US012662537B2

(12) United States Patent　　　(10) Patent No.: US 12,662,537 B2

He et al.　　　(45) Date of Patent: Jun. 23, 2026

(54) ANTI-PD-L1 ANTIGEN BINDING PROTEIN AND APPLICATION THEREOF

(71) Applicant: Harbour BioMed (Shanghai) Co., Ltd, Shanghai (CN)

(72) Inventors: Yun He, Suzhou (CN); Shuwen Ren, Suzhou (CN); Bin Liu, Suzhou (CN); Xin Gan, Suzhou (CN); Donghai Li, Suzhou (CN); Fei Chen, Suzhou (CN); Ling Wang, Suzhou (CN); Jin Li, Suzhou (CN); Yiping Rong, Suzhou (CN)

(73) Assignee: Harbour BioMed (Shanghai) Co., Ltd., Shanghai (CN)

( * ) Notice: Subject to any disclaimer, the term of this patent is extended or adjusted under 35 U.S.C. 154(b) by 1121 days.

(21) Appl. No.: 17/765,270

(22) PCT Filed: Sep. 29, 2020

(86) PCT No.: PCT/CN2020/118811

§ 371 (c)(1),
(2) Date: Mar. 30, 2022

(87) PCT Pub. No.: WO2021/063352

PCT Pub. Date: Apr. 8, 2021

(65) Prior Publication Data

US 2022/0411513 A1　　　Dec. 29, 2022

(30) Foreign Application Priority Data

Sep. 30, 2019　(CN) ......................... 201910944996.4

(51) Int. Cl.
| | |
|---|---|
| *C07K 16/28* | (2006.01) |
| *A61K 38/17* | (2006.01) |
| *A61K 39/00* | (2006.01) |
| *A61K 39/395* | (2006.01) |
| *A61K 45/06* | (2006.01) |
| *A61K 47/68* | (2017.01) |
| *A61P 1/00* | (2006.01) |
| *A61P 35/00* | (2006.01) |
| *C07K 14/71* | (2006.01) |

(52) U.S. Cl.
CPC ........ *C07K 16/2827* (2013.01); *A61K 38/179* (2013.01); *A61K 39/3955* (2013.01); *A61K 45/06* (2013.01); *A61K 47/6849* (2017.08); *A61P 1/00* (2018.01); *A61P 35/00* (2018.01); *C07K 14/71* (2013.01); *A61K 2039/505* (2013.01); *C07K 2317/21* (2013.01); *C07K 2317/565* (2013.01); *C07K 2317/73* (2013.01); *C07K 2317/732* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2018/0346571 A1　12/2018　Gurney et al.

FOREIGN PATENT DOCUMENTS

| | | |
|---|---|---|
| CN | 104961829 A | 10/2015 |
| CN | 106103488 A | 11/2016 |
| CN | 106939047 A | 7/2017 |
| TW | 202126700 A | 7/2021 |
| WO | WO 2007/005874 A2 | 1/2007 |
| WO | WO 2011/066389 A1 | 6/2011 |
| WO | WO 2013/079174 A1 | 6/2013 |

OTHER PUBLICATIONS

Bhattacharya et al., PLoS One 12(3): e0171355. https://doi.org/10.1371/journal.pone.0171355; 22 pages total (Year: 2017).*
Fenton et al., Medicinal Chemistry Research (2020) 29:1133-1146 (Year: 2020).*
Pucci et al., Current Opinion in Structural Biology 2022, 72: 161-168 (Year: 2022).*
Pak et al., PLoS One 18(3): e0282689. https://doi.org/10.1371/journal.pone.0282689 (Year: 2023).*
Mei et al., Current Opinion in Biotechnology 2024, 90:103223 (Year: 2024).*
Al-Lazikani et al., Standard conformations for the canonical structures of immunoglobulins. J Mol Biol. Nov. 7, 1997;273(4):927-48.
Altschul et al., Basic local alignment search tool. J Mol Biol. Oct. 5, 1990;215(3):403-10.
Carter et al., PD-1:PD-L inhibitory pathway affects both CD4(+) and CD8(+) T cells and is overcome by IL-2. Eur J Immunol. Mar. 2002;32(3):634-43.
Freeman et al., Engagement of the PD-1 immunoinhibitory receptor by a novel B7 family member leads to negative regulation of lymphocyte activation. J Exp Med. Oct. 2, 2000;192(7):1027-34.
Ishida et al., Induced expression of PD-1, a novel member of the immunoglobulin gene superfamily, upon programmed cell death. EMBO J. Nov. 1992;11(11):3887-95.
Kolibab et al., Protein Data Bank AAY57163: immunoglobulin heavy chain variable region, partial [*Homo sapiens*]. RCSB Protein Data Bank. Jan. 28, 2005. 2 pages.
Lee et al., A new addition to the PD-1 checkpoint inhibitors for non-small cell lung cancer-the anti-PDL1 antibody-MEDI4736. Transl Lung Cancer Res. Dec. 2014;3(6):408-10.

(Continued)

*Primary Examiner* — Christina M Borgeest

(74) *Attorney, Agent, or Firm* — Mintz Levin Cohn Ferris Glovsky and Popeo, P.C.

(57) ABSTRACT

Provided is an anti-PD-L1 antigen binding protein, capable of binding to primate-derived PD-L1 with a KD value of $1 \times 10^{-8}$ M or less. The antigen binding protein can block the binding of PD-1 and CD80 to PD-L1, stimulate the secretion of cytokines in immune cells, and can inhibit tumor growth and/or tumor cell proliferation. Also provided is a fusion protein, comprising human TGFBRII or a fragment thereof and the antigen binding protein. Also provided is an application of the antigen binding protein and/or the fusion protein in the prevention and treatment of tumors or cancers.

20 Claims, 20 Drawing Sheets

Specification includes a Sequence Listing.

(56) References Cited

OTHER PUBLICATIONS

Lipman et al., Rapid and sensitive protein similarity searches. Science. Mar. 22, 1985;227(4693):1435-41.

Luan et al., A fully human monoclonal antibody targeting PD-L1 with potent anti-tumor activity. Int Immunopharmacol. Feb. 2016;31:248-56. Epub Jan. 12, 2016.

Nishimura et al., Autoimmune dilated cardiomyopathy in PD-1 receptor-deficient mice. Science. Jan. 12, 2001;291(5502):319-22.

Pearson et al., Improved tools for biological sequence comparison. Proc Natl Acad Sci U S A. Apr. 1988;85(8):2444-8.

Tan et al., Protein Data Bank 5XJ4_H: Chain H, durvalumab-VH. RCSB Protein Data Bank. Apr. 25, 2018. 2 pages.

Valecha et al., Anti-PD-1/PD-L1 antibodies in non-small cell lung cancer: the era of immunotherapy. Expert Rev Anticancer Ther. Jan. 2017; 17(1):47-59. Epub Nov. 23, 2016.

Yang, Development and Identification of Monoclonal Antibody for Swine PD-1 and PD-L1. Thesis submitted to Zhengzhou University for Master's Degree. May 2017. 57 pages.

* cited by examiner

(A)     PR000265

Time (sec)

(B)     PR000266

Time (sec)

(C)

(D)

(E)

(A)

(B)

(C)

(D)

(A)

(B)

(A)

(B)

(A)

(B)

(A)

(B)

(C)

(A)

(B)

(A)

O  Group 1: Human IgG1, 10.4 mg/kg, q3d × 6, ip
+  Group 2: Positive control M7824, 12.3 mg/kg, q3d × 6, ip
⊞  Group 3: PR001902, 12.2 mg/kg, q3d × 6, ip (B)

⊖  Group 1: Human IgG1, 10.4 mg/kg, q3d × 6, ip
◆  Group 2: Positive control M7824, 12.3 mg/kg, q3d × 6, ip
⊟  Group 3: PR001902, 12.2 mg/kg, q3d × 6, ip

SEQUENCE LISTING

<160> NUMBER OF SEQ ID NOS: 194

<210> SEQ ID NO 1
<211> LENGTH: 25
<212> TYPE: PRT
<213> ORGANISM: Artificial Sequence
<220> FEATURE:
<223> OTHER INFORMATION: HFWR1

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: HFWR1

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: HFWR1

<400> SEQUENCE: 3

Gln Val Gln Leu Val Gln Ser Gly Ala Glu Val Lys Lys Pro Gly Gln
1               5                   10                  15

Ser Leu Arg Ile Ser Cys Lys Gly Ala
            20                  25

<210> SEQ ID NO 4
<211> LENGTH: 25
<212> TYPE: PRT
<213> ORGANISM: Artificial Sequence
<220> FEATURE:
<223> OTHER INFORMATION: HFWR1

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 5
<211> LENGTH: 7
<212> TYPE: PRT
<213> ORGANISM: Artificial Sequence
<220> FEATURE:
<223> OTHER INFORMATION: HCDR1

<400> SEQUENCE: 5

Gly Phe Thr Phe Ser Ser Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: HCDR1

```
<400> SEQUENCE: 6

Gly Phe Thr Phe Ser Asp Ser
1               5

<210> SEQ ID NO 7
<211> LENGTH: 7
<212> TYPE: PRT
<213> ORGANISM: Artificial Sequence
<220> FEATURE:
<223> OTHER INFORMATION: HCDR1

<400> SEQUENCE: 7

Gly Tyr Ser Phe Ser Thr Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: HCDR1

<400> SEQUENCE: 8

Gly Tyr Thr Phe Thr Ser Tyr
1               5

<210> SEQ ID NO 9
<211> LENGTH: 19
<212> TYPE: PRT
<213> ORGANISM: Artificial Sequence
<220> FEATURE:
<223> OTHER INFORMATION: HFWR2

<400> SEQUENCE: 9

Trp Met Ser Trp Val Arg Gln Ala Pro Gly Lys Gly Leu Glu Trp Val
1               5                   10                  15

Ala Asn Ile

<210> SEQ ID NO 10
<211> LENGTH: 19
<212> TYPE: PRT
<213> ORGANISM: Artificial Sequence
<220> FEATURE:
<223> OTHER INFORMATION: HFWR2

<400> SEQUENCE: 10

Trp Ile His Trp Val Arg Gln Ala Pro Gly Lys Gly Leu Glu Trp Val
1               5                   10                  15

Ala Trp Ile

<210> SEQ ID NO 11
<211> LENGTH: 19
<212> TYPE: PRT
<213> ORGANISM: Artificial Sequence
<220> FEATURE:
<223> OTHER INFORMATION: HFWR2

<400> SEQUENCE: 11

Ile Met Met Trp Val Arg Gln Ala Pro Gly Lys Gly Leu Glu Trp Val
1               5                   10                  15

Ser Ser Ile

<210> SEQ ID NO 12
```

```
<211> LENGTH: 19
<212> TYPE: PRT
<213> ORGANISM: Artificial Sequence
<220> FEATURE:
<223> OTHER INFORMATION: HFWR2

<400> SEQUENCE: 12

Trp Ile Gly Trp Val Arg Gln Met Pro Gly Lys Gly Leu Glu Trp Met
1               5                   10                  15

Gly Ile Ile

<210> SEQ ID NO 13
<211> LENGTH: 19
<212> TYPE: PRT
<213> ORGANISM: Artificial Sequence
<220> FEATURE:
<223> OTHER INFORMATION: HFWR2

<400> SEQUENCE: 13

Trp Met His Trp Val Arg Gln Ala Pro Gly Gln Gly Leu Glu Trp Met
1               5                   10                  15

Gly Arg Ile

<210> SEQ ID NO 14
<211> LENGTH: 6
<212> TYPE: PRT
<213> ORGANISM: Artificial Sequence
<220> FEATURE:
<223> OTHER INFORMATION: HCDR2

<400> SEQUENCE: 14

Lys Gln Asp Gly Ser Glu
1               5

<210> SEQ ID NO 15
<211> LENGTH: 6
<212> TYPE: PRT
<213> ORGANISM: Artificial Sequence
<220> FEATURE:
<223> OTHER INFORMATION: HCDR2

<400> SEQUENCE: 15

Ser Pro Tyr Gly Gly Ser
1               5

<210> SEQ ID NO 16
<211> LENGTH: 6
<212> TYPE: PRT
<213> ORGANISM: Artificial Sequence
<220> FEATURE:
<223> OTHER INFORMATION: HCDR2

<400> SEQUENCE: 16

Lys Gln Glu Gly Ser Glu
1               5

<210> SEQ ID NO 17
<211> LENGTH: 6
<212> TYPE: PRT
<213> ORGANISM: Artificial Sequence
<220> FEATURE:
<223> OTHER INFORMATION: HCDR2

<400> SEQUENCE: 17

Lys Gln Asp Ala Ser Glu
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: HCDR2

<400> SEQUENCE: 18

Tyr Pro Ser Gly Gly Ile
1               5

<210> SEQ ID NO 19
<211> LENGTH: 6
<212> TYPE: PRT
<213> ORGANISM: Artificial Sequence
<220> FEATURE:
<223> OTHER INFORMATION: HCDR2

<400> SEQUENCE: 19

Tyr Pro Asp Asp Ser Asp
1               5

<210> SEQ ID NO 20
<211> LENGTH: 6
<212> TYPE: PRT
<213> ORGANISM: Artificial Sequence
<220> FEATURE:
<223> OTHER INFORMATION: HCDR2

<400> SEQUENCE: 20

Gly Pro Asn Ser Gly Phe
1               5

<210> SEQ ID NO 21
<211> LENGTH: 41
<212> TYPE: PRT
<213> ORGANISM: Artificial Sequence
<220> FEATURE:
<223> OTHER INFORMATION: HFWR3

<400> SEQUENCE: 21

Lys Tyr Tyr Val Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Asp Thr Ala Val Tyr Tyr Cys Ala Arg
        35                  40

<210> SEQ ID NO 22
<211> LENGTH: 41
<212> TYPE: PRT
<213> ORGANISM: Artificial Sequence
<220> FEATURE:
<223> OTHER INFORMATION: HFWR3

<400> SEQUENCE: 22

Lys Tyr Tyr Val Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Asp Thr Ala Val Phe Tyr Cys Ala Arg
        35                  40
```

```
<210> SEQ ID NO 23
<211> LENGTH: 41
<212> TYPE: PRT
<213> ORGANISM: Artificial Sequence
<220> FEATURE:
<223> OTHER INFORMATION: HFWR3

<400> SEQUENCE: 23

Lys Tyr Tyr Val Asp Ser Val Lys Gly Arg Phe Thr Ile Ser Arg Asp
1               5                   10                  15

Asn Ala Lys Asn Ser Gln Tyr Leu Gln Met Asn Ser Leu Arg Ala Glu
            20                  25                  30

Asp Thr Ala Val Tyr Tyr Cys Ala Arg
        35                  40

<210> SEQ ID NO 24
<211> LENGTH: 41
<212> TYPE: PRT
<213> ORGANISM: Artificial Sequence
<220> FEATURE:
<223> OTHER INFORMATION: HFWR3

<400> SEQUENCE: 24

Lys Tyr Tyr Gly Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Glu Thr Ala Val Tyr Tyr Cys Ala Arg
        35                  40

<210> SEQ ID NO 25
<211> LENGTH: 41
<212> TYPE: PRT
<213> ORGANISM: Artificial Sequence
<220> FEATURE:
<223> OTHER INFORMATION: HFWR3

<400> SEQUENCE: 25

Thr Tyr Tyr Ala Asp Ser Val Lys Gly Arg Phe Thr Ile Ser Ala Asp
1               5                   10                  15

Thr Ser Lys Asn Thr Ala Tyr Leu Gln Met Asn Ser Leu Arg Ala Glu
            20                  25                  30

Asp Thr Ala Val Tyr Tyr Cys Ala Arg
        35                  40

<210> SEQ ID NO 26
<211> LENGTH: 41
<212> TYPE: PRT
<213> ORGANISM: Artificial Sequence
<220> FEATURE:
<223> OTHER INFORMATION: HFWR3

<400> SEQUENCE: 26

Thr Phe Tyr Ala Asp Thr Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Arg
        35                  40

<210> SEQ ID NO 27
<211> LENGTH: 41
<212> TYPE: PRT
```

-continued

```
<213> ORGANISM: Artificial Sequence
<220> FEATURE:
<223> OTHER INFORMATION: HFWR3

<400> SEQUENCE: 27

Thr Arg Tyr Ser Pro Ser Phe Glu Gly Gln Val Thr Ile Ser Val Asp
1               5                   10                  15

Lys Ser Ile Thr Thr Ala Tyr Leu His Trp Ser Ser Leu Lys Ala Ser
            20                  25                  30

Asp Thr Ala Ile Tyr Tyr Cys Ala Arg
        35                  40

<210> SEQ ID NO 28
<211> LENGTH: 41
<212> TYPE: PRT
<213> ORGANISM: Artificial Sequence
<220> FEATURE:
<223> OTHER INFORMATION: HFWR3

<400> SEQUENCE: 28

Thr Ser Tyr Asn Glu Lys Phe Lys Asn Arg Val Thr Met Thr Arg Asp
1               5                   10                  15

Thr Ser Thr Ser Thr Val Tyr Met Glu Leu Ser Ser Leu Arg Ser Glu
            20                  25                  30

Asp Thr Ala Val Tyr Tyr Cys Ala Arg
        35                  40

<210> SEQ ID NO 29
<211> LENGTH: 10
<212> TYPE: PRT
<213> ORGANISM: Artificial Sequence
<220> FEATURE:
<223> OTHER INFORMATION: HCDR3

<400> SEQUENCE: 29

Asp Arg Ala Val Ala Gly Ala Phe Asp Ile
1               5                   10

<210> SEQ ID NO 30
<211> LENGTH: 10
<212> TYPE: PRT
<213> ORGANISM: Artificial Sequence
<220> FEATURE:
<223> OTHER INFORMATION: HCDR3

<400> SEQUENCE: 30

Asp Arg Ala Val Ala Gly Ala Ser Ala Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: HCDR3

<400> SEQUENCE: 31

Asp Arg Pro Val Ala Gly Ala Ser Asp Ile
1               5                   10

<210> SEQ ID NO 32
<211> LENGTH: 10
<212> TYPE: PRT
<213> ORGANISM: Artificial Sequence
<220> FEATURE:
```

```
<223> OTHER INFORMATION: HCDR3

<400> SEQUENCE: 32

Asp Arg Ala Val Ala Gly Ala Phe Ala Ile
1               5                   10

<210> SEQ ID NO 33
<211> LENGTH: 10
<212> TYPE: PRT
<213> ORGANISM: Artificial Sequence
<220> FEATURE:
<223> OTHER INFORMATION: HCDR3

<400> SEQUENCE: 33

Asp Arg Ala Val Ala Gly Ala Ser Asp Ile
1               5                   10

<210> SEQ ID NO 34
<211> LENGTH: 9
<212> TYPE: PRT
<213> ORGANISM: Artificial Sequence
<220> FEATURE:
<223> OTHER INFORMATION: HCDR3

<400> SEQUENCE: 34

Arg His Trp Pro Gly Gly Phe Asp Tyr
1               5

<210> SEQ ID NO 35
<211> LENGTH: 11
<212> TYPE: PRT
<213> ORGANISM: Artificial Sequence
<220> FEATURE:
<223> OTHER INFORMATION: HCDR3

<400> SEQUENCE: 35

Ile Lys Leu Gly Thr Val Thr Thr Val Asp Tyr
1               5                   10

<210> SEQ ID NO 36
<211> LENGTH: 8
<212> TYPE: PRT
<213> ORGANISM: Artificial Sequence
<220> FEATURE:
<223> OTHER INFORMATION: HCDR3

<400> SEQUENCE: 36

Leu Val Gly Gly Ala Pro Ala Tyr
1               5

<210> SEQ ID NO 37
<211> LENGTH: 10
<212> TYPE: PRT
<213> ORGANISM: Artificial Sequence
<220> FEATURE:
<223> OTHER INFORMATION: HCDR3

<400> SEQUENCE: 37

Gly Gly Ser Ser Tyr Asp Tyr Phe Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: HFWR4
```

-continued

<400> SEQUENCE: 38

```
Trp Gly Gln Gly Thr Met Val Thr Val Ser Ser
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: HFWR4

<400> SEQUENCE: 39

```
Trp Gly Gln Gly Thr Leu Val Thr Val Ser Ser
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: HFWR4

<400> SEQUENCE: 40

```
Trp Gly Gln Gly Thr Thr Val Thr Val Ser Ser
1               5                   10
```

<210> SEQ ID NO 41
<211> LENGTH: 23
<212> TYPE: PRT
<213> ORGANISM: Artificial Sequence
<220> FEATURE:
<223> OTHER INFORMATION: LFWR1

<400> SEQUENCE: 41

```
Asp Ile Gln Met Thr Gln Ser Pro Ser Thr Leu Ser Thr Ser Val Gly
1               5                   10                  15

Asp Arg Val Thr Ile Thr Cys
            20
```

<210> SEQ ID NO 42
<211> LENGTH: 23
<212> TYPE: PRT
<213> ORGANISM: Artificial Sequence
<220> FEATURE:
<223> OTHER INFORMATION: LFWR1

<400> SEQUENCE: 42

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 43
<211> LENGTH: 23
<212> TYPE: PRT
<213> ORGANISM: Artificial Sequence
<220> FEATURE:
<223> OTHER INFORMATION: LFWR1

<400> SEQUENCE: 43

```
Asp Ile Gln Met Thr Gln Ser Pro Ser Thr Leu Ser Ala Ser Val Gly
1               5                   10                  15

His Arg Val Thr Ile Thr Cys
            20
```

```
<210> SEQ ID NO 44
<211> LENGTH: 23
<212> TYPE: PRT
<213> ORGANISM: Artificial Sequence
<220> FEATURE:
<223> OTHER INFORMATION: LFWR1

<400> SEQUENCE: 44

Asp Ile Gln Met Thr Gln Ser Pro Ser Thr Leu Ser Ala Ser Val Gly
1               5                   10                  15

Asp Arg Val Thr Val Thr Cys
            20

<210> SEQ ID NO 45
<211> LENGTH: 23
<212> TYPE: PRT
<213> ORGANISM: Artificial Sequence
<220> FEATURE:
<223> OTHER INFORMATION: LFWR1

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 46
<211> LENGTH: 22
<212> TYPE: PRT
<213> ORGANISM: Artificial Sequence
<220> FEATURE:
<223> OTHER INFORMATION: LFWR1

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 47
<211> LENGTH: 23
<212> TYPE: PRT
<213> ORGANISM: Artificial Sequence
<220> FEATURE:
<223> OTHER INFORMATION: LFWR1

<400> SEQUENCE: 47

Asp Ile Val Leu Thr Gln Ser Pro Ala Ser Leu Ala Val Ser Pro Gly
1               5                   10                  15

Gln Arg Ala Thr Ile Thr Cys
            20

<210> SEQ ID NO 48
<211> LENGTH: 11
<212> TYPE: PRT
<213> ORGANISM: Artificial Sequence
<220> FEATURE:
<223> OTHER INFORMATION: LCDR1

<400> SEQUENCE: 48

Arg Ala Ser Gln Ser Ile Ser Ile Trp Leu Ala
1               5                   10
```

```
<210> SEQ ID NO 49
<211> LENGTH: 11
<212> TYPE: PRT
<213> ORGANISM: Artificial Sequence
<220> FEATURE:
<223> OTHER INFORMATION: LCDR1

<400> SEQUENCE: 49

Arg Ala Ser Gln Ser Ile Phe Ile Trp Leu Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: LCDR1

<400> SEQUENCE: 50

Arg Ala Ser Gln Ser Ile Ser Ser Trp Leu Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: LCDR1

<400> SEQUENCE: 51

Arg Ala Ser Gln Ser Ile Tyr Ile Trp Leu Ala
1               5                   10

<210> SEQ ID NO 52
<211> LENGTH: 11
<212> TYPE: PRT
<213> ORGANISM: Artificial Sequence
<220> FEATURE:
<223> OTHER INFORMATION: LCDR1

<400> SEQUENCE: 52

Arg Ala Ser Gln Asp Val Ser Thr Ala Val Ala
1               5                   10

<210> SEQ ID NO 53
<211> LENGTH: 14
<212> TYPE: PRT
<213> ORGANISM: Artificial Sequence
<220> FEATURE:
<223> OTHER INFORMATION: LCDR1

<400> SEQUENCE: 53

Thr Gly Thr Ser Ser Asp Val Gly Gly Tyr Asn Tyr Val Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: LCDR1

<400> SEQUENCE: 54

Ser Gly Ser Ser Ser Asp Ile Gly Arg Tyr Asp Tyr Val Ser
1               5                   10

<210> SEQ ID NO 55
```

```
<211> LENGTH: 15
<212> TYPE: PRT
<213> ORGANISM: Artificial Sequence
<220> FEATURE:
<223> OTHER INFORMATION: LCDR1

<400> SEQUENCE: 55

Arg Ala Ser Glu Ser Val Ser Ile His Gly Thr His Leu Met His
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: LFWR2

<400> SEQUENCE: 56

Trp Tyr Gln Gln Lys Pro Gly Lys Ala Pro Lys Leu Leu Ile Tyr
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: LFWR2

<400> SEQUENCE: 57

Trp Tyr Gln Gln Lys Pro Gly Lys Ala Pro Asn Leu Leu Ile Tyr
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: LFWR2

<400> SEQUENCE: 58

Trp Tyr Gln Gln Lys Pro Gly Lys Ala Pro Asp Leu Leu Ile Tyr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: LFWR2

<400> SEQUENCE: 59

Trp Tyr Gln Gln His Pro Gly Lys Ala Pro Lys Leu Leu Ile Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: LFWR2

<400> SEQUENCE: 60

Trp Tyr Gln Gln His Pro Gly Lys Ala Pro Lys Leu Met Ile Tyr
1               5                   10                  15

<210> SEQ ID NO 61
<211> LENGTH: 15
```

-continued

```
<212> TYPE: PRT
<213> ORGANISM: Artificial Sequence
<220> FEATURE:
<223> OTHER INFORMATION: LFWR2

<400> SEQUENCE: 61

Trp Tyr Gln His Tyr Pro Asp Lys Ala Pro Lys Leu Ile Ile Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: LFWR2

<400> SEQUENCE: 62

Trp Tyr Gln Gln Lys Pro Gly Gln Pro Pro Lys Leu Leu Ile Tyr
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: LCDR2

<400> SEQUENCE: 63

Lys Ala Ser Ser Leu Glu Ser
1               5

<210> SEQ ID NO 64
<211> LENGTH: 7
<212> TYPE: PRT
<213> ORGANISM: Artificial Sequence
<220> FEATURE:
<223> OTHER INFORMATION: LCDR2

<400> SEQUENCE: 64

Lys Ala Ser Ser Leu Glu Thr
1               5

<210> SEQ ID NO 65
<211> LENGTH: 7
<212> TYPE: PRT
<213> ORGANISM: Artificial Sequence
<220> FEATURE:
<223> OTHER INFORMATION: LCDR2

<400> SEQUENCE: 65

Ser Ala Ser Phe Leu Tyr Ser
1               5

<210> SEQ ID NO 66
<211> LENGTH: 7
<212> TYPE: PRT
<213> ORGANISM: Artificial Sequence
<220> FEATURE:
<223> OTHER INFORMATION: LCDR2

<400> SEQUENCE: 66

Asp Val Ser Asn Arg Pro Ser
1               5

<210> SEQ ID NO 67
<211> LENGTH: 7
<212> TYPE: PRT
```

```
<213> ORGANISM: Artificial Sequence
<220> FEATURE:
<223> OTHER INFORMATION: LCDR2

<400> SEQUENCE: 67

Glu Val Lys His Arg Pro Ser
1               5

<210> SEQ ID NO 68
<211> LENGTH: 7
<212> TYPE: PRT
<213> ORGANISM: Artificial Sequence
<220> FEATURE:
<223> OTHER INFORMATION: LCDR2

<400> SEQUENCE: 68

Ala Ala Ser Asn Leu Glu Ser
1               5

<210> SEQ ID NO 69
<211> LENGTH: 32
<212> TYPE: PRT
<213> ORGANISM: Artificial Sequence
<220> FEATURE:
<223> OTHER INFORMATION: LFWR3

<400> SEQUENCE: 69

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: LFWR3

<400> SEQUENCE: 70

Gly Val Pro Ser Arg Phe Ser Gly Asn Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: LFWR3

<400> SEQUENCE: 71

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Thr Thr Tyr Tyr Cys
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: LFWR3
```

-continued

<400> SEQUENCE: 72

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Phe Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: LFWR3

<400> SEQUENCE: 73

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: LFWR3

<400> SEQUENCE: 74

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: LFWR3

<400> SEQUENCE: 75

Gly Ile Ser His Arg Phe Ser Ala Ser Lys Ser Gly Asn Thr Ala Ser
1               5                   10                  15

Leu Thr Ile Ser Glu Leu Gln Pro Gly Asp Glu Ala Asp Tyr Tyr Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: LFWR3

<400> SEQUENCE: 76

Gly Val Pro Ala Arg Phe Ser Gly Ser Gly Ser Gly Thr Asp Phe Thr
1               5                   10                  15

Leu Thr Ile Asn Pro Val Glu Ala Glu Asp Thr Ala Asn Tyr Tyr Cys
            20                  25                  30

<210> SEQ ID NO 77
<211> LENGTH: 9
<212> TYPE: PRT
<213> ORGANISM: Artificial Sequence
<220> FEATURE:

-continued

```
<223> OTHER INFORMATION: LCDR3

<400> SEQUENCE: 77

Gln Gln Tyr Tyr Gly Tyr Ser Arg Thr
1               5

<210> SEQ ID NO 78
<211> LENGTH: 9
<212> TYPE: PRT
<213> ORGANISM: Artificial Sequence
<220> FEATURE:
<223> OTHER INFORMATION: LCDR3

<400> SEQUENCE: 78

Gln Gln Tyr Tyr Gly Ser Ser Arg Thr
1               5

<210> SEQ ID NO 79
<211> LENGTH: 9
<212> TYPE: PRT
<213> ORGANISM: Artificial Sequence
<220> FEATURE:
<223> OTHER INFORMATION: LCDR3

<400> SEQUENCE: 79

Gln Gln Tyr Tyr Ser Tyr Ser Arg Thr
1               5

<210> SEQ ID NO 80
<211> LENGTH: 9
<212> TYPE: PRT
<213> ORGANISM: Artificial Sequence
<220> FEATURE:
<223> OTHER INFORMATION: LCDR3

<400> SEQUENCE: 80

Gln Gln Tyr His Thr Tyr Ser Arg Thr
1               5

<210> SEQ ID NO 81
<211> LENGTH: 9
<212> TYPE: PRT
<213> ORGANISM: Artificial Sequence
<220> FEATURE:
<223> OTHER INFORMATION: LCDR3

<400> SEQUENCE: 81

Gln Gln Tyr Leu Tyr His Pro Ala Thr
1               5

<210> SEQ ID NO 82
<211> LENGTH: 10
<212> TYPE: PRT
<213> ORGANISM: Artificial Sequence
<220> FEATURE:
<223> OTHER INFORMATION: LCDR3

<400> SEQUENCE: 82

Ser Ser Tyr Thr Ser Ser Ser Thr Arg Val
1               5                   10

<210> SEQ ID NO 83
<211> LENGTH: 10
<212> TYPE: PRT
<213> ORGANISM: Artificial Sequence
<220> FEATURE:
<223> OTHER INFORMATION: LCDR3
```

-continued

<400> SEQUENCE: 83

Ala Ser Tyr Thr Glu Ser Lys Thr Tyr Ile
1               5                   10

<210> SEQ ID NO 84
<211> LENGTH: 9
<212> TYPE: PRT
<213> ORGANISM: Artificial Sequence
<220> FEATURE:
<223> OTHER INFORMATION: LCDR3

<400> SEQUENCE: 84

Gln Gln Ser Phe Glu Asp Pro Leu Thr
1               5

<210> SEQ ID NO 85
<211> LENGTH: 10
<212> TYPE: PRT
<213> ORGANISM: Artificial Sequence
<220> FEATURE:
<223> OTHER INFORMATION: LFWR4

<400> SEQUENCE: 85

Phe Gly Gln Gly Thr Lys Val Glu Ile Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: LFWR4

<400> SEQUENCE: 86

Phe Gly Gln Gly Thr Lys Val Glu Ile Arg
1               5                   10

<210> SEQ ID NO 87
<211> LENGTH: 10
<212> TYPE: PRT
<213> ORGANISM: Artificial Sequence
<220> FEATURE:
<223> OTHER INFORMATION: LFWR4

<400> SEQUENCE: 87

Phe Gly Thr Gly Thr Lys Val Thr Val Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: LFWR4

<400> SEQUENCE: 88

Phe Gly Gly Gly Thr Lys Val Thr Val Leu
1               5                   10

<210> SEQ ID NO 89
<211> LENGTH: 10
<212> TYPE: PRT
<213> ORGANISM: Artificial Sequence
<220> FEATURE:
<223> OTHER INFORMATION: LFWR4

```
<400> SEQUENCE: 89

Phe Gly Gln Gly Thr Lys Leu Glu Ile Lys
1               5                   10

<210> SEQ ID NO 90
<211> LENGTH: 119
<212> TYPE: PRT
<213> ORGANISM: Artificial Sequence
<220> FEATURE:
<223> OTHER INFORMATION: VH

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: VH

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser
        115

<210> SEQ ID NO 92
<211> LENGTH: 119
<212> TYPE: PRT
<213> ORGANISM: Artificial Sequence
<220> FEATURE:
```

-continued

```
<223> OTHER INFORMATION: VH

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Val Ala Gly Ala Ser Asp Ile Trp Gly Gln Gly
            100                 105                 110

Thr Met Val Thr Val Ser Ser
        115

<210> SEQ ID NO 93
<211> LENGTH: 119
<212> TYPE: PRT
<213> ORGANISM: Artificial Sequence
<220> FEATURE:
<223> OTHER INFORMATION: VH

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
            100                 105                 110

Thr Met Val Thr Val Ser Ser
        115

<210> SEQ ID NO 94
<211> LENGTH: 119
<212> TYPE: PRT
<213> ORGANISM: Artificial Sequence
<220> FEATURE:
<223> OTHER INFORMATION: VH

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Gln Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Asp Ile Trp Gly Gln Gly
                100                 105                 110

Thr Met Val Thr Val Ser Ser
        115
```

<210> SEQ ID NO 95
<211> LENGTH: 119
<212> TYPE: PRT
<213> ORGANISM: Artificial Sequence
<220> FEATURE:
<223> OTHER INFORMATION: VH

<400> SEQUENCE: 95

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Glu Thr Ala Val Tyr Tyr Cys
                85                  90                  95

Ala Arg Asp Arg Ala Val Ala Gly Ala Ser Asp Ile Trp Gly Gln Gly
                100                 105                 110

Thr Met Val Thr Val Ser Ser
        115
```

<210> SEQ ID NO 96
<211> LENGTH: 118
<212> TYPE: PRT
<213> ORGANISM: Artificial Sequence
<220> FEATURE:
<223> OTHER INFORMATION: VH

<400> SEQUENCE: 96

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: VH

<400> SEQUENCE: 97

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser
        115

<210> SEQ ID NO 98
<211> LENGTH: 119
<212> TYPE: PRT
<213> ORGANISM: Artificial Sequence
<220> FEATURE:
<223> OTHER INFORMATION: VH

<400> SEQUENCE: 98

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser
        115

<210> SEQ ID NO 99
<211> LENGTH: 119
<212> TYPE: PRT
<213> ORGANISM: Artificial Sequence
<220> FEATURE:
<223> OTHER INFORMATION: VH

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Glu Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
                100                 105                 110

Thr Met Val Thr Val Ser Ser
            115
```

<210> SEQ ID NO 100
<211> LENGTH: 119
<212> TYPE: PRT
<213> ORGANISM: Artificial Sequence
<220> FEATURE:
<223> OTHER INFORMATION: VH

<400> SEQUENCE: 100

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Ala Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
                100                 105                 110

Thr Met Val Thr Val Ser Ser
            115
```

<210> SEQ ID NO 101
<211> LENGTH: 119
<212> TYPE: PRT
<213> ORGANISM: Artificial Sequence
<220> FEATURE:
<223> OTHER INFORMATION: VH

<400> SEQUENCE: 101

```
Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
        20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser
        115
```

```
<210> SEQ ID NO 102
<211> LENGTH: 119
<212> TYPE: PRT
<213> ORGANISM: Artificial Sequence
<220> FEATURE:
<223> OTHER INFORMATION: VH

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser
        115
```

```
<210> SEQ ID NO 103
<211> LENGTH: 119
<212> TYPE: PRT
<213> ORGANISM: Artificial Sequence
<220> FEATURE:
<223> OTHER INFORMATION: VH

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Gly Asp Ser Val
    50                  55                  60
```

-continued

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Glu Thr Ala Val Tyr Tyr Cys
                85                  90                  95

Ala Arg Asp Arg Ala Val Ala Gly Ala Ser Asp Ile Trp Gly Gln Gly
            100                 105                 110

Thr Met Val Thr Val Ser Ser
        115

<210> SEQ ID NO 104
<211> LENGTH: 119
<212> TYPE: PRT
<213> ORGANISM: Artificial Sequence
<220> FEATURE:
<223> OTHER INFORMATION: VH

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Glu Thr Ala Val Tyr Tyr Cys
                85                  90                  95

Ala Arg Asp Arg Ala Val Ala Gly Ala Ser Asp Ile Trp Gly Gln Gly
            100                 105                 110

Thr Met Val Thr Val Ser Ser
        115

<210> SEQ ID NO 105
<211> LENGTH: 120
<212> TYPE: PRT
<213> ORGANISM: Artificial Sequence
<220> FEATURE:
<223> OTHER INFORMATION: VH

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110
```

```
Gly Thr Leu Val Thr Val Ser Ser
        115                 120

<210> SEQ ID NO 106
<211> LENGTH: 117
<212> TYPE: PRT
<213> ORGANISM: Artificial Sequence
<220> FEATURE:
<223> OTHER INFORMATION: VH

<400> SEQUENCE: 106

Gln Val Gln Leu Val Gln Ser Gly Ala Glu Val Lys Lys Pro Gly Gln
1               5                   10                  15

Ser Leu Arg Ile Ser Cys Lys Gly Ala Gly Tyr Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Glu Gly Gln Val Thr Ile Ser Val Asp Lys Ser Ile Thr Thr Ala Tyr
65                  70                  75                  80

Leu His Trp Ser Ser Leu Lys Ala Ser Asp Thr Ala Ile Tyr Tyr Cys
                85                  90                  95

Ala Arg Leu Val Gly Gly Ala Pro Ala Tyr Trp Gly Gln Gly Thr Leu
            100                 105                 110

Val Thr Val Ser Ser
        115

<210> SEQ ID NO 107
<211> LENGTH: 119
<212> TYPE: PRT
<213> ORGANISM: Artificial Sequence
<220> FEATURE:
<223> OTHER INFORMATION: VH

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: VL
```

```
<400> SEQUENCE: 108

Asp Ile Gln Met Thr Gln Ser Pro Ser Thr Leu Ser Thr Ser Val Gly
1               5                   10                  15

Asp Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
                85                  90                  95

Thr Phe Gly Gln Gly Thr Lys Val Glu Ile Lys
            100                 105

<210> SEQ ID NO 109
<211> LENGTH: 107
<212> TYPE: PRT
<213> ORGANISM: Artificial Sequence
<220> FEATURE:
<223> OTHER INFORMATION: VL

<400> SEQUENCE: 109

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Phe Ile Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys
            100                 105

<210> SEQ ID NO 110
<211> LENGTH: 107
<212> TYPE: PRT
<213> ORGANISM: Artificial Sequence
<220> FEATURE:
<223> OTHER INFORMATION: VL

<400> SEQUENCE: 110

Asp Ile Gln Met Thr Gln Ser Pro Ser Thr Leu Ser Ala Ser Val Gly
1               5                   10                  15

His Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Asp Leu Leu Ile
        35                  40                  45

Tyr Lys Ala Ser Ser Leu Glu Thr Gly Val Pro Ser Arg Phe Ser Gly
    50                  55                  60

Asn Gly Ser Gly Thr Glu Phe Thr Leu Thr Ile Ser Ser Leu Gln Pro
65                  70                  75                  80
```

-continued

```
Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: VL

<400> SEQUENCE: 111

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
                85                  90                  95

Thr Phe Gly Gln Gly Thr Lys Val Glu Ile Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: VL

<400> SEQUENCE: 112

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Thr Thr Tyr Tyr Cys Gln Gln Tyr Tyr Ser Tyr Ser Arg
                85                  90                  95

Thr Phe Gly Gln Gly Thr Lys Val Glu Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: VL
```

-continued

```
<400> SEQUENCE: 113

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Tyr Ile Trp
            20                  25                  30

Leu Ala Trp Tyr Gln Gln His Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Tyr Gly Tyr Ser Arg
                85                  90                  95

Thr Phe Gly Gln Gly Thr Lys Val Glu Ile Arg
            100                 105
```

```
<210> SEQ ID NO 114
<211> LENGTH: 107
<212> TYPE: PRT
<213> ORGANISM: Artificial Sequence
<220> FEATURE:
<223> OTHER INFORMATION: VL

<400> SEQUENCE: 114

Asp Ile Gln Met Thr Gln Ser Pro Ser Thr Leu Ser Ala Ser Val Gly
1               5                   10                  15

Asp Arg Val Thr Val Thr Cys Arg Ala Ser Gln Ser Ile Tyr Ile Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys
            100                 105
```

```
<210> SEQ ID NO 115
<211> LENGTH: 107
<212> TYPE: PRT
<213> ORGANISM: Artificial Sequence
<220> FEATURE:
<223> OTHER INFORMATION: VL

<400> SEQUENCE: 115

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

-continued

```
Asp Asp Phe Ala Thr Tyr Tyr Cys Gln Gln Tyr His Thr Tyr Ser Arg
            85                  90                  95

Thr Phe Gly Gln Gly Thr Lys Val Glu Ile Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: VL

<400> SEQUENCE: 116

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
            85                  90                  95

Thr Phe Gly Gln Gly Thr Lys Val Glu Ile Lys
            100                 105

<210> SEQ ID NO 117
<211> LENGTH: 107
<212> TYPE: PRT
<213> ORGANISM: Artificial Sequence
<220> FEATURE:
<223> OTHER INFORMATION: VL

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
            85                  90                  95

Thr Phe Gly Gln Gly Thr Lys Val Glu Ile Lys
            100                 105

<210> SEQ ID NO 118
<211> LENGTH: 107
<212> TYPE: PRT
<213> ORGANISM: Artificial Sequence
<220> FEATURE:
<223> OTHER INFORMATION: VL
```

-continued

<400> SEQUENCE: 118

```
Asp Ile Gln Met Thr Gln Ser Pro Ser Thr Leu Ser Ala Ser Val Gly
1               5                   10                  15

His Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Asp Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys
            100                 105
```

<210> SEQ ID NO 119
<211> LENGTH: 110
<212> TYPE: PRT
<213> ORGANISM: Artificial Sequence
<220> FEATURE:
<223> OTHER INFORMATION: VL

<400> SEQUENCE: 119

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 120
<211> LENGTH: 110
<212> TYPE: PRT
<213> ORGANISM: Artificial Sequence
<220> FEATURE:
<223> OTHER INFORMATION: VL

<400> SEQUENCE: 120

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asp Ile Gly Arg Tyr
            20                  25                  30

Asp Tyr Val Ser Trp Tyr Gln His Tyr Pro Asp Lys Ala Pro Lys Leu
        35                  40                  45

Ile Ile Tyr Glu Val Lys His Arg Pro Ser Gly Ile Ser His Arg Phe
    50                  55                  60

Ser Ala Ser Lys Ser Gly Asn Thr Ala Ser Leu Thr Ile Ser Glu Leu
65                  70                  75                  80
```

```
Gln Pro Gly Asp Glu Ala Asp Tyr Tyr Cys Ala Ser Tyr Thr Glu Ser
                85                  90                  95

Lys Thr Tyr Ile Phe Gly Gly Gly Thr Lys Val Thr Val Leu
            100                 105                 110
```

<210> SEQ ID NO 121
<211> LENGTH: 111
<212> TYPE: PRT
<213> ORGANISM: Artificial Sequence
<220> FEATURE:
<223> OTHER INFORMATION: VL

<400> SEQUENCE: 121

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110
```

<210> SEQ ID NO 122
<211> LENGTH: 449
<212> TYPE: PRT
<213> ORGANISM: Artificial Sequence
<220> FEATURE:
<223> OTHER INFORMATION: HC

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 123
<211> LENGTH: 449
<212> TYPE: PRT
<213> ORGANISM: Artificial Sequence
<220> FEATURE:
<223> OTHER INFORMATION: HC

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60
```

-continued

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 124
<211> LENGTH: 449
<212> TYPE: PRT
<213> ORGANISM: Artificial Sequence -continued

```
<220> FEATURE:
<223> OTHER INFORMATION: HC

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Pro Val Ala Gly Ala Ser Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 125
<211> LENGTH: 449
<212> TYPE: PRT
<213> ORGANISM: Artificial Sequence
<220> FEATURE:
<223> OTHER INFORMATION: HC

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

-continued

```
Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys

<210> SEQ ID NO 126
<211> LENGTH: 449
<212> TYPE: PRT
<213> ORGANISM: Artificial Sequence
<220> FEATURE:
<223> OTHER INFORMATION: HC

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Gln Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205
```

-continued

```
Ser Asn Thr Lys Val Asp Lys Lys Val Glu Pro Lys Ser Cys Asp Lys
    210             215             220
```

```
Thr His Thr Cys Pro Pro Cys Pro Ala Pro Glu Leu Leu Gly Gly Pro
225             230             235             240
```

```
Ser Val Phe Leu Phe Pro Pro Lys Pro Lys Asp Thr Leu Met Ile Ser
            245             250             255
```

```
Arg Thr Pro Glu Val Thr Cys Val Val Val Asp Val Ser His Glu Asp
            260             265             270
```

```
Pro Glu Val Lys Phe Asn Trp Tyr Val Asp Gly Val Glu Val His Asn
            275             280             285
```

```
Ala Lys Thr Lys Pro Arg Glu Glu Gln Tyr Ala Ser Thr Tyr Arg Val
    290             295             300
```

```
Val Ser Val Leu Thr Val Leu His Gln Asp Trp Leu Asn Gly Lys Glu
305             310             315             320
```

```
Tyr Lys Cys Lys Val Ser Asn Lys Ala Leu Pro Ala Pro Ile Glu Lys
            325             330             335
```

```
Thr Ile Ser Lys Ala Lys Gly Gln Pro Arg Glu Pro Gln Val Tyr Thr
            340             345             350
```

```
Leu Pro Pro Ser Arg Glu Glu Met Thr Lys Asn Gln Val Ser Leu Thr
            355             360             365
```

```
Cys Leu Val Lys Gly Phe Tyr Pro Ser Asp Ile Ala Val Glu Trp Glu
    370             375             380
```

```
Ser Asn Gly Gln Pro Glu Asn Asn Tyr Lys Thr Thr Pro Pro Val Leu
385             390             395             400
```

```
Asp Ser Asp Gly Ser Phe Phe Leu Tyr Ser Lys Leu Thr Val Asp Lys
            405             410             415
```

```
Ser Arg Trp Gln Gln Gly Asn Val Phe Ser Cys Ser Val Met His Glu
            420             425             430
```

```
Ala Leu His Asn His Tyr Thr Gln Lys Ser Leu Ser Leu Ser Pro Gly
            435             440             445
```

```
Lys
```

```
<210> SEQ ID NO 127
<211> LENGTH: 449
<212> TYPE: PRT
<213> ORGANISM: Artificial Sequence
<220> FEATURE:
<223> OTHER INFORMATION: HC
```

```
<400> SEQUENCE: 127
```

```
Glu Val Gln Leu Val Glu Ser Gly Gly Gly Leu Val Gln Pro Gly Gly
1               5               10              15
```

```
Ser Leu Arg Leu Ser Cys Ala Ala Ser Gly Phe Thr Phe Ser Ser Tyr
            20              25              30
```

```
Trp Met Ser Trp Val Arg Gln Ala Pro Gly Lys Gly Leu Glu Trp Val
            35              40              45
```

```
Ala Asn Ile Lys Gln Asp Gly Ser Glu Lys Tyr Tyr Gly Asp Ser Val
    50              55              60
```

```
Lys Gly Arg Phe Thr Ile Ser Arg Asp Asn Ala Lys Asn Ser Leu Tyr
65              70              75              80
```

```
Leu Gln Met Asn Ser Leu Arg Ala Glu Glu Thr Ala Val Tyr Tyr Cys
            85              90              95
```

```
Ala Arg Asp Arg Ala Val Ala Gly Ala Ser Asp Ile Trp Gly Gln Gly
            100             105             110
```

-continued

```
Thr Met Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 128
<211> LENGTH: 448
<212> TYPE: PRT
<213> ORGANISM: Artificial Sequence
<220> FEATURE:
<223> OTHER INFORMATION: HC

<400> SEQUENCE: 128

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430
```

Leu His Asn His Tyr Thr Gln Lys Ser Leu Ser Leu Ser Pro Gly Lys
        435                 440                 445

<210> SEQ ID NO 129
<211> LENGTH: 449
<212> TYPE: PRT
<213> ORGANISM: Artificial Sequence
<220> FEATURE:
<223> OTHER INFORMATION: HC

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 130
<211> LENGTH: 449
<212> TYPE: PRT
<213> ORGANISM: Artificial Sequence
<220> FEATURE:
<223> OTHER INFORMATION: HC

<400> SEQUENCE: 130
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Ser Ala Phe Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

```
<210> SEQ ID NO 131
<211> LENGTH: 449
<212> TYPE: PRT
<213> ORGANISM: Artificial Sequence
<220> FEATURE:
<223> OTHER INFORMATION: HC

<400> SEQUENCE: 131
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 132
<211> LENGTH: 449
<212> TYPE: PRT
<213> ORGANISM: Artificial Sequence
<220> FEATURE:
<223> OTHER INFORMATION: HC

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Ala Ser Glu Lys Tyr Tyr Val Asp Ser Val
        50                  55                  60
```

-continued

```
Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Phe Tyr Cys
                85                  90                  95

Ala Arg Asp Arg Ala Val Ala Gly Ala Phe Ala Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 133
<211> LENGTH: 449
<212> TYPE: PRT

<213> ORGANISM: Artificial Sequence
<220> FEATURE:
<223> OTHER INFORMATION: HC

<400> SEQUENCE: 133

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

-continued

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 134
<211> LENGTH: 449
<212> TYPE: PRT
<213> ORGANISM: Artificial Sequence
<220> FEATURE:
<223> OTHER INFORMATION: HC

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

-continued

```
Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 135
<211> LENGTH: 449
<212> TYPE: PRT
<213> ORGANISM: Artificial Sequence
<220> FEATURE:
<223> OTHER INFORMATION: HC

<400> SEQUENCE: 135
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Glu Thr Ala Val Tyr Tyr Cys
                85                  90                  95

Ala Arg Asp Arg Ala Val Ala Gly Ala Ser Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

```
<210> SEQ ID NO 136
<211> LENGTH: 449
<212> TYPE: PRT
<213> ORGANISM: Artificial Sequence
<220> FEATURE:
<223> OTHER INFORMATION: HC

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Ala Ser Glu Lys Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Glu Thr Ala Val Tyr Tyr Cys
                85                  90                  95
```

-continued

```
Ala Arg Asp Arg Ala Val Ala Gly Ala Ser Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 137
<211> LENGTH: 449
<212> TYPE: PRT
<213> ORGANISM: Artificial Sequence
<220> FEATURE:
<223> OTHER INFORMATION: HC -continued

<400> SEQUENCE: 137

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 138
<211> LENGTH: 600
<212> TYPE: PRT
<213> ORGANISM: Artificial Sequence
<220> FEATURE:
<223> OTHER INFORMATION: HC

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Glu Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300
```

-continued

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
            435                 440                 445

Gly Gly Gly Gly Ser Gly Gly Gly Gly Ser Gly Gly Gly Gly Ser Thr
    450                 455                 460

Ile Pro Pro His Val Gln Lys Ser Val Asn Asn Asp Met Ile Val Thr
465                 470                 475                 480

Asp Asn Asn Gly Ala Val Lys Phe Pro Gln Leu Cys Lys Phe Cys Asp
                    485                 490                 495

Val Arg Phe Ser Thr Cys Asp Asn Gln Lys Ser Cys Met Ser Asn Cys
                    500                 505                 510

Ser Ile Thr Ser Ile Cys Glu Lys Pro Gln Glu Val Cys Val Ala Val
            515                 520                 525

Trp Arg Lys Asn Asp Glu Asn Ile Thr Leu Glu Thr Val Cys His Asp
            530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Lys Pro Gly Glu Thr Phe Phe Met
                    565                 570                 575

Cys Ser Cys Ser Ser Asp Glu Cys Asn Asp Asn Ile Ile Phe Ser Glu
                    580                 585                 590

Glu Tyr Asn Thr Ser Asn Pro Asp
            595                 600

<210> SEQ ID NO 139
<211> LENGTH: 605
<212> TYPE: PRT
<213> ORGANISM: Artificial Sequence
<220> FEATURE:
<223> OTHER INFORMATION: HC

<400> SEQUENCE: 139

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Glu Gly Ser Glu Lys Tyr Tyr Val Asp Ser Val
    50                  55                  60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Gly Gly Gly Gly Ser Gly Gly Gly Ser Gly Gly Gly Gly Ser Gly
    450                 455                 460

Gly Gly Gly Ser Gly Ile Pro Pro His Val Gln Lys Ser Val Asn Asn
465                 470                 475                 480
```

-continued

```
Asp Met Ile Val Thr Asp Asn Asn Gly Ala Val Lys Phe Pro Gln Leu
            485                 490                 495

Cys Lys Phe Cys Asp Val Arg Phe Ser Thr Cys Asp Asn Gln Lys Ser
            500                 505                 510

Cys Met Ser Asn Cys Ser Ile Thr Ser Ile Cys Glu Lys Pro Gln Glu
            515                 520                 525

Val Cys Val Ala Val Trp Arg Lys Asn Asp Glu Asn Ile Thr Leu Glu
            530                 535                 540

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Lys Pro Gly
                565                 570                 575

Glu Thr Phe Phe Met Cys Ser Cys Ser Ser Asp Glu Cys Asn Asp Asn
                580                 585                 590

Ile Ile Phe Ser Glu Glu Tyr Asn Thr Ser Asn Pro Asp
                595                 600                 605
```

<210> SEQ ID NO 140
<211> LENGTH: 450
<212> TYPE: PRT
<213> ORGANISM: Artificial Sequence
<220> FEATURE:
<223> OTHER INFORMATION: HC

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

<210> SEQ ID NO 141
<211> LENGTH: 607
<212> TYPE: PRT
<213> ORGANISM: Artificial Sequence
<220> FEATURE:
<223> OTHER INFORMATION: HC

<400> SEQUENCE: 141

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Ala Gly Gly Gly Ser Gly Gly Gly Gly Ser Gly Gly Gly Gly
    450                 455                 460

Ser Gly Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
            485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
            515                 520                 525

Gln Glu Val Cys Val Ala Val Trp Arg Lys Asn Asp Glu Asn Ile Thr
        530                 535                 540

Leu Glu Thr Val Cys His Asp Pro Lys Leu Pro Tyr His Asp Phe Ile
545                 550                 555                 560
```

-continued

```
Leu Glu Asp Ala Ala Ser Pro Lys Cys Ile Met Lys Glu Lys Lys Lys
            565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605

<210> SEQ ID NO 142
<211> LENGTH: 590
<212> TYPE: PRT
<213> ORGANISM: Artificial Sequence
<220> FEATURE:
<223> OTHER INFORMATION: HC

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Glu Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Gly Ser Gly Gly Ser Gly Ile Pro Pro His Val Gln Lys Ser Val Asn
        450                 455                 460

Asn Asp Met Ile Val Thr Asp Asn Asn Gly Ala Val Lys Phe Pro Gln
465                 470                 475                 480

Leu Cys Lys Phe Cys Asp Val Arg Phe Ser Thr Cys Asp Asn Gln Lys
                485                 490                 495

Ser Cys Met Ser Asn Cys Ser Ile Thr Ser Ile Cys Glu Lys Pro Gln
                500                 505                 510

Glu Val Cys Val Ala Val Trp Arg Lys Asn Asp Glu Asn Ile Thr Leu
                515                 520                 525

Glu Thr Val Cys His Asp Pro Lys Leu Pro Tyr His Asp Phe Ile Leu
        530                 535                 540

Glu Asp Ala Ala Ser Pro Lys Cys Ile Met Lys Glu Lys Lys Lys Pro
545                 550                 555                 560

Gly Glu Thr Phe Phe Met Cys Ser Cys Ser Ser Asp Glu Cys Asn Asp
                565                 570                 575

Asn Ile Ile Phe Ser Glu Glu Tyr Asn Thr Ser Asn Pro Asp
                580                 585                 590
```

```
<210> SEQ ID NO 143
<211> LENGTH: 584
<212> TYPE: PRT
<213> ORGANISM: Artificial Sequence
<220> FEATURE:
<223> OTHER INFORMATION: HC

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
                35                  40                  45

Ala Asn Ile Lys Gln Glu Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Asp Arg Ala Val Ala Gly Ala Phe Asp Ile Trp Gly Gln Gly
        100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Ile Pro Pro His Val Gln Lys Ser Val Asn Asn Asp Met Ile Val Thr
    450                 455                 460

Asp Asn Asn Gly Ala Val Lys Phe Pro Gln Leu Cys Lys Phe Cys Asp
465                 470                 475                 480

Val Arg Phe Ser Thr Cys Asp Asn Gln Lys Ser Cys Met Ser Asn Cys
                485                 490                 495

Ser Ile Thr Ser Ile Cys Glu Lys Pro Gln Glu Val Cys Val Ala Val
        500                 505                 510

-continued

Trp Arg Lys Asn Asp Glu Asn Ile Thr Leu Glu Thr Val Cys His Asp
            515                 520                 525

Pro Lys Leu Pro Tyr His Asp Phe Ile Leu Glu Asp Ala Ala Ser Pro
        530                 535                 540

Lys Cys Ile Met Lys Glu Lys Lys Lys Pro Gly Glu Thr Phe Phe Met
545                 550                 555                 560

Cys Ser Cys Ser Ser Asp Glu Cys Asn Asp Asn Ile Ile Phe Ser Glu
                565                 570                 575

Glu Tyr Asn Thr Ser Asn Pro Asp
            580

<210> SEQ ID NO 144
<211> LENGTH: 603
<212> TYPE: PRT
<213> ORGANISM: Artificial Sequence
<220> FEATURE:
<223> OTHER INFORMATION: HC

<400> SEQUENCE: 144

Gln Val Gln Leu Val Gln Ser Gly Ala Glu Val Lys Lys Pro Gly Gln
1               5                   10                  15

Ser Leu Arg Ile Ser Cys Lys Gly Ala Gly Tyr Ser Phe Ser Thr Tyr
            20                  25                  30

Trp Ile Gly Trp Val Arg Gln Met Pro Gly Lys Gly Leu Glu Trp Met
            35                  40                  45

Gly Ile Ile Tyr Pro Asp Asp Ser Asp Thr Arg Tyr Ser Pro Ser Phe
        50                  55                  60

Glu Gly Gln Val Thr Ile Ser Val Asp Lys Ser Ile Thr Thr Ala Tyr
65                  70                  75                  80

Leu His Trp Ser Ser Leu Lys Ala Ser Asp Thr Ala Ile Tyr Tyr Cys
                85                  90                  95

Ala Arg Leu Val Gly Gly Ala Pro Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

-continued

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Gly Gly
                435                 440                 445

Gly Gly Ser Gly Gly Gly Gly Ser Gly Gly Gly Gly Ser Gly Gly Gly
    450                 455                 460

Gly Ser Gly Ile Pro Pro His Val Gln Lys Ser Val Asn Asn Asp Met
465                 470                 475                 480

Ile Val Thr Asp Asn Asn Gly Ala Val Lys Phe Pro Gln Leu Cys Lys
                485                 490                 495

Phe Cys Asp Val Arg Phe Ser Thr Cys Asp Asn Gln Lys Ser Cys Met
                500                 505                 510

Ser Asn Cys Ser Ile Thr Ser Ile Cys Glu Lys Pro Gln Glu Val Cys
                515                 520                 525

Val Ala Val Trp Arg Lys Asn Asp Glu Asn Ile Thr Leu Glu Thr Val
    530                 535                 540

Cys His Asp Pro Lys Leu Pro Tyr His Asp Phe Ile Leu Glu Asp Ala
545                 550                 555                 560

Ala Ser Pro Lys Cys Ile Met Lys Glu Lys Lys Lys Pro Gly Glu Thr
                565                 570                 575

Phe Phe Met Cys Ser Cys Ser Ser Asp Glu Cys Asn Asp Asn Ile Ile
                580                 585                 590

Phe Ser Glu Glu Tyr Asn Thr Ser Asn Pro Asp
    595                 600

<210> SEQ ID NO 145
<211> LENGTH: 605
<212> TYPE: PRT
<213> ORGANISM: Artificial Sequence
<220> FEATURE:
<223> OTHER INFORMATION: HC

<400> SEQUENCE: 145

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
                35                  40                  45

-continued

```
Ala Asn Ile Lys Gln Glu Gly Ser Glu Lys Tyr Tyr Gly Asp Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Glu Thr Ala Val Tyr Tyr Cys
            85              90              95

Ala Arg Asp Arg Ala Val Ala Gly Ala Ser Asp Ile Trp Gly Gln Gly
            100             105             110

Thr Met Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Gly Gly Gly Gly Ser Gly Gly Gly Ser Gly Gly Gly Gly Ser Gly
    450             455             460
```

```
Gly Gly Gly Ser Gly Ile Pro Pro His Val Gln Lys Ser Val Asn Asn
465             470             475             480

Asp Met Ile Val Thr Asp Asn Asn Gly Ala Val Lys Phe Pro Gln Leu
                485             490             495

Cys Lys Phe Cys Asp Val Arg Phe Ser Thr Cys Asp Asn Gln Lys Ser
            500             505             510

Cys Met Ser Asn Cys Ser Ile Thr Ser Ile Cys Glu Lys Pro Gln Glu
            515             520             525

Val Cys Val Ala Val Trp Arg Lys Asn Asp Glu Asn Ile Thr Leu Glu
    530             535             540

Thr Val Cys His Asp Pro Lys Leu Pro Tyr His Asp Phe Ile Leu Glu
545             550             555             560

Asp Ala Ala Ser Pro Lys Cys Ile Met Lys Glu Lys Lys Pro Gly
            565             570             575

Glu Thr Phe Phe Met Cys Ser Cys Ser Ser Asp Glu Cys Asn Asp Asn
            580             585             590

Ile Ile Phe Ser Glu Glu Tyr Asn Thr Ser Asn Pro Asp
            595             600             605

<210> SEQ ID NO 146
<211> LENGTH: 605
<212> TYPE: PRT
<213> ORGANISM: Artificial Sequence
<220> FEATURE:
<223> OTHER INFORMATION: HC

<400> SEQUENCE: 146

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
        20              25              30

Trp Met Ser Trp Val Arg Gln Ala Pro Gly Lys Gly Leu Glu Trp Val
        35              40              45

Ala Asn Ile Lys Gln Asp Ala Ser Glu Lys Tyr Tyr Gly Asp Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Glu Thr Ala Val Tyr Tyr Cys
                85              90              95

Ala Arg Asp Arg Ala Val Ala Gly Ala Ser Asp Ile Trp Gly Gln Gly
            100             105             110

Thr Met Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220
```

```
Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Gly Gly Gly Gly Ser Gly Gly Gly Gly Ser Gly Gly Gly Ser Gly
        450             455             460

Gly Gly Gly Ser Gly Ile Pro Pro His Val Gln Lys Ser Val Asn Asn
465             470             475             480

Asp Met Ile Val Thr Asp Asn Asn Gly Ala Val Lys Phe Pro Gln Leu
            485             490             495

Cys Lys Phe Cys Asp Val Arg Phe Ser Thr Cys Asp Asn Gln Lys Ser
            500             505             510

Cys Met Ser Asn Cys Ser Ile Thr Ser Ile Cys Glu Lys Pro Gln Glu
            515             520             525

Val Cys Val Ala Val Trp Arg Lys Asn Asp Glu Asn Ile Thr Leu Glu
        530             535             540

Thr Val Cys His Asp Pro Lys Leu Pro Tyr His Asp Phe Ile Leu Glu
545             550             555             560

Asp Ala Ala Ser Pro Lys Cys Ile Met Lys Glu Lys Lys Pro Gly
            565             570             575

Glu Thr Phe Phe Met Cys Ser Cys Ser Ser Asp Glu Cys Asn Asp Asn
        580             585             590

Ile Ile Phe Ser Glu Glu Tyr Asn Thr Ser Asn Pro Asp
        595             600             605
```

<210> SEQ ID NO 147
<211> LENGTH: 605
<212> TYPE: PRT
<213> ORGANISM: Artificial Sequence
<220> FEATURE:
<223> OTHER INFORMATION: HC -continued

```
<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Ala Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Val Ala Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Gly Gly Gly Gly Ser Gly Gly Gly Gly Ser Gly Gly Gly Gly Ser Gly
    450             455             460

Gly Gly Gly Ser Gly Ile Pro Pro His Val Gln Lys Ser Val Asn Asn
465             470             475             480

Asp Met Ile Val Thr Asp Asn Asn Gly Ala Val Lys Phe Pro Gln Leu
            485             490             495

Cys Lys Phe Cys Asp Val Arg Phe Ser Thr Cys Asp Asn Gln Lys Ser
            500             505             510

Cys Met Ser Asn Cys Ser Ile Thr Ser Ile Cys Glu Lys Pro Gln Glu
            515             520             525

Val Cys Val Ala Val Trp Arg Lys Asn Asp Glu Asn Ile Thr Leu Glu
    530             535             540

Thr Val Cys His Asp Pro Lys Leu Pro Tyr His Asp Phe Ile Leu Glu
545             550             555             560

Asp Ala Ala Ser Pro Lys Cys Ile Met Lys Glu Lys Lys Lys Pro Gly
            565             570             575

Glu Thr Phe Phe Met Cys Ser Cys Ser Ser Asp Glu Cys Asn Asp Asn
            580             585             590

Ile Ile Phe Ser Glu Glu Tyr Asn Thr Ser Asn Pro Asp
        595             600             605

<210> SEQ ID NO 148
<211> LENGTH: 605
<212> TYPE: PRT
<213> ORGANISM: Artificial Sequence
<220> FEATURE:
<223> OTHER INFORMATION: HC

<400> SEQUENCE: 148

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Trp Met Ser Trp Val Arg Gln Ala Pro Gly Lys Gly Leu Glu Trp Val
            35              40              45

Ala Asn Ile Lys Gln Asp Gly Ser Glu Lys Tyr Tyr Val Asp Ser Val
        50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
            85              90              95

Ala Arg Asp Arg Ala Val Ala Gly Ala Phe Asp Ile Trp Gly Gln Gly
            100             105             110

Thr Met Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
        130             135             140

Gly Cys Leu Val Lys Asp Tyr Phe Pro Glu Pro Val Thr Val Ser Trp
145             150             155             160
```

-continued

```
Asn Ser Gly Ala Leu Thr Ser Gly Val His Thr Phe Pro Ala Val Leu
             165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
             195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
             245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
             275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
             325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
             355                 360                 365

Cys Leu Val Lys Gly Phe Tyr Pro Ser Asp Ile Ala Val Glu Trp Glu
             370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
             405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
             435                 440                 445

Gly Gly Gly Gly Ser Gly Gly Gly Gly Ser Gly Gly Gly Ser Gly
        450                 455                 460

Gly Gly Gly Ser Gly Ile Pro Pro His Val Gln Lys Ser Val Asn Asn
465                 470                 475                 480

Asp Met Ile Val Thr Asp Asn Asn Gly Ala Val Lys Phe Pro Gln Leu
             485                 490                 495

Cys Lys Phe Cys Asp Val Arg Phe Ser Thr Cys Asp Asn Gln Lys Ser
             500                 505                 510

Cys Met Ser Asn Cys Ser Ile Thr Ser Ile Cys Glu Lys Pro Gln Glu
             515                 520                 525

Val Cys Val Ala Val Trp Arg Lys Asn Asp Glu Asn Ile Thr Leu Glu
        530                 535                 540

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Lys Pro Gly
             565                 570                 575
```

Glu Thr Phe Phe Met Cys Ser Cys Ser Ser Asp Glu Cys Asn Asp Asn
            580                 585                 590

Ile Ile Phe Ser Glu Glu Tyr Asn Thr Ser Asn Pro Asp
            595                 600                 605

<210> SEQ ID NO 149
<211> LENGTH: 584
<212> TYPE: PRT
<213> ORGANISM: Artificial Sequence
<220> FEATURE:
<223> OTHER INFORMATION: HC

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

-continued

```
Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Ala Gly Gly
            435                 440                 445

Gly Gly Ser Gly Gly Gly Gly Ser Gly Gly Gly Gly Ser Gly Gly Gly
            450                 455                 460

Gly Ser Gly Gly Ala Val Lys Phe Pro Gln Leu Cys Lys Phe Cys Asp
465                 470                 475                 480

Val Arg Phe Ser Thr Cys Asp Asn Gln Lys Ser Cys Met Ser Asn Cys
                485                 490                 495

Ser Ile Thr Ser Ile Cys Glu Lys Pro Gln Glu Val Cys Val Ala Val
            500                 505                 510

Trp Arg Lys Asn Asp Glu Asn Ile Thr Leu Glu Thr Val Cys His Asp
            515                 520                 525

Pro Lys Leu Pro Tyr His Asp Phe Ile Leu Glu Asp Ala Ala Ser Pro
            530                 535                 540

Lys Cys Ile Met Lys Glu Lys Lys Lys Pro Gly Glu Thr Phe Phe Met
545                 550                 555                 560

Cys Ser Cys Ser Ser Asp Glu Cys Asn Asp Asn Ile Ile Phe Ser Glu
                565                 570                 575

Glu Tyr Asn Thr Ser Asn Pro Asp
                580

<210> SEQ ID NO 150
<211> LENGTH: 214
<212> TYPE: PRT
<213> ORGANISM: Artificial Sequence
<220> FEATURE:
<223> OTHER INFORMATION: LC

<400> SEQUENCE: 150

Asp Ile Gln Met Thr Gln Ser Pro Ser Thr Leu Ser Thr Ser Val Gly
1                   5                   10                  15

Asp Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
                85                  90                  95

Thr Phe Gly Gln Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 151
<211> LENGTH: 214
<212> TYPE: PRT
<213> ORGANISM: Artificial Sequence
<220> FEATURE:
<223> OTHER INFORMATION: LC

<400> SEQUENCE: 151

Asp Ile Gln Met Thr Gln Ser Pro Ser Thr Leu Ser Ala Ser Val Gly
1                   5                   10                  15

Asp Arg Val Thr Ile Thr Cys Arg Ala Ser Gln Ser Ile Phe Ile Trp
                20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 152
<211> LENGTH: 214
<212> TYPE: PRT
<213> ORGANISM: Artificial Sequence
<220> FEATURE:
```

-continued

<223> OTHER INFORMATION: LC

<400> SEQUENCE: 152

```
Asp Ile Gln Met Thr Gln Ser Pro Ser Thr Leu Ser Ala Ser Val Gly
1               5                   10                  15

His Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Asp Leu Leu Ile
        35                  40                  45

Tyr Lys Ala Ser Ser Leu Glu Thr Gly Val Pro Ser Arg Phe Ser Gly
    50                  55                  60

Asn Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 153
<211> LENGTH: 214
<212> TYPE: PRT
<213> ORGANISM: Artificial Sequence
<220> FEATURE:
<223> OTHER INFORMATION: LC
```

<400> SEQUENCE: 153

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 154
<211> LENGTH: 214
<212> TYPE: PRT
<213> ORGANISM: Artificial Sequence
<220> FEATURE:
<223> OTHER INFORMATION: LC

<400> SEQUENCE: 154
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Thr Thr Tyr Tyr Cys Gln Gln Tyr Tyr Ser Tyr Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 155
<211> LENGTH: 214
<212> TYPE: PRT
<213> ORGANISM: Artificial Sequence
<220> FEATURE:
<223> OTHER INFORMATION: LC
```

<400> SEQUENCE: 155

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Tyr Ile Trp
            20                  25                  30

Leu Ala Trp Tyr Gln Gln His Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Tyr Gly Tyr Ser Arg
                85                  90                  95

Thr Phe Gly Gln Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210
```

<210> SEQ ID NO 156
<211> LENGTH: 214
<212> TYPE: PRT
<213> ORGANISM: Artificial Sequence
<220> FEATURE:
<223> OTHER INFORMATION: LC

<400> SEQUENCE: 156

```
Asp Ile Gln Met Thr Gln Ser Pro Ser Thr Leu Ser Ala Ser Val Gly
1               5                   10                  15

Asp Arg Val Thr Val Thr Cys Arg Ala Ser Gln Ser Ile Tyr Ile Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 157
<211> LENGTH: 214
<212> TYPE: PRT
<213> ORGANISM: Artificial Sequence
<220> FEATURE:
<223> OTHER INFORMATION: LC

<400> SEQUENCE: 157

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Thr Tyr Ser Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 158
<211> LENGTH: 214
<212> TYPE: PRT
<213> ORGANISM: Artificial Sequence
<220> FEATURE:
<223> OTHER INFORMATION: LC
```

-continued

```
<400> SEQUENCE: 158

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Tyr Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 159
<211> LENGTH: 214
<212> TYPE: PRT
<213> ORGANISM: Artificial Sequence
<220> FEATURE:
<223> OTHER INFORMATION: LC

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 160
<211> LENGTH: 214
<212> TYPE: PRT
<213> ORGANISM: Artificial Sequence
<220> FEATURE:
<223> OTHER INFORMATION: LC

<400> SEQUENCE: 160

Asp Ile Gln Met Thr Gln Ser Pro Ser Thr Leu Ser Ala Ser Val Gly
1               5                   10                  15

His Arg Val Thr Ile Thr Cys Arg Ala Ser Gln Ser Ile Ser Ile Trp
                20                  25                  30

Leu Ala Trp Tyr Gln Gln Lys Pro Gly Lys Ala Pro Asp Leu Leu Ile
            35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 161
<211> LENGTH: 214
<212> TYPE: PRT
<213> ORGANISM: Artificial Sequence
<220> FEATURE:
<223> OTHER INFORMATION: LC
```

-continued

<400> SEQUENCE: 161

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Tyr Ile Trp
            20                  25                  30

Leu Ala Trp Tyr Gln Gln His Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Tyr Gly Tyr Ser Arg
                85                  90                  95

Thr Phe Gly Gln Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 162
<211> LENGTH: 214
<212> TYPE: PRT
<213> ORGANISM: Artificial Sequence
<220> FEATURE:
<223> OTHER INFORMATION: LC

<400> SEQUENCE: 162

```
Asp Ile Gln Met Thr Gln Ser Pro Ser Thr Leu Ser Ala Ser Val Gly
1               5                   10                  15

Asp Arg Val Thr Val Thr Cys Arg Ala Ser Gln Ser Ile Tyr Ile Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

-continued

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
    210
```

```
<210> SEQ ID NO 163
<211> LENGTH: 214
<212> TYPE: PRT
<213> ORGANISM: Artificial Sequence
<220> FEATURE:
<223> OTHER INFORMATION: LC

<400> SEQUENCE: 163
```

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
                20                  25                  30
Leu Ala Trp Tyr Gln Gln Lys Pro Gly Lys Ala Pro Asn Leu Leu Ile
            35                  40                  45
Tyr Lys Ala Ser Ser Leu Glu Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Tyr Gly Tyr Ser Arg
                85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
    210
```

```
<210> SEQ ID NO 164
<211> LENGTH: 216
<212> TYPE: PRT
<213> ORGANISM: Artificial Sequence
<220> FEATURE:
<223> OTHER INFORMATION: LC
```

<400> SEQUENCE: 164

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

<210> SEQ ID NO 165
<211> LENGTH: 216
<212> TYPE: PRT
<213> ORGANISM: Artificial Sequence
<220> FEATURE:
<223> OTHER INFORMATION: LC

<400> SEQUENCE: 165

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asp Ile Gly Arg Tyr
                20                  25                  30

Asp Tyr Val Ser Trp Tyr Gln His Tyr Pro Asp Lys Ala Pro Lys Leu
            35                  40                  45

Ile Ile Tyr Glu Val Lys His Arg Pro Ser Gly Ile Ser His Arg Phe
        50                  55                  60

Ser Ala Ser Lys Ser Gly Asn Thr Ala Ser Leu Thr Ile Ser Glu Leu
65                  70                  75                  80

Gln Pro Gly Asp Glu Ala Asp Tyr Tyr Cys Ala Ser Tyr Thr Glu Ser
                85                  90                  95

Lys Thr Tyr Ile Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125
```

-continued

```
Leu Gln Ala Asn Lys Ala Thr Leu Val Cys Leu Ile Ser Asp Phe Tyr
    130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
        195             200             205

Thr Val Ala Pro Thr Glu Cys Ser
    210             215
```

<210> SEQ ID NO 166
<211> LENGTH: 218
<212> TYPE: PRT
<213> ORGANISM: Artificial Sequence
<220> FEATURE:
<223> OTHER INFORMATION: LC

<400> SEQUENCE: 166

```
Asp Ile Val Leu Thr Gln Ser Pro Ala Ser Leu Ala Val Ser Pro Gly
1               5               10              15

Gln Arg Ala Thr Ile Thr Cys Arg Ala Ser Glu Ser Val Ser Ile His
            20              25              30

Gly Thr His Leu Met His Trp Tyr Gln Gln Lys Pro Gly Gln Pro Pro
        35              40              45

Lys Leu Leu Ile Tyr Ala Ala Ser Asn Leu Glu Ser Gly Val Pro Ala
    50              55              60

Arg Phe Ser Gly Ser Gly Ser Gly Thr Asp Phe Thr Leu Thr Ile Asn
65              70              75              80

Pro Val Glu Ala Glu Asp Thr Ala Asn Tyr Tyr Cys Gln Gln Ser Phe
                85              90              95

Glu Asp Pro Leu Thr Phe Gly Gln Gly Thr Lys Leu Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
                165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215
```

<210> SEQ ID NO 167
<211> LENGTH: 6
<212> TYPE: PRT
<213> ORGANISM: Artificial Sequence
<220> FEATURE:
<223> OTHER INFORMATION: linker -continued

```
<400> SEQUENCE: 167

Gly Gly Ser Gly Gly Ser
1               5

<210> SEQ ID NO 168
<211> LENGTH: 15
<212> TYPE: PRT
<213> ORGANISM: Artificial Sequence
<220> FEATURE:
<223> OTHER INFORMATION: linker

<400> SEQUENCE: 168

Gly Gly Gly Gly Ser Gly Gly Gly Gly Ser Gly Gly Gly Gly Ser
1               5                   10                  15

<210> SEQ ID NO 169
<211> LENGTH: 20
<212> TYPE: PRT
<213> ORGANISM: Artificial Sequence
<220> FEATURE:
<223> OTHER INFORMATION: linker

<400> SEQUENCE: 169

Gly Gly Gly Gly Ser Gly Gly Gly Gly Ser Gly Gly Gly Gly Ser Gly
1               5                   10                  15

Gly Gly Gly Ser
            20

<210> SEQ ID NO 170
<211> LENGTH: 107
<212> TYPE: PRT
<213> ORGANISM: Artificial Sequence
<220> FEATURE:
<223> OTHER INFORMATION: CK

<400> SEQUENCE: 170

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 171
<211> LENGTH: 106
<212> TYPE: PRT
<213> ORGANISM: Artificial Sequence
<220> FEATURE:
<223> OTHER INFORMATION: CL

<400> SEQUENCE: 171

Gly Gln Pro Lys Ala Asn Pro Thr Val Thr Leu Phe Pro Pro Ser Ser
1               5                   10                  15
```

-continued

```
Glu Glu Leu Gln Ala Asn Lys Ala Thr Leu Val Cys Leu Ile Ser Asp
        20              25              30

Phe Tyr Pro Gly Ala Val Thr Val Ala Trp Lys Ala Asp Gly Ser Pro
        35              40              45

Val Lys Ala Gly Val Glu Thr Thr Lys Pro Ser Lys Gln Ser Asn Asn
    50              55              60

Lys Tyr Ala Ala Ser Ser Tyr Leu Ser Leu Thr Pro Glu Gln Trp Lys
65              70              75              80

Ser His Arg Ser Tyr Ser Cys Gln Val Thr His Glu Gly Ser Thr Val
                85              90              95

Glu Lys Thr Val Ala Pro Thr Glu Cys Ser
        100             105
```

<210> SEQ ID NO 172
<211> LENGTH: 330
<212> TYPE: PRT
<213> ORGANISM: Artificial Sequence
<220> FEATURE:
<223> OTHER INFORMATION: CH

<400> SEQUENCE: 172

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
        20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
        100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
        180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
        260             265             270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 173
<211> LENGTH: 330
<212> TYPE: PRT
<213> ORGANISM: Artificial Sequence
<220> FEATURE:
<223> OTHER INFORMATION: CH

<400> SEQUENCE: 173

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 174
<211> LENGTH: 329
<212> TYPE: PRT
<213> ORGANISM: Artificial Sequence
<220> FEATURE:
<223> OTHER INFORMATION: CH

<400> SEQUENCE: 174

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

-continued

```
<210> SEQ ID NO 175
<211> LENGTH: 329
<212> TYPE: PRT
<213> ORGANISM: Artificial Sequence
<220> FEATURE:
<223> OTHER INFORMATION: CH

<400> SEQUENCE: 175

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 176
<211> LENGTH: 567
<212> TYPE: PRT
<213> ORGANISM: Artificial Sequence
```

-continued

```
<220> FEATURE:
<223> OTHER INFORMATION: TGFBR2

<400> SEQUENCE: 176

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65              70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400
```

```
Ser Leu Arg Leu Asp Pro Thr Leu Ser Val Asp Asp Leu Ala Asn Ser
            405             410             415

Gly Gln Val Gly Thr Ala Arg Tyr Met Ala Pro Glu Val Leu Glu Ser
            420             425             430

Arg Met Asn Leu Glu Asn Val Glu Ser Phe Lys Gln Thr Asp Val Tyr
            435             440             445

Ser Met Ala Leu Val Leu Trp Glu Met Thr Ser Arg Cys Asn Ala Val
        450             455             460

Gly Glu Val Lys Asp Tyr Glu Pro Pro Phe Gly Ser Lys Val Arg Glu
465             470             475             480

His Pro Cys Val Glu Ser Met Lys Asp Asn Val Leu Arg Asp Arg Gly
            485             490             495

Arg Pro Glu Ile Pro Ser Phe Trp Leu Asn His Gln Gly Ile Gln Met
            500             505             510

Val Cys Glu Thr Leu Thr Glu Cys Trp Asp His Asp Pro Glu Ala Arg
            515             520             525

Leu Thr Ala Gln Cys Val Ala Glu Arg Phe Ser Glu Leu Glu His Leu
        530             535             540

Asp Arg Leu Ser Gly Arg Ser Cys Ser Glu Glu Lys Ile Pro Glu Asp
545             550             555             560

Gly Ser Leu Asn Thr Thr Lys
            565

<210> SEQ ID NO 177
<211> LENGTH: 136
<212> TYPE: PRT
<213> ORGANISM: Artificial Sequence
<220> FEATURE:
<223> OTHER INFORMATION: TGFBR2

<400> SEQUENCE: 177

Ile Pro Pro His Val Gln Lys Ser Val Asn Asn Asp Met Ile Val Thr
1               5               10              15

Asp Asn Asn Gly Ala Val Lys Phe Pro Gln Leu Cys Lys Phe Cys Asp
            20              25              30

Val Arg Phe Ser Thr Cys Asp Asn Gln Lys Ser Cys Met Ser Asn Cys
        35              40              45

Ser Ile Thr Ser Ile Cys Glu Lys Pro Gln Glu Val Cys Val Ala Val
        50              55              60

Trp Arg Lys Asn Asp Glu Asn Ile Thr Leu Glu Thr Val Cys His Asp
65              70              75              80

Pro Lys Leu Pro Tyr His Asp Phe Ile Leu Glu Asp Ala Ala Ser Pro
            85              90              95

Lys Cys Ile Met Lys Glu Lys Lys Lys Pro Gly Glu Thr Phe Phe Met
            100             105             110

Cys Ser Cys Ser Ser Asp Glu Cys Asn Asp Asn Ile Ile Phe Ser Glu
            115             120             125

Glu Tyr Asn Thr Ser Asn Pro Asp
        130             135

<210> SEQ ID NO 178
<211> LENGTH: 137
<212> TYPE: PRT
<213> ORGANISM: Artificial Sequence
<220> FEATURE:
<223> OTHER INFORMATION: TGFBR2
```

<400> SEQUENCE: 178

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
    130                 135
```

<210> SEQ ID NO 179
<211> LENGTH: 6
<212> TYPE: PRT
<213> ORGANISM: Artificial Sequence
<220> FEATURE:
<223> OTHER INFORMATION: HCDR2 Formula 1
<220> FEATURE:
<221> NAME/KEY: X
<222> LOCATION: (3)..(3)
<223> OTHER INFORMATION: X=D or E
<220> FEATURE:
<221> NAME/KEY: X
<222> LOCATION: (4)..(4)
<223> OTHER INFORMATION: X=G or A

<400> SEQUENCE: 179

```
Lys Gln Xaa Xaa Ser Glu
1               5
```

<210> SEQ ID NO 180
<211> LENGTH: 10
<212> TYPE: PRT
<213> ORGANISM: Artificial Sequence
<220> FEATURE:
<223> OTHER INFORMATION: HCDR3 Formula 1
<220> FEATURE:
<221> NAME/KEY: X
<222> LOCATION: (3)..(3)
<223> OTHER INFORMATION: X=A or P
<220> FEATURE:
<221> NAME/KEY: X
<222> LOCATION: (8)..(8)
<223> OTHER INFORMATION: X=F or S
<220> FEATURE:
<221> NAME/KEY: X
<222> LOCATION: (9)..(9)
<223> OTHER INFORMATION: X=D or A
<220> FEATURE:
<221> NAME/KEY: X
<222> LOCATION: (10)..(10)
<223> OTHER INFORMATION: X=IF

<400> SEQUENCE: 180

```
Asp Arg Xaa Val Ala Gly Ala Xaa Xaa Xaa
1               5                   10
```

```
<210> SEQ ID NO 181
<211> LENGTH: 11
<212> TYPE: PRT
<213> ORGANISM: Artificial Sequence
<220> FEATURE:
<223> OTHER INFORMATION: LCDR1 Formula 1
<220> FEATURE:
<221> NAME/KEY: X
<222> LOCATION: (7)..(7)
<223> OTHER INFORMATION: X=FS or Y
<220> FEATURE:
<221> NAME/KEY: X
<222> LOCATION: (8)..(8)
<223> OTHER INFORMATION: X=I or S

<400> SEQUENCE: 181

Arg Ala Ser Gln Ser Ile Xaa Xaa Trp Leu Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: LCDR2 Formula 1
<220> FEATURE:
<221> NAME/KEY: X
<222> LOCATION: (7)..(7)
<223> OTHER INFORMATION: X=S or T

<400> SEQUENCE: 182

Lys Ala Ser Ser Leu Glu Xaa
1               5

<210> SEQ ID NO 183
<211> LENGTH: 9
<212> TYPE: PRT
<213> ORGANISM: Artificial Sequence
<220> FEATURE:
<223> OTHER INFORMATION: LCDR3 Formula 1
<220> FEATURE:
<221> NAME/KEY: X
<222> LOCATION: (4)..(4)
<223> OTHER INFORMATION: X=Y or H
<220> FEATURE:
<221> NAME/KEY: X
<222> LOCATION: (5)..(5)
<223> OTHER INFORMATION: X=GT or S
<220> FEATURE:
<221> NAME/KEY: X
<222> LOCATION: (6)..(6)
<223> OTHER INFORMATION: X=Y or S

<400> SEQUENCE: 183

Gln Gln Tyr Xaa Xaa Xaa Ser Arg Thr
1               5

<210> SEQ ID NO 184
<211> LENGTH: 41
<212> TYPE: PRT
<213> ORGANISM: Artificial Sequence
<220> FEATURE:
<223> OTHER INFORMATION: H-FR3 Formula 1
<220> FEATURE:
<221> NAME/KEY: X
<222> LOCATION: (4)..(4)
<223> OTHER INFORMATION: X=V or G
<220> FEATURE:
<221> NAME/KEY: X
<222> LOCATION: (22)..(22)
<223> OTHER INFORMATION: X=L or Q
<220> FEATURE:
```

-continued

```
<221> NAME/KEY: X
<222> LOCATION: (33)..(33)
<223> OTHER INFORMATION: X=D or E
<220> FEATURE:
<221> NAME/KEY: X
<222> LOCATION: (37)..(37)
<223> OTHER INFORMATION: X=Y or F

<400> SEQUENCE: 184

Lys Tyr Tyr Xaa Asp Ser Val Lys Gly Arg Phe Thr Ile Ser Arg Asp
1               5                   10                  15

Asn Ala Lys Asn Ser Xaa Tyr Leu Gln Met Asn Ser Leu Arg Ala Glu
            20                  25                  30

Xaa Thr Ala Val Xaa Tyr Cys Ala Arg
        35                  40

<210> SEQ ID NO 185
<211> LENGTH: 23
<212> TYPE: PRT
<213> ORGANISM: Artificial Sequence
<220> FEATURE:
<223> OTHER INFORMATION: L-FR1
<220> FEATURE:
<221> NAME/KEY: X
<222> LOCATION: (13)..(13)
<223> OTHER INFORMATION: X=T or A
<220> FEATURE:
<221> NAME/KEY: X
<222> LOCATION: (17)..(17)
<223> OTHER INFORMATION: X=D or H
<220> FEATURE:
<221> NAME/KEY: X
<222> LOCATION: (21)..(21)
<223> OTHER INFORMATION: X=I or V

<400> SEQUENCE: 185

Asp Ile Gln Met Thr Gln Ser Pro Ser Thr Leu Ser Xaa Ser Val Gly
1               5                   10                  15

Xaa Arg Val Thr Xaa Thr Cys
            20

<210> SEQ ID NO 186
<211> LENGTH: 15
<212> TYPE: PRT
<213> ORGANISM: Artificial Sequence
<220> FEATURE:
<223> OTHER INFORMATION: L-FR2 Formula 1
<220> FEATURE:
<221> NAME/KEY: X
<222> LOCATION: (5)..(5)
<223> OTHER INFORMATION: X=K or H
<220> FEATURE:
<221> NAME/KEY: X
<222> LOCATION: (11)..(11)
<223> OTHER INFORMATION: X=KN or D

<400> SEQUENCE: 186

Trp Tyr Gln Gln Xaa Pro Gly Lys Ala Pro Xaa Leu Leu Ile Tyr
1               5                   10                  15

<210> SEQ ID NO 187
<211> LENGTH: 32
<212> TYPE: PRT
<213> ORGANISM: Artificial Sequence
<220> FEATURE:
<223> OTHER INFORMATION: L-FR3 Formula 1
<220> FEATURE:
<221> NAME/KEY: X
<222> LOCATION: (9)..(9)
<223> OTHER INFORMATION: X=S or N
```

```
<220> FEATURE:
<221> NAME/KEY: X
<222> LOCATION: (28)..(28)
<223> OTHER INFORMATION: X=A or T
<220> FEATURE:
<221> NAME/KEY: X
<222> LOCATION: (31)..(31)
<223> OTHER INFORMATION: X=Y or F

<400> SEQUENCE: 187

Gly Val Pro Ser Arg Phe Ser Gly Xaa Gly Ser Gly Thr Glu Phe Thr
1               5                   10                  15

Leu Thr Ile Ser Ser Leu Gln Pro Asp Asp Phe Xaa Thr Tyr Xaa Cys
            20                  25                  30

<210> SEQ ID NO 188
<211> LENGTH: 10
<212> TYPE: PRT
<213> ORGANISM: Artificial Sequence
<220> FEATURE:
<223> OTHER INFORMATION: L-FR4 Formula 1
<220> FEATURE:
<221> NAME/KEY: X
<222> LOCATION: (10)..(10)
<223> OTHER INFORMATION: X=K or R

<400> SEQUENCE: 188

Phe Gly Gln Gly Thr Lys Val Glu Ile Xaa
1               5                   10

<210> SEQ ID NO 189
<211> LENGTH: 119
<212> TYPE: PRT
<213> ORGANISM: Artificial Sequence
<220> FEATURE:
<223> OTHER INFORMATION: VH Formula 1
<220> FEATURE:
<221> NAME/KEY: X
<222> LOCATION: (54)..(54)
<223> OTHER INFORMATION: X=D or E
<220> FEATURE:
<221> NAME/KEY: X
<222> LOCATION: (55)..(55)
<223> OTHER INFORMATION: X=G or A
<220> FEATURE:
<221> NAME/KEY: X
<222> LOCATION: (61)..(61)
<223> OTHER INFORMATION: X=V or G
<220> FEATURE:
<221> NAME/KEY: X
<222> LOCATION: (79)..(79)
<223> OTHER INFORMATION: X=L or Q
<220> FEATURE:
<221> NAME/KEY: X
<222> LOCATION: (90)..(90)
<223> OTHER INFORMATION: X=D or E
<220> FEATURE:
<221> NAME/KEY: X
<222> LOCATION: (94)..(94)
<223> OTHER INFORMATION: X=Y or F
<220> FEATURE:
<221> NAME/KEY: X
<222> LOCATION: (101)..(101)
<223> OTHER INFORMATION: X=A or P
<220> FEATURE:
<221> NAME/KEY: X
<222> LOCATION: (106)..(106)
<223> OTHER INFORMATION: X=F or S
<220> FEATURE:
<221> NAME/KEY: X
<222> LOCATION: (107)..(107)
<223> OTHER INFORMATION: X=D or A
<220> FEATURE:
<221> NAME/KEY: X
```

```
<222> LOCATION: (108)..(108)
<223> OTHER INFORMATION: X=I or F

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Xaa Xaa Ser Glu Lys Tyr Tyr Xaa Asp Ser Val
    50                  55                  60

Lys Gly Arg Phe Thr Ile Ser Arg Asp Asn Ala Lys Asn Ser Xaa Tyr
65                  70                  75                  80

Leu Gln Met Asn Ser Leu Arg Ala Glu Xaa Thr Ala Val Xaa Tyr Cys
                85                  90                  95

Ala Arg Asp Arg Xaa Val Ala Gly Ala Xaa Xaa Xaa Trp Gly Gln Gly
            100                 105                 110

Thr Met Val Thr Val Ser Ser
        115

<210> SEQ ID NO 190
<211> LENGTH: 107
<212> TYPE: PRT
<213> ORGANISM: Artificial Sequence
<220> FEATURE:
<223> OTHER INFORMATION: VL Formula 1
<220> FEATURE:
<221> NAME/KEY: X
<222> LOCATION: (13)..(13)
<223> OTHER INFORMATION: X13=T or A
<220> FEATURE:
<221> NAME/KEY: X
<222> LOCATION: (17)..(17)
<223> OTHER INFORMATION: X=D or H
<220> FEATURE:
<221> NAME/KEY: X
<222> LOCATION: (21)..(21)
<223> OTHER INFORMATION: X=I or V
<220> FEATURE:
<221> NAME/KEY: X
<222> LOCATION: (30)..(30)
<223> OTHER INFORMATION: X=FS or Y
<220> FEATURE:
<221> NAME/KEY: X
<222> LOCATION: (31)..(31)
<223> OTHER INFORMATION: X=I or S
<220> FEATURE:
<221> NAME/KEY: X
<222> LOCATION: (39)..(39)
<223> OTHER INFORMATION: X=K or H
<220> FEATURE:
<221> NAME/KEY: X
<222> LOCATION: (45)..(45)
<223> OTHER INFORMATION: X=KN or D
<220> FEATURE:
<221> NAME/KEY: X
<222> LOCATION: (56)..(56)
<223> OTHER INFORMATION: X=S or T
<220> FEATURE:
<221> NAME/KEY: X
<222> LOCATION: (65)..(65)
<223> OTHER INFORMATION: X=S or N
<220> FEATURE:
<221> NAME/KEY: X
<222> LOCATION: (84)..(84)
<223> OTHER INFORMATION: X=A or T
<220> FEATURE:
<221> NAME/KEY: X
<222> LOCATION: (87)..(87)
```

```
<223> OTHER INFORMATION: X=Y or F
<220> FEATURE:
<221> NAME/KEY: X
<222> LOCATION: (92)..(92)
<223> OTHER INFORMATION: X=Y or H
<220> FEATURE:
<221> NAME/KEY: X
<222> LOCATION: (93)..(93)
<223> OTHER INFORMATION: X=GT or S
<220> FEATURE:
<221> NAME/KEY: X
<222> LOCATION: (94)..(94)
<223> OTHER INFORMATION: X=Y or S
<220> FEATURE:
<221> NAME/KEY: X
<222> LOCATION: (107)..(107)
<223> OTHER INFORMATION: X=K or R

<400> SEQUENCE: 190

Asp Ile Gln Met Thr Gln Ser Pro Ser Thr Leu Ser Xaa Ser Val Gly
1               5                   10                  15

Xaa Arg Val Thr Xaa Thr Cys Arg Ala Ser Gln Ser Ile Xaa Xaa Trp
            20                  25                  30

Leu Ala Trp Tyr Gln Gln Xaa Pro Gly Lys Ala Pro Xaa Leu Leu Ile
        35                  40                  45

Tyr Lys Ala Ser Ser Leu Glu Xaa Gly Val Pro Ser Arg Phe Ser Gly
    50                  55                  60

Xaa Gly Ser Gly Thr Glu Phe Thr Leu Thr Ile Ser Ser Leu Gln Pro
65                  70                  75                  80

Asp Asp Phe Xaa Thr Tyr Xaa Cys Gln Gln Tyr Xaa Xaa Xaa Ser Arg
                85                  90                  95

Thr Phe Gly Gln Gly Thr Lys Val Glu Ile Xaa
            100                 105

<210> SEQ ID NO 191
<211> LENGTH: 9
<212> TYPE: PRT
<213> ORGANISM: Artificial Sequence
<220> FEATURE:
<223> OTHER INFORMATION: LCDR3 Formula 2
<220> FEATURE:
<221> NAME/KEY: X
<222> LOCATION: (5)..(5)
<223> OTHER INFORMATION: X=G or S
<220> FEATURE:
<221> NAME/KEY: X
<222> LOCATION: (6)..(6)
<223> OTHER INFORMATION: X=Y or S

<400> SEQUENCE: 191

Gln Gln Tyr Tyr Xaa Xaa Ser Arg Thr
1               5

<210> SEQ ID NO 192
<211> LENGTH: 41
<212> TYPE: PRT
<213> ORGANISM: Artificial Sequence
<220> FEATURE:
<223> OTHER INFORMATION: H-FR3 Formula 2
<220> FEATURE:
<221> NAME/KEY: X
<222> LOCATION: (4)..(4)
<223> OTHER INFORMATION: X=V or G
<220> FEATURE:
<221> NAME/KEY: X
<222> LOCATION: (33)..(33)
<223> OTHER INFORMATION: X=D or E
<220> FEATURE:
<221> NAME/KEY: X
```

-continued

```
<222> LOCATION: (37)..(37)
<223> OTHER INFORMATION: X=Y or F

<400> SEQUENCE: 192

Lys Tyr Tyr Xaa Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Xaa Thr Ala Val Xaa Tyr Cys Ala Arg
        35                  40

<210> SEQ ID NO 193
<211> LENGTH: 119
<212> TYPE: PRT
<213> ORGANISM: Artificial Sequence
<220> FEATURE:
<223> OTHER INFORMATION: VH Formula 2
<220> FEATURE:
<221> NAME/KEY: X
<222> LOCATION: (54)..(54)
<223> OTHER INFORMATION: X=D or E
<220> FEATURE:
<221> NAME/KEY: X
<222> LOCATION: (55)..(55)
<223> OTHER INFORMATION: X=G or A
<220> FEATURE:
<221> NAME/KEY: X
<222> LOCATION: (61)..(61)
<223> OTHER INFORMATION: X=V or G
<220> FEATURE:
<221> NAME/KEY: X
<222> LOCATION: (90)..(90)
<223> OTHER INFORMATION: X=D or E
<220> FEATURE:
<221> NAME/KEY: X
<222> LOCATION: (94)..(94)
<223> OTHER INFORMATION: X=Y or F
<220> FEATURE:
<221> NAME/KEY: X
<222> LOCATION: (101)..(101)
<223> OTHER INFORMATION: X=A or P
<220> FEATURE:
<221> NAME/KEY: X
<222> LOCATION: (106)..(106)
<223> OTHER INFORMATION: X=F or S
<220> FEATURE:
<221> NAME/KEY: X
<222> LOCATION: (107)..(107)
<223> OTHER INFORMATION: X=D or A
<220> FEATURE:
<221> NAME/KEY: X
<222> LOCATION: (108)..(108)
<223> OTHER INFORMATION: X=I or F

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Xaa Xaa Ser Glu Lys Tyr Tyr Xaa Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Xaa Thr Ala Val Xaa Tyr Cys
                85                  90                  95
```

-continued

```
Ala Arg Asp Arg Xaa Val Ala Gly Ala Xaa Xaa Xaa Trp Gly Gln Gly
            100                 105                 110

Thr Met Val Thr Val Ser Ser
        115

<210> SEQ ID NO 194
<211> LENGTH: 107
<212> TYPE: PRT
<213> ORGANISM: Artificial Sequence
<220> FEATURE:
<223> OTHER INFORMATION: VL Formula 2
<220> FEATURE:
<221> NAME/KEY: X
<222> LOCATION: (13)..(13)
<223> OTHER INFORMATION: X=T or A
<220> FEATURE:
<221> NAME/KEY: X
<222> LOCATION: (17)..(17)
<223> OTHER INFORMATION: X=D or H
<220> FEATURE:
<221> NAME/KEY: X
<222> LOCATION: (21)..(21)
<223> OTHER INFORMATION: X=I or V
<220> FEATURE:
<221> NAME/KEY: X
<222> LOCATION: (30)..(30)
<223> OTHER INFORMATION: X=FS or Y
<220> FEATURE:
<221> NAME/KEY: X
<222> LOCATION: (31)..(31)
<223> OTHER INFORMATION: X=I or S
<220> FEATURE:
<221> NAME/KEY: X
<222> LOCATION: (39)..(39)
<223> OTHER INFORMATION: X=K or H
<220> FEATURE:
<221> NAME/KEY: X
<222> LOCATION: (45)..(45)
<223> OTHER INFORMATION: X=KN or D
<220> FEATURE:
<221> NAME/KEY: X
<222> LOCATION: (56)..(56)
<223> OTHER INFORMATION: X=S or T
<220> FEATURE:
<221> NAME/KEY: X
<222> LOCATION: (65)..(65)
<223> OTHER INFORMATION: X=S or N
<220> FEATURE:
<221> NAME/KEY: X
<222> LOCATION: (84)..(84)
<223> OTHER INFORMATION: X=A or T
<220> FEATURE:
<221> NAME/KEY: X
<222> LOCATION: (87)..(87)
<223> OTHER INFORMATION: X=Y or F
<220> FEATURE:
<221> NAME/KEY: X
<222> LOCATION: (93)..(93)
<223> OTHER INFORMATION: X=G or S
<220> FEATURE:
<221> NAME/KEY: X
<222> LOCATION: (94)..(94)
<223> OTHER INFORMATION: X=Y or S
<220> FEATURE:
<221> NAME/KEY: X
<222> LOCATION: (107)..(107)
<223> OTHER INFORMATION: X=K or R

<400> SEQUENCE: 194

Asp Ile Gln Met Thr Gln Ser Pro Ser Thr Leu Ser Xaa Ser Val Gly
1               5                   10                  15

Xaa Arg Val Thr Xaa Thr Cys Arg Ala Ser Gln Ser Ile Xaa Xaa Trp
            20                  25                  30
```

-continued

```
Leu Ala Trp Tyr Gln Gln Xaa Pro Gly Lys Ala Pro Xaa Leu Leu Ile
        35              40                  45

Tyr Lys Ala Ser Ser Leu Glu Xaa Gly Val Pro Ser Arg Phe Ser Gly
    50              55                  60

Xaa Gly Ser Gly Thr Glu Phe Thr Leu Thr Ile Ser Ser Leu Gln Pro
65                  70                  75                  80

Asp Asp Phe Xaa Thr Tyr Xaa Cys Gln Gln Tyr Tyr Xaa Xaa Ser Arg
                85          90                  95

Thr Phe Gly Gln Gly Thr Lys Val Glu Ile Xaa
            100             105
```

ANTI-PD-L1 ANTIGEN BINDING PROTEIN AND APPLICATION THEREOF

RELATED APPLICATIONS

The present application is a United States National Phase under 35 U.S.C. § 371 of International Application No. PCT/CN2020/118811, filed Sep. 29, 2020, which claims priority to Chinese Application No. 201910944996.4, filed on Sep. 30, 2019, the contents of each which are incorporated by reference in their entirety.

FIELD OF THE INVENTION

The present application relates to the field of biomedicine, and specifically relates to an anti-PD-L1 antigen binding protein and use thereof, as well as a fusion protein against both PD-L1 and TGFB and use thereof.

BACKGROUND OF THE INVENTION

Programmed death receptor ligand 1 (PD-L1), also known as cluster of differentiation 274 (CD274) or B7 homologous protein 1 (B7-H1), is a type I transmembrane protein of 40 kDa which is generally expressed on activated T cells, B cells, monocytes, dendritic cells, macrophages and many non-hematopoietic cells.

PD-L1 can bind to programmed death receptor 1 (PD-1) and B7-1 (CD80). Wherein the PD-L1/PD-1 signaling pathway is a very important co-inhibitory signaling pathway in immune response, which negatively regulates the immune response of T cells, suppresses the activity of T cells and reduces the secretion of cytokines. Studies have found that PD-L1 can be expressed in various tumor tissues, including gastric cancer, lung cancer, breast cancer, pancreatic cancer, ovarian cancer, colon cancer, mast cell tumor, malignant melanoma and the like, and can be expressed in bone marrow cells which infiltrate in tumor microenvironment, thereby protecting the tumor cells from immune system attack. Transforming growth factor-B (TGFB) is a powerful cytokine that has a significant impact on the immune system, and participates in many proliferative and non-proliferative cellular processes, such as cell proliferation and differentiation, embryonic development, extracellular matrix formation, bone development, wound healing, hematopoiesis, as well as immune and inflammatory response. Among the prior treatment technologies, whether chemotherapy or tumor-targeted therapy, an important bottleneck affecting their efficacies is the immune tolerance developed by tumor cells. Tumor cells escape from the recognition and attack by the body's immune system by using a variety of immunosuppressive mechanisms in the tumor microenvironment, including immunosuppressive cytokines (such as TGFB), regulatory T cells (Tregs), co-inhibitory signaling pathway molecules, and myeloid inhibitory cells and the like.

Multiple immunosuppression mechanisms may hinder the effectiveness of immunotherapy. In some cases, tumors are refractory to single-drug immunotherapy, and only a small percentage of cancers have a complete response. Thus, research and development of a medicament with the ability to block the PD-1/PD-L1 signaling pathway, as well as targeting the neutralization of immunosuppressive cytokine TGFB in the tumor microenvironment on the basis of inhibiting PD-1/PD-L1 pathway, could bring novel solutions for treating tumors and various immune system-associated diseases.

SUMMARY OF THE INVENTION

The present application provides a PD-L1 antigen binding protein that is capable of binding to PD-L1 derived from a primate with a KD value of $1\times10^{-8}$ M or less. The antigen binding protein can block the binding of PD-1 and CD80 with PD-L1, can stimulate the secretion of IFN-$\gamma$ and/or IL2 in immune cells, and can inhibit tumor growth and/or tumor cell proliferation. The present application also provides a fusion protein comprising human TGFBRII or the fragment thereof and the antigen binding protein. The present application also provides use of the antigen binding protein and/or the fusion protein in the prevention and treatment of tumors or cancers.

In one aspect, the present application provides an isolated antigen binding protein that binds to PD-L1, comprising at least one CDR of an antibody heavy chain variable region VH, wherein the VH comprises the amino acid sequence set forth in SEQ ID NO: 193; preferably, the VH comprises the amino acid sequence set forth in any one of SEQ ID NOs: 90-93, 95 and 97-104.

In some embodiments, the isolated antigen binding protein comprises at least one CDR of an antibody light chain variable region VH, wherein the VL comprises the amino acid sequence set forth in SEQ ID NO: 194; preferably, the VL comprises the amino acid sequence set forth in any one of SEQ ID NOs: 108-114, 116 and 118.

In some embodiments, the isolated antigen binding protein comprises an antibody or antigen binding fragment thereof; preferably, the antibody is selected from the group consisting of: a monoclonal antibody, a chimeric antibody, a humanized antibody and a fully human antibody; preferably, the antigen binding fragment comprises Fab, Fab', Fv fragment, F(ab')2, scFv, di-scFv and/or dAb.

In some embodiments, the isolated antigen binding protein comprises a light chain variable region VL and a heavy chain variable region VH, wherein the light chain variable region VL comprises LCDR1 comprising the amino acid sequence set forth in SEQ ID NO: 181, LCDR2 comprising the amino acid sequence set forth in SEQ ID NO: 182, and LCDR3 comprising the amino acid sequence set forth in SEQ ID NO: 191; and wherein the heavy chain variable region VH comprises HCDR1 comprising the amino acid sequence set forth in SEQ ID NO: 5, HCDR2 comprising the amino acid sequence set forth in SEQ ID NO: 179, and HCDR3 comprising the amino acid sequence set forth in SEQ ID NO: 180.

In some embodiments, the LCDR1 comprises the amino acid sequence set forth in any one of SEQ ID NOs: 181, and 48-51; the LCDR2 comprises the amino acid sequence set forth in any one of SEQ ID NOs: 182, and 63-64; the LCDR3 comprises the amino acid sequence set forth in any one of SEQ ID NOs: 191, and 77-79; the HCDR1 comprises the amino acid sequence set forth in SEQ ID NO: 5; the HCDR2 comprises the amino acid sequence set forth in any one of SEQ ID NOs: 179, 14, 16 and 17; the HCDR3 comprises the amino acid sequence set forth in any one of SEQ ID NOs: 180, and 29-33.

In some embodiments, the LCDR1 comprises the amino acid sequence set forth in SEQ ID NO: 48; the LCDR2 comprises the amino acid sequence set forth in SEQ ID NO: 63; the LCDR3 comprises the amino acid sequence set forth in SEQ ID NO: 77; the HCDR1 comprises the amino acid sequence set forth in SEQ ID NO: 5; the HCDR2 comprises the amino acid sequence set forth in SEQ ID NO: 14; and the HCDR3 comprises the amino acid sequence set forth in SEQ ID NO: 29; or the LCDR1 comprises the amino acid sequence set forth in SEQ ID NO: 49, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29; or the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 30; or the LCDR1 comprises the amino acid sequence set forth in SEQ ID NO: 50, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29; or the LCDR1 comprises the amino acid sequence set forth in SEQ ID NO: 50, the LCDR2 comprises the amino acid sequence set forth in SEQ ID NO: 63, the LCDR3 comprises the amino acid sequence set forth in SEQ ID NO: 79, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 31; or the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 32; or the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14 and the HCDR3 comprises the amino acid sequence set forth in SEQ ID NO: 33; or the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 30; or the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 30; or the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 32; or the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 32; or the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 29; or the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 29; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 33; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 33.

In some embodiments, the antibody heavy chain variable region VH comprises framework regions H-FR1, H-FR2, H-FR3 and H-FR4; preferably, the H-FR1 is linked at the C-terminus to the N-terminus of the HCDR1, and comprises the amino acid sequence set forth in SEQ ID NO: 1; and/or the H-FR2 is located between the HCDR1 and the HCDR2, and comprises the amino acid sequence set forth in SEQ ID NO: 9; and/or the H-FR3 is located between the HCDR2 and the HCDR3, and comprises the amino acid sequence set forth in SEQ ID NO: 192; and/or the H-FR4 is at the N-terminus linked to the C-terminus of the HCDR3, and comprises the amino acid sequence set forth in SEQ ID NO: 38; further preferably, the H-FR3 comprises the amino acid sequence set forth in any one of SEQ ID NOs: 21, 22 and 24.

In some embodiments, the antibody light chain variable region VL comprises framework regions L-FR1, L-FR2, L-FR3 and L-FR4; preferably, the L-FR1 is linked at the C-terminus to the N-terminus of the LCDR1, and comprises the amino acid sequence set forth in SEQ ID NO: 185; and/or the L-FR2 is located between the LCDR1 and the LCDR2, and comprises the amino acid sequence set forth in SEQ ID NO: 186; and/or the L-FR3 is located between the LCDR2 and the LCDR3, and comprises the amino acid sequence set forth in SEQ ID NO: 187; and/or the L-FR4 is at the N-terminus linked to the C-terminus of the LCDR3, and comprises the amino acid sequence set forth in SEQ ID NO: 188.

In some embodiments, the L-FR1 comprises the amino acid sequence set forth in any one of SEQ ID NOs: 41-44; and/or the L-FR2 comprises the amino acid sequence set forth in any one of SEQ ID NOs: 56-59; and/or the L-FR3 comprises the amino acid sequence set forth in any one of SEQ ID NOs: 69-72; and/or the L-FR4 comprises the amino acid sequence set forth in any one of SEQ ID NOs: 85-86.

In some embodiments, the antibody heavy chain variable region VH comprises the amino acid sequence set forth in SEQ ID NO: 193; the antibody light chain variable region VH comprises the amino acid sequence set forth in SEQ ID NO: 194;

preferably, the antibody heavy chain variable region VH comprises the amino acid sequence set forth in any one of SEQ ID NOs: 90-93, 95 and 97-104;

preferably, the antibody light chain variable region VL comprises the amino acid sequence set forth in any one of SEQ ID NOs: 108-114, 116 and 118.

In some embodiments, the antibody heavy chain variable region VH comprises the amino acid sequence set forth in SEQ ID NO: 90, the antibody light chain variable region VL comprises the amino acid sequence set forth in SEQ ID NO: 108; or the antibody heavy chain variable region VH comprises the amino acid sequence set forth in SEQ ID NO: 90, the antibody light chain variable region VL comprises the amino acid sequence set forth in SEQ ID NO: 109; or the antibody heavy chain variable region VH comprises the amino acid sequence set forth in SEQ ID NO: 91, the antibody light chain variable region VL comprises the amino acid sequence set forth in SEQ ID NO: 110; or the antibody heavy chain variable region VH comprises the amino acid sequence set forth in SEQ ID NO: 90, the antibody light chain variable region VL comprises the amino acid sequence set forth in SEQ ID NO: 111; or,

the antibody heavy chain variable region VH comprises the amino acid sequence set forth in SEQ ID NO: 92, the antibody light chain variable region VL comprises the amino acid sequence set forth in SEQ ID NO: 112; or the antibody heavy chain variable region VH comprises the amino acid sequence set forth in SEQ ID NO: 93, the antibody light chain variable region VL comprises the amino acid sequence set forth in SEQ ID NO: 113; or the antibody heavy chain variable region VH comprises the amino acid sequence set forth in SEQ ID NO: 90, the antibody light chain variable region VL comprises the amino acid sequence set forth in SEQ ID NO: 114; or the antibody heavy chain variable region VH comprises the amino acid sequence set forth in SEQ ID NO: 95, the antibody light chain variable region VL comprises the amino acid sequence set forth in SEQ ID NO: 116; or the antibody heavy chain variable region VH comprises the amino acid sequence set forth in SEQ ID NO: 97, the antibody light chain variable region VL comprises the amino acid sequence set forth in SEQ ID NO: 118; or the antibody heavy chain variable region VH comprises the amino acid sequence set forth in SEQ ID NO: 98, the antibody light chain variable region VL comprises the amino acid sequence set forth in SEQ ID NO: 118; or, the antibody heavy chain variable region VH comprises the amino acid sequence set forth in SEQ ID NO: 99, the antibody light chain variable region VL comprises the amino acid sequence set forth in SEQ ID NO: 113; or the antibody heavy chain variable region VH comprises the amino acid sequence set forth in SEQ ID NO: 100, the antibody light chain variable region VL comprises the amino acid sequence set forth in SEQ ID NO: 113; or the antibody heavy chain variable region VH comprises the amino acid sequence set forth in SEQ ID NO: 101, the antibody light chain variable region VL comprises the amino acid sequence set forth in SEQ ID NO: 114; or the antibody heavy chain variable region VH comprises the amino acid sequence set forth in SEQ ID NO: 102, the antibody light chain variable region VL comprises the amino acid sequence set forth in SEQ ID NO: 114; or the antibody heavy chain variable region VH comprises the amino acid sequence set forth in SEQ ID NO: 103, the antibody light chain variable region VL comprises the amino acid sequence set forth in SEQ ID NO: 116; or the antibody heavy chain variable region VH comprises the amino acid sequence set forth in SEQ ID NO: 104, the antibody light chain variable region VL comprises the amino acid sequence set forth in SEQ ID NO: 116.

In some embodiments, the isolated antigen binding protein comprises an antibody heavy chain constant region, and the antibody heavy chain constant region comprises a human IgG constant region; preferably, wherein the antibody heavy chain constant region comprises the amino acid sequence set forth in any one of SEQ ID NOs: 172-175.

In some embodiments, the isolated antigen binding protein comprises an antibody heavy chain HC, and the HC comprises the amino acid sequence set forth in any one of SEQ ID NOs: 122-125, 127, and 129-137.

In some embodiments, the isolated antigen binding protein comprises an antibody light chain constant region, wherein the antibody light chain constant region comprises the amino acid sequence set forth in SEQ ID NO: 170.

In some embodiments, the isolated antigen binding protein comprises an antibody light chain LC, and the LC comprises the amino acid sequence set forth in any one of SEQ ID NOs: 150-156, 158 and 160-163.

In some embodiments, the isolated antigen binding protein has one or more of the following properties:

1) capable of binding to PD-L1 derived from a primate with a KD value of $1\times10^{-8}$ M or less;
2) capable of blocking the binding of PD-1 to PD-L1;
3) capable of blocking the binding of CD80 to PD-L1;
4) capable of stimulating the secretion of IFN-γ and/or IL2 in an immune cell;
5) capable of inhibiting tumor growth and/or tumor cell proliferation;
6) binding to an epitope of PD-L1 derived from a primate that does not completely overlap with the epitope of a control antibody, wherein the control antibody comprises a LCDR1 set forth in SEQ ID NO: 52, a LCDR2 set forth in SEQ ID NO: 65, and a LCDR3 set forth in SEQ ID NO: 81, and the control antibody comprises a HCDR1 set forth in SEQ ID NO: 6, a HCDR2 set forth in SEQ ID NO: 15 and a HCDR3 set forth in SEQ ID NO: 34;

or wherein the control antibody comprises a LCDR1 set forth in SEQ ID NO: 53, a LCDR2 set forth in SEQ ID NO: 66 and a LCDR3 set forth in SEQ ID NO: 82, and the control antibody comprises a HCDR1 set forth in SEQ ID NO: 5, a HCDR2 set forth in SEQ ID NO: 18 and a HCDR3 set forth in SEQ ID NO: 35;

or wherein the control antibody comprises a LCDR1 set forth in SEQ ID NO: 55, a LCDR2 set forth in SEQ ID NO: 68 and a LCDR3 set forth in SEQ ID NO: 84, and the control antibody comprises a HCDR1 set forth in SEQ ID NO: 8, a HCDR2 set forth in SEQ ID NO: 20 and a HCDR3 set forth in SEQ ID NO: 37.

In some embodiments, the primate comprises a human and/or a monkey.

In another aspect, the present application provides a fusion protein comprising: a) a human TGFBRII or a fragment thereof; and b) the isolated antigen binding protein.

In some embodiments, the fusion protein comprises a first polypeptide and a second polypeptide, wherein the first polypeptide comprises a heavy chain of the isolated antigen binding protein, or a fragment thereof, and the human TGFBRII or fragment thereof; and the second polypeptide comprises the light chain of the isolated antigen binding protein, or a fragment thereof; preferably, the antibody heavy chain or fragment thereof is fused in frame with the human TGFBRII or fragment thereof to form the first polypeptide; further preferably, wherein the antibody heavy chain or fragment thereof is directly or indirectly linked at the C-terminus to the N-terminus of the human TGFBRII or fragment thereof.

In some embodiments, the heavy chain or fragment thereof of the first polypeptide comprises a HCDR1, a HCDR2 and a HCDR3, wherein the HCDR1 comprises the amino acid sequence set forth in SEQ ID NO: 5; the HCDR2 comprises the amino acid sequence set forth in any one of SEQ ID NOs: 179, 14, 16 and 17; the HCDR3 comprises the amino acid sequence set forth in any one of SEQ ID NOs: 180, and 29-33; and/or the second peptide comprises a LCDR1, a LCDR2 and a LCDR3, wherein the LCDR1 comprises the amino acid sequence set forth in any one of SEQ ID NOs: 181, and 48-51; the LCDR2 comprises the amino acid sequence set forth in any one of SEQ ID NOs: 182, and 63-64; and the LCDR3 comprises the amino acid sequence set forth in any one of SEQ ID NOs: 191, and 77-79.

In some embodiments, the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78; the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 29; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77; the HCDR1 comprises the amino acid sequence set forth in SEQ ID NO: 5, the HCDR2 comprises the amino acid sequence set forth in SEQ ID NO: 16, the HCDR3 comprises the amino acid sequence set forth in SEQ ID NO: 33; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77; the HCDR1 comprises the amino acid sequence set forth in SEQ ID NO: 5, the HCDR2 comprises the amino acid sequence set forth in SEQ ID NO: 17, the HCDR3 comprises the amino acid sequence set forth in SEQ ID NO: 33; or the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78; the HCDR1 comprises the amino acid sequence set forth in SEQ ID NO: 5, the HCDR2 comprises the amino acid sequence set forth in SEQ ID NO: 17, the HCDR3 comprises the amino acid sequence set forth in SEQ ID NO: 29; or the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78; the HCDR1 comprises the amino acid sequence set forth in SEQ ID NO: 5, the HCDR2 comprises the amino acid sequence set forth in SEQ ID NO: 14, the HCDR3 comprises the amino acid sequence set forth in SEQ ID NO: 29.

In some embodiments, the antibody heavy chain or fragment thereof is linked to the human TGFBRII or fragment thereof via a linker; preferably, wherein the linker is a peptide linker, and the peptide linker comprises the amino acid sequence set forth in any one of SEQ ID NOs: 167-169.

In some embodiments, the human TGFBRII and fragment thereof comprises an extracellular domain of a human TGFBRII; preferably, the human TGFBRII and fragment thereof comprises the amino acid sequence set forth in any one of SEQ ID NOs: 176-178.

In some embodiments, the heavy chain or fragment thereof of the first polypeptide is combined with the light chain or fragment thereof of the second polypeptide to form an antigen binding portion that specifically binds to PD-L1.

In some embodiments, the first polypeptide comprises the amino acid sequence set forth in any one of SEQ ID NOs: 138, 139, 142, 143 and 145-148; wherein the second polypeptide comprises the amino acid sequence set forth in any one of SEQ ID NOs: 162-163.

In some embodiments, the first polypeptide comprises the amino acid sequence set forth in SEQ ID NO: 138, and the second polypeptide comprises the amino acid sequence set forth in SEQ ID NO: 162; or the first polypeptide comprises the amino acid sequence set forth in SEQ ID NO: 139, and the second polypeptide comprises the amino acid sequence set forth in SEQ ID NO: 162; or the first polypeptide comprises the amino acid sequence set forth in SEQ ID NO: 142, and the second polypeptide comprises the amino acid sequence set forth in SEQ ID NO: 162; or the first polypeptide comprises the amino acid sequence set forth in SEQ ID NO: 143, and the second polypeptide comprises the amino acid sequence set forth in SEQ ID NO: 162; or the first polypeptide comprises the amino acid sequence set forth in SEQ ID NO: 145, and the second polypeptide comprises the amino acid sequence set forth in SEQ ID NO: 163; or the first polypeptide comprises the amino acid sequence set forth in SEQ ID NO: 146, and the second polypeptide comprises the amino acid sequence set forth in SEQ ID NO: 163; or the first polypeptide comprises the amino acid sequence set forth in SEQ ID NO: 147, and the second polypeptide comprises the amino acid sequence set forth in SEQ ID NO: 162; or the first polypeptide comprises the amino acid sequence set forth in SEQ ID NO: 148, and the second polypeptide comprises the amino acid sequence set forth in SEQ ID NO: 162.

In another aspect, the present application provides one or more nucleic acid molecules encoding the isolated antigen binding protein or the fusion protein.

In another aspect, the present application provides a vector comprising the nucleic acid molecule.

In another aspect, the present application provides a cell comprising the nucleic acid molecule or the vector.

In another aspect, the present application provides a method of preparing the isolated antigen binding protein or the fusion protein, comprising culturing the cell under the condition that the isolated antigen binding protein or the fusion protein is expressed.

In another aspect, the present application provides a chimeric antigen receptor comprising the isolated antigen binding protein.

In another aspect, the present application provides a genetically modified cell comprising the chimeric antigen receptor.

In another aspect, the present application provides an antibody-drug conjugate comprising a cytotoxic agent and the isolated antigen binding protein.

In another aspect, the present application provides a pharmaceutical composition comprising the isolated antigen binding protein, the fusion protein, the nucleic acid molecule, the vector, the cell, the chimeric antigen receptor, the genetically modified cell and/or the antibody-drug conjugate, and optionally, a pharmaceutically acceptable carrier; more preferably, the pharmaceutical composition further comprises one or more selected from the group consisting of: a hormone preparation, a targeted small molecule preparation, a proteasome inhibitor, an imaging agent, a diagnostic agent, a chemotherapeutic agent, an oncolytic medicament, a cytotoxic agent, a cytokine, an activator of co-stimulatory molecule, an inhibitor of inhibitory molecule and a vaccine.

In another aspect, the present application provides use of the isolated antigen binding protein, the fusion protein, the nucleic acid molecule, the vector, the cell, the chimeric antigen receptor, the genetically modified cell and/or the antibody-drug conjugate and/or the pharmaceutical composition in the manufacture of a medicament which is used for preventing, alleviating and/or treating a tumor or a cancer, inhibiting tumor growth and/or inhibiting tumor cell proliferation; preferably, the tumor or cancer is the tumor or cancer with abnormal expression of PD-L1; preferably, the tumor or cancer comprises a colorectal cancer.

In another aspect, the present application provides a method of preventing, alleviating or treating a tumor, inhibiting tumor growth and/or inhibiting tumor cell proliferation, comprising the administration of the isolated antigen binding protein, the fusion protein, the nucleic acid molecule, the vector, the cell, the chimeric antigen receptor, the genetically modified cell and/or the antibody-drug conjugate and/or the pharmaceutical composition to a subject in need thereof; preferably, wherein the tumor or cancer is the tumor or cancer with abnormal expression of PD-L1; preferably, the tumor or cancer comprises a colorectal cancer.

In another aspect, the present application provides the isolated antigen binding protein, the fusion protein, the nucleic acid molecule, the vector, the cell, the chimeric antigen receptor, the genetically modified cell and/or the antibody-drug conjugate and/or the pharmaceutical composition for use in treating cancer, inhibiting tumor growth and/or inhibiting tumor cell proliferation.

In another aspect, the present application provides a method of inhibiting the binding of PD-L1 and/or CD80 to PD-1, comprising the administration of the isolated antigen binding protein, the fusion protein, the nucleic acid molecule, the vector, the cell, the chimeric antigen receptor, the genetically modified cell and/or the antibody-drug conjugate and/or the pharmaceutical composition.

In another aspect, the present application provides a kit comprising the isolated antigen binding protein, the fusion protein, the nucleic acid molecule, the vector, the cell, the chimeric antigen receptor, the genetically modified cell and/or the antibody-drug conjugate and/or the pharmaceutical composition; preferably, the kit further comprises (i) a delivery device; and/or (ii) an instruction. The skilled in the art can easily notice other aspects and advantages of the present application from the detailed description below. The detailed description below only shows and describes the exemplary embodiments of the present application. As those skilled in the art will recognize, the contents of the present application enable those skilled in the art to modify the disclosed specific embodiments without departing from the spirit and scope of the invention involved in the present application. Accordingly, the figures and descriptions in the specification of the present application are only exemplary and not restrictive.

DESCRIPTION OF THE DRAWINGS

The specific characteristics of the invention involved in the present application are set forth in the attached claims. The characteristics and advantages of the invention involved in the present application can be better understood by referring to the exemplary embodiments and figures that are described in detail below. A brief description of the figures is as follows:

DETAILED DESCRIPTION OF THE INVENTION

Figure 1:
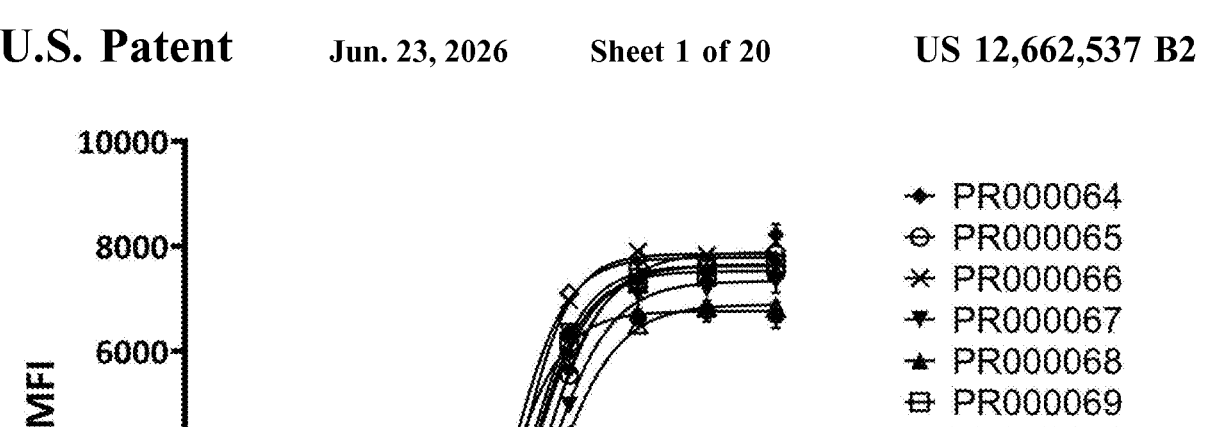
FIG. 1 shows that the antigen binding proteins of the present application bind to the CHO-K1 cells overexpressing human PD-L1.

Hereinafter the embodiments of the invention of the present application are illustrated by certain specific examples. Those familiar with this technology can easily understand the other advantages and effects of the invention of the present application from the contents disclosed in the present specification.

In the present application, the term "antigen binding protein" generally refers to a protein comprising an antigen binding portion, and optionally allowing the antigen binding portion to adopt a scaffold or framework portion that promotes the conformation in which the antigen binding protein binds to the antigen. It can typically comprise an antibody light chain variable region (VL), an antibody heavy chain variable region (VH) or both of the above. The VH and VL regions can be further divided into hypervariable regions called complementarity determining regions (CDRs), which are interspersed in more conserved regions called framework regions (FRs). Each of VH and VL can be composed of three CDRs and four FR regions, which can be arranged in the following order from the amino terminus to the carboxy terminus: FR1, CDR1, FR2, CDR2, FR3, CDR3, and FR4. The variable regions of the heavy and light chains contain binding domains that interact with an antigen. Examples of the antigen binding protein include, but are not limited to, antibodies, antigen binding fragments (Fab, Fab', F(ab)₂, Fv fragment, F(ab')₂, scFv, di-scFv and/or dAb), immunoconjugates, multi-specific antibodies (such as bis-pecific antibodies), antibody fragments, antibody derivatives, antibody analogs or fusion proteins, etc., provided that they exhibit the desired antigen binding activity.

In the present application, the term "fusion protein" generally refers to a protein that is composed of two or more polypeptides, which are usually not linked in the natural state, but the respective amino terminus and carboxyl terminus of which can be directly or indirectly linked together to form one continuous polypeptide. In some cases, the terms "fusion protein" and "antibody" can be used interchangeably when referring to the fusion proteins of the present application. In some cases, the terms "fusion protein" and "antigen binding protein" can be used interchangeably when referring to the fusion proteins of the present application.

In the present application, the term "Fab" generally refers to a fragment comprising a heavy chain variable domain and a light chain variable domain, and also comprising a constant domain of light chain and the first constant domain of heavy chain (CH1); the term "Fab'" generally refers to a fragment in which a few residues (including one or more cysteines from an antibody hinge region) are added to the carboxyl terminus of CH1 domain of heavy chain to be different from Fab; the term "F(ab')$_2$" generally refers to a dimer of Fab', comprising an antibody fragment of two Fab fragments that are connected by a disulfide bridge on the hinge region. The term "Fv" generally refers to the smallest antibody fragment containing a complete antigen recognition and binding site. In some cases, the fragment can consist of a dimer in which one heavy chain variable region and one light chain variable region are tightly non-covalently bound; the term "dsFv" generally refers to a disulfide bond-stabilized Fv fragment, in which the bond between a single light chain variable region and a single heavy chain variable region is a disulfide bond. The term "dAb fragment" generally refers to an antibody fragment consisting of a VH domain. In the present application, the term "scFv" generally refers to a monovalent molecule formed by covalently connecting and pairing one heavy chain variable domain and one light chain variable domain of an antibody via a flexible peptide linker; such scFv molecules may have a general structure: NH$_2$-VL-linker-VH—COOH or NH$_2$-VH-linker-VL-COOH.

In the present application, the term "variable" generally refers to the fact that certain portions of a variable domain sequence of an antibody change strongly, and form the binding and specificity of various specific antibodies to specific antigens thereof. However, the variability is not evenly distributed throughout an antibody variable region. It is concentrated in the three segments of the variable regions of light chain and heavy chain, called the complementarity determining regions (CDRs) or hypervariable regions (HVRs). The highly conserved portions in the variable domain are called the framework regions (FRs). Each of the variable domains of natural heavy chain and light chain comprises four FR regions (H-FR1, H-FR2, H-FR3, H-FR4, L-FR1, L-FR2, L-FR3, L-FR4), most of which adopt a (3-sheet configuration and are connected by three CDR structure loop regions. The CDRs in each chain close together via the FR regions, and form the antigen binding site of the antibody together with the CDRs from the other chain. The constant regions do not directly participate in the binding of an antibody and an antigen, but they exhibit various effector functions, for example, they participate in antibody-dependent cytotoxicity. In the art, CDRs of an antibody can be defined by a variety of methods, for example the Kabat definition rules based on sequence variability (see Kabat et al., Protein Sequences of Immunology, Fifth Edition, National Institutes of Health, Bethesda, Maryland (1991)) and Chothia definition rules based on the location of structural loop regions (see Al-Lazikani et al., J Mol Biol 273:927-48, 1997). In the present application, the Combined definition rule comprising Kabat definition and Chothia definition are also used to determine the amino acid residues in a variable domain sequence and a full-length antibody sequence. The definition method of antibody CDR can be found in Table 1.

TABLE 1

| Definition method of antibody CDR | | | |
|---|---|---|---|
| | Kabat | Chothia | Combined |
| LCDR1 | L24--L34 | L24--L34 | L24-L34 |
| LCDR2 | L50--L56 | L50--L56 | L50-L56 |
| LCDR3 | L89--L97 | L89--L97 | L89-L97 |
| HCDR1 | H31--H35 | H26--H32 | H26-H35 |
| HCDR2 | H50--H65 | H52--H56 | H50-H65 |
| HCDR3 | H95--H102 | H95--H102 | H95-H102 | wherein, Laa-Lbb may refer to the amino acid sequence from the position aa (Chothia numbering rule) to the position bb (Chothia numbering rule) starting from the N-terminus of a light chain of an antibody; Haa-Hbb may refers to the amino acid sequence from the position aa (Chothia numbering rule) to the position bb (Chothia numbering rule) starting from the N-terminus of a heavy chain of an antibody. For example, L24-L34 may refers to the amino acid sequence from the position 24 to the position 34 according to Chothia numbering rule starting from the N-terminus of a light chain of an antibody; and H26-H32 may refers to the amino acid sequence from the position 26 to the position 32 according to Chothia numbering rule starting from the N-terminus of a heavy chain of an antibody.

In the present application, the term "isolated" antigen binding protein generally refers to an antigen binding protein that has already been identified, isolated and/or recovered from the components of the production environment thereof (for example, natural or recombinant). The pollution components of the production environment thereof are usually the substances that interfere with the research, diagnosis and use of treatment thereof, which may include enzymes, hormones and other proteins or non-proteinous solutes. The isolated antigen binding proteins and antibodies are usually prepared by at least one purification step.

In the present application, the term "monoclonal antibody" usually refers to an antibody that obtained from a group of essentially homogeneous antibodies, i.e., the individual antibodies in a group are the same, except for a small number of natural mutations that may exist. Monoclonal antibodies are usually highly specific to a single antigen site. Furthermore, each monoclonal antibody is directed to the single determinant on an antigen, which is different from conventional polyclonal antigen agents (usually comprising different antibodies that are directed to different determinants) Besides their specificity, an advantage of a monoclonal antibody lies in that they can be synthesized by hybridoma culture and thus will not be polluted by other immunoglobins. The adjunct "monoclonal" represents the characteristic of an antibodies that are obtained from a population of essentially homogeneous antibodies, and will not be interpreted as any specific methods are needed to produce an antibody. For example, the monoclonal antibodies used according to the present application can be prepared in hybridoma cells, or can be prepared by DNA recombination method.

In the present application, the term "fully human antibody" generally refers to an antibody that is expressed by an animal which are obtained by transferring a human antibody-encoding gene into a genetically engineered animal with an antibody gene-deficiency. All portions of an antibody (including a variable region and a constant region of an antibody) are encoded by the human-derived genes. The fully human antibody can greatly reduce the immune side effects on the human body caused by heterologous antibodies. The methods of obtaining a fully human antibody in the art may include phage display technology, transgenic mouse technology, ribosome display technology, RNA-polypeptide technology, and the like.

In the present application, the term "specifically bind" generally refers to the binding of an antibody to an epitope via the antigen binding domain thereof, and some complementarities between the antigen binding domain and the epitope are needed for binding. According to this definition, an antibody is termed as "specifically binding" to an antigen when the antibody binds to an epitope via the antigen binding domain thereof more easily than binding to a random, unrelated epitope. "Epitope" refers to a specific atomic radical (for example, sugar side chain, phosphoryl, sulfonyl) or an amino acid on an antigen the binds to an antigen binding protein (such as an antibody).

In the present application, the terms "KD", "$K_D$" can be used interchangeably, usually refer to equilibrium dissociation constant, "KD" is the ratio of the dissociation rate constant (kdis, also known as "dissociation rate (off-rate) (koff)" or "kd") to the association rate constant (kon, also known as "association rate (kon)" or "ka"). The association rate constant (kon), the dissociation rate constant (kdis), and the equilibrium dissociation constant (KD) can be used to indicate the binding affinity of an antigen binding protein (such as an antibody) to an antigen. The methods for determining the association and dissociation rate constants are well known in the art, including, but not limited to, biofilm interference technology (BLI), radioimmunoassay (RIA), equilibrium dialysis, surface plasmon resonance (SPR), fluorescence resonance energy transfer (FRET), co-immunoprecipitation (Co-IP) and protein chip technology. The measured affinity of a specific protein-protein interaction can be different if measured under different conditions (for example, salt concentration, pH).

In the present application, the term "PD-L1" usually refers to programmed death ligand 1 protein, a functional variant thereof and/or a functional fragment thereof. PD-L1 is also known as cluster of differentiation 274 (CD274) or B7 homolog 1 (B7-H1), and is the protein encoded by CD274 gene (in human) PD-L1 binds to the ligand thereof, for example, programmed death 1 (PD-1) which is expressed in activated T cells, B cells and macrophages (Ishida et al., 1992 EMBO J, 11:3887-3395; Okazaki et al., Autoimmune dilated cardiomyopathy in PD-1 receptor-deficient mice. Science, 2001; 291: 319-22). The complexation of PD-L1 and PD-1 exerts immunosuppressive effect by inhibiting the proliferation of T cells and producing cytokines IL-1 and IFN-γ (Freeman et al., Engagement of PD-1 immunoinhibitory receptor by a novel B7 family member leads to negative regulation of lymphocyte activation, J. Exp. Med. 2000, 192:1027-1034; Carter et al., PD-1: PD-L inhibitory pathway affects both CD4(+) and CD8(+) T cells and is overcome by IL-2. Eur. J. Immunol. 2002, 32:634-643). The term "PD-L1" encompasses any natural PD-L1 of any vertebrate source including mammals, such as primates (for example, human) and rodents (for example, mouse and rat). Said term encompasses "full-length", unprocessed PD-L1 and any forms of PD-L1 produced by the processing in cells. PD-L1 may exist as a transmembrane protein or as a soluble protein. Said term also encompasses naturally-existing variants of PD-L1, for example, splicing variants or allele variants. The basic structure of PD-L1 comprises 4 domains: an extracellular Ig-like V-type domain and an Ig-like C2-type domain, a transmembrane domain and a cytoplasmic domain. The sequence of PD-L1 is known in the art. For example, the information concerning human PD-L1 gene (including genome DNA sequence) can be found under NCBI Gene ID No. 29126. Further for example, the information concerning mouse PD-L1 gene (including genome DNA sequence) can be found under NCBI Gene ID No. 60533. Further for example, the information concerning cynomolgus PD-L1 gene (including genome DNA sequence) can be found under NCBI Gene ID No. 102145573. The amino acid sequence of exemplary full-length human PD-L1 protein can be found under NCBI accession number NP_054862 or Uniprot accession number Q9NZQ7. The protein sequence of exemplary full-length mouse PD-L1 can be found under NCBI accession number NP_068693 or Uniprot accession number Q9EP73. The protein sequence of exemplary full-length cynomolgus PD-L1 can be found under NCBI accession number XP_005581836 or Uniprot accession number G7PSE7.

In the present application, the term "PD-1" generally refers to programmed death 1 receptor (also known as CD279), a functional variant thereof and/or a functional fragment thereof. PD-1 is usually expressed on T cells, B cells, natural killer cells, activated monocytes and dendritic cells (DCs). PD-1 may bind to the ligands thereof, PD-L1 and PD-L2. The variants with different amino acid sequences to naturally-existing PD-1 but maintaining the ability of specifically binding to PD-L1 are also included within the definition of PD-1. Within the definition of PD-1, it further includes the variants enhancing the biological activity of PD-L1. The sequences of PD-1 are known in the art. For example, the protein sequence of an exemplary full-length human PD-1 can be found under NCBI accession number NP_005009, the protein sequence of an exemplary full-length cynomolgus PD-1 can be found under NCBI accession number NP_001271065 or Uniprot accession number B0LAJ3.

In the present application, the term "CD80" generally refers to cluster of differentiation protein 80 (also known as B7-1), a functional variant thereof and/or a functional fragment thereof. CD80 is usually expressed on obligate antigen presenting cells (APCs). CD80 can bind to PD-L1. The variants with different amino acid sequences to naturally-existing CD80 but maintaining the ability of specifically binding to PD-L1 are also included within the definition of CD80. The term "CD80" as used herein includes human CD80 (hCD80), variants, isomers and species homologs of hCD80, and analogs containing at least one common epitope of hCD80. For example, the term "CD80" also encompasses CD80s from other species such as other mammals (for example, rats, mouses, rabbits, non-human primates, pigs or bovines). The intact human CD80 sequence can be found in Uniprot accession number P33681.

In the present application, the term "TGFBRII" usually refers to a receptor of transforming growth factor B (also known as TGFBR2). The TGFBR on the surface of a cell can be bound and activated by transforming growth factor (TGFB) and can perform signal transduction via SMAD pathway, which has the activity of regulating growth, antiinflammatory and immune regulation. The intact human TGFBRII sequence can be found in Uniprot accession number P37173.

In the present application, the term "specific anti-PD-L1 antibody" generally refers to an antibody that can compete with the antibody of the present application for binding to PD-L1. The antigen binding protein of the present application may include those antibodies with the same amino acid sequence as a specific anti-PD-L1 antibody.

In the present application, the term "control antibody" usually refers to a standard PD-L1 antibody against which the experimental results are evaluated in the examples of the present application. In some cases, the control antibody may refer to the positive control in the examples of the present application, for example, PR000151, PR001598 and PR002466.

In the present application, the term "primate" usually refers to monkey and ape species, and includes monkey species, such as the monkeys from the *Macaca* (such as, and specifically, cynomolgus (*Macaca fascicularis*) and/or rhesus monkey (*Macaca mulatta*)) and baboon (*Papio ursinus*), as well as marmoset (a species from *Callithrix*), squirrel monkey (a species from *Saimiri*), and tamarin (a species from *Saguinus*), and ape species, such as chimpanzee (*Pan troglodytes*), and also includes *Homo sapiens*.

In the present application, the term "epitope" usually refers to a certain area or region of an antigen that is specifically bound by an antigen binding protein (such as an antibody). The epitope usually consists of such as the chemically active surface groups of amino acids or carbohydrates or sugar side chain molecules, and usually has a specific three-dimensional structural characteristic as well as a specific charge characteristic. The epitope may be a "linear epitope" or a "conformational epitope". In a linear epitope, all the interaction sites between a protein and an interacting molecule (such as an antibody) occur linearly along the primary amino acid sequence of the protein. In a conformational epitope, the interaction sites occur cross-over on the amino acids of a protein separated from each other. The methods for determining which type of epitopes are bound by a given antigen binding protein (such as an antibody) (such as Epitope Mapping) are well known in the art, including, for example, Western Blotting and Immunoprecipitation assay, for example, testing the reactivity of overlapped or adjacent peptides (for example, from PD-L1) with a given antigen binding protein (such as an anti-PD-L1 antibody). The methods for determining the spatial conformation of an epitope include the technologies in the art and those described in the present application, for example, X-ray Crystallography, Two Dimensional NMR and HDX-MS (see, for example, Epitope Mapping Protocols in Methods in Molecular Biology, Vol. 66, G. E. Morris, Ed. (1996)). The term "not completely overlapping" epitopes usually refer to, when referring to two or more antigen binding proteins (such as antibodies), the respective antibodies bind to a population of amino acid residues that are not completely identical or are not completely overlapping, such as determined by a given method. Technologies for determining whether the antigen binding protein of the present application binds to the same epitope as the reference antibody include, e.g., Epitope Mapping methods, such as X-ray analysis of crystals of antigen: antibody complexes, which provides atomic resolution of epitopes, and Hydrogen/Deuterium Exchange Mass Spectrometry (HDX-MS). Other methods monitor the binding of an antibody to an antigen fragment or a mutant variant form of antigen, wherein the loss of binding due to the modification in amino acid residue in an antigen sequence is often regarded as an indication of an epitope component (for example, alanine scanning mutagenesis—Cunningham and Wells (1985) Science 244:1081). In addition, the computational combination method of epitope positioning can also be used.

In the present application, the term "subject" usually refers to a mammal animal. The mammal animals include but are not limited to domesticated animals (e.g., cows, sheep, cats, dogs and horses), primates (e.g., humans and non-human primates, such as monkeys), rabbits, and rodents (e.g., mice and rats).

In the present application, the term "nucleic acid molecule" usually refers to any length of isolated form of a nucleotide, a deoxyribonucleotide or a ribonucleotide or an analog thereof that is isolated from the natural environment thereof or is artificially synthesized.

In the present application, the term "vector" usually refers to a nucleic acid molecule capable of self-replication in a suitable host, which transfers the inserted nucleic acid molecule into a host cell and/or among host cells. The vectors may include the vectors mainly used to insert DNA or RNA into cells, the vectors mainly used to replicate DNA or RNA, and the expressed vectors mainly used to DNA or RNA replication and/or translation. The vectors also include the vectors having multiple functions of the above. The vectors may be polynucleotides that are capable of transcription and translation into polypeptides when introduced into suitable host cells. Generally, the vectors can produce desired expression products by culturing the suitable host cells comprising the vectors.

In the present application, the term "cell" usually refers to an individual cell, a cell line or a cell culture that may contain or already contained a plasmid or a vector comprising the nucleic acid molecules of the present application, or that are capable of expressing the antibodies or the antigen binding fragment thereof of the present application. The cells can include the progeny of a single host cell. Because of the natural, accidental or deliberate mutations, the progeny cells may not necessarily be identical to the original parental cells in morphology or genome, provided that they are capable of expressing the antibodies or antigen binding fragments thereof described in the present application. The cells can be obtained by in vitro transfection using the vectors described in the present application. The cells can be procaryotes (e.g., *Escherichia coli*), and also can be eukaryotes (e.g., yeast cells, e.g., COS cells, Chinese Hamster Ovary (CHO) cells, HeLa cells, HEK293 cells, COS-1 cells, NS0 cells or myeloma cells). In some cases, the cells may be mammal animal cells. For example, the mammal animal cells may be CHO-K1 cells. In the present application, the term "recombinant cell" usually refers to a cell into which a recombinant expression vector has been introduced. The recombinant host cells not only include a certain kind of cells, but also include the progeny of these cells.

In the present application, the term "pharmaceutical composition" usually refers to a formulation, which exists in a form that allows the biological activity of the active ingredients to be effective, and does not comprise the additional ingredients that are unacceptably toxic to the subject to which the composition is administered. The composition is aseptic. The "aseptic" composition is sterile, or is free of all living microorganisms or spores thereof.

In the present application, the term "treatment" generally refers to the desire to alter the natural course of a disease in an individual being treated, and may be a clinical intervention to achieve prevention or during the course of a clinical disease. Desirable therapeutic effects include, but are not limited to, preventing the occurrence or recurrence of disease, reducing symptoms, attenuating any direct or indirect pathological consequences of the disease, preventing metastasis, reducing the rate of disease progression, improving or ameliorating the disease state, and alleviating or improving prognosis. In some cases, antibodies (e.g., anti-PD-L1 antibodies) can be used to delay disease progression or slow disease progression.

In the present application, the term "administration" usually refers to a method of giving a certain dose of compound (e.g., an anti-tumor therapeutic agent) or pharmaceutical composition (e.g., a pharmaceutical composition comprising an anti-tumor therapeutic agent) to a subject (e.g., a patient). The administration can be carried out through any suitable means, including parenteral, intrapulmonary and intranasal, and (if topical treatment is needed) intralesional administration. Parenteral infusions include, for example, intramuscular, intravenous, intraarterial, intraperitoneal or subcutaneous administration. The dosing can be carried out by any suitable routes, for example, by injection (such as intravenous or subcutaneous injection), partially depending on whether the administrations is transient or long-term. Various dosing processes are encompassed herein, including but not limited to a single administration or multiple administrations over various time points, bolus administration and pulse infusion.

In the present application, the term "tumor" usually refers to all neoplastic cell growth and proliferation (whether malignant or benign), and all precancerous and cancerous cells and tissues. In the present application, tumors may include a colon cancer.

In the present application, the term "between" usually refers to a certain amino acid fragment is directly or indirectly linked at the C-terminus to the N-terminus of the first amino acid fragment, and is at the N-terminus directly or indirectly linked to the C-terminus of the second amino acid fragment. In a light chain, for example, the N-terminus of the L-FR2 is directly or indirectly linked to the C-terminus of the LCDR1, and the C-terminus of the L-FR2 is directly or indirectly linked to the N-terminus of LCDR2. Further for example, the N-terminus of the L-FR3 is directly or indirectly linked to the C-terminus of the LCDR2, and the C-terminus of the L-FR3 is directly or indirectly linked to the N-terminus of LCDR3. In a heavy chain, for example, the N-terminus of the H-FR2 is directly or indirectly linked to the C-terminus of the HCDR1, and the C-terminus of H-FR2 is directly or indirectly linked to the N-terminus of HCDR2. Also for example, the N-terminus of the H-FR3 is directly or indirectly linked to the C-terminus of the HCDR2, and the C-terminus of the H-FR3 is directly or indirectly linked to the N-terminus of HCDR3. In the present application, "the first amino acid fragment" and "the second amino acid fragment" can be any amino acid fragments that may be the same or different.

In the present application, the term "comprise" usually refers to the meanings of "comprise", "include", "contain" or "encompass". In some cases, it also represents the meanings of "is", and "consist of".

In the present application, the term "about" usually refers to a range of 0.5%-10% of variation above or below a specific value, for example, a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of variation above or below a specific value.

Antigen Binding Protein

In one aspect, the present application provides an antigen binding protein comprising at least one CDR of an antibody light chain variable region VL.

In the present application, the antigen binding protein may comprise LCDR1, and the LCDR1 may comprise the amino acid sequence set forth in SEQ ID NO: 181:

RASQSIX$_7$X$_8$WLA (SEQ ID NO: 181); wherein, X$_7$=F, S or Y; X$_8$=I or S. For example, this sequence can be the sequence determined according to the Chothia definition rule.

In some cases, when compared with the LCDR1 of an antigen binding protein set forth in SEQ ID NO: 48, the LCDR1 may at least comprise an amino acid substitution selected from the following positions: an amino acid substitution at X$_7$ and/or X$_8$.

In some cases, when compared with the LCDR1 of an antigen binding protein set forth in SEQ ID NO: 48, the LCDR1 may at least comprise an amino acid substitution at X$_7$ and/or X$_8$, wherein the amino acid of X$_7$ may be substituted by Y or F; the amino acid of X$_8$ may be substituted by S.

For example, the LCDR1 may comprise the amino acid sequence set forth in any one of SEQ ID NOs: 48-51.

In the present application, the antigen binding protein may comprise LCDR2, and the LCDR2 may comprise the amino acid sequence set forth in SEQ ID NO: 182:

KASSLEX$_7$ (SEQ ID NO: 182); wherein, X$_7$=T or S. For example, this sequence may be the sequence determined according to the Chothia definition rule.

In some cases, when compared with the LCDR2 of an antigen binding protein set forth in SEQ ID NO: 63, the LCDR2 may at least comprise an amino acid substitution selected from the following position: an amino acid substitution at X$_7$.

In some cases, when compared with the LCDR2 of an antigen binding protein set forth in SEQ ID NO: 63, the LCDR2 may at least comprise an amino acid substitution at X$_7$, wherein the amino acid of X$_7$ may be substituted by T.

For example, the LCDR2 may comprise the amino acid sequence set forth in any one of SEQ ID NOs: 63-64.

In the present application, the antigen binding protein may comprise LCDR3, and the LCDR3 may comprise the amino acid sequence set forth in SEQ ID NO: 183:

QQYX$_4$X$_5$X$_6$SRT (SEQ ID NO: 183); wherein, X$_4$=Y or H, X$_5$=G, T or S, X$_6$=Y or S. For example, this sequence may be the sequence determined according to the Chothia definition rule.

In some cases, when compared with the LCDR3 of an antigen binding protein set forth in SEQ ID NO: 77, the LCDR3 may at least comprise an amino acid substitution selected from the following positions: an amino acid substitution at X$_4$, X$_5$ and/or X$_6$.

In some cases, when compared with the LCDR3 of an antigen binding protein set forth in SEQ ID NO: 77, the LCDR3 may at least comprise an amino acid substitution at X$_4$, X$_5$, and/or X$_6$, wherein the amino acid of X$_4$ may be substituted by H; the amino acid of X$_5$ may be substituted by S or T; the amino acid of X$_6$ may be substituted by S.

For example, the LCDR3 may comprise the amino acid sequence set forth in any one of SEQ ID NOs: 77-80.

In some other cases, the LCDR3 may comprise the amino acid sequence set forth in SEQ ID NO: 191:

QQYYX$_5$X$_6$SRT (SEQ ID NO: 191); wherein, X$_5$=G or S, X$_6$=Y or S. For example, this sequence may be the sequence determined according to the Chothia definition rule.

In some specific cases, when compared with the LCDR3 of an antigen binding protein set forth in SEQ ID NO: 77, the LCDR3 may at least comprise an amino acid substitution selected from the following positions: an amino acid substitution at $X_5$ and/or $X_6$.

In some specific cases, when compared with the LCDR3 of an antigen binding protein set forth in SEQ ID NO: 77, the LCDR3 may at least comprise an amino acid substitution at $X_5$ and/or $X_6$, wherein the amino acid of $X_5$ may be substituted by S; the amino acid of $X_6$ may be substituted by S.

For example, the LCDR3 may comprise the amino acid sequence set forth in any one of SEQ ID NOs: 77-79.

In the present application, the antigen binding protein may comprise a framework region L-FR1. The C-terminus of L-FR1 is linked to the N-terminus of LCDR1, and the L-FR1 may comprise the amino acid sequence set forth in SEQ ID NO: 185:

DIQMTQSPSTLSX$_{13}$SVGX$_{17}$RVTX$_{21}$TC (SEQ ID NO: 185); wherein, $X_{13}$=T or A; $X_{17}$=D or H; $X_{21}$=I or V. For example, this sequence may be the sequence determined according to the Chothia definition rule.

In some cases, when compared with the L-FR1 of an antigen binding protein set forth in SEQ ID NO: 41, the L-FR1 may at least comprise an amino acid substitution selected from the following positions: an amino acid substitution at $X_{13}$, $X_{17}$ and/or $X_{21}$.

In some cases, when compared with the L-FR1 of an antigen binding protein set forth in SEQ ID NO: 41, the L-FR1 may at least comprise an amino acid substitution at $X_{13}$, $X_{17}$ and/or $X_{21}$, wherein the amino acid of $X_{13}$ may be substituted by A; the amino acid of $X_{17}$ may be substituted by H; the amino acid of $X_{21}$ may be substituted by V.

For example, the L-FR1 may comprise the amino acid sequence set forth in any one of SEQ ID NOs: 41-44.

In the present application, the antigen binding protein may comprise L-FR2. The L-FR2 is located between the LCDR1 and the LCDR2, and the L-FR2 may comprise the amino acid sequence set forth in SEQ ID NO: 186:

WYQQX$_5$PGKAPX$_{11}$LLIY (SEQ ID NO: 186); wherein, $X_5$=K or H; $X_{11}$=K, N or D. For example, this sequence may be the sequence determined according to the Chothia definition rule.

In some cases, when compared with the L-FR2 of an antigen binding protein set forth in SEQ ID NO: 56, the L-FR2 may at least comprise an amino acid substitution selected from the following positions: an amino acid substitution at $X_5$ and/or $X_{11}$.

In some cases, when compared with the L-FR2 of an antigen binding protein set forth in SEQ ID NO: 56, the L-FR2 can at least comprise an amino acid substitution at $X_5$ and/or $X_{11}$, wherein the amino acid of $X_5$ can be substituted by H; the amino acid of $X_{11}$ can be substituted by D or N.

For example, the L-FR2 may comprise the amino acid sequence set forth in any one of SEQ ID NOs: 56-59.

In the present application, the antigen binding protein may comprise L-FR3. The L-FR3 is located between the LCDR2 and the LCDR3, and the L-FR3 comprises the amino acid sequence set forth in SEQ ID NO: 187:

GYPSRFSGX$_9$GSGTEFTLTISSLQPDDFX$_{28}$TYX$_{31}$C (SEQ ID NO: 187); wherein, $X_9$=S or N; $X_{28}$=A or T; $X_{31}$=Y or F. For example, this sequence may be the sequence determined according to the Chothia definition rule.

In some cases, when compared with the L-FR3 of an antigen binding protein set forth in SEQ ID NO: 69, the L-FR3 may at least comprise an amino acid substitution selected from the following positions: an amino acid substitution at $X_9$, $X_{28}$ and/or $X_{31}$.

In some cases, when compared with the L-FR3 of an antigen binding protein set forth in SEQ ID NO: 69, the L-FR3 may at least comprise an amino acid substitution at $X_9$, $X_{28}$ and/or $X_{31}$, wherein the amino acid of $X_9$ may be substituted by N; the amino acid of $X_{28}$ may be substituted by T; the amino acid of $X_{31}$ may be substituted by F.

For example, the L-FR3 may comprise the amino acid sequence set forth in any one of SEQ ID NOs: 69-72.

In the present application, the antigen binding protein may comprise L-FR4, the N-terminus of the L-FR4 is linked to the C-terminus of the LCDR3, and the L-FR4 may comprise the amino acid sequence set forth in SEQ ID NO: 188:

FGQGTKVEIX$_{10}$ (SEQ ID NO: 188); wherein, $X_{10}$=K or R. For example, this sequence may be the sequence determined according to the Chothia definition rule.

In some cases, when compared with the L-FR4 of an antigen binding protein set forth in SEQ ID NO: 85, the L-FR4 may at least comprise an amino acid substitution selected from the following position: an amino acid substitution at $X_{10}$.

In some cases, when compared with the L-FR4 of an antigen binding protein set forth in SEQ ID NO: 85, the L-FR4 may at least comprise an amino acid substitution at $X_{10}$, wherein, the amino acid of $X_{10}$ may be substituted by R.

For example, the L-FR4 may comprise the amino acid sequence set forth in any one of SEQ ID NOs: 85-86.

In the present application, the antigen binding protein may comprise a light chain variable region VL, and the VL may comprise the amino acid sequence set forth in SEQ ID NO: 190:

DIQMTQSPSTLSX$_{13}$SVGX$_{17}$RVTX$_{21}$TCRASQSIX$_{30}$X$_{31}$WLAWYQQX$_{39}$PGKAPX$_{45}$L LIYKASSLEX$_{56}$GYPSRFSGX$_{65}$GSGTEFTLTISSL-QPDDFX$_{84}$TYX$_{87}$CQQYX$_{92}$X$_{93}$X$_{94}$SRTF GQGTKVEIX$_{107}$ (SEQ ID NO: 190); wherein, $X_{13}$=T or A; $X_{17}$=D or H; $X_{21}$=I or V; $X_{30}$=F, S or Y; $X_{31}$=I or S; $X_{39}$=K or H; $X_{45}$=K, N or D; $X_{56}$=S or T; $X_{65}$=S or N; $X_{84}$=A or T; $X_{87}$=Y or F; $X_{92}$=Y or H; $X_{93}$=G, T or S; $X_{94}$=Y or S; $X_{107}$=K or R. For example, this sequence may be the sequence determined according to the Chothia definition rule.

In some cases, when compared with the VL set forth in SEQ ID NO: 108, the VL may at least comprise an amino acid substitution selected from the following positions: an amino acid substitution at $X_{13}$, $X_{17}$, $X_{21}$, $X_{30}$, $X_{31}$, $X_{39}$, $X_{45}$, $X_{56}$, $X_{65}$, $X_{84}$, $X_{87}$, $X_{92}$, $X_{93}$, $X_{94}$, $X_{107}$.

In some cases, when compared with the VL set forth in SEQ ID NO: 108, the VL may at least comprise amino acid substitutions at $X_{13}$, $X_{17}$, $X_{21}$, $X_{30}$, $X_{31}$, $X_{39}$, $X_{45}$, $X_{56}$, $X_{65}$, $X_{84}$, $X_{87}$, $X_{92}$, $X_{93}$, $X_{94}$, and $X_{107}$, wherein, the amino acid of $X_{13}$ may be substituted by A, the amino acid of $X_{17}$ may be substituted by H, the amino acid of $X_{21}$ may be substituted by V, the amino acid of $X_{30}$ may be substituted by S or Y, the amino acid of $X_{31}$ may be substituted by S, the amino acid of $X_{39}$ may be substituted by H, the amino acid of $X_{45}$ may be substituted by N or D, the amino acid of $X_{56}$ may be substituted by T, the amino acid of $X_{65}$ may be substituted by N, the amino acid of $X_{84}$ may be substituted by T, the amino acid of $X_{87}$ may be substituted by F, the amino acid of $X_{92}$ may be substituted by H, the amino acid of $X_{93}$ may be substituted by T or S, the amino acid of $X_{94}$ may be substituted by S, and the amino acid of $X_{107}$ may be substituted by R.

For example, the VL region may comprise the amino acid sequence set forth in any one of SEQ ID NOs: 108-116 and 118.

In some cases, the VL of the present application may comprise the amino acid sequence set forth in SEQ ID NO: 194:

DIQMTQSPSTLSX$_{13}$SVGX$_{17}$RVTX$_{21}$TCRASQSIX$_{30}$X$_{31}$WLAWYQQX$_{39}$PGKAPX$_{45}$L LIYKASSLEX$_{56}$GVPSRFSGX$_{65}$GSGTEFTLTISSL-QPDDFX$_{84}$TYX$_{87}$CQQYYX$_{93}$X$_{94}$SRTF GQGTKVEIX$_{107}$ (SEQ ID NO: 194); wherein, X$_{13}$=T or A; X$_{17}$=D or H; X$_{21}$=I or V; X$_{30}$=F, S or Y; X$_{31}$=I or S; X$_{39}$=K or H; X$_{45}$=K, N or D; X$_{56}$=S or T; X$_{65}$=S or N; X$_{84}$=A or T; X$_{87}$=Y or F; X$_{93}$=G or S; X$_{94}$=Y or S; X$_{107}$=K or R. For example, this sequence may be the sequence determined according to the Chothia definition rule.

In some cases, when compared with the VL set forth in SEQ ID NO: 108, the VL may at least comprise an amino acid substitution selected from the following positions amino acid substitutions at X$_{13}$, X$_{17}$, X$_{21}$, X$_{30}$, X$_{31}$, X$_{39}$, X$_{45}$, X$_{56}$, X$_{65}$, X$_{84}$, X$_{87}$, X$_{93}$, X$_{94}$, and X$_{107}$.

In some cases, when compared with the VL set forth in SEQ ID NO: 108, the VL may at least comprise an amino acid substitution at X$_{13}$, X$_{17}$, X$_{21}$, X$_{30}$, X$_{31}$, X$_{39}$, X$_{45}$, X$_{56}$, X$_{65}$, X$_{84}$, X$_{87}$, X$_{93}$, X$_{94}$, and X$_{107}$, wherein, the amino acid of X$_{13}$ may be substituted by A, the amino acid of X$_{17}$ may be substituted by H, the amino acid of X$_{21}$ may be substituted by V, the amino acid of X$_{30}$ may be substituted by S or Y, the amino acid of X$_{31}$ may be substituted by S, the amino acid of X$_{39}$ may be substituted by H, the amino acid of X$_{45}$ may be substituted by N or D, the amino acid of X$_{56}$ may be substituted by T, the amino acid of X$_{65}$ may be substituted by N, the amino acid of X$_{84}$ may be substituted by T, the amino acid of X$_{87}$ may be substituted by F, the amino acid of X$_{93}$ may be substituted by S, the amino acid of X$_{94}$ may be substituted by S, the amino acid of X$_{107}$ may be substituted by R.

For example, the VL region may comprise the amino acid sequence set forth in any one of SEQ ID NOs: 108-114, 116 and 118.

The antigen binding protein of the present application may comprise a light chain constant region CL, and the antibody light chain constant region may comprise a human Igκ constant region. For example, the CL region may comprise the amino acid sequence set forth in the following: SEQ ID NO: 170.

The antigen binding protein of the present application may comprise an antibody light chain LC, the antibody light chain may comprise the amino acid sequence set forth in any one of SEQ ID NOs: 150-158 and 160-163. Alternatively, the antibody light chain of the antigen binding protein of the present application may comprise the amino acid sequence set forth in any one of SEQ ID NOs: 150-156, 158 and 160-163.

The antigen binding protein of the present application may comprise at least one CDR of an antibody heavy chain variable region VH.

In the present application, the antigen binding protein may comprise HCDR1, and the HCDR1 may comprise the amino acid sequence set forth in SEQ ID NO: 5:

GFTFSSY (SEQ ID NO: 5). For example, this sequence may be the sequence determined according to the Chothia definition rule.

In the present application, the antigen binding protein may comprise HCDR2, and the HCDR2 may comprise the amino acid sequence set forth in SEQ ID NO: 179:

KQX$_3$X$_4$SE (SEQ ID NO: 179); wherein, X$_3$=D or E; X$_4$=G or A. For example, this sequence may be the sequence determined according to the Chothia definition rule.

In some cases, when compared with the HCDR2 of the antigen binding protein set forth in SEQ ID NO: 14, the HCDR2 may at least comprise an amino acid substitution selected from the following positions: an amino acid substitution at X$_3$ and/or X$_4$.

In some cases, when compared with the HCDR2 of the antigen binding protein set forth in SEQ ID NO: 14, the HCDR2 may at least comprise an amino acid substitution at X$_3$ and/or X$_4$, wherein, the amino acid of X$_3$ may be substituted by E, the amino acid of X$_4$ may be substituted by A.

For example, the HCDR2 may comprise the amino acid sequence set forth in any one of SEQ ID NOs: 14, 16 and 17.

In the present application, the antigen binding protein may comprise HCDR3, and the HCDR3 may comprise the amino acid sequence set forth in SEQ ID NO: 180:

DRX$_3$VAGAX$_8$X$_9$X$_{10}$ (SEQ ID NO: 180); wherein, X$_3$=A or P; X$_8$=F or S; X$_9$=D or A; X$_{10}$=I or F. For example, this sequence may be the sequence determined according to the Chothia definition rule.

In some cases, when compared with the HCDR3 of the antigen binding protein set forth in SEQ ID NO: 29, the HCDR3 may at least comprise an amino acid substitution selected from the following positions: an amino acid substitution at X$_3$, X$_8$, X$_9$ and/or X$_{10}$.

In some cases, when compared with the HCDR3 of the antigen binding protein set forth in SEQ ID NO: 29, the HCDR3 may at least comprise an amino acid substitution at X$_3$, X$_8$, X$_9$ and/or X$_{10}$, wherein the amino acid of X$_3$ may be substituted by P; the amino acid of X$_8$ may be substituted by S; the amino acid of X$_9$ may be substituted by A; the amino acid of X$_{10}$ may be substituted by F.

For example, the HCDR3 may comprise the amino acid sequence set forth in any one of SEQ ID NOs: 29-33.

In the present application, the antigen binding protein may comprise a framework region H-FR1. The C-terminus of the H-FR1 is linked to the N-terminus of the HCDR1, and the H-FR1 may comprise the amino acid sequence set forth in SEQ ID NO: 1:

EVQLVESGGGLVQPGGSLRLSCAAS (SEQ ID NO: 1). For example, this sequence may be the sequence determined according to the Chothia definition rule.

In the present application, the antigen binding protein may comprise H-FR2, the H-FR2 is located between the HCDR1 and the HCDR2, and the H-FR2 may comprise the amino acid sequence set forth in SEQ ID NO: 9:

WMSWVRQAPGKGLEWVANI (SEQ ID NO: 9). For example, this sequence may be the sequence determined according to the Chothia definition rule.

In the present application, the antigen binding protein may comprise H-FR3, the H-FR3 is located between the HCDR2 and the HCDR3, and the H-FR3 may comprise the amino acid sequence set forth in SEQ ID NO: 184:

KYYX$_4$DSVKGRFTISRDNAKNSX$_{22}$YLQMNSLRA-EX$_{33}$TAVX$_{37}$YCAR (SEQ ID NO: 184); wherein, X$_4$=V or G; X$_{22}$=L or Q; X$_{33}$=D or E; X$_{37}$=Y or F. For example, this sequence may be the sequence determined according to the Chothia definition rule.

In some cases, when compared with the H-FR3 set forth in SEQ ID NO: 21, the H-FR3 may at least comprise an amino acid substitution selected from the following positions: an amino acid substitution at X$_4$, X$_{22}$, X$_{33}$ and/or X$_{37}$.

In some cases, when compared with the H-FR3 set forth in SEQ ID NO: 21, the H-FR3 may at least comprise an amino acid substitution at $X_4$, $X_{22}$, $X_{33}$ and/or $X_{37}$, wherein, the amino acid of $X_4$ may be substituted by G, the amino acid of $X_{22}$ may be substituted by Q, the amino acid of $X_{33}$ may be substituted by E, the amino acid of $X_{37}$ may be substituted by F.

For example, the H-FR3 may comprise the amino acid sequence set forth in any one of SEQ ID NOs: 21-24.

Alternatively, the H-FR3 of the present application may comprise the amino acid sequence set forth in SEQ ID NO: 192:

KYYX$_4$DSVKGRFTISRDNAKNSLYLQMNSLRAE-X$_{33}$TAVX$_{37}$YCAR (SEQ ID NO: 192); wherein, $X_4$=V or G; $X_{33}$=D or E; $X_{37}$=Y or F. For example, this sequence may be the sequence determined according to the Chothia definition rule.

In some cases, when compared with the H-FR3 set forth in SEQ ID NO: 21, the H-FR3 may at least comprise an amino acid substitution selected from the following positions: an amino acid substitution at $X_4$, $X_{33}$ and/or $X_{37}$.

In some cases, when compared with the H-FR3 set forth in SEQ ID NO: 21, the H-FR3 may at least comprise an amino acid substitution at $X_4$, $X_{33}$ and/or $X_{37}$, wherein, the amino acid of $X_4$ may be substituted by G, the amino acid of $X_{33}$ may be substituted by E, the amino acid of $X_{37}$ may be substituted by F.

For example, the H-FR3 may comprise the amino acid sequence set forth in any one of SEQ ID NOs: 21-22 and 24.

In the present application, the antigen binding protein may comprise H-FR4, the N-terminus of the H-FR4 is linked to the C-terminus of the HCDR3, and the H-FR4 may comprise the amino acid sequence set forth in SEQ ID NO: 38:

WGQGTMVTVSS (SEQ ID NO: 38). For example, this sequence may be the sequence determined according to the Chothia definition rule.

In the present application, the antigen binding protein may comprise a heavy chain variable region VH, and the VH may comprise the amino acid sequence set forth in SEQ ID NO: 189:

EVQLVESGGGLVQPGGSLRLS-CAASGFTFSSYWMSWVRQAPGKGLEWVANIKQ X$_{54}$X$_{55}$SEKYYX$_{61}$DSVKGRFTISRDNAKNSX$_{79}$Y-LQMNSLRAEX$_{90}$TAVX$_{94}$YCARDRX$_{101}$VAGAX$_{106}$ X$_{107}$X$_{108}$WGQGTMVTVSS (SEQ ID NO: 189); wherein, $X_{54}$=D or E; $X_{55}$=G or A; $X_{61}$=V or G; $X_{79}$=L or Q; $X_{90}$=D or E; $X_{94}$=Y or F; $X_{101}$=A or P; $X_{106}$=F or S; $X_{107}$=D or A; $X_{108}$=I or F. For example, this sequence may be the sequence determined according to the Chothia definition rule.

In some cases, when compared with the VH set forth in SEQ ID NO: 90, the VH may at least comprise an amino acid substitution selected from the following positions: an amino acid substitution at $X_{54}$, $X_{55}$, $X_{61}$, $X_{79}$, $X_{90}$, $X_{94}$, $X_{101}$, $X_{106}$, $X_{107}$ and/or $X_{108}$.

In some cases, when compared with the VH set forth in SEQ ID NO: 90, the VH may at least comprise an amino acid substitution at $X_{54}$, $X_{55}$, $X_{61}$, $X_{79}$, $X_{90}$, $X_{94}$, $X_{101}$, $X_{106}$, $X_{107}$ and/or $X_{108}$, wherein, the amino acid of $X_{54}$ may be substituted by E, the amino acid of $X_{55}$ may be substituted by A, the amino acid of $X_{61}$ may be substituted by G, $X_{79}$ may be substituted by Q, the amino acid of $X_{90}$ may be substituted by E, the amino acid of $X_{94}$ may be substituted by F, $X_{101}$ may be substituted by P, the amino acid of $X_{106}$ may be substituted by S, the amino acid of $X_{107}$ may be substituted by A, the amino acid of $X_{108}$ may be substituted by F.

For example, the VH region may comprise the amino acid sequence set forth in any one of SEQ ID NOs: 90-95 and 97-104.

In some cases, the VH of the present application may comprise the amino acid sequence set forth in SEQ ID NO:193:

EVQLVESGGGLVQPGGSLRLS-CAASGFTFSSYWMSWVRQAPGKGLEWVANIKQ X$_{54}$X$_{55}$SEKYYX$_{61}$DSVKGRFTISRDNAKNSLYLQ-MNSLRAEX$_{90}$TAVX$_{94}$YCARDRX$_{101}$V AGAX$_{106}$X$_{107}$X$_{108}$WGQGTMVTVSS (SEQ ID NO: 193); wherein, $X_{54}$=D or E; $X_{55}$=G or A; $X_{61}$=V or G; $X_{90}$=D or E; $X_{94}$=Y or F; $X_{101}$=A or P; $X_{106}$=F or S; $X_{107}$=D or A; $X_{108}$=I or F. For example, this sequence may be the sequence determined according to the Chothia definition rule.

In some cases, when compared with the VH set forth in SEQ ID NO: 90, the VH may at least comprise an amino acid substitution selected from the following positions: an amino acid substitution at $X_{54}$, $X_{55}$, $X_{61}$, $X_{90}$, $X_{94}$, $X_{101}$, $X_{106}$, $X_{107}$ and/or $X_{108}$.

In some cases, when compared with the VH set forth in SEQ ID NO: 90, the VH may at least comprise an amino acid substitution at $X_{54}$, $X_{55}$, $X_{61}$, $X_{90}$, $X_{94}$, $X_{101}$, $X_{106}$, $X_{107}$ and/or $X_{108}$, wherein, the amino acid of $X_{54}$ may be substituted by E, the amino acid of $X_{55}$ may be substituted by A, the amino acid of $X_{61}$ may be substituted by G, the amino acid of $X_{90}$ may be substituted by E, the amino acid of $X_{94}$ may be substituted by F, $X_{101}$ may be substituted by P, the amino acid of $X_{106}$ may be substituted by S, the amino acid of $X_{107}$ may be substituted by A, the amino acid of $X_{108}$ may be substituted by F.

For example, the VH region may comprise the amino acid sequence set forth in any one of SEQ ID NOs: 90-93, 95 and 97-104.

The antigen binding protein of the present application may comprise a heavy chain constant region CH, and the antibody heavy chain constant region may comprise human IgG constant region. In some cases, the human IgG constant region may comprise human IgG1 constant region. The human IgG1 constant region may include natural and artificially synthesized IgG1 constant region or mutants thereof. The mutation may comprise a mutation at the following one or more positions: L234, L235, N297 or K447. For example, it may comprise a mutation at one, two or more positions. The mutation may comprise deletion, insertion or substitution of an amino acid. For example, the human IgG1 constant region may comprise the following mutations: 1) N297A, 2) K447 deletion, 3) N297A and K447 deletions, 4) L234A, L235A and K447 deletions. For example, the human IgG1 constant region of the fusion protein may comprise the amino acid sequence set forth in any one of SEQ ID NOs: 172-175.

In the present application, the isolated antigen binding protein may comprise LCDR1-3. Wherein, the LCDR1 may comprise the amino acid sequence set forth in SEQ ID NO: 181; the LCDR2 may comprise the amino acid sequence set forth in SEQ ID NO: 182; and the LCDR3 may comprise the amino acid sequence set forth in SEQ ID NO: 183. Alternatively, the LCDR1 of the antigen binding protein of the present application may comprise the amino acid sequence set forth in SEQ ID NO: 181; the LCDR2 may comprise the amino acid sequence set forth in SEQ ID NO: 182; and the LCDR3 may comprise the amino acid sequence set forth in SEQ ID NO: 191.

In some cases, the LCDR1 of the antigen binding protein of the present application may comprise the amino acid sequence set forth in any one of the following: SEQ ID NOs:

48-51; the LCDR2 may comprise the amino acid sequence set forth in any one of the following: SEQ ID NOs: 63-64; and the LCDR3 may comprise the amino acid sequence set forth in any one of the following: SEQ ID NOs: 77-80. In some other cases, the LCDR1 of the antigen binding protein of the present application may comprise the amino acid sequence set forth in any one of the following: SEQ ID NOs: 48-51; the LCDR2 may comprise the amino acid sequence set forth in any one of the following: SEQ ID NOs: 63-64; and the LCDR3 may comprise the amino acid sequence set forth in any one of the following: SEQ ID NOs: 77-79.

For example, the antigen binding protein of the present application may comprise the same LCDR1-3 as PR000064. Wherein the LCDR1 may comprise the amino acid sequence set forth in SEQ ID NO: 48, the LCDR2 may comprise the amino acid sequence set forth in SEQ ID NO: 63, and the LCDR3 may comprise the amino acid sequence set forth in SEQ ID NO: 77.

For example, the antigen binding protein of the present application may comprise the same LCDR1-3 as PR000065, wherein the LCDR1 may comprise the amino acid sequence set forth in SEQ ID NO: 49, the LCDR2 may comprise the amino acid sequence set forth in SEQ ID NO: 64, and the LCDR3 may comprise the amino acid sequence set forth in SEQ ID NO: 78.

For example, the antigen binding protein of the present application may comprise the same LCDR1-3 as PR000066, PR000261, PR000262. Wherein the LCDR1 may comprise the amino acid sequence set forth in SEQ ID NO: 48, the LCDR2 may comprise the amino acid sequence set forth in SEQ ID NO: 64, and the LCDR3 may comprise the amino acid sequence set forth in SEQ ID NO: 78.

For example, the antigen binding protein of the present application may comprise the same LCDR1-3 as PR000067, wherein the LCDR1 may comprise the amino acid sequence set forth in SEQ ID NO: 50, the LCDR2 may comprise the amino acid sequence set forth in SEQ ID NO: 63, and the LCDR3 may comprise the amino acid sequence set forth in SEQ ID NO: 77.

For example, the antigen binding protein of the present application may comprise the same LCDR1-3 as PR000068. Wherein the LCDR1 may comprise the amino acid sequence set forth in SEQ ID NO: 50, the LCDR2 may comprise the amino acid sequence set forth in SEQ ID NO: 63, and the LCDR3 may comprise the amino acid sequence set forth in SEQ ID NO: 79.

For example, the antigen binding protein of the present application may comprise the same LCDR1-3 as PR000069, PR000263, PR000264, wherein the LCDR1 may comprise the amino acid sequence set forth in SEQ ID NO: 51, the LCDR2 may comprise the amino acid sequence set forth in SEQ ID NO: 63, and the LCDR3 may comprise the amino acid sequence set forth in SEQ ID NO: 77.

For example, the antigen binding protein of the present application may comprise the same LCDR1-3 as PR000070, PR000265, PR000266. Wherein the LCDR1 may comprise the amino acid sequence set forth in SEQ ID NO: 51, the LCDR2 may comprise the amino acid sequence set forth in SEQ ID NO: 64, and the LCDR3 may comprise the amino acid sequence set forth in SEQ ID NO: 78.

For example, the antigen binding protein of the present application may comprise the same LCDR1-3 as PR000071, wherein the LCDR1 may comprise the amino acid sequence set forth in SEQ ID NO: 50, the LCDR2 may comprise the amino acid sequence set forth in SEQ ID NO: 63, and the LCDR3 may comprise the amino acid sequence set forth in SEQ ID NO: 80.

For example, the antigen binding protein of the present application may comprise the same LCDR1-3 as PR000072, PR000267, PR000268. Wherein the LCDR1 may comprise the amino acid sequence set forth in SEQ ID NO: 50, the LCDR2 may comprise the amino acid sequence set forth in SEQ ID NO: 64, and the LCDR3 may comprise the amino acid sequence set forth in SEQ ID NO: 77.

In the present application, the isolated antigen binding protein may comprise L-FR1-4. Wherein, the L-FR1 may comprise the amino acid sequence set forth in SEQ ID NO: 185; the L-FR2 may comprise the amino acid sequence set forth in SEQ ID NO: 186; the L-FR3 may comprise the amino acid sequence set forth in SEQ ID NO: 187; and the L-FR4 may comprise the amino acid sequence set forth in SEQ ID NO: 188.

In some cases, the L-FR1 of the antigen binding protein of the present application may comprise the amino acid sequence set forth in any one of the following: SEQ ID NOs: 41-44; the L-FR2 may comprise the amino acid sequence set forth in any one of the following: SEQ ID NOs: 56-59; the L-FR3 may comprise the amino acid sequence set forth in any one of the following: SEQ ID NOs: 69-72; and the L-FR4 may comprise the amino acid sequence set forth in any one of the following: SEQ ID NOs: 85-86.

For example, the antigen binding protein of the present application may comprise the same L-FR1-4 as PR000064. Wherein the L-FR1 may comprise the amino acid sequence set forth in SEQ ID NO: 41, the L-FR2 may comprise the amino acid sequence set forth in SEQ ID NO: 56, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000065. Wherein the L-FR1 may comprise the amino acid sequence set forth in SEQ ID NO: 42, the L-FR2 may comprise the amino acid sequence set forth in SEQ ID NO: 57, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000066. Wherein the L-FR1 may comprise the amino acid sequence set forth in SEQ ID NO: 43, the L-FR2 may comprise the amino acid sequence set forth in SEQ ID NO: 58, the L-FR3 may comprise the amino acid sequence set forth in SEQ ID NO: 70, and the L-FR4 may comprise the amino acid sequence set forth in SEQ ID NO: 85.

For example, the antigen binding protein of the present application may comprise the same L-FR1-4 as PR000067. Wherein the L-FR1 may comprise the amino acid sequence set forth in SEQ ID NO: 42, the L-FR2 may comprise the amino acid sequence set forth in SEQ ID NO: 56, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000068. Wherein the L-FR1 may comprise the amino acid sequence set forth in SEQ ID NO: 42, the L-FR2 may comprise the amino acid sequence set forth in SEQ ID NO: 56, the L-FR3 may comprise the amino acid sequence set forth in SEQ ID NO: 71, and the L-FR4 may comprise the amino acid sequence set forth in SEQ ID NO: 85.

For example, the antigen binding protein of the present application may comprise the same L-FR1-4 as PR000071. Wherein the L-FR1 may comprise the amino acid sequence set forth in SEQ ID NO: 42, the L-FR2 may comprise the amino acid sequence set forth in SEQ ID NO: 56, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000069, PR000263, PR000264. Wherein the L-FR1 may comprise the amino acid sequence set forth in SEQ ID NO: 42, the L-FR2 may comprise the amino acid sequence set forth in SEQ ID NO: 59, the L-FR3 may comprise the amino acid sequence set forth in SEQ ID NO: 72, and the L-FR4 may comprise the amino acid sequence set forth in SEQ ID NO: 86.

For example, the antigen binding protein of the present application may comprise the same L-FR1-4 as PR000070, PR000265, PR000266. Wherein the L-FR1 may comprise the amino acid sequence set forth in SEQ ID NO: 44, the L-FR2 may comprise the amino acid sequence set forth in SEQ ID NO: 57, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000072, PR000267, PR000268. Wherein the L-FR1 may comprise the amino acid sequence set forth in SEQ ID NO: 42, the L-FR2 may comprise the amino acid sequence set forth in SEQ ID NO: 57, the L-FR3 may comprise the amino acid sequence set forth in SEQ ID NO: 69, and the L-FR4 may comprise the amino acid sequence set forth in SEQ ID NO: 85.

For example, the antigen binding protein of the present application may comprise the same L-FR1-4 as PR000261, PR000262. Wherein the L-FR1 may comprise the amino acid sequence set forth in SEQ ID NO: 43, the L-FR2 may comprise the amino acid sequence set forth in SEQ ID NO: 58, the L-FR3 may comprise the amino acid sequence set forth in SEQ ID NO: 69, and the L-FR4 may comprise the amino acid sequence set forth in SEQ ID NO: 85.

In the present application, the isolated antigen binding protein may comprise HCDR1-3. Wherein, the HCDR1 may comprise the amino acid sequence set forth in SEQ ID NO: 5; the HCDR2 may comprise the amino acid sequence set forth in SEQ ID NO: 179; and the HCDR3 may comprise the amino acid sequence set forth in SEQ ID NO: 180.

In some cases, the HCDR1 of the antigen binding protein of the present application may comprise the amino acid sequence set forth in the following: SEQ ID NO: 5; the HCDR2 may comprise the amino acid sequences set forth in any one of the following: SEQ ID NOs: 14, 16 and 17; and the HCDR3 may comprise the amino acid sequences set forth in any one of the following: SEQ ID NOs: 29-33.

For example, the antigen binding protein of the present application may comprise the same HCDR1-3 as PR000064, PR000065, PR000067, PR000070. Wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 29.

For example, the antigen binding protein of the present application may comprise the same HCDR1-3 as PR000066. Wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 30.

For example, the antigen binding protein of the present application may comprise the same HCDR1-3 as PR000068. Wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 31.

For example, the antigen binding protein of the present application may comprise the same HCDR1-3 as PR000069. Wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 32.

For example, the antigen binding protein of the present application may comprise the same HCDR1-3 as PR000071, PR000072. Wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 33.

For example, the antigen binding protein of the present application may comprise the same HCDR1-3 as PR000261. Wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 30.

For example, the antigen binding protein of the present application may comprise the same HCDR1-3 as PR000262. Wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 30.

For example, the antigen binding protein of the present application may comprise the same HCDR1-3 as PR000263. Wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 32.

For example, the antigen binding protein of the present application may comprise the same HCDR1-3 as PR000264. Wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 32.

For example, the antigen binding protein of the present application may comprise the same HCDR1-3 as PR000265. Wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 29.

For example, the antigen binding protein of the present application may comprise the same HCDR1-3 as PR000266. Wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 29.

For example, the antigen binding protein of the present application may comprise the same HCDR1-3 as PR000267. Wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 33.

For example, the antigen binding protein of the present application may comprise the same HCDR1-3 as PR000268. Wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 33.

In the present application, the isolated antigen binding protein may comprise H-FR1-4. Wherein, the H-FR1 may comprise the amino acid sequence set forth in SEQ ID NO: 1; the H-FR2 may comprise the amino acid sequence set forth in SEQ ID NO: 9; the H-FR3 may comprise the amino acid sequence set forth in SEQ ID NO: 184; and the H-FR4 may comprise the amino acid sequence set forth in SEQ ID NO: 38. Alternatively, the H-FR1 may comprise the amino acid sequence set forth in SEQ ID NO: 1; the H-FR2 may comprise the amino acid sequence set forth in SEQ ID NO: 9; the H-FR3 may comprise the amino acid sequence set forth in SEQ ID NO: 192; and the H-FR4 may comprise the amino acid sequence set forth in SEQ ID NO: 38.

In some cases, the H-FR1 of the antigen binding protein of the present application may comprise the amino acid sequence set forth in the following: SEQ ID NO: 1; the H-FR2 may comprise the amino acid sequence set forth in the following: SEQ ID NO: 9; the H-FR3 may comprise the amino acid sequence set forth in any one of the following: SEQ ID NOs: 21-24; and the H-FR4 may comprise the amino acid sequence set forth in any one of the following: SEQ ID NO: 38. In some other cases, the H-FR1 of the antigen binding protein of the present application may comprise the amino acid sequence set forth in the following: SEQ ID NO: 1; the H-FR2 may comprise the amino acid sequence set forth in the following: SEQ ID NO: 9; the H-FR3 may comprise the amino acid sequence set forth in any one of the following: SEQ ID NOs: 21-22 and 24; and the H-FR4 may comprise the amino acid sequence set forth in any one of the following: SEQ ID NO: 38.

For example, the antigen binding protein of the present application may comprise H-FR1-4, wherein the H-FR1 may comprise the amino acid sequence set forth in SEQ ID NO: 1, the H-FR2 may comprise the amino acid sequence set forth in SEQ ID NO: 9, the H-FR3 may comprise the amino acid sequence set forth in SEQ ID NO: 21, and the H-FR4 may comprise the amino acid sequence set forth in SEQ ID NO: 38.

For example, the antigen binding protein of the present application may comprise H-FR1-4, wherein the H-FR1 may comprise the amino acid sequence set forth in SEQ ID NO: 1, the H-FR2 may comprise the amino acid sequence set forth in SEQ ID NO: 9, the H-FR3 may comprise the amino acid sequence set forth in SEQ ID NO: 22, and the H-FR4 may comprise the amino acid sequence set forth in SEQ ID NO: 38.

For example, the antigen binding protein of the present application may comprise H-FR1-4, wherein the H-FR1 may comprise the amino acid sequence set forth in SEQ ID NO: 1, the H-FR2 may comprise the amino acid sequence set forth in SEQ ID NO: 9, the H-FR3 may comprise the amino acid sequence set forth in SEQ ID NO: 23, and the H-FR4 may comprise the amino acid sequence set forth in SEQ ID NO: 38.

For example, the antigen binding protein of the present application may comprise H-FR1-4, wherein the H-FR1 may comprise the amino acid sequence set forth in SEQ ID NO: 1, the H-FR2 may comprise the amino acid sequence set forth in SEQ ID NO: 9, the H-FR3 may comprise the amino acid sequence set forth in SEQ ID NO: 24, and the H-FR4 may comprise the amino acid sequence set forth in SEQ ID NO: 38.

In the present application, the isolated antigen binding protein may comprise LCDR1-3 and HCDR1-3. Wherein, the LCDR1 may comprise the amino acid sequence set forth in SEQ ID NO: 181; the LCDR2 may comprise the amino acid sequence set forth in SEQ ID NO: 182; and the LCDR3 may comprise the amino acid sequence set forth in SEQ ID NO: 183; the HCDR1 may comprise the amino acid sequence set forth in SEQ ID NO: 5; the HCDR2 may comprise the amino acid sequence set forth in SEQ ID NO: 179; and the HCDR3 may comprise the amino acid sequence set forth in SEQ ID NO: 180. Alternatively, the LCDR1 may comprise the amino acid sequence set forth in SEQ ID NO: 181; the LCDR2 may comprise the amino acid sequence set forth in SEQ ID NO: 182; and the LCDR3 may comprise the amino acid sequence set forth in SEQ ID NO: 191; the HCDR1 may comprise the amino acid sequence set forth in SEQ ID NO: 5; the HCDR2 may comprise the amino acid sequence set forth in SEQ ID NO: 179; and the HCDR3 may comprise the amino acid sequence set forth in SEQ ID NO: 180.

In some cases, the LCDR1 of the antigen binding protein of the present application may comprise the amino acid sequence set forth in any one of the following: SEQ ID NOs: 48-51; the LCDR2 may comprise the amino acid sequence set forth in any one of the following: SEQ ID NOs: 63-64; and the LCDR3 may comprise the amino acid sequence set forth in any one of the following: SEQ ID NOs: 77-80; the HCDR1 may comprise the amino acid sequence set forth in the following: SEQ ID NO: 5; the HCDR2 may comprise the amino acid sequence set forth in any one of the following: SEQ ID NOs: 14, 16 and 17; and the HCDR3 may comprise the amino acid sequence set forth in any one of the following: SEQ ID NOs: 29-33. In some other cases, the LCDR1 of the antigen binding protein of the present application may comprise the amino acid sequence set forth in any one of the following: SEQ ID NOs: 48-51; the LCDR2 may comprise the amino acid sequence set forth in any one of the following: SEQ ID NOs: 63-64; and the LCDR3 may comprise the amino acid sequence set forth in any one of the following: SEQ ID NOs: 77-79; the HCDR1 may comprise the amino acid sequence set forth in the following: SEQ ID NO: 5; the HCDR2 may comprise the amino acid sequence set forth in any one of the following: SEQ ID NOs: 14, 16 and 17; and the HCDR3 may comprise the amino acid sequence set forth in any one of the following: SEQ ID NOs: 29-33.

For example, the antigen binding protein of the present application may comprise the same LCDR1-3 and HCDR1-3 as PR000064. Wherein the LCDR1 may comprise the amino acid sequence set forth in SEQ ID NO: 48, the LCDR2 may comprise the amino acid sequence set forth in SEQ ID NO: 63, and the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 29.

For example, the antigen binding protein of the present application may comprise the same LCDR1-3 and HCDR1-3 as PR000065. Wherein the LCDR1 may comprise the amino acid sequence set forth in SEQ ID NO: 49, the LCDR2 may comprise the amino acid sequence set forth in SEQ ID NO: 64, the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 29.

For example, the antigen binding protein of the present application may comprise the same LCDR1-3 and HCDR1-3 as PR000066. Wherein the LCDR1 may comprise the amino acid sequence set forth in SEQ ID NO: 48, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 30.

For example, the antigen binding protein of the present application may comprise the same LCDR1-3 and HCDR1-3 as PR000067. Wherein the LCDR1 may comprise the amino acid sequence set forth in SEQ ID NO: 50, the LCDR2 may comprise the amino acid sequence set forth in SEQ ID NO: 63; the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 29.

For example, the antigen binding protein of the present application may comprise the same LCDR1-3 and HCDR1-3 as PR000068. Wherein the LCDR1 may comprise the amino acid sequence set forth in SEQ ID NO: 50, the LCDR2 may comprise the amino acid sequence set forth in SEQ ID NO: 63, and the LCDR3 may comprise the amino acid sequence set forth in SEQ ID NO: 79, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 31.

For example, the antigen binding protein of the present application may comprise the same LCDR1-3 and HCDR1-3 as PR000069. Wherein the LCDR1 may comprise the amino acid sequence set forth in SEQ ID NO: 51, the LCDR2 may comprise the amino acid sequence set forth in SEQ ID NO: 63, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 32.

For example, the antigen binding protein of the present application may comprise the same LCDR1-3 and HCDR1-3 as PR000070. Wherein the LCDR1 may comprise the amino acid sequence set forth in SEQ ID NO: 51, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 29.

For example, the antigen binding protein of the present application may comprise the same LCDR1-3 and HCDR1-3 as PR000071. Wherein the LCDR1 may comprise the amino acid sequence set forth in SEQ ID NO: 50, the LCDR2 may comprise the amino acid sequence set forth in SEQ ID NO: 63, and the LCDR3 may comprise the amino acid sequence set forth in SEQ ID NO: 80, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 33.

For example, the antigen binding protein of the present application may comprise the same LCDR1-3 and HCDR1-3 as PR000072. Wherein the LCDR1 may comprise the amino acid sequence set forth in SEQ ID NO: 50, the LCDR2 may comprise the amino acid sequence set forth in SEQ ID NO: 64, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 14, and the HCDR3 may comprise the amino acid sequence set forth in SEQ ID NO: 33.

For example, the antigen binding protein of the present application may comprise the same LCDR1-3 and HCDR1-3 as PR000261. Wherein the LCDR1 may comprise the amino acid sequence set forth in SEQ ID NO: 48, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 30.

For example, the antigen binding protein of the present application may comprise the same LCDR1-3 and HCDR1-3 as PR000262. Wherein the LCDR1 may comprise the amino acid sequence set forth in SEQ ID NO: 48, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 30.

For example, the antigen binding protein of the present application may comprise the same LCDR1-3 and HCDR1-3 as PR000263. Wherein the LCDR1 may comprise the amino acid sequence set forth in SEQ ID NO: 51, the LCDR2 may comprise the amino acid sequence set forth in SEQ ID NO: 63, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 32.

For example, the antigen binding protein of the present application may comprise the same LCDR1-3 and HCDR1-3 as PR000264. Wherein the LCDR1 may comprise the amino acid sequence set forth in SEQ ID NO: 51, the LCDR2 may comprise the amino acid sequence set forth in SEQ ID NO: 63, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 32.

For example, the antigen binding protein of the present application may comprise the same LCDR1-3 and HCDR1-3 as PR000265 and PR000416. Wherein the LCDR1 may comprise the amino acid sequence set forth in SEQ ID NO: 51, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 29.

For example, the antigen binding protein of the present application may comprise the same LCDR1-3 and HCDR1-3 as PR000266. Wherein the LCDR1 may comprise the amino acid sequence set forth in SEQ ID NO: 51, the LCDR2 may comprise the amino acid sequence set forth in SEQ ID NO: 64, and the LCDR3 may comprise the amino acid sequence set forth in SEQ ID NO: 78, wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 29.

For example, the antigen binding protein of the present application may comprise the same LCDR1-3 and HCDR1-3 as PR000267. Wherein the LCDR1 may comprise the amino acid sequence set forth in SEQ ID NO: 50, the LCDR2 may comprise the amino acid sequence set forth in SEQ ID NO: 64, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 16, and the HCDR3 may comprise the amino acid sequence set forth in SEQ ID NO: 33.

For example, the antigen binding protein of the present application may comprise the same LCDR1-3 and HCDR1-3 as PR000268. Wherein the LCDR1 may comprise the amino acid sequence set forth in SEQ ID NO: 50, the LCDR2 may comprise the amino acid sequence set forth in SEQ ID NO: 64, the LCDR3 may comprise the amino acid sequence set forth in SEQ ID NO: 77, wherein the HCDR1 may comprise the amino acid sequence set forth in SEQ ID NO: 5, the HCDR2 may comprise the amino acid sequence set forth in SEQ ID NO: 17, and the HCDR3 may comprise the amino acid sequence set forth in SEQ ID NO: 33.

In the present application, the antigen binding protein may comprise a light chain variable region VL and a heavy chain variable region VH. The VL may comprise the amino acid sequence set forth in SEQ ID NO: 194, and the VH may comprise the amino acid sequence set forth in SEQ ID NO: 193. Alternatively, the VL may comprise the amino acid sequence set forth in SEQ ID NO: 190, and the VH may comprise the amino acid sequence set forth in SEQ ID NO: 189.

In some cases, the VL of the antigen binding protein may comprise the amino acid sequence set forth in any one of SEQ ID NOs: 108-116 and 118, and the VH may comprise the amino acid sequence set forth in any one of SEQ ID NOs: 90-95, and 97-104. In some other cases, the VL of the antigen binding protein may comprise the amino acid sequence set forth in any one of SEQ ID NOs: 108-114, 116 and 118, and the VH may comprise the amino acid sequence set forth in any one of SEQ ID NOs: 90-93, 95, and 97-104.

For example, the antigen binding protein of the present application may comprise the same VL and VH as PR000064, wherein, the VL may comprise the amino acid sequence set forth in SEQ ID NO: 108, and the VH may comprise the amino acid sequence set forth in SEQ ID NO: 90.

For example, the antigen binding protein of the present application may comprise the same VL and VH as PR000065, wherein, the VL may comprise the amino acid sequence set forth in SEQ ID NO: 109, and the VH may comprise the amino acid sequence set forth in SEQ ID NO: 90.

For example, the antigen binding protein of the present application may comprise the same VL and VH as PR000066, wherein, the VL may comprise the amino acid sequence set forth in SEQ ID NO: 110, and the VH may comprise the amino acid sequence set forth in SEQ ID NO: 91.

For example, the antigen binding protein of the present application may comprise the same VL and VH as PR000067, wherein, the VL may comprise the amino acid sequence set forth in SEQ ID NO: 111, and the VH may comprise the amino acid sequence set forth in SEQ ID NO: 90.

For example, the antigen binding protein of the present application may comprise the same VL and VH as PR000068, wherein, the VL may comprise the amino acid sequence set forth in SEQ ID NO: 112, and the VH may comprise the amino acid sequence set forth in SEQ ID NO: 92.

For example, the antigen binding protein of the present application may comprise the same VL and VH as PR000069, wherein, the VL may comprise the amino acid sequence set forth in SEQ ID NO: 113, and the VH may comprise the amino acid sequence set forth in SEQ ID NO: 93.

For example, the antigen binding protein of the present application may comprise the same VL and VH as PR000070, wherein, the VL may comprise the amino acid sequence set forth in SEQ ID NO: 114, and the VH may comprise the amino acid sequence set forth in SEQ ID NO: 90.

For example, the antigen binding protein of the present application may comprise the same VL and VH as PR000071, wherein, the VL may comprise the amino acid sequence set forth in SEQ ID NO: 115, and the VH may comprise the amino acid sequence set forth in SEQ ID NO: 94.

For example, the antigen binding protein of the present application may comprise the same VL and VH as PR000072, wherein, the VL may comprise the amino acid sequence set forth in SEQ ID NO: 116, and the VH may comprise the amino acid sequence set forth in SEQ ID NO: 95.

For example, the antigen binding protein of the present application may comprise the same VL and VH as PR000261, wherein, the VL may comprise the amino acid sequence set forth in SEQ ID NO: 118, and the VH may comprise the amino acid sequence set forth in SEQ ID NO: 97.

For example, the antigen binding protein of the present application may comprise the same VL and VH as PR000262, wherein, the VL may comprise the amino acid sequence set forth in SEQ ID NO: 118, and the VH may comprise the amino acid sequence set forth in SEQ ID NO: 98.

For example, the antigen binding protein of the present application may comprise the same VL and VH as PR000263, wherein, the VL may comprise the amino acid sequence set forth in SEQ ID NO: 113, and the VH may comprise the amino acid sequence set forth in SEQ ID NO: 99.

For example, the antigen binding protein of the present application may comprise the same VL and VH as PR000264, wherein, the VL may comprise the amino acid sequence set forth in SEQ ID NO: 113, and the VH may comprise the amino acid sequence set forth in SEQ ID NO: 100.

For example, the antigen binding protein of the present application may comprise the same VL and VH as PR000265 or PR000416, wherein, the VL may comprise the amino acid sequence set forth in SEQ ID NO: 114, and the VH may comprise the amino acid sequence set forth in SEQ ID NO: 101.

For example, the antigen binding protein of the present application may comprise the same VL and VH as PR000266, wherein, the VL may comprise the amino acid sequence set forth in SEQ ID NO: 114, and the VH may comprise the amino acid sequence set forth in SEQ ID NO: 102.

For example, the antigen binding protein of the present application may comprise the same VL and VH as PR000267, wherein, the VL may comprise the amino acid sequence set forth in SEQ ID NO: 116, and the VH may comprise the amino acid sequence set forth in SEQ ID NO: 103.

For example, the antigen binding protein of the present application may comprise the same VL and VH as PR000268, wherein, the VL may comprise the amino acid sequence set forth in SEQ ID NO: 116, and the VH may comprise the amino acid sequence set forth in SEQ ID NO: 104.

In some cases, the antigen binding protein may comprise a light chain constant region and a heavy chain constant region, wherein, the light chain constant region may comprise the amino acid sequence set forth in SEQ ID NO: 170, and the heavy chain constant region may comprise the amino acid sequence set forth in any one of SEQ ID NOs: 172-175.

In some cases, the antigen binding protein may comprise an antibody light chain LC and an antibody heavy chain HC, wherein, the antibody light chain LC may comprise the amino acid sequence set forth in any one of the following: SEQ ID NOs: 150-158 and 160-163, and the antibody heavy chain HC may comprise the amino acid sequence set forth in any one of the following: SEQ ID NOs: 122-127 and 129-137.

In some cases, the antigen binding protein may comprise an antibody light chain LC and an antibody heavy chain HC, wherein, the antibody light chain LC may comprise the amino acid sequence set forth in any one of the following: SEQ ID NOs: 150-156, 158 and 160-163, and the antibody heavy chain HC may comprise the amino acid sequence set forth in any one of the following: SEQ ID NOs: 122-125, 127 and 129-137.

For example, the antigen binding protein of the present application may comprise the same LC and HC as PR000064, wherein, the LC may comprise the amino acid sequence set forth in SEQ ID NO: 150, and the HC may comprise the amino acid sequence set forth in SEQ ID NO: 122.

For example, the antigen binding protein of the present application may comprise the same LC and HC as PR000065, wherein, the LC may comprise the amino acid sequence set forth in SEQ ID NO: 151, and the HC may comprise the amino acid sequence set forth in SEQ ID NO: 122.

For example, the antigen binding protein of the present application may comprise the same LC and HC as PR000066, wherein, the LC may comprise the amino acid sequence set forth in SEQ ID NO: 152, and the HC may comprise the amino acid sequence set forth in SEQ ID NO: 123.

For example, the antigen binding protein of the present application may comprise the same LC and HC as PR000067, wherein, the LC may comprise the amino acid sequence set forth in SEQ ID NO: 153, and the HC may comprise the amino acid sequence set forth in SEQ ID NO: 122.

For example, the antigen binding protein of the present application may comprise the same LC and HC as PR000068, wherein, the LC may comprise the amino acid sequence set forth in SEQ ID NO: 154, and the HC may comprise the amino acid sequence set forth in SEQ ID NO: 124.

For example, the antigen binding protein of the present application may comprise the same LC and HC as PR000069, wherein, the LC may comprise the amino acid sequence set forth in SEQ ID NO: 155, and the HC may comprise the amino acid sequence set forth in SEQ ID NO: 125.

For example, the antigen binding protein of the present application may comprise the same LC and HC as PR000070, wherein, the LC may comprise the amino acid sequence set forth in SEQ ID NO: 156, and the HC may comprise the amino acid sequence set forth in SEQ ID NO: 122.

For example, the antigen binding protein of the present application may comprise the same LC and HC as PR000071, wherein, the LC may comprise the amino acid sequence set forth in SEQ ID NO: 157, and the HC may comprise the amino acid sequence set forth in SEQ ID NO: 126.

For example, the antigen binding protein of the present application may comprise the same LC and HC as PR000072, wherein, the LC may comprise the amino acid sequence set forth in SEQ ID NO: 158, and the HC may comprise the amino acid sequence set forth in SEQ ID NO: 127.

For example, the antigen binding protein of the present application may comprise the same LC and HC as PR000261, wherein, the LC may comprise the amino acid sequence set forth in SEQ ID NO: 160, and the HC may comprise the amino acid sequence set forth in SEQ ID NO: 129.

For example, the antigen binding protein of the present application may comprise the same LC and HC as PR000262, wherein, the LC may comprise the amino acid sequence set forth in SEQ ID NO: 160, and the HC may comprise the amino acid sequence set forth in SEQ ID NO: 130.

For example, the antigen binding protein of the present application may comprise the same LC and HC as PR000263, wherein, the LC may comprise the amino acid sequence set forth in SEQ ID NO: 161, and the HC may comprise the amino acid sequence set forth in SEQ ID NO: 131.

For example, the antigen binding protein of the present application may comprise the same LC and HC as PR000264, wherein, the LC may comprise the amino acid sequence set forth in SEQ ID NO: 161, and the HC may comprise the amino acid sequence set forth in SEQ ID NO: 132.

For example, the antigen binding protein of the present application may comprise the same LC and HC as PR000265, wherein, the LC may comprise the amino acid sequence set forth in SEQ ID NO: 162, and the HC may comprise the amino acid sequence set forth in SEQ ID NO: 133.

For example, the antigen binding protein of the present application may comprise the same LC and HC as PR000266, wherein, the LC may comprise the amino acid sequence set forth in SEQ ID NO: 162, and the HC may comprise the amino acid sequence set forth in SEQ ID NO: 134.

For example, the antigen binding protein of the present application may comprise the same LC and HC as PR000267, wherein, the LC may comprise the amino acid sequence set forth in SEQ ID NO: 163, and the HC may comprise the amino acid sequence set forth in SEQ ID NO: 135.

For example, the antigen binding protein of the present application may comprise the same LC and HC as PR000268, wherein, the LC may comprise the amino acid sequence set forth in SEQ ID NO: 163, and the HC may comprise the amino acid sequence set forth in SEQ ID NO: 136.

For example, the antigen binding protein of the present application may comprise the same LC and HC as PR000416, wherein, the LC may comprise the amino acid sequence set forth in SEQ ID NO: 162, and the HC may comprise the amino acid sequence set forth in SEQ ID NO: 137.

Particular Anti-PD-L1 Antibody

The isolated antigen binding protein of the present application may competitively bind to PD-L1 with a particular anti-PD-L1 antibody. In the present application, the particular anti-PD-L1 antibody may comprise LCDR1-3. Wherein, the LCDR1 may comprise the amino acid sequence set forth in SEQ ID NO: 181; the LCDR2 may comprise the amino acid sequence set forth in SEQ ID NO: 182; and the LCDR3 may comprise the amino acid sequence set forth in SEQ ID NO: 191. In some cases, the LCDR1 of the particular anti-PD-L1 antibody of the present application may comprise the amino acid sequences set forth in any one of the following: SEQ ID NOs: 48-51; the LCDR2 may comprise the amino acid sequences set forth in any one of the following: SEQ ID NOs: 63-64; and the LCDR3 may comprise the amino acid sequences set forth in any one of the following: SEQ ID NOs: 77-79.

In the present application, the particular anti-PD-L1 antibody may comprise HCDR1-3. Wherein, the HCDR1 may comprise the amino acid sequence set forth in SEQ ID NO: 5; the HCDR2 may comprise the amino acid sequence set forth in SEQ ID NO: 179; and the HCDR3 may comprise the amino acid sequence set forth in SEQ ID NO: 180. In some cases, the HCDR1 of the particular anti-PD-L1 antibody of the present application may comprise the amino acid sequence set forth in the following: SEQ ID NO: 5; the HCDR2 may comprise the amino acid sequences set forth in any one of the following: SEQ ID NOs: 14, 16 and 17; and the HCDR3 may comprise the amino acid sequences set forth in any one of the following: SEQ ID NOs: 29-33.

In the present application, the particular anti-PD-L1 antibody may comprise LCDR1-3 and HCDR1-3. Wherein, the LCDR1 may comprise the amino acid sequence set forth in SEQ ID NO: 181: the LCDR2 may comprise the amino acid sequence set forth in SEQ ID NO: 182; and the LCDR3 may comprise the amino acid sequence set forth in SEQ ID NO: 191; the HCDR1 may comprise the amino acid sequence set forth in SEQ ID NO: 5; the HCDR2 may comprise the amino acid sequence set forth in SEQ ID NO: 179; and the HCDR3 may comprise the amino acid sequence set forth in SEQ ID NO: 180. In some cases, the LCDR1 of the particular anti-PD-L1 antibody of the present application may comprise the amino acid sequence set forth in any one of the following: SEQ ID NOs: 48-51; the LCDR2 may comprise the amino acid sequence set forth in any one of the following: SEQ ID NOs: 63-64; and the LCDR3 may comprise the amino acid sequence set forth in any one of the following: SEQ ID NOs: 77-79; the HCDR1 of may comprise the amino acid sequence set forth in the following: SEQ ID NO: 5; the HCDR2 may comprise the amino acid sequence set forth in any one of the following: SEQ ID NOs: 14, 16 and 17; and the HCDR3 may comprise the amino acid sequence set forth in any one of the following: SEQ ID NOs: 29-33.

In the present application, the particular anti-PD-L1 antibody may comprise a light chain variable region VL and a heavy chain variable region VH. The VL may comprise the amino acid sequence set forth in SEQ ID NO: 194, and the VH may comprise the amino acid sequence set forth in SEQ ID NO: 193. In some cases, the VL of the particular anti-PD-L1 antibody may comprise the amino acid sequence set forth in any one of SEQ ID NOs: 108-114, 116 and 118, and the VH may comprise the amino acid sequence set forth in any one of SEQ ID NOs: 90-93, 95, 97-104.

Determination Method

The physical/chemical properties and/or biological activities of the PD-L1 antigen binding proteins or fusion proteins of the present application may be determined, screened or characterized by various assays known in the art.

In one aspect, for example, the antigen binding activities of the antigen binding proteins or fusion proteins of the present application may be tested by known methods such as Enzyme-Linked Immunosorbent assay (ELISA), Immunoblotting (e.g., Western Blotting), Flow Cytometry (e.g., FACS), Immunohistochemistry, and Immunofluorescence, etc.

In the present application, the isolated antigen binding protein may bind to a PD-L1 derived from primates in a KD value of $1\times10^{-8}$ M or less. The binding affinity of the primate PD-L1 antigen-binding protein to PD-L1 may be determined by any methods known in the art. In some cases, the binding affinity may be determined by Surface Plasmon Resonance (SPR), Enzyme-linked Immunosorbent assay (ELISA), Binding Antigen Precipitation, Equilibrium Dialysis, Biolayer Interferometry (BLI). In some cases, the binding affinity and KD value of PD-L1 antigen binding protein to PD-L1 may be determined by Biolayer Interferometry (BLI). For example, ForteBio Octet molecular interaction analysis meter may be used to perform the analysis of binding dynamics between antigens and antibodies.

In the present application, the isolated antigen binding protein may bind to a PD-L1 derived from primates in a KD value of $1\times10^{-8}$ M or less. For example, a PD-L1 derived from human may be bound in the KD value of about $1\times10^{-8}$ M or less, about $9\times10^{-9}$ M or less, about $8\times10^{-9}$ M or less, about $7\times10^{-9}$ M or less, about $6\times10^{-9}$ M or less, about $5 \times 10^{-9}$ M or less, about $4 \times 10^{-9}$ M or less, about $3 \times 10^{-9}$ M or less, about $2 \times 10^{-9}$ M or less, about $1 \times 10^{-9}$ M or less, as detected by such ForteBio Octet molecular interaction analysis meter.

In another case, the binding activity of the PD-L1 antigen binding protein of the present application to PD-L1 may by determined by Flow Cytometry or Enzyme-linked Immunosorbent assay. For example, in FACS assay, the host cells (such as CHOK1 cells) that stably express human PD-L1 are used, and the EC50 value of the PD-L1 antigen binding protein and PD-L1 is between about 0.0001 nM and about 100 nM, for example, about 0.001 nM and about 10 nM, about 0.01 nM and about 10 nM, about 0.05 nM and about 5 nM, about 0.05 nM and about 1 nM. Further for example, in ELISA, human PD-L1 antigen proteins are used, and the EC50 value of the PD-L1 antigen binding protein and PD-L1 is between about 0.0001 nM and about 100 nM, for example, between about 0.001 nM and about 10 nM, between about 0.001 nM and about 5 nM, between about 0.001 nM and about 1 nM, between about 0.01 nM and about 0.5 nM, between about 0.01 nM and about 0.1 nM.

In another aspect, a competition assay may be used to identify the antibodies that compete with any one of the antigen binding proteins of the present application for binding to PD-L1. In some cases, such competitive antibodies bind to an overlapping epitope (for example, a linear or a conformational epitope) that bound by any one of the antigen binding proteins of the present application. Exemplary methods for mapping an epitope to which an antigen binding protein binds include but are not limited to X-ray Co-crystal and Cryo-electron Microscopy (cryo-EM), Array-based Oligopeptide Scanning, Site-directed Mutagenesis Mapping, Cross-linking Coupled Mass Spectrometry, and Bio-layer Interferometry.

In another aspect, the antigen binding proteins of the present application are capable of blocking the binding of PD-1 to PD-L1. In some cases, the blocking of the binding of PD-1 to PD-L1 by the antigen binding proteins may be determined by Flow Cytometry FACS, Enzyme-linked Immunosorbent assay ELISA. For example, first the host cells (such as CHOK1 cells) that stable express PD-L1 are incubated with the decreasing amounts of the unlabeled antigen binding proteins, followed by incubation with biotinylated PD-1 proteins. Then, FACS is used to analyze the cells to verify the blocking of the binding of PD-1 to PD-L1 by the antigen binding proteins. Further for example, first the PD-L1 antigen binding proteins are coated on the plate, the decreasing amounts of unlabeled antigen binding proteins and the biotinylated PD-1 proteins are mixed and incubated together. Then, ELISA is used to analyze the cells to verify the blocking of the binding of PD-1 to PD-L1 by the antigen binding proteins.

In another aspect, the antigen binding proteins of the present application are capable of blocking the binding of CD80 to PD-L1. In some cases, the blocking the binding of CD80 to PD-L1 by the antigen binding proteins may be determined by Flow Cytometry FACS, Enzyme-linked Immunosorbent assay ELISA. For example, first the host cells (such as CHOK1 cells) that stable express PD-L1 are incubated with the decreasing amounts of unlabeled antigen binding proteins, followed by incubation with the biotinylated CD80 proteins. Then, FACS is used to analyze the cells to verify the blocking of the binding of CD80 to PD-L1 by the antigen binding proteins. Further for example, first the PD-L1 antigen binding proteins are coated on the plate, the decreasing amounts of unlabeled antigen binding proteins and the biotinylated CD80 proteins are mixed and incubated together. Then, ELISA is used to analyze the cells to verify the blocking of the binding of CD80 to PD-L1 by the antigen binding proteins.

The antigen binding proteins of the present application are capable of stimulating the secretion of IFN-γ and/or IL2 in immune cells. The immune cells may include lymphocytes, for example, B cells, T cells, natural killer cells, myeloid cells, e.g., monocytes, macrophages, mast cells, basophils and granulocytes. Any methods known by those skilled in the art may be used to determine the secretion of cytokines in immune cells, for example, the proliferation of immune cells (e.g., T cells) or the cytokines produced by immune cells (e.g., IFN-γ or IL2 produced by T cells.) may be quantitively determined via Enzyme-linked Immunosorbent assay (ELISA).

Control Antibody

The antigen binding protein of the present application are capable of binding to an epitope of the PD-L1 derived from a primate that does not completely overlap with the epitope of a control antibody. In some cases, the control antibody may be anti-PD-L1 antibody avelumab, i.e., the antibody PR001598 of the present application. PR001598 may comprise a light chain variable region and a heavy chain variable region, the light chain variable region of the control antibody may comprise LCDR1, LCDR2 and LCDR3, the LCDR1 comprises the amino acid sequence set forth in SEQ ID NO: 53, the LCDR2 comprises the amino acid sequence set forth in SEQ ID NO: 66, the LCDR3 comprises the amino acid sequence set forth in SEQ ID NO: 82; the heavy chain variable region of the control antibody may comprise HCDR1, HCDR2 and HCDR3, the HCDR1 comprises the amino acid sequence set forth in SEQ ID NO: 5, the HCDR2 comprises the amino acid sequence set forth in SEQ ID NO: 18, the HCDR3 comprises the amino acid sequence set forth in SEQ ID NO: 35; the light chain variable region of the control antibody comprises the amino acid sequence set forth in SEQ ID NO: 119, the heavy chain variable region of the control antibody comprises the amino acid sequence set forth in SEQ ID NO: 105.

In some other cases, the control antibody may be anti-PD-L1 antibody atezolizumab, i.e., the antibody PR000151 of the present application. PR000151 may comprise a light chain variable region and a heavy chain variable region, the light chain variable region of the control antibody comprises LCDR1, LCDR2 and LCDR3, the LCDR1 comprises the amino acid sequence set forth in SEQ ID NO: 52, the LCDR2 comprises the amino acid sequence set forth in SEQ ID NO: 65, the LCDR3 comprises the amino acid sequence set forth in SEQ ID NO: 81; the heavy chain variable region of the control antibody comprises HCDR1, HCDR2 and HCDR3, the HCDR1 comprises the amino acid sequence set forth in SEQ ID NO: 6, the HCDR2 comprises the amino acid sequence set forth in SEQ ID NO: 15, the HCDR3 comprises the amino acid sequence set forth in SEQ ID NO: 34; the light chain variable region of the control antibody comprises the amino acid sequence set forth in SEQ ID NO: 117, the heavy chain variable region of the control antibody comprises the amino acid sequence set forth in SEQ ID NO: 96.

In some other cases, the control antibody may be Hengrui fusion protein 9, i.e., the antibody PR002466 of the present application. PR002466 may comprise a light chain variable region and a heavy chain variable region, the light chain variable region of the control antibody comprises LCDR1, LCDR2 and LCDR3, the LCDR1 comprises the amino acid sequence set forth in SEQ ID NO: 55, the LCDR2 comprises the amino acid sequence set forth in SEQ ID NO: 68, the LCDR3 comprises the amino acid sequence set forth in SEQ ID NO: 84; the heavy chain variable region of the control antibody comprises HCDR1, HCDR2 and HCDR3, the HCDR1 comprises the amino acid sequence set forth in SEQ ID NO: 8, the HCDR2 comprises the amino acid sequence set forth in SEQ ID NO: 20, the HCDR3 comprises the amino acid sequence set forth in SEQ ID NO: 37; the light chain variable region of the control antibody comprises the amino acid sequence set forth in SEQ ID NO: 121, the heavy chain variable region of the control antibody comprises the amino acid sequence set forth in SEQ ID NO: 107.

The methods for determining epitopes in the art include but are not limited to synthetic peptide method, immunoinformatic prediction method, polypeptide activity assay, epitope peptide scanning technology, protein cleavage method, phage display technology, X-ray diffraction and nuclear magnetic resonance analysis, and epitope prediction using computer software. In some embodiments, the Biolayer Interferometry (BLI)-based Octet molecular interaction analysis platform may be used to perform the competitive binding of the antigen binding protein of the present application and the control antibody to an antigen epitope. For example, the first antibody is mixed with an antigen, then the second antibody is added, ForteBio Octet is used for determining the competitive inhibition rate of the second antibody against the first antibody, when the competitive inhibition rate is less than 85% (e.g., less than 84%, less than 83%, less than 80%, or less), it is believed that the epitopes of an antigen, to which the first antibody and the second antibody bind respectively, do not completely overlap.

Fusion Protein

In another aspect, the present application provides a fusion protein which may comprise: a) a human TGFBRII or a fragment thereof; and b) the antigen binding proteins described above in the present application.

The human TGFBRII or fragment thereof of the fusion proteins of the present application may comprise the extracellular domain of human TGFBRII. In some cases, the human TGFBRII or fragment thereof may comprise the amino acid sequence set forth in any one of SEQ ID NOs: 176-178.

In the present application, the fusion proteins may comprise the isolated antigen binding proteins of the present application. The isolated antigen binding protein may comprise a light chain variable region VL and a heavy chain variable region VH. In some cases, the VL may comprise the amino acid sequence set forth in SEQ ID NO: 190, and the VH may comprise the amino acid sequence set forth in SEQ ID NO: 189.

The isolated antigen binding protein may also comprise an antibody heavy chain constant region, and the heavy chain constant region may comprise a human IgG constant region. In some cases, the human IgG constant region may comprise a human IgG1 constant region. The human IgG constant region may comprise natural and artificially synthesized IgG1 constant region or a mutant thereof. The mutations may comprise one or more mutations at following positions: L234, L235, N297 or K447. For example, it may comprise mutations at one, two or more positions. The mutations may comprise deletion, insertion or substitution of an amino acid. For example, the human IgG1 constant region may comprise following mutations: 1) N297A, 2) K447 deletion, 3) N297A and K447 deletions, 4) L234A, L235A and K447 deletions. For example, the human IgG1 constant region of the fusion protein may comprise the amino acid sequence set forth in any one of SEQ ID NOs: 172-175.

The isolated antigen binding protein of the fusion protein of the present application may comprise an antibody heavy chain or a fragment thereof. In some cases, the antibody heavy chain or fragment thereof may comprise the amino acid sequence set forth in any one of the following or a part thereof: SEQ ID NOs: 122-127 and 129-137. For example, the antibody heavy chain or fragment thereof may comprise the amino acid sequence set forth in any one of the following or a part thereof: SEQ ID NOs: 122 and 133-137. The isolated antigen binding protein of the fusion protein of the present application may comprise an antibody light chain or a fragment thereof. In some cases, the antibody light chain or fragment thereof may comprise the amino acid sequence set forth in any one of the following or a part thereof: SEQ ID NOs: 150-158 and 160-163. For example, the antibody light chain or fragment thereof may comprise the amino acid sequence set forth in any one of the following or a part thereof: SEQ ID NOs: 156 and 162-163. The heavy chain or fragment thereof of the fusion protein is combined with the light chain or fragment thereof to form an antigen binding portion that specifically binds to PD-L1.

The antibody heavy chain or fragment thereof of the antigen binding protein comprised in the fusion protein of the present application is fused in-frame with the human TGFBRII or fragment thereof to form a fusion polypeptide. In some cases, the antibody heavy chain or the fragment thereof may be at the N-terminus directly or indirectly linked to the C-terminus of the human TGFBRII or fragment thereof. In some cases, the antibody heavy chain or the fragment thereof may be directly or indirectly linked at the C-terminus to the N-terminus of the human TGFBRII or the fragment thereof. For example, the antibody heavy chain or the fragment thereof may be directly linked at the C-terminus to the N-terminus of the human TGFBRII or the fragment thereof. In some other cases, the antibody heavy chain or fragment thereof may be linked to the human TGFBRII or the fragment thereof via a linker, for example, the peptide linker may comprise the amino acid sequence set forth in any one of SEQ ID NOs: 167-169.

In the present application, the fusion protein may comprise a first polypeptide and a second polypeptide. The first polypeptide may comprise the heavy chain or the fragment thereof of the isolated antigen binding protein and the human TGFBRII or fragment thereof. In some cases, the first polypeptide may comprise the heavy chain of the antigen binding protein or fragment thereof, the peptide linker, and the human TGFBRII or fragment thereof from N-terminus to C-terminus. For example, the first polypeptide may comprise the amino acid sequence set forth in any one of SEQ ID NOs: 138-139, 142-143 and 145-148. The second polypeptide may comprise the light chain of the isolated antigen binding protein or fragment thereof, for example, the second polypeptide may comprise the amino acid sequence set forth in any one of SEQ ID NOs: 162-163.

For example, the first polypeptide of the fusion protein may comprise the amino acid sequence set forth in SEQ ID NO: 138, and the second polypeptide may comprise the amino acid sequence set forth in SEQ ID NO: 162, e.g., the fusion protein may comprise the same first polypeptide and second polypeptide as PR001487;

the first polypeptide may comprise the amino acid sequence set forth in SEQ ID NO: 139, and the second polypeptide may comprise the amino acid sequence set forth in SEQ ID NO: 162, e.g., the fusion protein may comprise the same first polypeptide and second polypeptide as PR001488;

the first polypeptide may comprise the amino acid sequence set forth in SEQ ID NO: 142, and the second polypeptide may comprise the amino acid sequence set forth in SEQ ID NO: 162, e.g., the fusion protein may comprise the same first polypeptide and second polypeptide as PR001901;

the first polypeptide may comprise the amino acid sequence set forth in SEQ ID NO: 143, and the second polypeptide may comprise the amino acid sequence set forth in SEQ ID NO: 162, e.g., the fusion protein may comprise the same first polypeptide and second polypeptide as PR001902;

the first polypeptide may comprise the amino acid sequence set forth in SEQ ID NO: 145, and the second polypeptide may comprise the amino acid sequence set forth in SEQ ID NO: 163, e.g., the fusion protein may comprise the same first polypeptide and second polypeptide as PR002247;

the first polypeptide may comprise the amino acid sequence set forth in SEQ ID NO: 146, and the second polypeptide may comprise the amino acid sequence set forth in SEQ ID NO: 163, e.g., the fusion protein may comprise the same first polypeptide and second polypeptide as PR002248;

the first polypeptide may comprise the amino acid sequence set forth in SEQ ID NO: 147, and the second polypeptide may comprise the amino acid sequence set forth in SEQ ID NO: 162, e.g., the fusion protein may comprise the same first polypeptide and second polypeptide as PR002249;

the first polypeptide may comprise the amino acid sequence set forth in SEQ ID NO: 148, and the second polypeptide may comprise the amino acid sequence set forth in SEQ ID NO: 162, e.g., the fusion protein may comprise the same first polypeptide and second polypeptide as PR002251.

The fusion protein of the present application may comprise two of the first polypeptide and two of the second polypeptide.

In the present application, one part of the amino acid sequence of each heavy chain or light chain of the antigen binding protein is homologous to the corresponding amino acid sequence in an antibody derived from a certain species, or belongs to a certain class. For example, the variable region and constant portion of a light chain and a heavy chain are all derived from the variable region and constant region of an antibody of an animal species (such as human). In the present application, the homolog may be a protein or a polypeptide that has at least about 85% (e.g., has at least about 85%, about 90%, about 91%, about 92%, about 93%, about 94%, about 95%, about 96%, about 97%, about 98%, about 99% or higher) sequence homology with the amino acid sequence of the protein and/or the polypeptide (e.g., the antibody or fragment thereof that specifically binds to PD-L1 protein).

In the present application, the homology usually refers to the similarity, likeness or relevance between two or more sequences. The "sequence homology percentage" may be calculated by following way: comparing the two sequences to be aligned in comparison window, determining the number of the positions at which there are identical nucleobases (e.g., A, T, C, G) or identical amino acid residues (e.g., Ala, Pro, Ser, Thr, Gly, Val, Leu, Ile, Phe, Tyr, Trp, Lys, Arg, His, Asp, Glu, Asn, Gln, Cys, and Met) in the two sequences to obtain the number of matching positions, dividing the number of matching positions by the total numbers of positions in the comparison window (i.e., the window size) and then multiplying the result by 100 to obtain sequence homology percentage. The alignment that is performed to determine sequence homology percentage may be achieved according to various ways known in the art, for example, by using publicly available computer software such as BLAST, BLAST-2, ALIGN or Megalign (DNASTAR) software. The skilled in the art may determine suitable parameters for aligning sequences, including any algorithms needed to achieve the maximal alignment within the scope of full-length sequences being compared or within the region of the sequence of interest. The homology also may be determined by following methods: FASTA and BLAST. The description of FASTA algorithm may be found in W. R. Pearson and D. J. Lipman, Improved tools for biological sequence comparison, Proc. Natl. Acad. Sci., 85: 2444-2448, 1988; and D. J. Lipman and W. R. Pearson, Rapid and sensitive protein similarity searches, Science, 227: 1435-1441, 1989. The description of BLAST algorithm may be found in S. Altschul, W. Gish, W. Miller, E. W. Myers and D. Lipman, A basic local alignment search tool, J. Mol. Biol., 215: 403-410, 1990.

Nucleic Acid, Vector, Host Cell and Manufacture Method

In another aspect, the present application also provides one or more isolated nucleic acid molecules. The one or more nucleic acids may encode the antigen binding protein of the present application. For example, each nucleic acid molecule of the one or more nucleic acid molecules may encode the intact antigen binding protein, and may also encode a part thereof (e.g., one or more of HCDR1-3, LCDR1-3, VL, VH, light chain or heavy chain).

The nucleic acid molecule of the present application may be isolated. For example, it may be produced or synthesized by following methods: (i) amplification in vitro, e.g., production by amplification via Polymerase Chain Reaction (PCR), (ii) production by clonal recombination, (iii) purification, e.g., by enzyme cleavage and fraction separation via gel electrophoresis, or (iv) synthesizing, e.g., by chemical synthesis. In some embodiments, the isolated nucleic acid is the nucleic acid molecule that is prepared by a DNA recombination technique.

In the present application, the nucleic acids encoding the antibody and antigen binding fragment thereof may be prepared by various methods known in the art, including but not limited to, using restriction fragment manipulation or using overlapping extension PCR by synthetic oligonucleotides, the specific operations may be found in Sambrook et al., Molecular Cloning, A Laboratory Manual, Cold Spring Harbor Laboratory Press, Cold Spring Harbor, N.Y., 1989; and Ausube et al., Current Protocols in Molecular Biology, Greene Publishing and Wiley-Interscience, New York N.Y., 1993.

In another aspect, the present application provides one or more vectors comprising one or more nucleic acid molecules described in the present application. Each vector may comprise one or more of the nucleic acid molecules. Besides, the vector may also comprise other genes, for example a marker gene that allows the vectors to be selected in an appropriate host cell and under an appropriate condition. Besides, the vector may also comprise an expression control element that allows the coding region to be correctly expressed in an appropriate host. Such control elements are known by the skilled in the art, for example, it may comprise promoters, ribosome binding sites, enhancers and other control elements that regulate gene transcription or mRNA translation and the like. In some embodiments, the sequence for expression control may be an adjustable element. The specific structure of the expression control sequence may be changed according to species or the function of cell types, but usually comprises 5' non-transcriptional sequences and 5' and 3' untranslated sequences, e.g., TATA box, capping sequence, CAAT sequence etc. For example, 5' non-transcriptional expression control sequence may comprise a promoter region which may comprise the promoter sequence for transcriptional control of a functionally linked nucleic acid. The expression control sequence may also comprise an enhancer sequence or an upstream activator sequence. In the present application, the appropriate promoter may comprise, e.g., the promoters for SP6, T3 and T7 polymerases, human U6TNA promoter, CMW promoter and artificially heterozygous promoters (such as CMV), wherein a certain part of the promoter may be fused with a certain part of a gene promoter for other cell proteins (such as human GAPDH, glyceraldehyde-3-phosphate dehydrogenase), which may comprise or may not comprise other introns. The one or more nucleic acid molecules of the present application may be operatively connected to the expression control elements.

The vector may comprise, e.g., plasmid, cosmid, virus, phage or other vectors commonly used in genetic engineering. For example, the vector is an expression vector.

In another aspect, the present application provides a cell host which may comprise one or more nucleic acid molecules of the present application and/or one or more vectors of the present application. In some embodiments, each type or each of the host cells may comprise one or more nucleic acid molecules or vectors of the present application. In some embodiments, each type or each of the host cells may comprise multiple (e.g., 2 or more) or multiple types of (e.g., 2 or more types of) of the nucleic acid molecules or vectors of the present application. For example, the vectors of the present application may be introduced into the host cells, e.g., eukaryotic cells, such as the cells from plants, fungi or yeast cells and the like. The vectors of the present application may be introduced into the host cells by the methods known in the art, e.g., electroporation, lipofectine transfection, lipofectamin transfection and the like.

In another aspect, the present application provides a method for preparing the antibody or antigen binding fragment thereof. The method may comprise culturing the host cells of the present application under the condition that the antibody or antigen binding fragment thereof is expressed. For example, it may be achieved by using appropriate medium, appropriate temperature and cultivation time and so on, and these methods are known by those skilled in the art.

In some cases, the method may also comprise the step of isolating and/or purifying the antibody or antigen binding fragment thereof. For example, protein G-agarose or protein A-agarose may be used to perform affinity chromatography, and the antibody or antigen binding fragment thereof of the present application may also be purified and isolated by gel electrophoresis and/or high performance liquid chromatography, etc.

Pharmaceutical Composition, Method, and Use

In another aspect, the present application provides a pharmaceutical composition which may comprise the antigen binding protein and/or fusion protein, the nucleic acid molecule, the vector, the host cell of the present application, and optionally, the pharmaceutically acceptable adjuvant.

The pharmaceutically acceptable adjuvant is non-toxic to recipients at the doses and concentrations employed, and may include buffers such as phosphates, citrates and other organic acids; antioxidants, including ascorbic acid and methionine acid; preservatives (such as octadecyl dimethyl benzyl ammonium chloride, hexamethonium chloride, benzalkonium chloride, benzethonium chloride, phenol, butanol or benzyl alcohol; alkyl parabens such as methyl or propyl paraben; catechol; resorcinol; cyclohexanol; 3-pentanol and m-cresol); polypeptides of low molecular weight (with less than about 10 residues); proteins such as serum albumin, gel or immunoglobulin; hydrophilic polymers such as polyvinylpyrrolidone; amino acids such as glycine, glutamine, asparagine, histidine, arginine, or lysine; monosaccharides, disaccharides, and other carbohydrates, including glucose, mannose, or dextrin; chelating agents, such as EDTA; sugars, such as sucrose, mannitol, trehalose, or sorbitol; salt-forming counterions, such as sodium ions; metal complex (e.g., Zn-protein complex); and/or nonionic surfactants, such as TWEEN™, PLURONICS™, or polyethylene glycol (PEG). The pharmaceutical composition of the present application may also comprise more than one active compound which are those active compounds having complementary activities without adversely affecting each other. The types and the effective amounts of such medicaments depend on, e.g., the amount and type of the antagonist existing in a formulation, and the clinical parameter of a subject.

The pharmaceutical composition may be used to inhibit tumor growth. For example, the pharmaceutical composition of the present application may inhibit or delay the development or progression of a disease, may reduce tumor size (even substantially eliminate tumor), and/or may alleviate and/or stabilize a disease state.

The pharmaceutical composition of the present application may comprise a prophylactically and/or therapeutically effective amount of the antibody, antigen binding fragment thereof. The prophylactically and/or therapeutically effective amount is the dosage that is required to prevent and/or treat (at least partially treat) a disease or disorder and/or any complications thereof in a subject having or at risk of developing the disease or disorder.

In another aspect, the present application provides use of the antigen binding protein and/or the fusion protein in the manufacture of a medicament. The medicament is used for treating cancer, inhibiting tumor growth and/or inhibiting tumor cell proliferation. In some embodiments, the tumor or cancer comprises a colorectal tumor or cancer. In some embodiments, the tumor or cancer is the tumor or cancer that abnormally expresses PD-L1. The present application also provides a method of detecting the expression of PD-L1 in a biological sample as described below. In some cases, the method comprises contacting a biological sample with the antigen binding protein and/or fusion protein of the present application under conditions that allow the antigen binding protein and/or fusion protein to bind to PD-L1, and detecting whether a complex is formed between the antigen binding protein and/or fusion protein and PD-L1. For example, the tumor or cancer is the one in which the expression of PD-L1 is increased as compared with a non-tumor or cancer sample. Such method may be an in vitro or in vivo method. The antigen binding protein and/or fusion protein of the present application may be used to, for example, an immunoassay, including, for example, immunohistochemistry (IHC), immunofluorescence (IF), immunoblotting (e.g., Western blotting), Flow Cytometry (e.g., FACS), and Enzyme-linked Immunosorbent Assay (ELISA). In some cases, for example, when PD-L1 is used as a biological marker for choosing a patient, the antigen binding protein and/or fusion protein is used to choose a subject that is suitable for performing the therapy using the antigen binding protein and/or fusion protein of the present application. The present application also provides use of the antigen binding protein and/or fusion protein in a method of diagnosing a subject suffering from a disorder (for example, a cancer or an immune dysfunction), comprising: determining the presence or expression level of PD-L1 in a sample obtained from the subject by contacting the sample with the antigen binding protein and/or fusion protein of the present application and detecting the presence of the bound antigen binding protein and/or fusion protein.

In another aspect, the present application provides a method of inhibiting the binding of PD-L1 to PD-1 comprising administrating the antigen binding protein of the present application. The method may be an ex vivo or in vitro method. In some cases, the method may comprise contacting a biological sample with the antigen binding protein and/or PD-1 of the present application under a condition that allows the binding of the antigen binding protein and/or PD-1 to PD-L1, detecting whether a complex is formed between the antigen binding protein and PD-L1, and detecting whether a complex is formed between PD-1 and PD-L1.

In another aspect, the present application provides a method of inhibiting the binding of PD-L1 to CD80, comprising administering the antigen binding protein of the present application. The method may be an ex vivo or in vitro method. In some cases, the method comprises contacting a biological sample with the antigen binding protein and/or CD80 of the present application under a condition that allows the binding of the antigen binding protein and/or CD80 to PD-L1, detecting whether a complex is formed between the antigen binding protein and PD-L1, and detecting whether a complex is formed between CD80 and PD-L1.

In another aspect, the present application provides a method of inhibiting the binding of TGFB to TGFBRII comprising administering the fusion protein of the present application. The method may be an ex vivo or in vitro method. In some cases, the method comprises contacting a biological sample with the fusion protein and/or the cell expressing reporter gene of TGFBRII of the present application under a condition that allows the binding of the fusion protein and/or the cell expressing reporter gene of TGFBRII to TGFB, detecting whether the fusion protein inhibits Smad signaling pathway that is induced by the binding of TGFB to TGFBRII.

In some cases, the biological sample includes a tissue or cell sample. For example, a biological sample may comprise cells or tissues from a normal subject or a cancer patient. In some cases, the origin of the tissue or cell sample may be solid tissues such as from fresh, frozen and/or preserved organs or tissue samples or biopsies or aspirates; blood or any blood component; body fluids such as cerebrospinal fluid, amniotic fluid, peritoneal fluid or interstitial fluid; cells from any time in the subject's pregnancy or development. In some other cases, the biological sample is obtained from in vitro tissues or cell cultures. The examples of the biological samples of the present application include but are not limited to tumor biopsies, circulating tumor cells, serum or plasma, circulating plasma proteins, ascites, primary cell cultures or cell lines derived from tumors or exhibiting tumor-like properties, and preserved tumor samples such as formalin-fixed paraffin-embedded tumor samples or frozen tumor samples.

The present application also provides use of the antigen binding protein in a method of diagnosing a subject suffering from a tumor or a cancer, comprising: determining the presence or expression level of PD-L1 in a sample obtained from a subject by contacting the sample with the antigen binding protein of the present application and detecting the presence of the bound antibody. In some cases, the sample may be selected from a group consisting of: tissue samples, whole blood samples, serum samples and plasma samples. In some cases, the tissue sample may be tumor samples. In some cases, the tumor sample may comprise tumor-infiltrating immune cells, tumor cells, stromal cells, and any combinations thereof.

In another aspect, the present application provides a method of treating a cancer in a subject, inhibiting tumor growth in a subject and/or inhibiting tumor cell proliferation, comprising administering the antigen binding fragment and/or the fusion protein, the nucleic acid molecule, the vector, the host cell and/or the pharmaceutical composition of the present application to a subject in need thereof or the tumor cell. It may be administered by any suitable methods, including, for example: intravenously, intramuscularly, subcutaneously, intradermally, percutaneously, intraarterially, intraperitoneally, intralesionally, intracranially, intraarticularly, intra-prostaticly, intrapleurally, intratracheally, intrathecally, intranasally, intravaginally, intrarectally, topically, intratumorally, peritoneally, subconjunctivally, intracapsularly, mucosally, intrapericardially, intraumbilically, intraocularly, intraorbitally, orally, topically, transdermally, intravitreally (e.g., by intravitreal injection), by eye drops, by inhalation, by injection, by implantation, by infusion, by continuous infusion, by local infusion via directly bathing of target cells, by catheter, by lavage, in the form of cream or in the form of lipid composition. The composition used in the method described herein may also be administered systemically or topically. The method of administration may be changed depending on various factors (e.g., the compound or composition being administered and the severity of the condition, disease or disorder being treated). In certain embodiments, the anti-cancer therapy (e.g., anti-PD-L1 antibody) is administered intravenously, intramuscularly, subcutaneously, topically, orally, transdermally, intraperitoneally, intraorbitally, by implantation, by inhalation, intrathecally, intraventricularly, or intranasally. Depending in part on whether the administration is transient or long-term, administration may be performed by any suitable way, e.g., by injection, such as intravenous or subcutaneous injection. Various dosing schedules encompassed herein, include but are not limited to a single administration or multiple administrations at various time points, bolus administrations, and pulse infusions.

The antigen binding protein or pharmaceutical composition described herein may be formulated, dosed and administered in a manner consistent with good medical practice. Considerations in this case include the particular disorder being treated, the particular mammal being treated, the clinical condition of the individual patient, the cause of the disorder, the site of drug delivery, the method of administration, the schedule of administration, and other factors known to medical practitioners. A therapeutic agent (e.g., an anti-PD-L1 antibody) need not but optionally be formulated and/or administered concurrently with one or more agents currently used to prevent or treat the disorder in considerations. The effective amounts of such other agents depend on the amount of a therapeutic agent (e.g., an anti-PD-L1 antibody) existing in a formulation, the type of the disorder or treatment, and other factors discussed above. These agents may usually be empirically/clinically determined to be administered at any appropriate dosage and may be empirically/clinically determined to be administered by any appropriate way. The dosage of the antibody administered in combination therapy may be reduced, as compared to a single therapy. The progress of this therapy is readily monitored by conventional techniques.

Chimeric Antigen Receptor

In another aspect, the present application provides a chimeric antigen receptor (CAR) which may comprise the nucleic acid molecule of the present application or the antigen binding protein of the present application. In some embodiments, it may comprise an extracellular domain (an extracellular binding domain) that are capable of binding to an antigen, a hinge domain, a transmembrane domain (trans-membrane region) and a polypeptide that transduces the cytoplasmic signal to the domain (i.e., intracellular signaling domain). The hinge domain may be considered to be a part for providing flexibility to an extracellular antigen binding region. The intracellular signaling domain refers to the protein that transmit information into cells to regulate cel-lular activity by generating a second messenger via a defined signaling pathway, or the protein that act as an effector by corresponding to such messengers to generate signals that may promote immune effector function of CAR cells (e.g., CAR-T cells). The intracellular signaling domain may com-prise a signaling transduction domain, also may comprise a co-stimulatory intracellular domain derived from a co-stimulatory molecule. For example, the co-stimulatory molecule may be selected from 4-1BB, CD27, ICOS and/or CD28. In another aspect, the present application provides a genetically modified cell which may comprise said chimeric antigen receptor. In some embodiments, the genetically modified cell may comprise a eukaryotic cell. In some embodiments, the genetically modified cell may comprise an isolated human cell. In some embodiments, the gene-modi-fied cells may comprise an immune cell such as T cell, or NK cell.

Antibody-Drug Conjugate

In another aspect, the present application provides an antibody-drug conjugate which may comprise a cytotoxic agent and the antigen binding fragment of the present application. An antibody-drug conjugate usually refers to an antibody is linked to a small molecule cytotoxic drug using a specific linker, the main components of which may com-prise an antibody, a linker and a small molecule cytotoxic drug. The targeting of an antibody-drug conjugate may come from the antibody portion thereof, and the toxicity may mostly come from the toxic portion of a small molecule chemical drug (payload), while the antibody portion may also have toxicity (ADCC and CDC).

Kit

In another aspect, the present application provides a kit which may comprise the antigen binding protein, the chi-meric antigen receptor, the genetically modified cell, the antibody-drug conjugate of the present application, and/or the pharmaceutically composition of the present application. It may comprise the antigen binding protein, the chimeric antigen receptor, the genetically modified cell, and/or the antibody drug conjugate of the present application in a single conventional container, and also may optionally com-bine with one or more therapeutic agents, optionally they may be formulated together in a pharmaceutical composi-tion.

In some cases, the kit may also comprise the device for the administration of the antigen binding protein, the chimeric antigen receptor, the genetically modified cell, the antibody-drug conjugate or the pharmaceutical composition of the present application; for example, the device depends on the way for administration of the contents. In some cases, the kit may comprise package insert which comprising information about the antigen binding protein, the pharmaceutical composition and the dosage form in the kit. Generally, such information assists patients and physicians in the effective and safe use of the encapsulated antigen binding protein, pharmaceutical composition and dosage form. The contain-ers used in such kit may usually comprise at least one vial, tube, flask, bottle, syringe, or other suitable containers into which one or more in the detecting and/or therapeutic composition may be placed, and is preferably suitably divided equally. Where a second therapeutic agent is also provided, the kit may also contain a second different con-tainer in which the second detecting and/or therapeutic composition may be placed. Alternatively, multiple com-pounds may be prepared as a single pharmaceutical com-position and may be packaged in a single container device such as a vial, flask, syringe, bottle or other suitable single container.

Drug Delivery Device

In another aspect, the present application provides a drug delivery device (for example, plastic bottle or vial, e.g., hollow pin or syringe barrel), which may be used for administration of the antigen binding protein or pharmaceu-tical composition thereof described in the present applica-tion. This device may introduce a substance into a patient via a parenteral route, such as intramuscularly, subcutaneously, or intravenously). For example, the injection device may be a syringe (e.g., a pre-filled syringe with the antigen binding protein or the pharmaceutical composition thereof described in the present application, such as an auto-injector), which may include a syringe barrel and a needle (which may be used to pierce skin and/or blood vessel) for containing a fluid to be injected (e.g., the antigen binding protein or the pharmaceutical composition thereof described in the present application). The mode of administration may be changed. The routes of administration may include orally, intramus-cularly, subcutaneously, rectally and the like.

In another aspect, the present application provides fol-lowing embodiments:

1. An isolated antigen binding protein comprising at least one CDR of an antibody heavy chain variable region VH, wherein the VH comprises the amino acid sequence set forth in SEQ ID NO: 193.
2. The isolated antigen binding protein of embodiment 1, wherein the VH comprises the amino acid sequence set forth in any one of SEQ ID NOs: 90-93, 95 and 97-104.
3. The isolated antigen binding protein of any one of embodiments 1-2, comprising at least one CDR of an antibody light chain variable region VL, wherein the VL comprises the amino acid sequence set forth in SEQ ID NO: 194.
4. The isolated antigen binding protein of embodiment 3, wherein the VL comprises the amino acid sequence set forth in any one of SEQ ID NOs: 108-114, 116 and 118.
5. The isolated antigen binding protein of any one of embodiments 1-4, comprising an antibody or an anti-gen binding fragment thereof.
6. The isolated antigen binding protein of embodiment 5, wherein the antigen binding fragment comprises Fab, Fab', Fv fragment, F(ab')$_2$, scFv, di-scFv and/or dAb.
7. The isolated antigen binding protein of any one of embodiments 5-6, wherein the antibody is selected from the group consisting of: a monoclonal antibody, a chimeric antibody, a humanized antibody and a fully human antibody.
8. The isolated antigen binding protein of any one of embodiments 1-7, which competes with a specific anti-PD-L1 antibody for binding to PD-L1, wherein the specific anti-PD-L1 antibody comprises a light chain variable region and a heavy chain variable region, the light chain variable region of the specific anti-PD-L1 antibody comprises LCDR1, LCDR2 and LCDR3, the LCDR1 comprises the amino acid sequence set forth in SEQ ID NO: 181, the LCDR2 comprises the amino acid sequence set forth in SEQ ID NO: 182, the LCDR3 comprises the amino acid sequence set forth in SEQ ID NO: 191; the heavy chain variable region of the specific anti-PD-L1 antibody comprises HCDR1, HCDR2 and HCDR3, the HCDR1 comprises the amino acid sequence set forth in SEQ ID NO: 5, the HCDR2 comprises the amino acid sequence set forth in SEQ ID NO: 179, and the HCDR3 comprises the amino acid sequence set forth in SEQ ID NO: 180.

9. The isolated antigen binding protein of embodiment 8, wherein the light chain variable region of the specific anti-PD-L1 antibody comprises the amino acid sequence set forth in SEQ ID NO: 194, the heavy chain variable region of the specific anti-PD-L1 antibody comprises the amino acid sequence set forth in SEQ ID NO: 193.

10. The isolated antigen binding protein of any one of embodiments 1-9, wherein the VH comprises HCDR1, HCDR2 and HCDR3, wherein the HCDR1 comprises the amino acid sequence set forth in SEQ ID NO: 5.

11. The isolated antigen binding protein of embodiment 10, wherein the HCDR2 comprises the amino acid sequence set forth in SEQ ID NO: 179.

12. The isolated antigen binding protein of embodiments 10-11, wherein the HCDR2 comprises the amino acid sequence set forth in any one of SEQ ID NOs: 14, 16 and 17.

13. The isolated antigen binding protein of any one of embodiments 10-12, wherein the HCDR3 comprises the amino acid sequence set forth in SEQ ID NO: 180.

14. The isolated antigen binding protein of embodiments 10-13, wherein the HCDR3 comprises the amino acid sequence set forth in any one of SEQ ID NOs: 29-33.

15. The isolated antigen binding protein of any one of embodiments 1-14, wherein the VH comprises framework regions H-FR1, H-FR2, H-FR3 and H-FR4.

16. The isolated antigen binding protein of embodiment 15, wherein the C-terminus of the H-FR1 is linked to the N-terminus of the HCDR1, and the H-FR1 comprises the amino acid sequence set forth in SEQ ID NO: 1.

17. The isolated antigen binding protein of any one of embodiments 15-16, wherein the H-FR2 is located between the HCDR1 and the HCDR2, and the H-FR2 comprises the amino acid sequence set forth in SEQ ID NO: 9.

18. The isolated antigen binding protein of any one of embodiments 15-17, wherein the H-FR3 is located between the HCDR2 and the HCDR3, and the H-FR3 comprises the amino acid sequence set forth in SEQ ID NO: 192.

19. The isolated antigen binding protein of any one of embodiments 15-18, wherein the H-FR3 comprise the amino acid sequence set forth in any one of SEQ ID NOs: 21, 22 and 24.

20. The isolated antigen binding protein of any one of embodiments 15-19, wherein the N-terminus of the H-FR4 is linked to the C-terminus of the HCDR3, and the H-FR4 comprises the amino acid sequence set forth in SEQ ID NO: 38.

21. The isolated antigen binding protein of any one of embodiments 1-20, comprising an antibody heavy chain variable region VH, wherein the VH comprises the amino acid sequence set forth in SEQ ID NO: 193.

22. The isolated antigen binding protein of embodiment 21, wherein the VH comprises the amino acid sequence set forth in any one of SEQ ID NOs: 90-93, 95 and 97-104.

23. The isolated antigen binding protein of any one of embodiments 1-22, comprising an antibody heavy chain constant region, and the antibody heavy chain constant region comprises a human IgG constant region.

24. The isolated antigen binding protein of embodiment 23, wherein the antibody heavy chain constant region comprises the amino acid sequence set forth in any one of SEQ ID NOs: 172-175.

25. The isolated antigen binding protein of any one of embodiments 1-24, comprising an antibody heavy chain HC, and the HC comprises the amino acid sequence set forth in any one of SEQ ID NOs: 122-125, 127 and 129-137.

26. The isolated antigen binding protein of any one of embodiments 3-25, wherein the VL comprises LCDR1, LCDR2 and LCDR3, wherein the LCDR1 comprises the amino acid sequence set forth in SEQ ID NO: 181.

27. The isolated antigen binding protein of embodiment 26, wherein the LCDR1 comprises the amino acid sequence set forth in any one of SEQ ID NOs: 48-51.

28. The isolated antigen binding protein of any one of embodiments 26-27, wherein the LCDR2 comprises the amino acid sequence set forth in SEQ ID NO: 182.

29. The isolated antigen binding protein of any one of embodiments 26-28, wherein the LCDR2 comprises the amino acid sequence set forth in any one of SEQ ID NOs: 63-64.

30. The isolated antigen binding protein of any one of embodiments 26-29, wherein the LCDR3 comprises the amino acid sequence set forth in SEQ ID NO: 191.

31. The isolated antigen binding protein of any one of embodiments 26-30, wherein the LCDR3 comprises the amino acid sequence set forth in any one of SEQ ID NOs: 77-79.

32. The isolated antigen binding protein of any one of embodiments 3-31, wherein the VL comprises framework regions L-FR1, L-FR2, L-FR3 and L-FR4.

33. The isolated antigen binding protein of embodiment 32, wherein the C-terminus of the L-FR1 is linked to the N-terminus of the LCDR1, and the L-FR1 comprises the amino acid sequence set forth in SEQ ID NO: 185.

34. The isolated antigen binding protein of any one of embodiments 32-33, wherein the L-FR1 comprises the amino acid sequence set forth in any one of SEQ ID NOs: 41-44.

35. The isolated antigen binding protein of any one of embodiments 32-34, wherein the L-FR2 is located between the LCDR1 and the LCDR2, and the L-FR2 comprises the amino acid sequence set forth in SEQ ID NO: 186.

36. The isolated antigen binding protein of any one of embodiments 32-35, wherein the L-FR2 comprises the amino acid sequence set forth in any one of SEQ ID NOs: 56-59.

37. The isolated antigen binding protein of any one of embodiments 32-36, wherein the L-FR3 is located between the LCDR2 and the LCDR3, and the L-FR3 comprises the amino acid sequence set forth in SEQ ID NO: 187.

38. The isolated antigen binding protein of any one of embodiments 32-37, wherein the L-FR3 comprises the amino acid sequence set forth in any one of SEQ ID NOs: 69-72.

39. The isolated antigen binding protein of any one of embodiments 32-38, wherein the N-terminus of the L-FR4 is linked to the C-terminus of the LCDR3, and the L-FR4 comprises the amino acid sequence set forth in SEQ ID NO: 188.

40. The isolated antigen binding protein of any one of embodiments 32-39, wherein the L-FR4 comprises the amino acid sequences set forth in any one of SEQ ID NOs: 85-86.

41. The isolated antigen binding protein of any one of embodiments 1-40, comprising an antibody light chain variable region VL, wherein the VL comprises the amino acid sequence set forth in SEQ ID NO: 194.

42. The isolated antigen binding protein of embodiment 41, wherein the VL comprises the amino acid sequence set forth in any one of SEQ ID NOs: 108-114, 116 and 118.

43. The isolated antigen binding protein of any one of embodiments 1-42, comprising an antibody light chain constant region, wherein the antibody light chain constant region comprises the amino acid sequence set forth in SEQ ID NO: 170.

44. The isolated antigen binding protein of any one of embodiments 1-43, comprising an antibody light chain LC, and the LC comprises the amino acid sequence set forth in any one of SEQ ID NOs: 150-156, 158 and 160-163.

45. The isolated antigen binding protein of any one of embodiments 1-44, having one or more of the following properties:

1) capable of binding to PD-L1 derived from a primate in a $K_D$ value of $1 \times 10^{-8}$ M or less;

2) capable of blocking the binding of PD-1 with PD-L1;

3) capable of blocking the binding of CD80 with PD-L1;

4) capable of stimulating the secretion of IFN-γ and/or IL2 in an immune cell;

5) capable of inhibiting tumor growth and/or tumor cell proliferation;

6) binding to an epitope of PD-L1 derived from a primate that does not completely overlap with the epitope of a control antibody, wherein the control antibody comprises LCDR1 set forth in SEQ ID NO: 52, LCDR2 set forth in SEQ ID NO: 65 and LCDR3 set forth in SEQ ID NO: 81, and the control antibody comprises HCDR1 set forth in SEQ ID NO: 6, HCDR2 set forth in SEQ ID NO: 15 and HCDR3 set forth in SEQ ID NO: 34;

or, wherein the control antibody comprises LCDR1 set forth in SEQ ID NO: 53, LCDR2 set forth in SEQ ID NO: 66 and LCDR3 set forth in SEQ ID NO: 82, and the control antibody comprises HCDR1 set forth in SEQ ID NO: 5, HCDR2 set forth in SEQ ID NO: 18 and HCDR3 set forth in SEQ ID NO: 35;

or, the control antibody comprises LCDR1 set forth in SEQ ID NO: 55, LCDR2 set forth in SEQ ID NO: 68 and LCDR3 set forth in SEQ ID NO: 84, and the control antibody comprises HCDR1 set forth in SEQ ID NO: 8, HCDR2 set forth in SEQ ID NO: 20 and HCDR3 set forth in SEQ ID NO: 37.

46. The isolated antigen binding protein of embodiment 45, wherein the primate comprises a human and/or a monkey.

47. A fusion protein comprising: a) a human TGFBRII or a fragment thereof; and b) the isolated antigen binding protein of any one of embodiments 1-46.

48. The fusion protein of embodiment 47, wherein the isolated antigen binding protein comprises an antibody heavy chain or a fragment thereof, and the antibody heavy chain or fragment thereof is fused in-frame with the human TGFBRII or fragment thereof to form the fusion polypeptide.

49. The fusion protein of embodiment 48, wherein the C-terminus of the antibody heavy chain or fragment thereof is directly or indirectly linked to the N-terminus of the human TGFBRII or fragment thereof.

50. The fusion protein of any one of embodiments 48-49, wherein the antibody heavy chain or fragment thereof is linked to the human TGFBRII or fragment thereof via a linker.

51. The fusion protein of embodiment 50, wherein the linker is a peptide linker, and the peptide linker comprises the amino acid sequence set forth in any one of SEQ ID NOs: 167-169.

52. The fusion protein of any one of embodiments 47-51, wherein the human TGFBRII or fragment thereof comprises the extracellular domain of the human TGFBRII.

53. The fusion protein of any one of embodiments 47-52, wherein the human TGFBRII or fragment thereof comprises the amino acid sequence set forth in any one of SEQ ID NOs: 176-178.

54. The fusion protein of any one of embodiments 47-53, comprising a first polypeptide and a second polypeptide, wherein the first polypeptide comprises a heavy chain of the isolated antigen binding protein or a fragment thereof and the human TGFBRII or fragment thereof; and the second polypeptide comprises a light chain of the isolated antigen binding protein or a fragment thereof.

55. The fusion protein of embodiment 54, wherein the heavy chain of the first polypeptide or fragment thereof is combined with the light chain of the second polypeptide or fragment thereof to form an antigen binding portion that specifically binds to PD-L1.

56. The fusion protein of any one of embodiments 54-55, wherein the first polypeptide comprises the amino acid sequence set forth in any one of SEQ ID NOs: 138, 139, 142, 143 and 145-148.

57. The fusion protein of any one of embodiments 54-56, wherein the second polypeptide comprises the amino acid sequence set forth in any one of SEQ ID NOs: 162-163.

58. The fusion protein of any one of embodiments 54-57, wherein, the first polypeptide comprises the amino acid sequence set forth in SEQ ID NO: 138, and the second polypeptide comprises the amino acid sequence set forth in SEQ ID NO: 162; or, the first polypeptide comprises the amino acid sequence set forth in SEQ ID NO: 139, and the second polypeptide comprises the amino acid sequence set forth in SEQ ID NO: 162; or, the first polypeptide comprises the amino acid sequence set forth in SEQ ID NO: 142, and the second polypeptide comprises the amino acid sequence set forth in SEQ ID NO: 162; or,

the first polypeptide comprises the amino acid sequence set forth in SEQ ID NO: 143, and the second polypeptide comprises the amino acid sequence set forth in SEQ ID NO: 162; or, the first polypeptide comprises the amino acid sequence set forth in SEQ ID NO: 145, and the second polypeptide comprises the amino acid sequence set forth in SEQ ID NO: 163; or, the first polypeptide comprises the amino acid sequence set forth in SEQ ID NO: 146, and the second polypeptide comprises the amino acid sequence set forth in SEQ ID NO: 163; or, the first polypeptide comprises the amino acid sequence set forth in SEQ ID NO: 147, and the second polypeptide comprises the amino acid sequence set forth in SEQ ID NO: 162; or, the first polypeptide comprises the amino acid sequence set forth in SEQ ID NO: 148, and the second polypeptide comprises the amino acid sequence set forth in SEQ ID NO: 162.

59. The fusion protein of any one of embodiments 54-58, comprising two of the first polypeptides and two of the second polypeptides.

60. Isolated one or more nucleic acids encoding the isolated antigen binding protein of any one of embodiments 1-46, and/or the fusion protein of any one of embodiments 47-59.

61. A vector comprising the nucleic acid of embodiment 60.

62. A cell comprising the nucleic acid of embodiment 60 or the vector of embodiment 61.

63. A method of preparing of the isolated antigen binding protein of any one of embodiments 1-46 and/or the fusion protein of any one of embodiments 47-59, the method comprises culturing the cell of embodiment 49 under the condition that the isolated antigen binding protein of any one of embodiments 1-46 or the fusion protein of any one of embodiments 47-59 is expressed.

64. A chimeric antigen receptor comprising the isolated antigen binding protein of any one of embodiments 1-46.

65. A genetically modified cell comprising the chimeric antigen receptor of embodiment 64.

66. An antibody-drug conjugate comprising a cytotoxic agent and the isolated antigen binding protein of any one of embodiments 1-46.

67. A pharmaceutical composition comprising the isolated antigen binding protein of any one of embodiments 1-46, the fusion protein of any one of embodiments 47-59, the nucleic acid molecule of embodiment 60, the vector of embodiment 61, the cell of embodiment 62, the chimeric antigen receptor of embodiment 64, the genetically modified cell of embodiment 65 and/or the antibody-drug conjugate of embodiment 66, and optionally, a pharmaceutically acceptable carrier.

68. Use of the isolated antigen binding protein of any one of embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67 in the manufacture of a medicament for preventing, alleviating and/or treating tumor or cancer, inhibiting tumor growth and/or inhibiting tumor cell proliferation.

69. The use of embodiment 68, wherein the tumor or cancer is the tumor or cancer that abnormally expresses PD-L1.

70. The use of any one of embodiments 68-69, wherein the tumor or cancer comprises a colorectal cancer.

71. A method of preventing, alleviating or treating a tumor, inhibiting tumor growth and/or inhibiting tumor cell proliferation, comprising the administration of the isolated antigen binding protein of any one of embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67 to a subject in need thereof.

72. The method of embodiment 71, wherein the tumor or cancer is the tumor or cancer that abnormally expresses PD-L1.

73. The method of any one of embodiments 71-72, wherein the tumor or cancer comprises a colorectal cancer.

74. The isolated antigen binding protein of any one of the embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67, for use in treating a cancer, inhibiting tumor growth and/or inhibiting tumor growth proliferation.

75. A method of inhibiting the binding of PD-L1 with PD-1, comprising the administration of the isolated antigen binding protein of any one of the embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67.

76. A method of inhibiting the binding of CD80 with PD-1, comprising the administration of the isolated antigen binding protein of any one of the embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67.

77. A kit comprising the isolated antigen binding protein of any one of embodiments 1-46, the nucleic acid molecule of embodiment 60, the vector of embodiment 61, the cell of embodiment 62, the chimeric antigen receptor of embodiment 64, the genetically modified cell of embodiment 65, the antibody-drug conjugate of embodiment 66 and/or the pharmaceutical composition of embodiment 67, and/or (i) administration device.

Without intending to be limited by any theory, the following Examples are only used to illustrate the fusion proteins, the preparation methods, and the use of the present application and the like, and are not used to limit the scopes of the inventions of the present application.

EXAMPLES

The Examples shown below are used to illustrate the specific embodiments of the present application, and are not intended to limit the scope of the present description or claims in any way. The Examples do not comprise the detailed descriptions of the conventional methods, such as those methods for constructing vectors and plasmids, methods for inserting the genes encoding proteins into such vectors and plasmids, or methods for introducing the plasmids into host cells. Such methods are well known to the person with ordinary skills in the art, and are described in many publications, including Sambrook J., Fritsch, E. F. and Maniais, T. (1989) Molecular Cloning: A Laboratory Manual, 2nd edition, Cold spring Harbor Laboratory Press.

Example 1. Preparation and Characterization
Analysis of the Antigen Binding Proteins or Fusion
Proteins The PD-L1 antigen may be used to immunize the experimental animals to obtain the antibody molecules specifically binding to PD-L1, the experimental animals may be mice, rats, rabbits, sheep, camels and the like. Generally, the obtained antibody molecules are of non-human origin. After obtaining the non-human antibodies, these molecules need to be humanization modified using antibody engineering techniques, in order to reduce the immunogenicity and improve druggability. However, the process of humanization of antibodies has its technical complexity, and the molecules that have been humanization modified will often reduce the affinity to antigens. In another aspect, the advances of transgenic technology have made it possible to breed genetically engineered mice that carry human immunoglobin immune libraries and have their endogenous mouse immune libraries missing. The antibodies produced by this kind of transgenic mice have fully human sequences, so there is no need for further humanization modifications, greatly improving the efficiency of the development of therapeutic antibodies. The Harbour H2L2 mouse (Harbour Antibodies BV) is a transgenic mouse that carries a human immunoglobin immune library, and the antibodies produced by the mouse have intact human antibody variable domains and rat constant domains.

1.1 Immunizing Mice with PD-L1 Antigen

Harbor H2L2 mice were immunized for multiple rounds with soluble recombinant human PD-L1-mFc fusion protein (Novo Protein Inc. Cat. No. CM06, lot number 0330837). The antigen protein was mixed with an immunologic adjuvant to form an immunogen reagent, which was then injected subcutaneously through the groin or through the peritoneal. In each round of immunization, the total injection dose received by each mouse is 100 μL. In the first round of immunization, each mouse was immunized with the immunogen reagent prepared by mixing with 50 μg of the antigen protein (human PD-L1-mFc) and Complete Freund's Adjuvant (Sigma, Cat. No. F5881) in a volume ratio of 1:1. In each subsequent round of booster immunization, each mouse was immunized with the immunogen reagent prepared by mixing with 25 μg of the antigen protein and Sigma Adjuvant System adjuvant (Sigma, Cat. No. S6322). The interval time of each round of booster immunization was at least two weeks, usually there were no more than five rounds of booster immunization. The immunization time was on Days 0, 14, 28, 42, 56, and 70; and the titers of antibody in the mouse serum were detected on Days 49 and 77. Three days before the fusion of cells, the last time of booster immunization was performed at a dose of 25 μg of the antigen protein per mouse.

60

1.2 Obtaining Monoclonal Hybridomas and Antibody Sequences

After the titers of the antibody specific to PD-L1 detected in the mouse serum reached a certain level, the spleen cells of the mice were taken out and were fused with the myeloma cell line to obtain the hybridoma cells; after the hybridoma cells were screened and cloned for several rounds, several hybridoma cells expressing anti-PD-L1 monoclonal antibody molecules were isolated. The isolated hybridoma cells and the monoclonal antibodies expressed by the cells were all represented by the corresponding clone numbers, for example: 63G11H3G9, 91G3H5H3 and the like. The isolated hybridoma cells express the antibody molecules that have intact human variable domains and rat constant domains in heavy chains and light chains. The above-mentioned monoclonal antibodies were further identified, several hybridoma clones were screened for sequencing according to the parameters, i.e., the binding ability thereof to human PD-L1, the binding ability thereof to cynomolgus PD-L1, inhibiting the binding ability of PD-L1 to PD-1 and the like. Conventional hybridoma sequencing techniques were used to obtain the nucleotide sequences encoding the variable domains of the antibody molecules and the corresponding amino acid sequences. In this example, the sequences of the variable domains of the anti-PD-L1 monoclonal antibody molecules obtained from the immunized Harbour H2L2 mice are human antibody sequences. The CDR sequences of the variable domains of the antibodies may be analyzed by Kabat or Chothia or other CDR definition rules (such as Combined definition rule) (see Table 1 for the definition of CDRs). Table 2 lists the hybridoma cells and the SEQ ID NO numbers for the sequences of variable domains of the recombinant antibodies and the CDR sequences, wherein CDRs are defined using the Chothia definition rule.

1.3 Preparation of Fully Human Recombinant Antibodies

After obtaining the sequences encoding the sequences of light chain and heavy chain variable domains of the antibody molecules, conventional DNA recombination techniques may be used to fuse and express the sequences of variable domains of light chains and heavy chains and the sequences of constant domains of light chains and heavy chains of the corresponding human antibodies to obtain the recombinant antibody molecules. In this example, the sequences of antibody heavy chain variable domains (VHs) were genetically synthesized and cloned into an expression plasmid vector of mammalian cells encoding the sequence of human IgG1 antibody heavy chain constant domain (SEQ ID NO: 172) or the variant sequences thereof comprising amino acid mutations (SEQ ID NO: 173-175), to encode and produce the full-length heavy chains (or variants thereof) of human IgG antibodies; the sequences of antibody light chain variable domains (VLs) were genetically synthesized and cloned into an expression plasmid vector of mammalian cells encoding the sequence of an human antibody κ light chain constant domain (SEQ ID NO: 170), to encode and produce the full-length κ light chains of antibodies; or the VLs were genetically synthesized and cloned into an expression plasmid vector of mammalian cells encoding the sequence of a human antibody 2 light chain constant domain (SEQ ID NO: 171), to encode and produce the full-length 2 light chains of antibodies. Table 2 lists the amino acid sequences of the light chains and heavy chains variable domains, the full-length amino acid sequences of light chains, the full-length amino acid sequences of heavy chains (human IgG1) of the PD-L1 antibodies in this example and the amino acid sequences of CDRs defined according to the Chothia definition rule.

The plasmids that encode the heavy chains of the antibodies and the plasmids that encode the light chains of the antibodies were simultaneously transfected into mammalian host cells (such as human embryonic kidney cells HEK293). Conventional recombinant protein expression and purification techniques were used to obtain the purified PD-L1 recombinant antibodies with the correctly paired and assembled light chains and heavy chains. Specifically, the HEK293 cells were expanded and cultured in the medium of FreeStyle™ F17 Expression Medium (Thermo, A1383504). Before starting transient transfection, the cells were adjusted to the concentrations of $6-8\times10^5$ cells/mL, were cultured in a shaker at 37° C. under 8% $CO_2$ for 24 hrs with the cell concentrations of $1.2\times10^6$ cells/mL. 30 mL of cultured cells were prepared. The above plasmids encoding the antibody heavy chains and the plasmids encoding the antibody light chains were mixed in a ratio of 2:3 in a total of 30 µg of plasmids, and were dissolved in 1.5 mL Opti-MEM reduced serum medium (Thermo, 31985088), and were subjected to filtration sterilization through 0.22 µm filter. Then 1.5 mL of Opti-MEM was taken and dissolved into 120 µL of 1 mg/mL PEI (Polysciences, 23966-2), standing for 5 mins. The PEI was added to the plasmids slowly, incubated for 10 mins at room temperature. the mix solution of the plasmids and PEI was slowly dropped into the culture flask while shaking the culture flask, and were cultured in a shaker at 37° C. 8% for 5 days. The survival of cells was observed after 5 days. The cultures were collected and centrifuged at 3300 g for 10 mins, the supernatants were taken. Then the supernatants were subjected to high-speed centrifugation to remove impurities. The gravity column (Bio-Rad, 7311550) containing MabSelect™ (GE Healthcare Life Science, 71-5020-91 AE) was equilibrated with PBS (pH 7.4) buffer and washed with 2-5 times of column volumes. The supernatant samples were passed through the column; 5-10 times of column volumes of PBS was used to wash the column, and 0.1 M glycine at pH 3.5 was used to elute the protein of interest, then Tris-HCl at pH 8.0 was used to adjust to neutral, finally the ultrafiltration tube (Millipore, UFC901024) was used to concentrate and change to PBS buffer to obtain a purified recombinant protein solution. Finally, NanoDrop (Thermo Scientific™ NanoDrop™ One) was used to determine the concentration, the purified recombinant protein solution was aliquoted and stored for later use.

frequency mutations and so on; the sequences of light chain variable domains are derived from events such as the gene rearrangements of germline gene V, J gene fragments of a light chain gene group and somatic high frequency mutations and so on. Gene rearrangements and somatic high frequency mutations are the main factors for increasing the diversity of antibodies. The antibodies derived from the same germline V gene fragment may also produce different sequences, but the overall similarity is high. Some algorithms, such as IMGT/DomainGapAlign (http://imgt.org/3Dstructure-DB/cgi/DomainGapAlign.cgi) or NCBI/Ig-BLAST (https://www.ncbi.nlm.nih.gov/igblast/), may be used to speculate the possible germline gene fragments, when the gene arrangements thereof occurred, from the sequences of variable domains of antibodies. The sequences of the antibodies in Example 1.3 and in Table 2 were analyzed, the gene fragments of germline gene V of heavy chain variable domains (VHs) and light chain variable domains (VLs) thereof were listed in Table 3.

Sometimes chemical modifications will be introduced into the amino acid chains of proteins or polypeptides after translation and synthesis in cells, called a post-translational modification (PTM). As for antibodies, some sites for PTM are very conserved. For example, the conserved amino acid asparagine Asn at position 297 (EU numbering) of the constant domain of human IgG1 antibody undergoes glycosylation modification to form a sugar chain, while the structure of the sugar chain is critical for the structure of the antibody and the relative effector functions. However, if there are PTMs in variable domains of antibodies, especially the antigen binding regions (such as CDRs), the presence of these PTMs may have a great effect on the binding to antigens, also may bring changes in the physicochemical properties of the antibodies. For example, glycosylation, deamidation, isomerization, oxidation, etc. may all increase the instability or heterogeneity of antibody molecules, thereby increasing the difficulty and risk in antibody development. Therefore, avoiding some potential PTMs is very important for the development of therapeutic antibodies. With the accumulation of experience, people have found that some PTMs are highly related to the composition of amino acid sequences, especially the "patterns" of the composition of adjacent amino acids, so that potential PTMs may be predicted from the primary amino acid sequences of pro-

TABLE 2

| Clone Number | Antibody | Light Chain | Heavy Chain | VL | VH | VL CDR1 | VL CDR2 | VL CDR3 | VH CDR1 | VH CDR2 | VH CDR3 |
|---|---|---|---|---|---|---|---|---|---|---|---|
| | | | | The screened anti-PD-L1 monoclonal hybridomas and the sequence numbers SEQ ID NOs of the recombinant antibodies thereof | | | | | | | |
| 63G11H3G9 | PR000064 | 150 | 122 | 108 | 90 | 48 | 63 | 77 | 5 | 14 | 29 |
| 67C1F7G6 | PR000065 | 151 | 122 | 109 | 90 | 49 | 64 | 78 | 5 | 14 | 29 |
| 69B8G8C2 | PR000066 | 152 | 123 | 110 | 91 | 48 | 64 | 78 | 5 | 14 | 30 |
| 73G3G9B11 | PR000067 | 153 | 122 | 111 | 90 | 50 | 63 | 77 | 5 | 14 | 29 |
| 82F8H7E1 | PR000068 | 154 | 124 | 112 | 92 | 50 | 63 | 79 | 5 | 14 | 31 |
| 85C5E4G3 | PR000069 | 155 | 125 | 113 | 93 | 51 | 63 | 77 | 5 | 14 | 32 |
| 91G3H5H3 | PR000070 | 156 | 122 | 114 | 90 | 51 | 64 | 78 | 5 | 14 | 29 |
| 95C7C4A9 | PR000071 | 157 | 126 | 115 | 94 | 50 | 63 | 80 | 5 | 14 | 33 |
| 98E11H1C9 | PR000072 | 158 | 127 | 116 | 95 | 50 | 64 | 77 | 5 | 14 | 33 |

1.4 Sequence Analysis and Expression Purification of the PD-L1 Antibodies

The sequences of heavy chain variable domains of antibodies are derived from events such as the gene rearrangements of germline gene V, D, J gene fragments of a heavy chain gene group on the chromosome and somatic high teins. For example, N-linked glycosylation site can be predicted from the sequence pattern of N-x-S/T (at the first position is asparagine, at the second position is any amino acid other than proline, and at the third position is serine or threonine). The amino acid sequence patterns that cause PTMs may be derived from the sequences of germline genes (for example, human germline gene fragment IGHV3-33 naturally has a glycosylation pattern NST in the FR3 region); it may also be derived from somatic high frequency mutations. Table 3 lists the predicted PTMs of the variable domains VHs and VLs of the antibodies of Example 1.3. Specifically, NGS or NLT may be the glycosylation site, DG may cause the isomerization of aspartic acid.

The amino acid sequence patterns of PTMs may be destroyed by amino acid mutations, thereby reducing or removing the formation of specific PTMs. According to different antibody sequences and PTM sequence patterns, there are different methods for mutations design. One method is to replace the "hotspot" amino acids (such as N or S in the NS pattern) with amino acids with similar physico-chemical properties (e.g., N is replaced with Q). If the PTM sequence pattern is derived from somatic high frequency mutations and does not exist in germline gene sequence, another method may be to replace the sequence pattern with the corresponding germline gene sequence. In actual operation, multiple mutation design methods may be used for the same PTM sequence pattern.

Table 4 lists the new antibody molecules (term as PTM variants) obtained by amino acid mutations on the sequences of the six antibodies with potential PTM sites from Example 1.3. Table 5-1 lists the amino acid sequences of light and heavy chains variable domains, the full-length amino acid sequences of light chains, the full-length amino acid sequences of heavy chains (human IgG1s(N297A)) of these PTM variants in this example, and the amino acid sequences of CDRs defined according to the Chothia definition rule. For all the designed PTM variants, the purified recombinant antibodies were obtained according to the method described in Example 1.3, and were further verified in the subsequent functional experiments.

TABLE 3

Germline gene analysis of the sequences of the PD-L1 antigen binding proteins and analysis of post-translational modification (PTM) sites

| Clone number | Antibody | VH germline V gene | VL germline V gene | VH PTM | VL PTM |
|---|---|---|---|---|---|
| 63G11H3G9 | PR000064 | IGHV3-7 | IGKV1-5 | DG (HCDR2) | — |
| 67C1F7G6 | PR000065 | IGHV3-7 | IGKV1-5 | DG (HCDR2) | — |
| 69B8G8C2 | PR000066 | IGHV3-7 | IGKV1-5 | DG (HCDR2) | NGS (LFR3) |
| 73G3G9B11 | PR000067 | IGHV3-7 | IGKV1-5 | DG (HCDR2) | — |
| 82F8H7E1 | PR000068 | IGHV3-7 | IGKV1-5 | DG (HCDR2) | — |
| 85C5E4G3 | PR000069 | IGHV3-7 | IGKV1-5 | DG (HCDR2) | — |
| 91G3H5H3 | PR000070 | IGHV3-7 | IGKV1-5 | DG (HCDR2) | — |
| 95C7C4A9 | PR000071 | IGHV3-7 | IGKV1-5 | DG (HCDR2) | — |
| 98E11H1C9 | PR000072 | IGHV3-7 | IGKV1-5 | DG (HCDR2) | — |

TABLE 4

Design of the mutation sites of the PD-L1 antigen binding protein sequences

| Initial antibody | PTM variant | mutation site | variant VH PTMs | variant VL PTMs |
|---|---|---|---|---|
| PR000066 | PR000261 | H: D54E; L: N65S | / | / |
| PR000066 | PR000262 | H: G55A; L: N65S | / | / |
| PR000069 | PR000263 | H: D54E | / | / |
| PR000069 | PR000264 | H: G55A | / | / |
| PR000070 | PR000265 | H: D54E | / | / |
| PR000070 | PR000266 | H: G55A | / | / |
| PR000072 | PR000267 | H: D54E | / | / |
| PR000072 | PR000268 | H: G55A | / | / |

TABLE 5-1

SEQ ID NOs of the antibodies obtained after mutations of PTM

| Initial antibody | PTM variant | Light chain | Heavy chain | VL | VH | VL CDR1 | VL CDR2 | VL CDR3 | VH CDR1 | VH CDR2 | VH CDR3 |
|---|---|---|---|---|---|---|---|---|---|---|---|
| PR000066 | PR000261 | 160 | 129 | 118 | 97 | 48 | 64 | 78 | 5 | 16 | 30 |
| PR000066 | PR000262 | 160 | 130 | 118 | 98 | 48 | 64 | 78 | 5 | 17 | 30 |
| PR000069 | PR000263 | 161 | 131 | 113 | 99 | 51 | 63 | 77 | 5 | 16 | 32 |
| PR000069 | PR000264 | 161 | 132 | 113 | 100 | 51 | 63 | 77 | 5 | 17 | 32 |
| PR000070 | PR000265 | 162 | 133 | 114 | 101 | 51 | 64 | 78 | 5 | 16 | 29 |
| PR000070 | PR000266 | 162 | 134 | 114 | 102 | 51 | 64 | 78 | 5 | 17 | 29 |
| PR000072 | PR000267 | 163 | 135 | 116 | 103 | 50 | 64 | 77 | 5 | 16 | 33 |
| PR000072 | PR000268 | 163 | 136 | 116 | 104 | 50 | 64 | 77 | 5 | 17 | 33 |

Table 5-2 lists the sequence numbers of the molecules of the control antibodies PR000151, PR001598 and the Fc-type switching antibody of PR000265, i.e., PR000416, that appeared in the Examples of the present application, wherein PR000151 is an analog of Roche's anti-PD-L1 antibody atezolizumab, PR000151 and atezolizumab may be used interchangeably herein; PR001598 is an analog of Merck KGaA's anti-PD-L1 antibody avelumab, PR001598 and avelumab may be used interchangeably herein. The above antibodies were prepared and purified by the method of Example 1.3.

TABLE 5-2

The Fc-type switching of PR000265 and control antibodies

| Antibody descriptions | Antibody numbering | Light chain | Heavy chain | VL | VH | Constant region class |
|---|---|---|---|---|---|---|
| atezolizumab analog | PR000151 | 159 | 128 | 117 | 96 | hIgG1(N297A) |
| avelumab analog | PR001598 | 164 | 140 | 119 | 105 | hIgG1 |
| Fc-type switching of PR000265 | PR000416 | 162 | 137 | 114 | 101 | hIgG1 |

Example 2 Binding of Antigen Binding Proteins to Cells Overexpressing Human/Cynomolgus PD-L1 (FACS)

To study the binding activity of the PD-L1 antigen binding proteins to human/cynomolgus PD-L1 in vitro, this example uses the CHOK1 cell line overexpressing human PD-L1 (CHO-K1/hPD-L1, Nanjing Genscript, M00543) or the CHOK1 cell line overexpressing cynomolgus PD-L1 (CHO-K1/cynoPD-L1, Nanjing Genscript, M00573) to perform binding experiments at cellular level. In brief, the PD-L1 cells were digested, and resuspended in F-12K complete medium, and the cell density was adjusted to $1\times10^6$ cells/mL. Cells were seeded on 96-well V bottom plate (Corning, 3894) at 100 µL cells/well, then 5-fold concentration gradients serial dilutions of the antigen binding proteins to be tested at the concentration of 2-fold of the final concentration were added at 100 µL/well, and mixed well, wherein the highest final concentration of the antigen binding proteins was 100 nM, and there were 8 concentrations in total. The isotype antibody hIgG1 iso was used as a control. The cells were placed at 4° C., incubated away from light for 1 hr. Then, 100 µL/well of pre-cooled PBS was added to wash cells twice. The cells were centrifuged at 500 g, 4° C. for 5 mins, and the supernatant was discarded. The fluorescent secondary antibody (goat anti-human IgG (H+L) secondary antibody, Alexa Fluor 488 conjugate, Invitrogen, A11013, 1:1000 dilution) was added at 100 µL/well, and incubated away from light at 4° C. for 30 mins. 200 µL/well of pre-cooled PBS was added to wash cells twice, and the cells were centrifuged at 500 g, 4° C. for 5 mins, and the supernatant was discarded. Finally, the cells were resuspended with 200 µL/well of pre-cooled PBS. The signal values of fluorescent luminescence were read using BD FACS MAYTOII. The flow cytometer BD FAC MAYTOII was used to read the signal values of fluorescent luminescence, and the software FlowJo v10 (FlowJo, LLC) was used to process and analyze data. The software GraphPad Prism 8 was applied to perform data processing and plotting analysis, and the parameters such as binding curves and EC50 values were obtained by four-parameter non-linear fitting.

Figure 2:
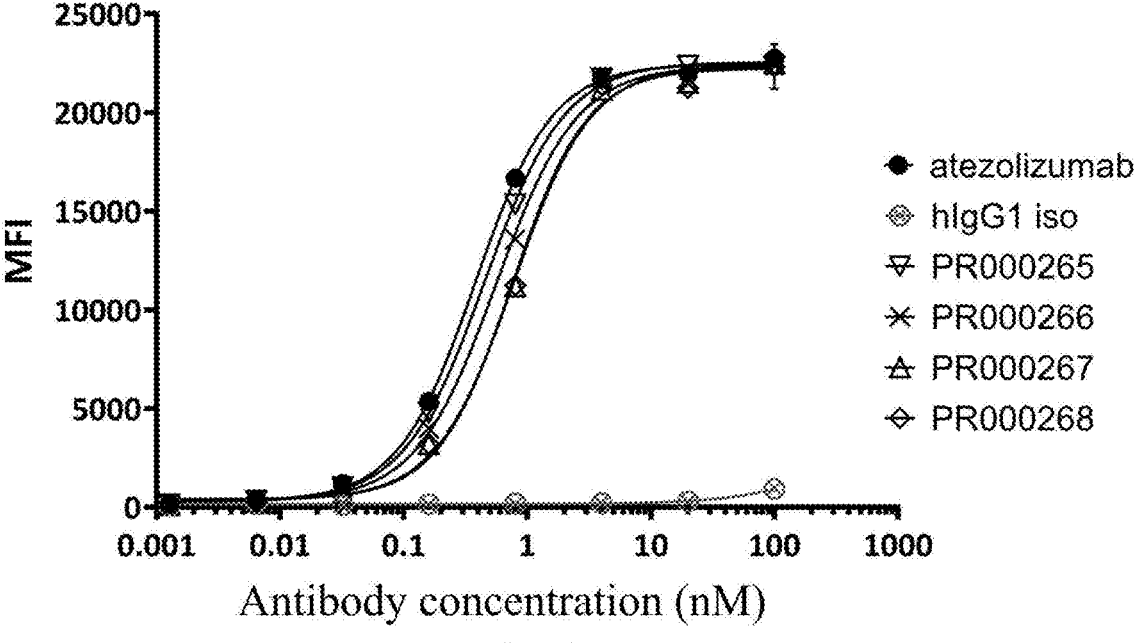
FIG. 2 shows that the antigen binding proteins of the present application bind to the CHO-K1 cells overexpressing cynomolgus PD-L1.

The results of FIG. 1 and Table 6 indicate that all the PD-L1 antigen binding proteins described in the present application are capable of binding to human PD-L1; the results of FIG. 2 and Table 7 indicate that all the PD-L1 antigen binding proteins are capable of binding to cynomolgus PD-L1; and the results are shown in a concentration-dependent effect.

TABLE 6

Binding to human PD-L1 which is on the cell surface

| Antigen binding protein | MFI maximum value | EC50 (nM) |
|---|---|---|
| PR000064 | 7885 | 0.417 |
| PR000065 | 7657 | 0.412 |
| PR000066 | 7859 | 0.255 |
| PR000067 | 7342 | 0.456 |
| PR000068 | 7636 | 0.326 |
| PR000069 | 7529 | 0.312 |
| PR000070 | 7787 | 0.210 |
| PR000071 | 6894 | 0.521 |
| PR000072 | 7629 | 0.292 |
| atezolizumab | 6765 | 0.188 |
| hIgG1 control | 305 | N.A. |

TABLE 7

Binding to Cynomolgus PD-L1 that is on the cell surface

| Antigen binding protein | MFI maximum value | EC50 (nM) |
|---|---|---|
| atezolizumab | 22447 | 0.379 |
| hIgG1 control | 935 | N.A. |
| PR000265 | 22556 | 0.451 |
| PR000266 | 22362 | 0.562 |
| PR000267 | 22401 | 0.775 |
| PR000268 | 22244 | 0.759 |

Example 3 Binding of Antigen Binding Proteins to Human/Cynomolgus PD-L1 Protein

This example studies the in vitro binding activity of the PD-L1 antigen binding proteins to human/cynomolgus PD-L1 protein by enzyme-linked immunosorbent assay (ELISA).

3.1 Binding of the Antigen Binding Proteins to Human PD-L1 Protein (ELISA)

Human PD-L1 (Acrobiosystems, PD1-H5229) was diluted in PBS to 2 μg/ml, added into 96-well plate (Corning 9018) at 100 μL per well, and was incubated at 4° C. overnight. After the liquid was discarded, the PBST buffer (pH 7.4, containing 0.05% tween-20) was used to wash the plate for 3 times. 250 μL of 2% BSA blocking buffer was added, and was incubated at the condition of 37° C. for 1 hr. The blocking buffer was discarded, and the PBST buffer (pH 7.4, containing 0.05% tween-20) was used to wash the plate for 3 times. The antigen binding proteins to be tested, serially diluted 5-fold starting from the concentration of 100 nM, 8 concentration gradients in total, were added at 100 μL per well, and were then incubated at 37° C. for 1 hr. The isotype antibody hIgG1 iso was used as a control. After washing with PBST buffer (pH 7.4, containing 0.05% tween-20) for three times, the goat anti-human HRP secondary antibody (Invitrogen, A18805) that was diluted 4000-fold was added, and was incubated away from light at the condition of 37° C. for 1 hr. After washing by PBST buffer (pH 7.4, containing 0.05% tween-20) for three times, 100 μL/well of TMB (Biopanda, TMB-S-003) was added, and was placed away from light at room temperature for about 5 mins; stop solution (BBI life sciences, E661006-0200) was added to each well at 50 μL/well to stop the reaction. The Microplate Reader Enspire (PerkinElemer) was used to detect the absorption values at 450 nm (OD450). The software GraphPad Prism 8 was applied to perform data processing and plotting analysis, the parameters such as binding curves and EC50 values were obtained by four-parameter non-linear fitting.

Figure 3:
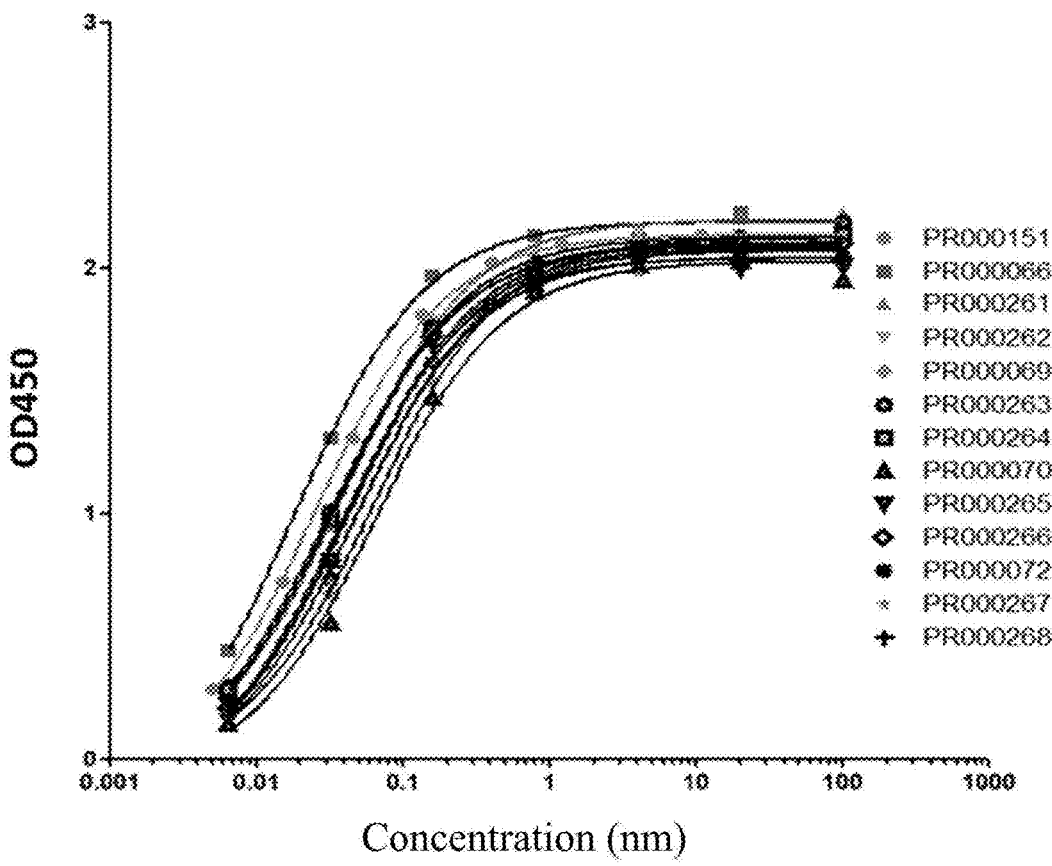
FIG. 3 shows that the antigen binding proteins of the present application bind to human PD-L1 protein.

FIG. 3 and Table 8 show all the PD-L1 antigen binding proteins of the present application are capable of binding to human PD-L1 protein, and the PTM variants still retain the binding activity of the parent antibodies.

TABLE 8

| Binding to human PD-L1 protein | |
| --- | --- |
| Antigen binding protein | EC50 (nM) |
| PR000151 | 0.0259 |
| PR000066 | 0.0189 |
| PR000261 | 0.0385 |
| PR000262 | 0.0338 |
| PR000069 | 0.0637 |
| PR000263 | 0.0321 |
| PR000264 | 0.0343 |
| PR000070 | 0.0641 |
| PR000265 | 0.0373 |
| PR000266 | 0.0415 |
| PR000072 | 0.0474 |
| PR000267 | 0.0462 |
| PR000268 | 0.0412 |

3.2 Binding of the Antigen Binding Proteins to Cynomolgus PD-L1 Protein (ELISA)

Cynomolgus PD-L1 (Acrobiosystems, PD1-052H4) was diluted with PBS to 2 μg/ml, added into 96-well plate (Corning 9018) at 100 μL per well, and was incubated at 4° C. overnight. After the liquid was discarded, the plate was washed with the PBST buffer for 3 times, 250 μL of 2% BSA was added to block, and was incubated at the condition of room temperature for 1 hr. The blocking buffer was discarded, and the plate was washed with the PBST buffer (pH 7.4, containing 0.05% tween-20) for 3 times. The concentrations of the antigen binding proteins to be tested were diluted to 5 μg/mL, was added at 100 μL/well, and was incubated at 37° C. for 1 hr. After washing with PBST buffer (pH 7.4, containing 0.05% tween-20) for 3 times, the goat anti-human HRP secondary antibody (Invitrogen, A18805) that was diluted 4000-fold was added, and was incubated at 37° C. for 1 hr. After washing, TMB (Biopanda, TMB-S-003) was added at 100 μL/well, placed away from light at room temperature for 5 mins; stop solution (BBI life sciences, E661006-0200) was added into each well at 50 μL/well to stop the reaction. The Microplate Reader Enspire (PerkinElemer) was used to detect the absorption values at 450 nm (OD450).

Figure 4:
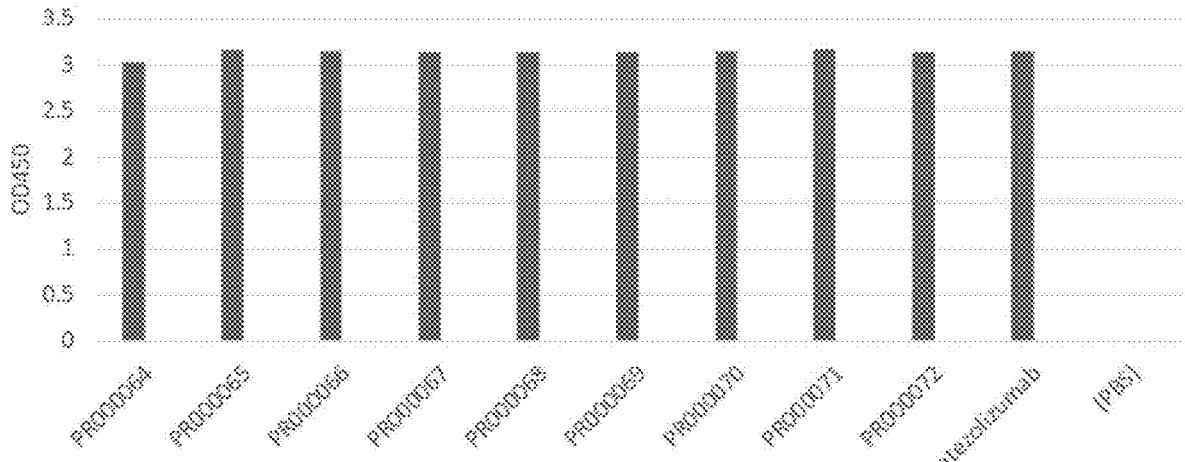
FIG. 4 shows that the antigen binding proteins of the present application bind to cynomolgus PD-L1 protein.

The results were shown in FIG. 4, indicating that all the PD-L1 antigen binding proteins of the present application are capable of binding to cynomolgus PD-L1 protein.

Example 4 the Antigen Binding Proteins Block the Binding of Human PD-1 to the CHO-K1 Cells Overexpressing Human PD-L1

To study the activity of human PD-L1 binding proteins to block the binding of human PD-1 to human PD-L1 in vitro, the CHOK1 cell line overexpressing human PD-L1 (CHO-K1/hPD-L1, Nanjing Genscript, M00543) was used to perform the experiments for the blocking of the binding of human PD-1/human PD-L1 at cellular level. In brief, the CHO-K1/hPD-L1 cells were digested, and resuspended in F-12K complete medium. The cell density was adjusted to $1 \times 10^6$ cells/mL. Cells were seeded in 96-well V bottom plate (Corning, 3894) at 100 μL cells/well, then the 3-fold concentration gradients serial dilutions of the antigen binding proteins to be tested at the concentration of 2-fold of the final concentration were added, and mixed well, wherein the highest final concentration of the antigen binding proteins was 100 nM, and there were 8 concentrations in total. The isotype antibody hIgG1 iso was used as a control. Cells were placed at 4° C., and were incubated away from light for 1 hr. Then, the cells were centrifugated at 4° C. for 5 mins, and the supernatant was discarded. Then, 1 μg/mL of the biotin-labeled human PD-1 protein (Acrobiosystems, PD1-H82F2) was added at 50 μL/well, incubated away from light at 4° C. for 30 mins. The cells were washed with 100 μL/well of pre-cooled PBS twice, centrifuged at 500 g, 4° C. for 5 mins, and the supernatant was discarded. 100 μL/well of fluorescent secondary antibody PE Streptavidin (BD Pharmingen, 554061, 1:200 dilution) was added, incubated away from light at 4° C. for 30 mins 200 μL/well of pre-cooled PBS was used to wash cells twice, cells were centrifuged at 500 g, 4° C. for 5 mins, the supernatant was discarded. Finally, 200 μL/well of pre-cooled PBS was used to resuspend cells. The BD FACS MAYTOII was used to read the signal value of fluorescent luminescence. The software GraphPad Prism 8 was applied to perform data processing and plotting analysis, and the parameters such as binding curves and IC50 values were obtained by four-parameter non-linear fitting.

Figure 5:
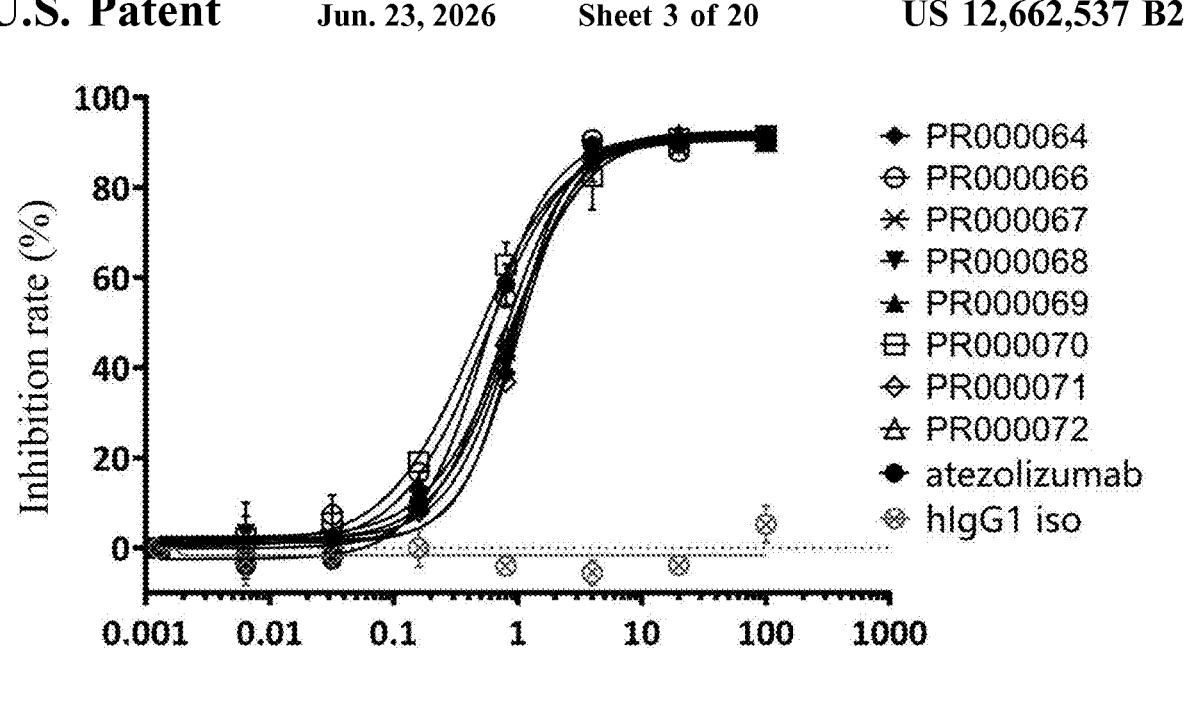
FIG. 5 shows that the antigen binding proteins of the present application block the binding of human PD-1 to the CHO-K1 cells overexpressing human PD-L1.
Figure 6:
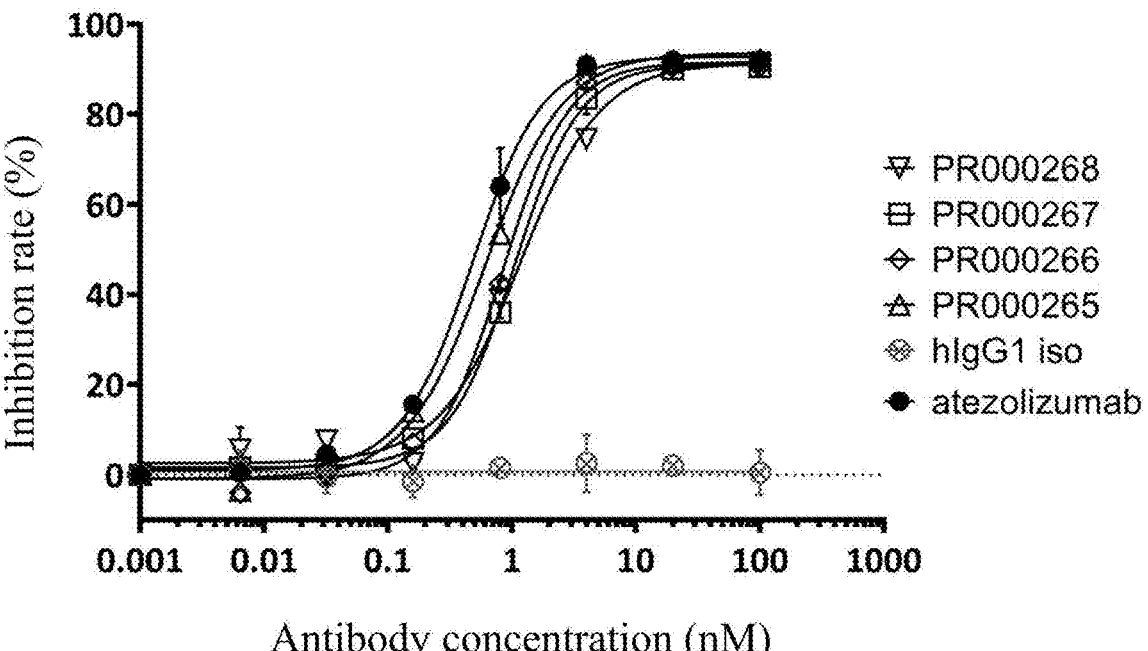
FIG. 6 shows that the antigen binding proteins of the present application block the binding of human PD-1 to the CHO-K1 cells overexpressing human PD-L1.

FIG. 5 and Table 9 show that all the antigen binding proteins before PTM mutation described in the present application are capable of blocking the binding of human PD-1 to human PD-L1 on the cell surface; FIG. 6 and Table 10 show that all the antigen binding proteins of the PTM variants described in the present application are capable of blocking the binding of human PD-1 to human PD-L1 on the cell surface; the blocking ability is comparable to that of atezolizumab analog.

TABLE 9

Blocking the binding of human PD-1 to human PD-L1 on the cell surface

| Antigen binding protein | Maximum inhibition rate (%) | IC50 (nM) |
|---|---|---|
| PR000064 | 91.46 | 0.938 |
| PR000066 | 91.81 | 0.539 |
| PR000067 | 91.16 | 0.894 |
| PR000068 | 91.37 | 0.853 |
| PR000069 | 92.35 | 0.836 |
| PR000070 | 90.74 | 0.449 |
| PR000071 | 91.58 | 0.987 |
| PR000072 | 92.49 | 0.746 |
| atezolizumab | 91.45 | 0.536 |
| hIgG1 Control | N.A. | N.A. |

TABLE 10

Blocking the binding of human PD-1 to human PD-L1 on the cell surface

| Antigen binding protein | Maximum inhibition rate (%) | IC50 (nM) |
|---|---|---|
| atezolizumab | 92.79 | 0.476 |
| hIgG1 Control | 0.68 | N.A. |
| PR000265 | 93.57 | 0.604 |
| PR000266 | 91.54 | 0.838 |
| PR000267 | 91.04 | 1.040 |
| PR000268 | 91.34 | 1.160 |

Example 5 the Antigen Binding Proteins Block the Binding of Human PD-L1 Protein to the Ligand Protein Thereof This example uses Enzyme-linked Immunosorbent Assay (ELISA) to study the ability of the PD-L1 antigen binding proteins of blocking the binding of human PD-L1 protein to the ligand protein thereof PD-1 or CD80 in vitro.

5.1 The Antigen Binding Proteins Block the Binding of Human PD-L1 to Human PD-1 (ELISA)

Human PD-L1 (Acrobiosystems, EP-101-96tests, A001-214) was diluted with PBS to 2 μg/ml, added into 96-well plate (Corning 9018) at 100 μL per well. The plate was coated at 4° C. overnight. After the liquid was discarded, the PBST buffer (pH 7.4, containing 0.05% tween-20) was used to wash the plate for 3 times, 250 μL of 2% BSA blocking buffer was added, incubated at the condition of 37° C. for 1 hr. The blocking buffer was discarded, and the PBST buffer (pH 7.4, containing 0.05% tween-20) was used to wash the plate for 3 times. The antigen binding proteins to be tested were diluted in PBST containing 0.5% (w/v) BSA to different concentration gradients, and after mixed with 0.6 μg/mL of human PD-1-Biotin protein (Acrobiosystems, EP-101-96tests, A002-214), added to the well plate. The isotype antibody hIgG1 iso was used as a control. They were incubated under the condition of 37° C. for 1 hr. After 3 times of washing, 100 μL of Streptavidin-HRP (Acrobiosystems, EP-101-96tests, A003-214) was added to each well, under the condition of 37° C., kept away from light for reaction for 1 hr. After 3 times of washing, 100 μL of TMB color-substrate solution was added, kept away from light for coloration reaction at room temperature for 5 mins. The stop solution was added to stop the reaction. The Microplate Reader Enspire (PerkinElemer) was used to detect the absorption values at 450 nm (OD450). The software Graph-Pad Prism 8 was applied to perform data processing and plotting analysis, the parameters such as binding curves and IC50 values were obtained by four-parameter non-linear fitting.

Figure 7:
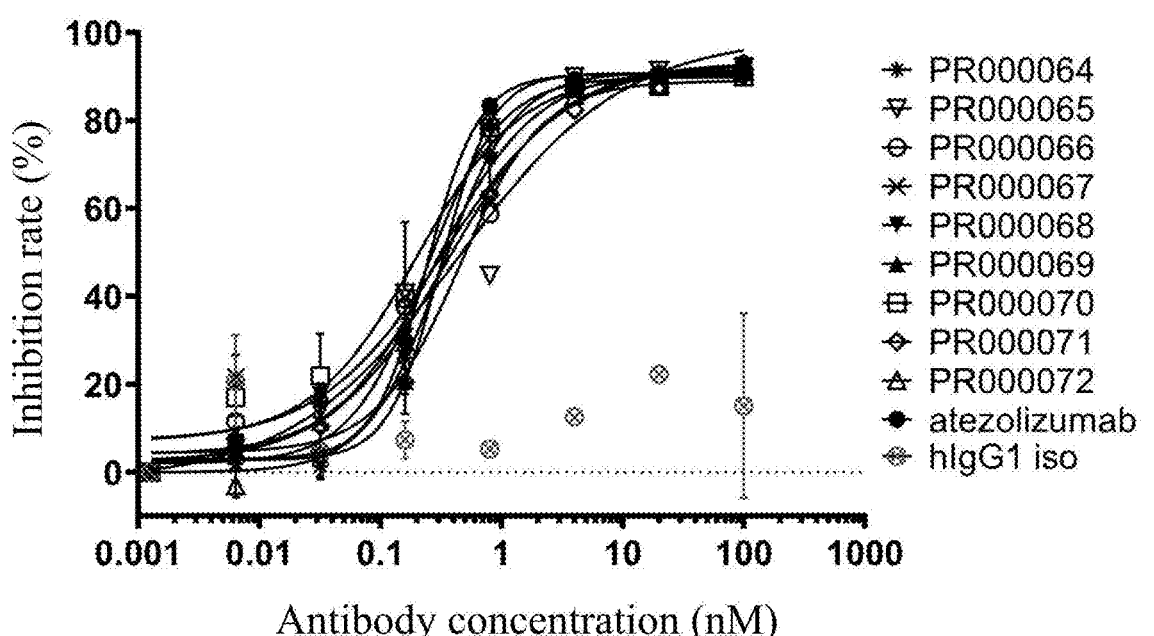
FIG. 7 shows that the antigen binding proteins of the present application block the binding of biotinylated human PD-1 protein to human PD-L1 protein.

FIG. 7 and Table 11 show that the antigen binding proteins described in the present application are capable of blocking the binding of human PD-1 to human PD-L1 protein; the blocking ability is comparable to that of atezolizumab analog.

TABLE 11

Blocking the binding of human PD-1 to human PD-L1 protein

| Antigen binding protein | Maximum inhibition rate (%) | IC50 (nM) |
|---|---|---|
| PR000064 | 91.06 | 0.313 |
| PR000065 | 99.03 | 0.432 |
| PR000066 | 93.05 | 0.350 |
| PR000067 | 92.91 | 0.333 |
| PR000068 | 91.59 | 0.288 |
| PR000069 | 90.71 | 0.313 |
| PR000070 | 90.62 | 0.200 |
| PR000071 | 88.98 | 0.448 |
| PR000072 | 89.85 | 0.237 |
| atezolizumab | 90.48 | 0.240 |
| hIgG1 Control | N.A. | N.A. |

5.2 The Antigen Binding Proteins Block the Binding of Human PD-L1 to Human B7-1 (CD80) (ELISA)

Human PD-L1-hFc protein (Acrobiosystems, PD1-H5258) was diluted in PBS to 1 μg/ml, added into 96-well plate (Corning 9018) at 100 μL per well. The plate was coated at 4° C. overnight. After the liquid was discarded, the PBST buffer (pH 7.4, containing 0.05% tween-20) was used to wash the plate for 3 times, 250 μL of 2% BSA blocking buffer was added, incubated under the condition of 37° C. for 1.5 hrs. The blocking buffer was discarded, and the PBST buffer (pH 7.4, containing 0.05% tween-20) was used to wash the plate for 3 times. The antigen binding proteins to be tested were diluted in PBST with 0.5% (w/v) BSA to different concentration gradients, after mixed with 10 μg/mL of human B7-1-Biotin protein (Acrobiosystems, B71-H82F2), added to the well plate. The isotype antibody hIgG1 iso was used as a control. They were incubated under the condition of 37° C. for 1.5 hrs. After 3 times of washing, 100 μL of Streptavidin-HRP (SIGMA, S2438) was added to each well, and was kept away from light for reaction under the condition of 37° C. for 1 hr. After 3 times of washing, 100 μL of TMB color-substrate solution was added, kept away from light for coloration reaction for 5 mins at room temperature. The stop solution was added to stop the reaction. The Microplate Reader Enspire (PerkinElemer) was used to detect the absorption values at 450 nm (OD450). The software GraphPad Prism 8 was applied to perform data processing and plotting analysis, the parameters such as binding curves and IC50 values were obtained by four-parameter non-linear fitting.

Figure 8:
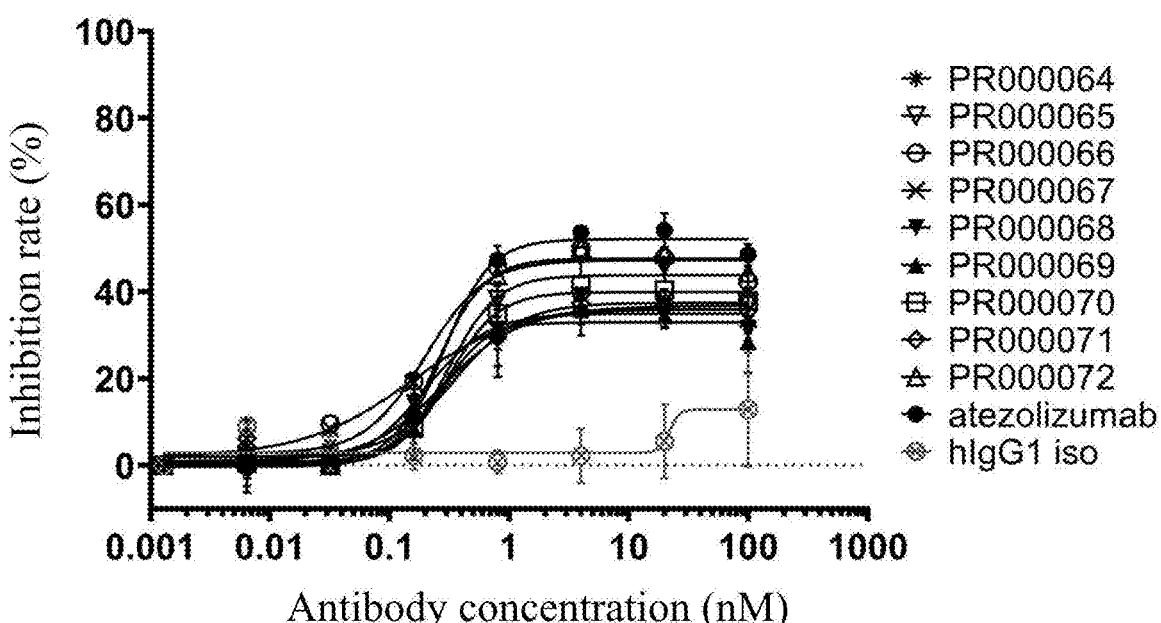
FIG. 8 shows that the antigen binding proteins of the present application block the binding of biotinylated human B7-1(CD80) protein to human PD-L1 protein.

FIG. 8 and Table 12 show that all the antigen binding proteins described in the present application are capable of blocking the binding of human B7-1 (CD80) to human PD-L1 protein.

US 12,662,537 B2

71 72

TABLE 12

Blocking the binding of human B7-1 (CD80) to human PD-L1

| Antigen binding protein | Maximum inhibition rate (%) | IC50 (nM) |
|---|---|---|
| PR000064 | 35.93 | 0.284 |
| PR000065 | 43.77 | 0.312 |
| PR000066 | 47.24 | 0.198 |
| PR000067 | 36.88 | 0.153 |
| PR000068 | 34.95 | 0.199 |
| PR000069 | 32.95 | 0.280 |
| PR000070 | 39.93 | 0.305 |
| PR000071 | 37.48 | 0.351 |
| PR000072 | 47.63 | 0.253 |
| atezolizumab | 52.11 | 1.622 |
| hIgG1 Control | N.A. | N.A. |

Example 6 Detection of the Inhibiting Effect of the Antigen Binding Proteins on PD-1 Signaling Pathway Using Reporter Gene Cell Line The Hep3B cells co-expressing human PD-L1 and OS8 (CD3 single chain antibody transmembrane protein) (constructed by ChemPartner (Shanghai)) were seeded on 96-well plate at 100 μL/well, with the cell amount of $1.25 \times 10^4$/well. Cells were incubated at 37° C. under the condition of 5% $CO_2$ overnight. The supernatant was discarded, and 50 μL/well of the diluents of the antigen binding proteins to be tested, which were diluted 5-fold starting from the initial concentration of 100 nM, were added. The isotype antibody hIgG1 iso was as a control. $5 \times 10^4$/well of the Jurkat reporter cells that could continuously express PD-1 and NFAT-luciferase reporter genes (constructed by ChemPartner (Shanghai)) were added at 50 μL/well. The plated was incubated at 37° C. under the condition of 5% $CO_2$ for 6 hrs. ONE-Glo™ luciferase reagent (Promega, Cat. No. E6110) was added, incubated at room temperature for 5 mins, and then the Microplate Reader was used to detect luminescence values.

Figure 9:
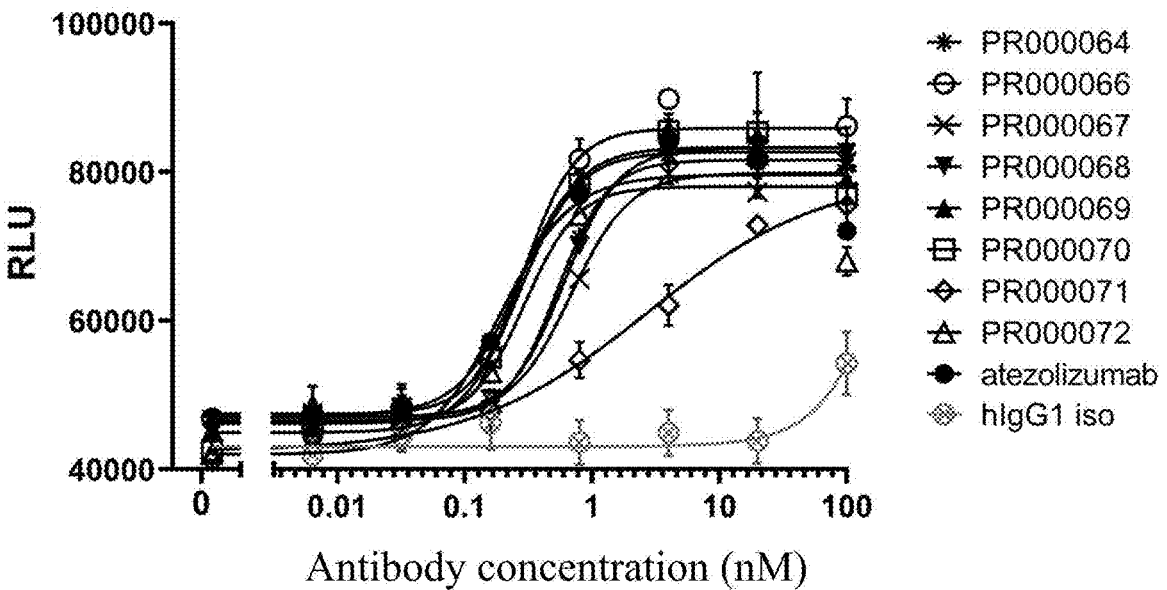
FIG. 9 shows that the inhibition of PD-1 signaling pathway by the antigen binding proteins of the present application.
Figure 10:
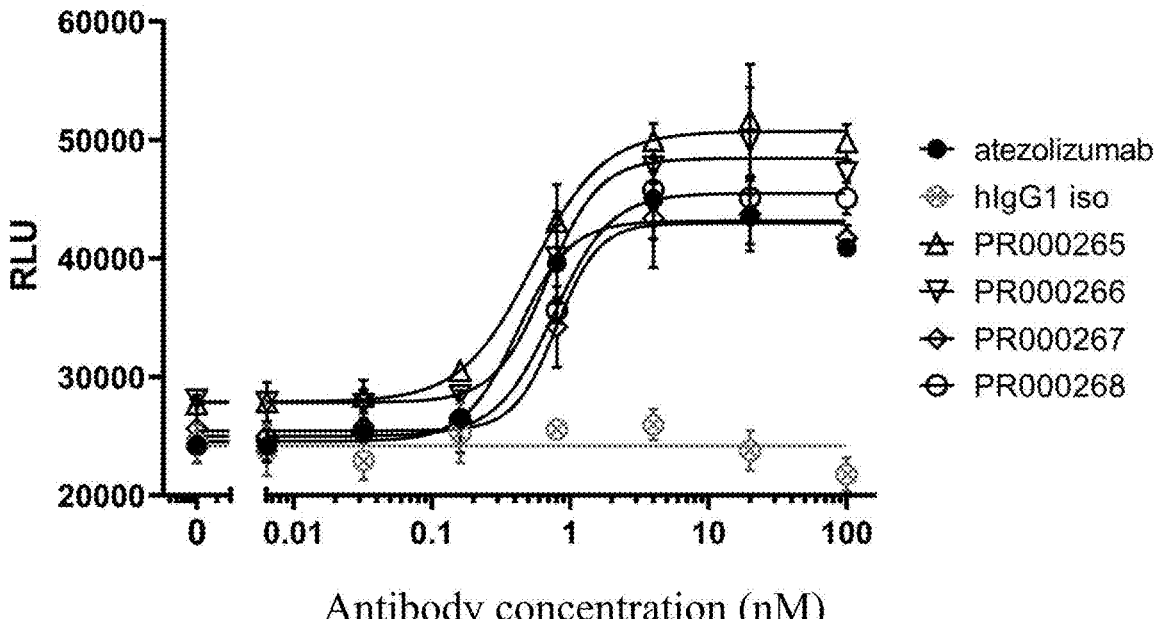
FIG. 10 shows that the inhibition of PD-1 signaling pathway by the antigen binding proteins of the present application.

FIG. 9 and Table 13 as well as FIG. 10 and Table 14 show that the antigen binding proteins described in the present application have inhibiting effects on PD-1 signaling pathway; except for PR000071, the inhibition of other molecules on PD-1 signaling pathway are comparable to that of atezolizumab analog.

TABLE 13

The inhibiting effect on PD-1 signaling pathway

| Antigen binding protein | Maximum fluorescence value (RLU) | EC50 (nM) |
|---|---|---|
| PR000064 | 81597 | 0.533 |
| PR000066 | 85890 | 0.292 |
| PR000067 | 79845 | 0.682 |
| PR000068 | 83254 | 0.603 |
| PR000069 | 83317 | 0.271 |
| PR000070 | 82697 | 0.269 |
| PR000071 | 79738 | 2.707 |
| PR000072 | 78043 | 0.293 |
| atezolizumab | 79621 | 0.190 |
| hIgG1 Control | N.A. | N.A. |

TABLE 14

The inhibiting effect on PD-1 signaling pathway

| Antigen binding protein | Maximum fluorescence value (RLU) | EC50 (nM) |
|---|---|---|
| atezolizumab | 43162 | 0.416 |
| hIgG1 control | N.A. | N.A. |
| PR000265 | 50732 | 0.533 |
| PR000266 | 48436 | 0.680 |
| PR000267 | 42982 | 0.796 |
| PR000268 | 45501 | 0.759 |

Example 7 Determination of the Affinity of the Antigen Binding Proteins with Human PD-L1 Using BLI Method 7.1 Determination of the Dissociation Constant of the Antigen Binding Proteins with Human PD-L1, and the Comparison of Dissociation Rates of Antigens at a Single Concentration The human PD-L1 protein with histidine tag was purchased from the manufacturer NovoProtein (Cat. No. C315); the test buffer was 1×kinetic buffer (diluted from 10×kinetic buffer (ForteBio, Cat. No. 18-1105)) for testing affinity and dilution of antigens and antibodies; Biolayer Interferometry (BLI) technology and Octet Molecular Interaction Analyzer (ForteBio, Octet Red96e) were used to analyze the binding kinetics between an antigen and an antibody.

When determining the affinity of the antigen with the antibody, the rotation speed of the sensor was 1000 rpm. First, the two AHC sensors placed in a column were equilibrated in the test buffer for 10 mins, and then the AHC sensors were used to capture the antigen binding proteins to be tested with the capture height of 0.9-1.1 nm. Then the AHC sensors were equilibrated in the test buffer for 2 mins. Then the AHC sensors were bound to the antigen (60 nM and 0 nM) for 3 mins, finally were dissociated for 15 mins. The AHC sensors were immersed in a 10 mM glycine (pH 1.5) solution for regeneration to elute the proteins bound to the sensors.

When using Octet Data Analysis software (Fortebio, version 11.0) for data analysis, the single deduction mode (reference well) was selected to deduct the reference signal, the "1:1 Local/full fitting" method was selected for data fitting, and kinetic parameters of the binding of antigens and antibodies were calculated, the $k_{on}$ (1/Ms) values, $k_{dis}$ (1/s) values and $K_D$ (M) values were obtained.

Figure 11:
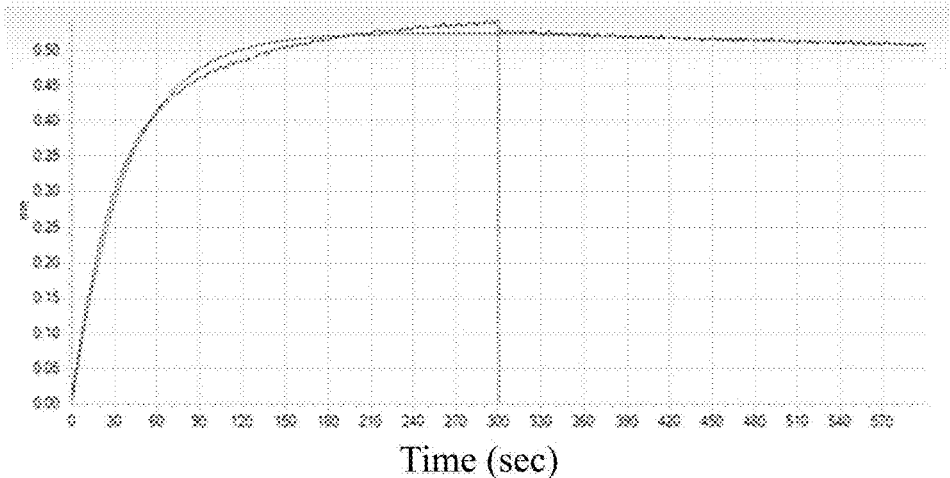
FIG. 11 shows that the affinity of the antigen binding proteins of the present application to human PD-L1; (A) antigen binding and dissociation curve of PR000265 at a single concentration, (B) antigen binding and dissociation curve of PR000266 at a single concentration, (C) antigen binding and dissociation curve of PR000265 at multiple concentrations, (D) antigen binding and dissociation curve of PR000151 at multiple concentrations, (E) antigen binding and dissociation curve of PR001598 at multiple concentrations.
Figure 11:
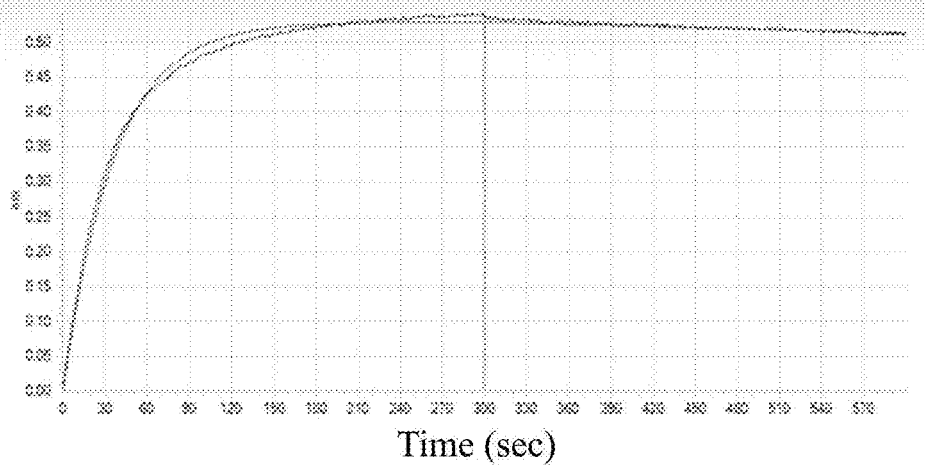
Figure 11:
Figure 11:
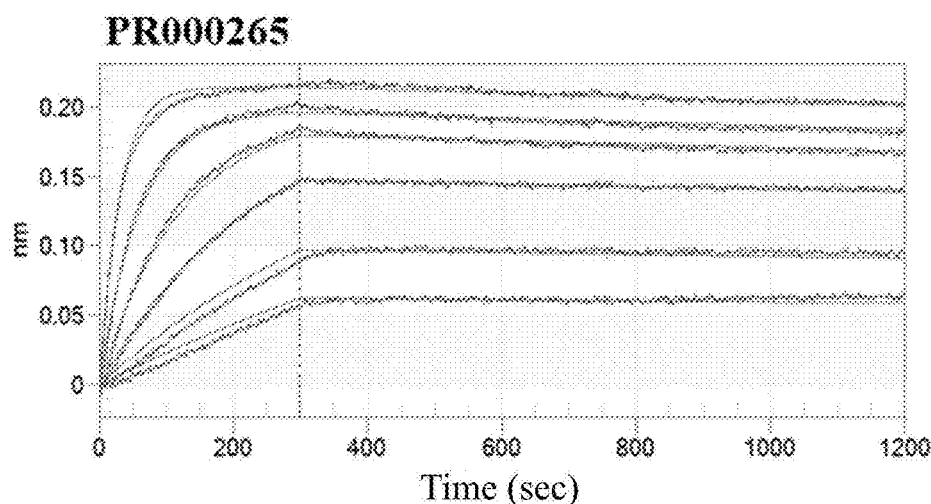
Figure 11:
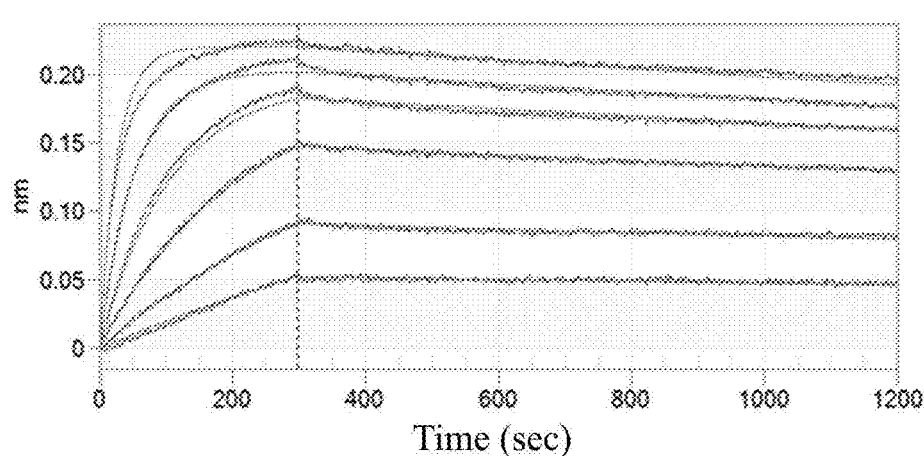
Figure 11:
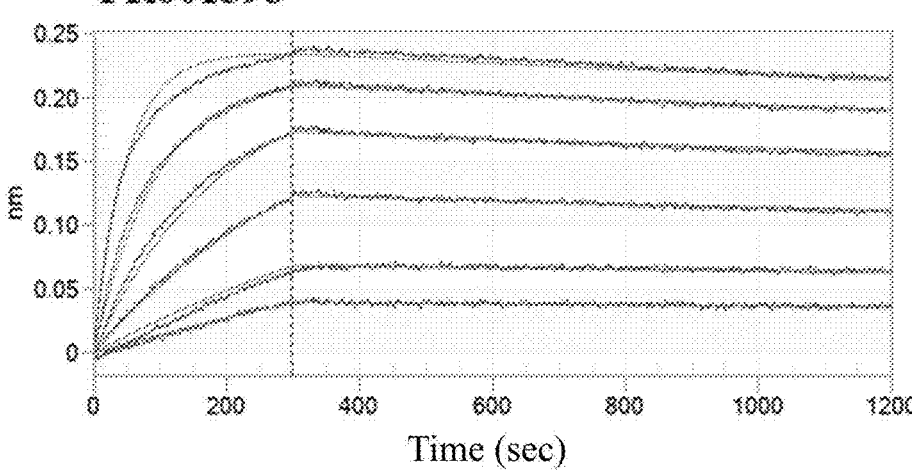

The results are shown in FIG. 11 (A-B) and Table 15-1, both PR000265 and PR000266 have higher affinity with PD-L1.

TABLE 15-1

The affinity of the antigen binding proteins with human PD-L1

| Antigen binding protein | $K_{on}$ (1/Ms) | $K_{dis}$ (1/s) | $K_D$ (M) |
|---|---|---|---|
| PR000265 | 2.60E+05 | 1.06E−04 | 4.09E−10 |
| PR000266 | 2.76E+05 | 9.62E−05 | 3.49E−10 |

7.2 Determination of the Association Constant and Affinity of the Antigen Binding Proteins with Human PD-L1 (Multi-Concentration Antigen)

According to the method of Example 7.1, the affinity of antigen (multi-concentration) with antibody was determined. When determining the affinity of antigen (multi-concentration) with antibody, the rotation speed of the sensor was 1000 rpm. First, the two columns of AHC sensors (8 sensors were placed in each column; the sensors in the first column were called reference AHC sensors, the sensors in the second column were called test AHC sensors) were equilibrated in the test buffer for 10 mins. Then, the 8 test AHC sensors were used to capture the antigen binding proteins to be tested (at the concentration of 40 nM), with the capture time of 30 s, the capture height of about 0.7 nm; after the 8 test AHC sensors were equilibrated in the test buffer for 2 minutes, they were bound to the antigen proteins which were serially diluted (for example, the antigen concentrations may be the gradient dilutions by 2-fold starting from 50-1.56 nM and 0 nM), wherein the 8 sensors may be immersed to up to 8 different concentrations of antigen; were bound to the antigen for 5 minutes, then dissociated for 15 minutes; finally, the AHC sensors were immersed in a 10 mM glycine (pH 1.5) solution for regeneration to elute the proteins bound to the sensors. The experimental procedure of the reference AHC sensor was the same as that of the test AHC sensor, with the only difference that in the first step, the 8 reference AHC sensors were immersed in the test buffer without the molecule to be tested for 30 seconds.

When using Octet Data Analysis software (Fortebio, version 11.0) for data analysis, the double deduction mode (double reference) was selected to deduct the reference signal, the "1:1 Global fitting" method was selected for data fitting, the kinetic parameters of the binding of the antigen and the antigen binding proteins were calculated, and the $k_{on}$ (1/Ms) values, $k_{dis}$ (1/s) values and $K_D$ (M) values were obtained.

The results are shown in FIG. 11 (C-E) and Table 15-2, the affinity of PR000265 with PD-L1 is higher than those of PR000151 (atezolizumab analog) and PR001598 (avelumab analog).

immersed in the antibody (50 nM) for 500 s, and the final signal of the binding of the antibody to PD-L1 was recorded as the 100% signal of this antibody. Step 2, epitope competition experiment: the SA sensor was used to capture the biotinylated PD-L1 protein with the capture height of 0.25 nm. The sensor was immersed in the first antibody (50 nM) for 500 s, and then the SA sensor was immersed in the mixture of the first antibody and the second antibody (the final concentrations of both antibodies were 50 nM) for 500 s, and the final signal was recorded as the signal of the second antibody. The inhibition rate was calculated by the following formula, $$\text{Inhibition rate } (\%)=(A-B)/A*100$$

A: 100% signal of a certain antibody (obtained from Step 1), B: signal of this antibody as the second antibody (obtained from Step 2).

If the obtained inhibition rate is greater than 85(%), it means that the epitopes bound by the two antibodies completely overlap; if the inhibition rate is less than 85(%), it means that the epitopes bound by the two antibodies do not completely overlap.

Among them, the antibody PR000416 is an antibody obtained by replacing the heavy chain constant region of the antigen binding protein PR000265 described in the present application with the human IgG1 constant region which does not have mutation.

The results show that the epitope of PR000265 (or PR000416) and the epitope of the control antibody PR000151 or PR001598 do not completely overlap, see Table 16-1 and Table 16-2.

TABLE 16-1

| Epitope competition of the antigen binding proteins | | | |
|---|---|---|---|
| Competitive | | The second antibody | |
| inhibition rate (%) | | PR000265 | PR000151 | PR001598 |
| The first antibody | PR000265 | 94.33 | 78.95 | 75.87 |

TABLE 15-2

| The affinity of the antigen binding proteins with human PD-L1 | | | | | | | |
|---|---|---|---|---|---|---|---|
| Antigen binding protein | Antigen concentration (nM) | $K_D$ (M) | $K_D$ error | $k_{on}$ (1/Ms) | $k_{on}$ error | $k_{dis}$ (1/s) | $k_{dis}$ error |
| PR000265 | 50~1.56 | 1.06E−10 | 1.55E−12 | 6.69E+05 | 2.37E+03 | 7.09E−05 | 1.01E−06 |
| PR000151 | 50~1.56 | 1.95E−10 | 1.35E−12 | 7.55E+05 | 2.34E+03 | 1.47E−04 | 9.10E−07 |
| PR001598 | 50~1.56 | 2.51E−10 | 2.62E−12 | 4.18E+05 | 1.45E+03 | 1.05E−04 | 1.04E−06 |

Example 8 Determination of the Epitope Competition of Binding of the Antigen Binding Proteins to PD-L1 Using BLI Method First, the human PD-L1 protein (NovoProtein, C315) was biotinylated using a biotinylation kit (EZ-Link Sulfo-NHS-LC-Biotin, ThermoFisher, A39257) according to the requirements of instructions. Then the ForteBio Octet platform was used to perform epitope competition experiments on the obtained antigen binding proteins with PR000151 (atezolizumab analog) and PR001598 (avelumab analog). Step 1, obtaining the 100% signal of the antibody: the SA sensor was used to capture the biotinylated PD-L1 protein with the capture height of 0.25 nm. The sensor was

TABLE 16-2

| Epitope competition of the antigen binding proteins | | | |
|---|---|---|---|
| Competitive | | The second antibody | |
| inhibition rate (%) | | PR000416 | PR001598 |
| The first antibody | PR000416 | 93.20 | 77.41 |

Example 9 the Antigen Binding Proteins Stimulate the Secretion of Cytokines in Mixed Lymphocyte Reaction (MLR)

The PBMC cells were isolated from the whole blood of the first donor using Ficoll-Paque Plus (GE Healthcare, 17144002). After 6 days of induction by adding recombinant human IL-4 (R&D Systems, 204-GMP) and recombinant human GM-CSF (R&D Systems, 215-GM/CF), immature human CD14+ dendritic cells (iDC cells) were obtained; then 1 µg/mL of lipopolysaccharide (Lipopolysaccharide, LPS; Sigma, L2630) was added, induction was performed for 24 hrs, and the mature dendritic cells (mDC cells) were obtained. T cell isolation kits (StemCell, 17951) were used to isolate and obtain T lymphocytes from the PBMC cells from the second donor. $1 \times 10^5$/well of T lymphocytes and $1 \times 10^4$/well of mDC cells were seeded in 96-well plate in a ratio of 10:1, 10 µg/mL of each of the antigen binding proteins and the control antibody were added, which were diluted 10-fold or corresponding folds. They were incubated at 37° C. in 5% $CO_2$ incubator for 5 days. The supernatant after 72 hrs and 120 hrs was collected separately. The IL2 ELISA kit (Thermo, 88-7025-88) was used to detect the level of IL-2 in the supernatant after 72 hrs; the IFN-γ ELISA kit (Thermo, 88-7316-88) was used to detect the level of IFN-γ in the supernatant after 120 hrs. the reagent instructions were referenced for specific operations.

Figure 12:
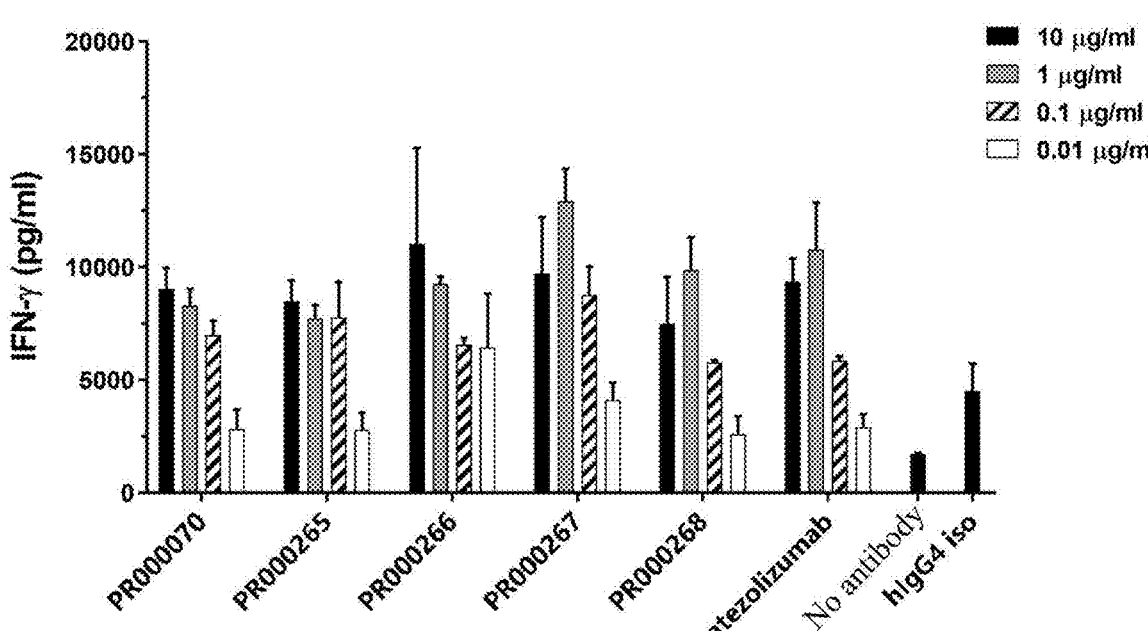
FIG. 12 shows that the antigen binding protein of the present application stimulates the secretion of cytokines in mixed lymphocyte reaction (MLR): in the first group of donor-paired MLR experiments, (A) the levels of IFN-γ in the supernatants after 120 hrs, (B) the levels of IL-2 in the supernatants after 72 hrs; in the second group of donor-paired MLR experiments, (C) the levels of IFN-γ in the supernatants after 120 hrs, (D) the levels of IL-2 in the supernatants after 72 hrs.
Figure 12:
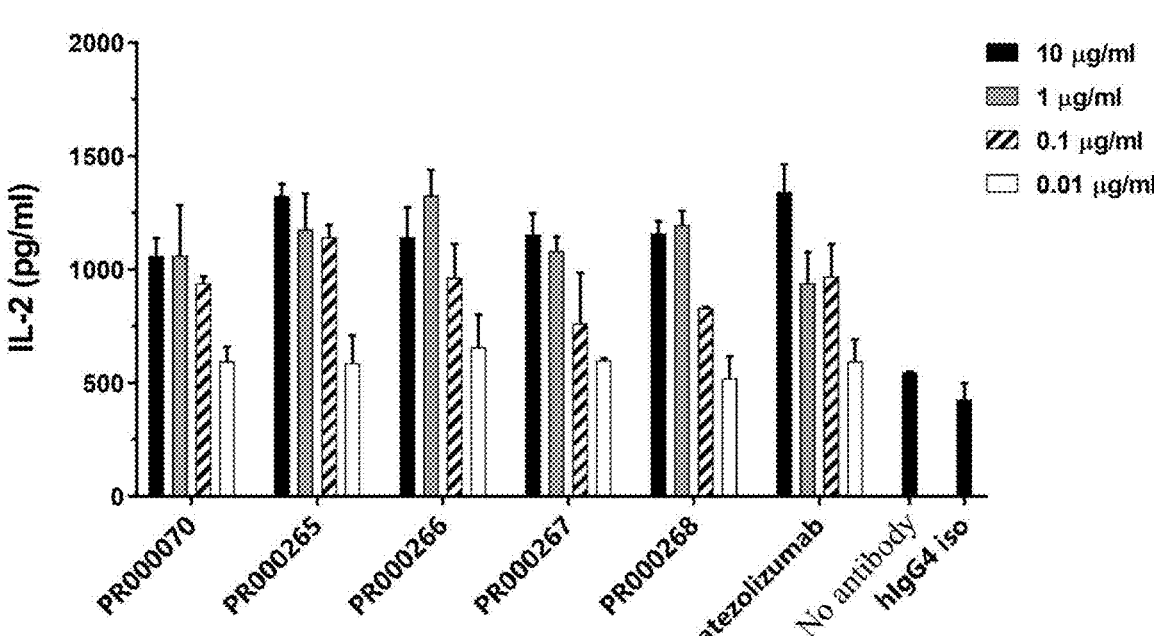
Figure 12:
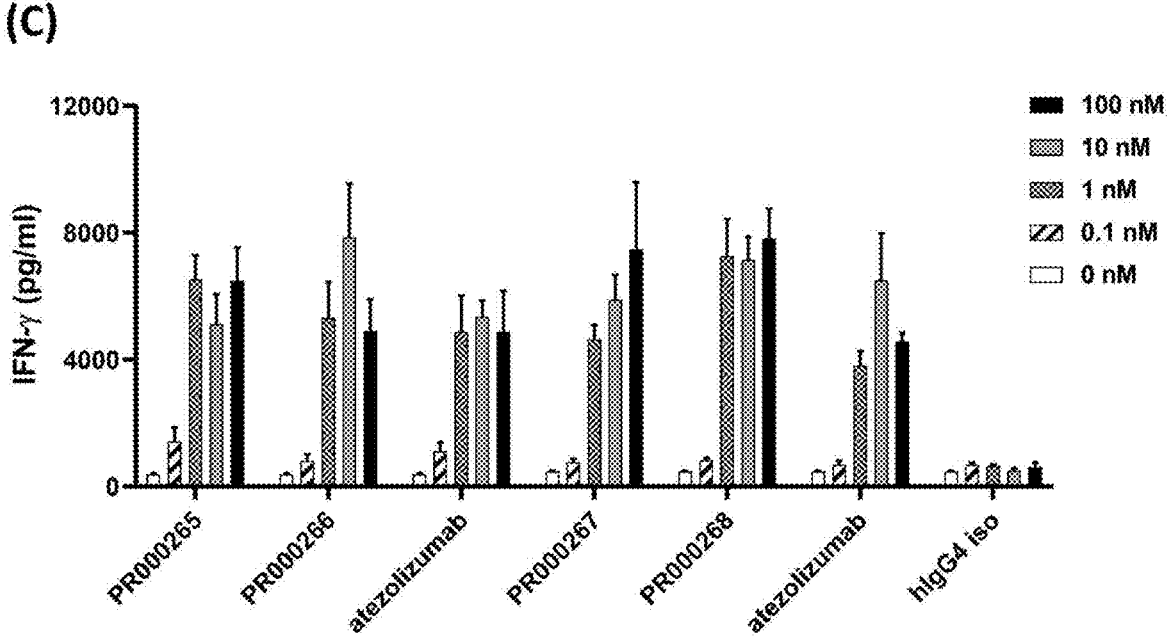
Figure 12:
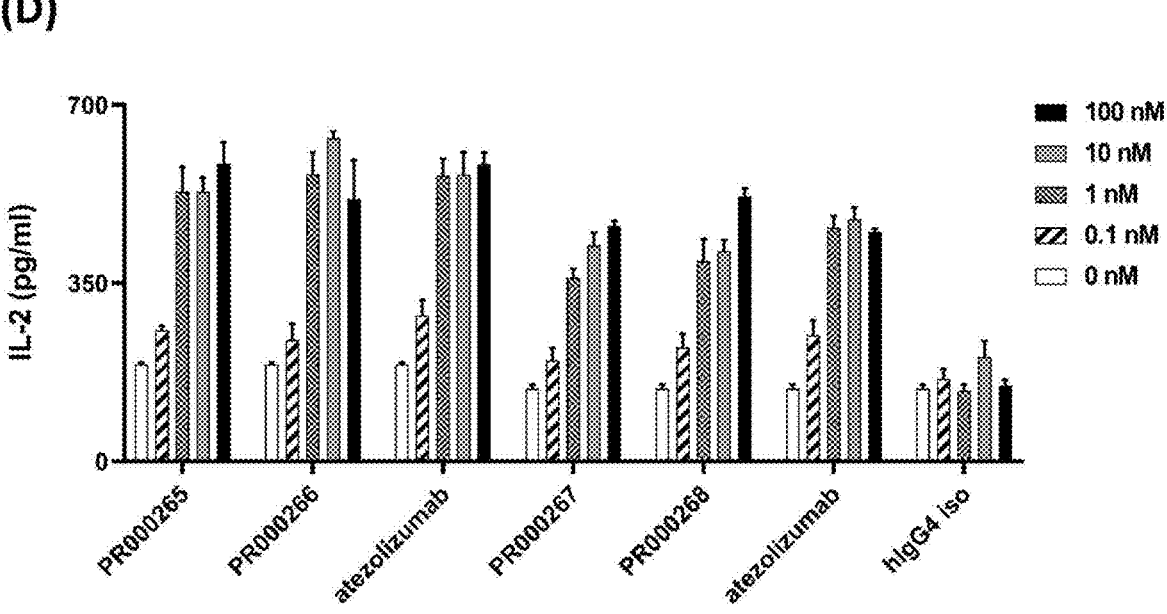

In this example, PBMCs of four donors were divided into two groups of donor pairs for mixed lymphocyte reaction (MLR). The results are shown in FIG. 12 (A-D). In two independent MLR experiments, all the antigen binding proteins are capable of enhancing the secretion of cytokines IL-2 and IFN-γ by the activated T lymphocytes.

Example 10 Antibody-Dependent Cytotoxicity Experiment

Figure 13:
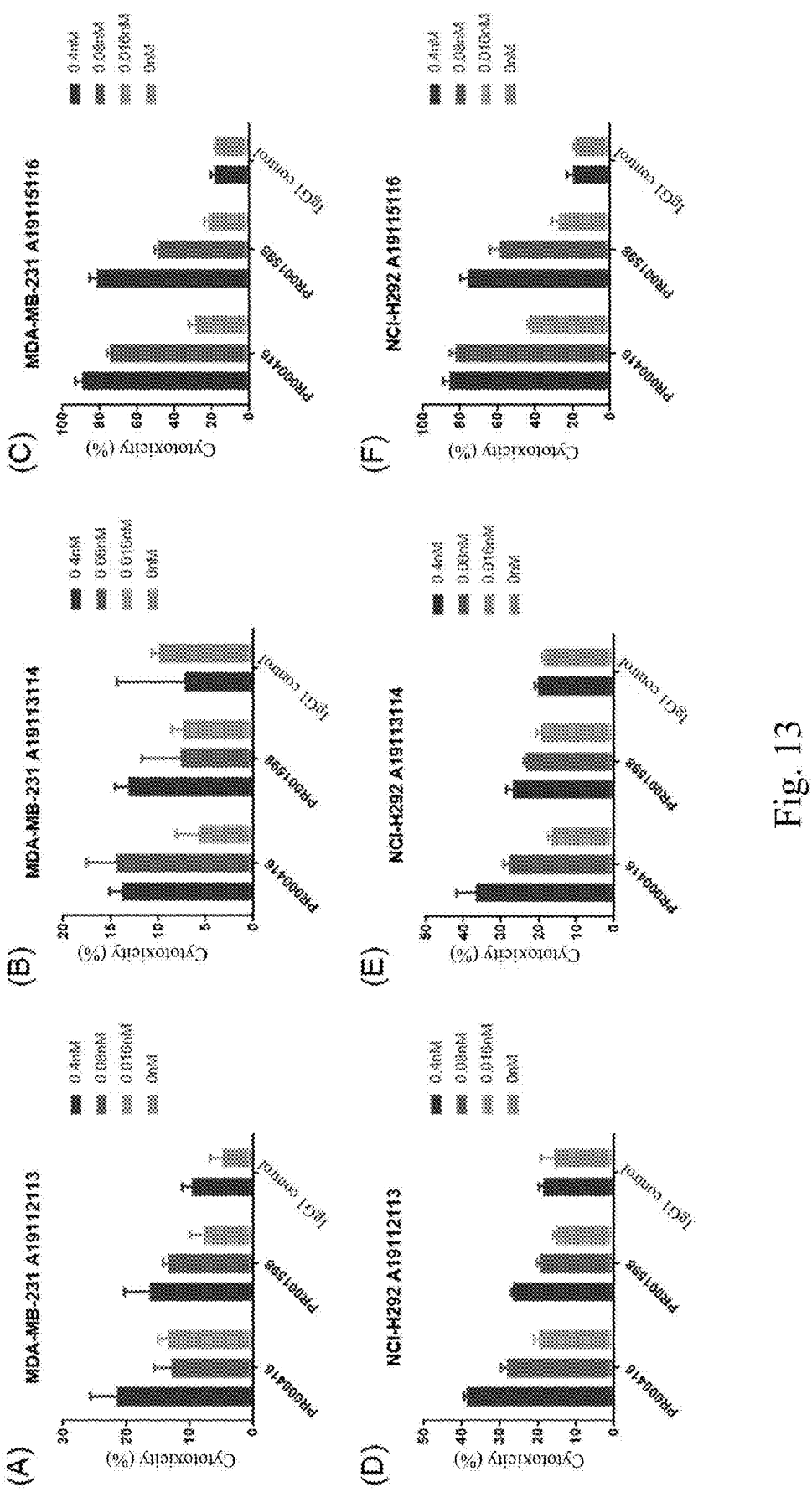
FIG. 13 shows that the results of antibody-dependent cytotoxicity of the antigen binding proteins of the present application: (A-C) the killing of the tumor cells MDA-MB-231 by the PBMCs from three different donors; (D-F) the killing of the tumor cells NCI-H292 by the PBMCs from three different donors.

This example measures the antibody-dependent cytotoxicity (ADCC). In this example, PBMCs were used as effector cells, multiple types of tumor cell lines with high expression of PD-L1 were used as target cells (such as MDA-MB-231 cells (ATCC, HTB-26), NCI-H292 cells (ATCC, CRL-1848)). Specifically, the fresh PBMCs were centrifuged to discard the supernatant, resuspended in 10% FBS-RPMI1640 medium, and incubated overnight in a 37° incubator. The PBMC cells were collected, centrifuged to discard the supernatant, resuspended in 2% FBS-RPMI1640 medium, and counted, then the cell density was adjusted to $1 \times 10^7$/mL, PBMCs were added into a U-shaped bottom 96-well plate at 50 µL/well. The target cells were collected, centrifugated to discard supernatant, resuspended in 2% FBS-RPMI1640 medium, and counted, and then the cell density was adjusted to $4 \times 10^5$/mL, the target cells were added into a U-shaped bottom 96-well plate at 25 µL/well. The ratio of effector cells and target cells was 50:1. The antibody was diluted to an intermediate concentration, wherein the initial concentration of 1.6 nM was diluted 5-fold serially to obtain 3 concentrations in total. The samples were added into a U-shaped bottom 96-well plate at 25 µL/well, the final initiation concentration of the samples was 0.4 nM. The cell plate was placed in an incubator to incubate for 3.5 hrs, 10 µL of lysis buffer was added into the target cell maximum release well and the volume reference well, and incubation was continued for 30 mins, with the total time of incubating cells and samples together of 4 hrs. 50 µL/well of supernatant was taken into a transparent flat-bottomed 96-well plate, the detection reagent in Promega LDH kit (Promega LDH-Glo™, J2380) was added at 50 µL/well. They were incubated at room temperature for 20 mins, 50 µL of reaction stop solution was added to stop the reaction. The microplate reader was used to read the absorbance value $OD_{450\ nm}$. The cytotoxicity was calculated according to the following calculation formula.

$$\text{cytotoxicity } (\%) = ((ER-CMB)-(ESR-CMB)-(TSR-CMB))/(TMR-VCC) \times 100\%$$

wherein:
ER=experiment well, sample+ effector cells+target cells
ESR=effector cell spontaneous release well, effector cells+culture medium
TSR=target cell spontaneous release well, target cells+culture medium
TMR=target cell maximum release well, target cells+culture medium+lysis buffer
VCC=volume reference well, culture medium+lysis buffer
CMB=culture medium reference well, culture medium
PBMCs of three donors and two tumor cell lines were used in this example, with six independent ADCC experiments in total. The results are show in FIG. 13 (A-F). PR000416 (PR000416 is an antibody obtained by replacing PR000265 with human IgG1 constant region which has no mutation) has a stronger ADCC effect than PR001598 (avelumab analog).

Example 11 In Vivo Inhibiting Tumor Activity of the Antigen Binding Proteins $5 \times 10^5$ cells/0.1 mL MC38-hPD-L1 (MC38 cells overexpressing human PD-L1) colon cancer cells were inoculated subcutaneously on the right side of female B-hPD-1 humanized mice (Biocytogen). When the tumor grown to about 118 $mm^3$, the mice were randomly divided into groups according to the tumor volume. There are 10 mice in each group, a total of 5 groups, that is: Human IgG1 (3 mg/kg, human IgG1 isotype control group), PR000151 (3 mg/kg, Atezolizumab low-dose group), PR000151 (10 mg/kg, Atezolizumab high-dose group), PR000265 (3 mg/kg, low-dose group of the antibody of the present application) and PR000265 (10 mg/kg, high-dose group of the antibody of the present application). The route of administration was intraperitoneal injection, once every 2 days, for a total of 13 administrations (q2d×13). The tumor volume and body weight were measured twice a week, and the mouse body weight and tumor volume were recorded.

On the $20^{th}$ day of administration in group, the tumor volume of the hIgG1 control group was 1359±171 $mm^3$. The tumor volumes of the anti-PD-L1 antibody PR000151 at the doses of 3 mg/kg and 10 mg/kg were 898±233 $mm^3$ and 741±203 $mm^3$, respectively, and the TGIs were 33.9% and 45.5%, respectively. The tumor volumes of the anti-PD-L1 antibody PR000265 at the doses of 3 mg/kg and 10 mg/kg were 881±169 $mm^3$ and 1035±472 $mm^3$, respectively, and the TGIs were 35.1% and 23.8%, respectively. On the $24^{th}$ day of administration in group, the tumor volume of the human IgG1 control group was 1876±203 mm³. The tumor volumes of the anti-PD-L1 antibody PR000151 at the doses of 3 mg/kg and 10 mg/kg were 1349±306 mm³ and 949±266 mm³, respectively, and the TGIs were 28.1% and 49.4%, respectively. The tumor volumes of the anti-PD-L1 antibody PR000265 at the doses of 3 mg/kg and 10 mg/kg were 1228±187 mm³ and 937±225 mm³, respectively, and the TGIs were 34.5% and 50.1%, respectively. Both PR000151 and PR000265 had significant tumor inhibitory effects at the doses of 3 mg/kg and 10 mg/kg, and compared with hIgG1, there was a statistical difference (P<0.05). The efficacy of PR000151 and PR000265 were similar, and there was no statistical difference between the groups (P>0.05).

Figure 14:
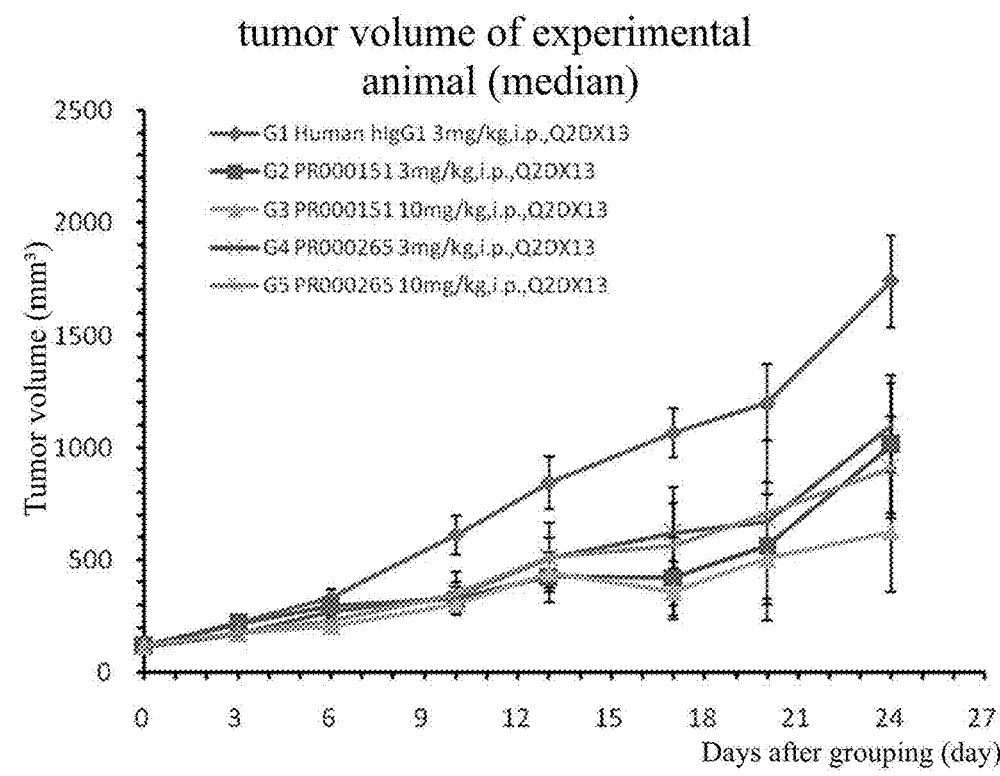
FIG. 14 shows that the activity of inhibiting tumor in vivo of the antigen binding proteins of the present application, the change in tumor volume (A) and the change in mouse body weight (B), respectively.
Figure 14:
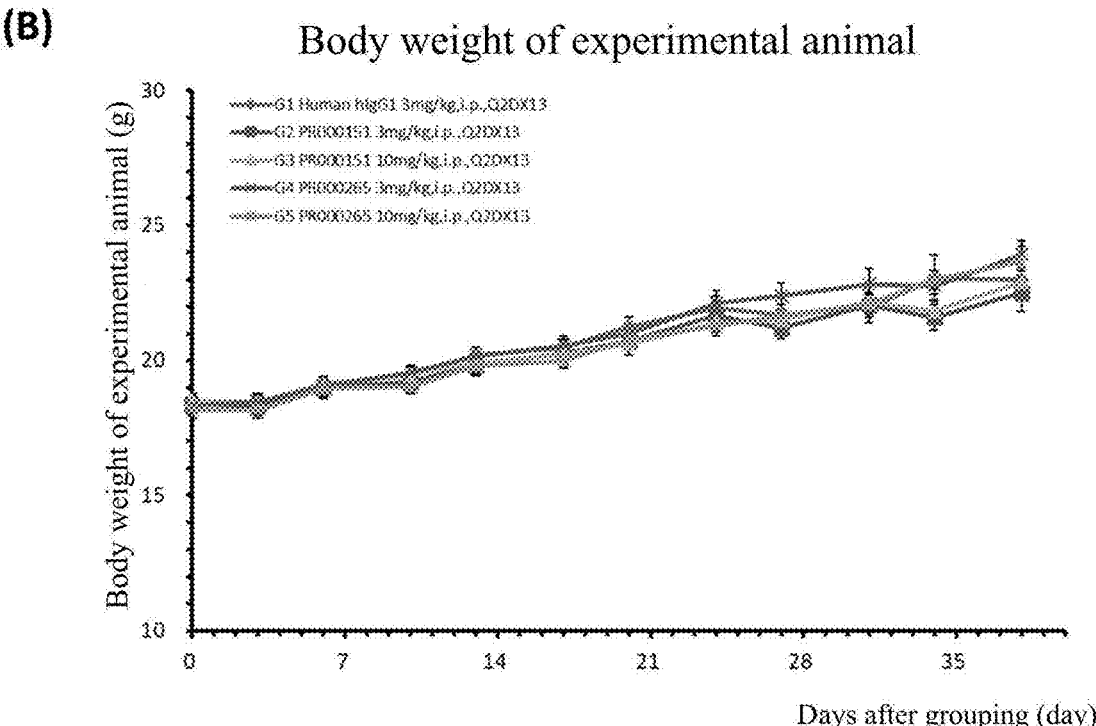

The results are shown in FIG. 14. Both PR000151 and PR000265 have significant tumor inhibitory effects. During the experiments, the body weight of each group of animals all increased, indicating that the animals tolerated the test product well. There is no significant toxic effect in animals with good safety.

Example 12 Preparation and Characterization Analysis of the Anti-PD-L1 and Anti-TGFB Bifunctional Fusion Proteins 12.1 Construction of the Fusion Protein Molecules The sequence of the extracellular region of human TGFB receptor (TGFBRII) was fused to the C-terminus of the antigen binding proteins obtained in Example 1 via a suitable length of flexible peptide (Linker) to construct bifunctional fusion protein molecules. The mammal host cells (such as HEK293 or ExpiCHO) were transfected with the plasmid encoding the sequence of polypeptide. The method of Example 1.3 was used to perform the recombinant expression and purification of fusion proteins. The fusion proteins of the present application PR001487, PR001488, PR001901, PR001902, PR002247, PR002248, PR002249 and PR002251 were obtained, and the structure of each portion is shown in Table 17. The sequence numberings of antibody light chains, antibody heavy chains and each domain are shown in Table 18. In addition, the protein molecule M7824 (also referred to as PR001599, which is a bintrafusp alfa analog), the protein molecule Hengrui fusion protein 9 (also referred to as PR002466, whose sequence is derived from patent WO2018205985A1), and TGFBRII Trap (also referred to as PR002040, which were obtained by fusing the sequence of anti-chicken lysozyme antibody clone TEL16 with the truncated sequence of the extracellular region of TGFBRII), were used as controls in this Example, and the structure and sequence numbering of each portion thereof are shown in Table 17 and Table 18.

TABLE 17

The structure of each portion of the fusion proteins of the present application

| Fusion protein | Initial PD-L1 antibody | Fc type (mutation) | Linker peptide | TGFBRII extracellular region (amino acid initial position) |
|---|---|---|---|---|
| PR001599 | PR001598 | hIgG1 | (G4S)4 | 24-159 |
| PR002466 | — | hIgG4 (S228P, F234A, L235A) | (G4S)4 | 43-159 |
| PR002040 | non-PD-L1 antibody | hIgG1 | (G4S)4 | 24-159 |
| PR001487 | PR000265 | hIgG1 | (G4S)3 | 23-159 |
| PR001488 | PR000265 | hIgG1 | (G4S)4 | 24-159 |
| PR001901 | PR000265 | hIgG1 | (G2S)2 | 24-159 |
| PR001902 | PR000265 | hIgG1 | none | 24-159 |
| PR002247 | PR000267 | hIgG1 | (G4S)4 | 24-159 |
| PR002248 | PR000268 | hIgG1 | (G4S)4 | 24-159 |
| PR002249 | PR000266 | hIgG1 | (G4S)4 | 24-159 |
| PR002251 | PR000070 | hIgG1 | (G4S)4 | 24-159 |

TABLE 18

The sequence numberings SEQ ID NOs of the fusion proteins of the present application

| Fusion protein | Second polypeptide | First polypeptide | VL | VH | VL CDR1 | VL CDR2 | VL CDR3 | VH CDR1 | VH CDR2 | VH CDR3 |
|---|---|---|---|---|---|---|---|---|---|---|
| PR001599 | 164 | 141 | 119 | 105 | 53 | 66 | 82 | 5 | 18 | 35 |
| PR002466 | 166 | 149 | 121 | 107 | 55 | 68 | 84 | 8 | 20 | 37 |
| PR002040 | 165 | 144 | 120 | 106 | 54 | 67 | 83 | 7 | 19 | 36 |
| PR001487 | 162 | 138 | 114 | 101 | 51 | 64 | 78 | 5 | 16 | 29 |
| PR001488 | 162 | 139 | 114 | 101 | 51 | 64 | 78 | 5 | 16 | 29 |
| PR001901 | 162 | 142 | 114 | 101 | 51 | 64 | 78 | 5 | 16 | 29 |
| PR001902 | 162 | 143 | 114 | 101 | 51 | 64 | 78 | 5 | 16 | 29 |
| PR002247 | 163 | 145 | 116 | 103 | 50 | 64 | 77 | 5 | 16 | 33 |
| PR002248 | 163 | 146 | 116 | 104 | 50 | 64 | 77 | 5 | 17 | 33 |
| PR002249 | 162 | 147 | 114 | 102 | 51 | 64 | 78 | 5 | 17 | 29 |
| PR002251 | 162 | 148 | 114 | 90 | 51 | 64 | 78 | 5 | 14 | 29 |

12.2 Analysis of Protein Purity and Polymer Using HPLC-SEC

Analytical molecule size exclusion chromatography (SEC) was used to analyze the purity and aggregate form of protein samples. The analytical column TSKgel G3000SWx1 (Tosoh Bioscience, 08541, 5 μm, 7.8 mm×30 cm) was connected to a High Pressure Liquid Chromatograph (HPLC) (model number: Agilent Technologies, Agilent 1260 Infinity II), equilibrated with PBS buffer at room temperature for at least 1 hr. An appropriate amount of protein samples (at least 10 μg, the sample concentration was adjusted to 1 mg/mL) was filtered with a 0.22 μm filter membrane and then injected into the system, and the HPLC program was set as follows: the sample in PBS (pH 7.4) buffer flowed through the chromatographic column at a flow rate of 1.0 mL/min, the longest time was 20 mins; the detection wavelength was 280 nm. After collection, Chem-Station software was used to integrate the chromatogram and calculate the relevant data, generating an analysis report which reported the retention times of the components of different molecular sizes in the sample.

12.3 Analysis of Protein Purity and Hydrophobicity Using HPLC-HIC

Analytical hydrophobic interaction chromatography (HIC) was used to analyze the purity and hydrophobicity of mine the thermal denaturation temperature (Tm) of protein molecules. 10 μg of the protein was added into a 96-well PCR plate (Thermo, AB-0700/W), then 2 μl of 100× diluted dye SYPRO™ (Invitrogen, 2008138) was added, and then buffer was added to make the final volume 40 μL per well. The PCR plate was sealed, placed in a real-time fluorescent quantitative PCR instrument (Bio-Rad CFX96 PCR System), incubated at 25° C. for 5 minutes, then the temperature was gradually increased from 25° C. to 95° C. with a gradient of 0.2° C./0.2 mins, the temperature was reduced to 25° C. at the end of the test. The FRET scanning mode was used and the Bio-Rad CFX Maestro software was used to analyze data and calculate the Tm of the sample.

12.5 Expression and Characterization Analysis of the Fusion Proteins

The expression and physicochemical properties of the fusion proteins obtained in Example 12.1 are shown in Table 19. The results show that PR001488 and PR001902 have higher yields than the control proteins PR002466 and PR001599, and PR001488 and PR001902 have better hydrophilicity than the control protein PR001599 (represented by a shorter retention time on HPLC-HIC). In general, PR001488 and PR001902 show more stable physicochemical properties than PR001599.

TABLE 19

| The expression and physicochemical properties of fusion proteins | | | | | | | |
|---|---|---|---|---|---|---|---|
| Fusion protein | Expression system and volume | Yield (mg/L) | SEC Purity (%) | HIC Purity (%) | HIC Retention time (min) | DSF (° C.) | |
| | | | | | | $Tm_1$ | $Tm_2$ |
| PR001488 | Expi-CHO (1 L) | 215.0 | 96.67% | 100.00% | 16.493 | 68.2 | 77.4 |
| PR001902 | Expi-CHO (1 L) | 217.9 | 99.60% | 98.62% | 16.453 | 67.6 | 77.2 |
| PR002466 | Expi-CHO (1 L) | 61.2 | 96.70% | 91.30% | 16.099 | 65.8 | 79.2 |
| PR001599 | Expi-CHO (1 L) | 126.5 | 98.14% | 96.68% | 18.660 | 68.2 | — | protein samples. The analytical column TSKgel Butyl-NPR (Tosoh Bioscience, 14947, 4.6 mm×3.5 cm) was connected to a High Pressure Liquid Chromatograph (HPLC) (model number: Agilent Technologies, Agilent 1260 Infinity II), and was equilibrated with PBS buffer at room temperature for at least 1 hr. The method was set as a linear gradient from 100% mobile phase A (20 mM histidine, 1.8 M ammonium sulfate, pH 6.0) to 100% mobile phase B (20 mM histidine, pH 6.0) within 16 mins, and the flow rate was set as 0.7 mL/min, the concentration of protein sample was 1 mg/ml, the injection volume was 20 μL, the detection wavelength was 280 nm. After collection, ChemStation software was used to integrate the chromatogram and calculate the relevant data, generating an analysis report which reported the retention times of the components of different molecular sizes in the sample.

12.4 Determination of Thermostability of Protein Molecules Using DSF

Differential Scanning Fluorimetry (DSF) is a commonly used high-throughput method for determining the thermostability of a protein. It uses a real-time fluorescent quantitative PCR instrument to reflect the denaturation process of the protein by monitoring the change in the fluorescence intensity of the dye bound to the unfolded protein molecule, thereby reflecting the thermostability of the protein molecule. In this example, the DSF method was used to deter- Example 13 Binding of the Fusion Proteins to CHO-K1 Cells Overexpressing Human PD-L1

The in vitro binding activity of the fusion proteins described in the present application to human PD-L1 was tested according to the method of Example 2.

Figure 15:
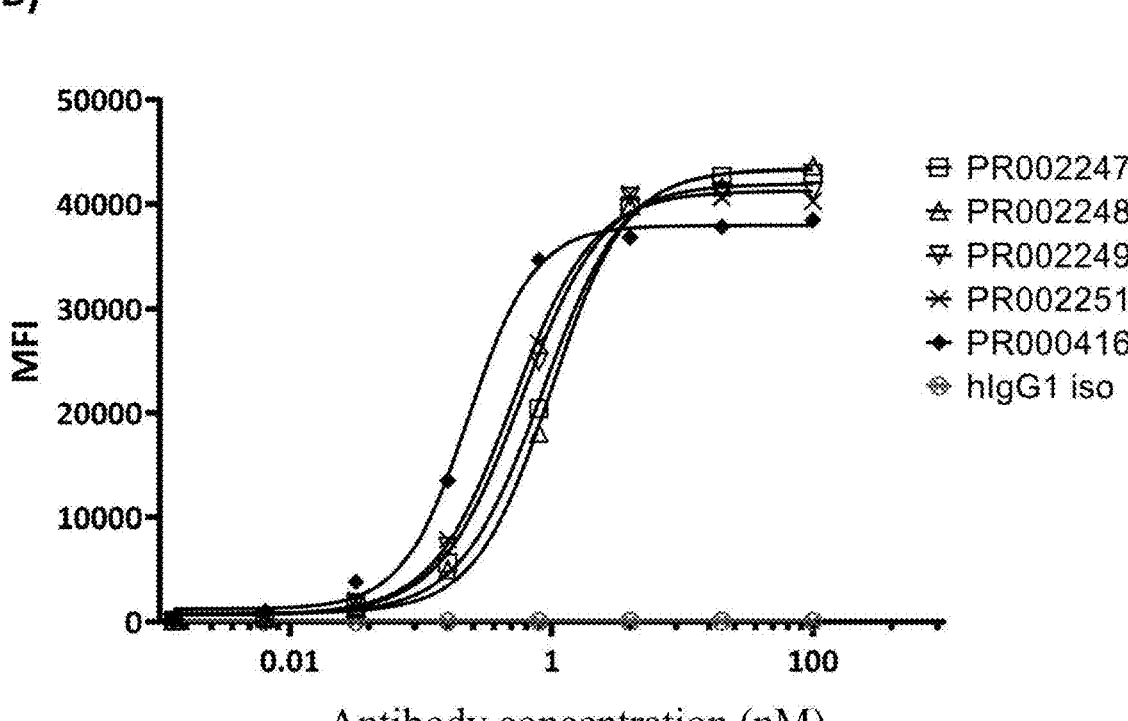
FIG. 15 shows that the fusion proteins of the present application bind to the CHO-K1 cells overexpressing human PD-L1: (A) the fusion proteins listed in Table 20-1, (B) the fusion proteins listed in Table 20-2.

FIG. 15 (A) and Table 20-1 as well as FIG. 15 (B) and Table 20-2 show that all the fusion proteins described in the present application are capable of binding to CHO-K1 cells overexpressing human PD-L1.

TABLE 20-1

| Binding to human PD-L1 that is on the cell surface | | |
|---|---|---|
| Fusion protein | MFI maximum value | EC50 (nM) |
| atezolizumab | 50075 | 0.3785 |
| PR001487 | 52996 | 0.3137 |
| PR001488 | 51536 | 0.5311 |
| PR001598 | 42395 | 0.5069 |
| PR001599 | 46184 | 0.7181 |
| PR001901 | 46836 | 0.4884 |
| PR001902 | 45373 | 0.5147 |
| PR000416 | 40359 | 0.2585 |

TABLE 20-2

| | Binding to human PD-L1 that is on the cell surface | |
|---|---|---|
| Fusion protein | MFI maximum value | EC50 (nM) |
| PR002247 | 43412 | 0.8518 |
| PR002248 | 43291 | 0.9836 |
| PR002249 | 41931 | 0.5844 |
| PR002251 | 41242 | 0.5012 |
| PR000416 | 37937 | 0.2313 |

Example 14 the Fusion Proteins Block the Binding of Human PD-1 to CHO-K1 Cells Overexpressing Human PD-L1

The in vitro activity of the fusion proteins described in the present application in blocking the binding of human PD-1 to human PD-L1 was tested according to the method of Example 4.

Figure 16:
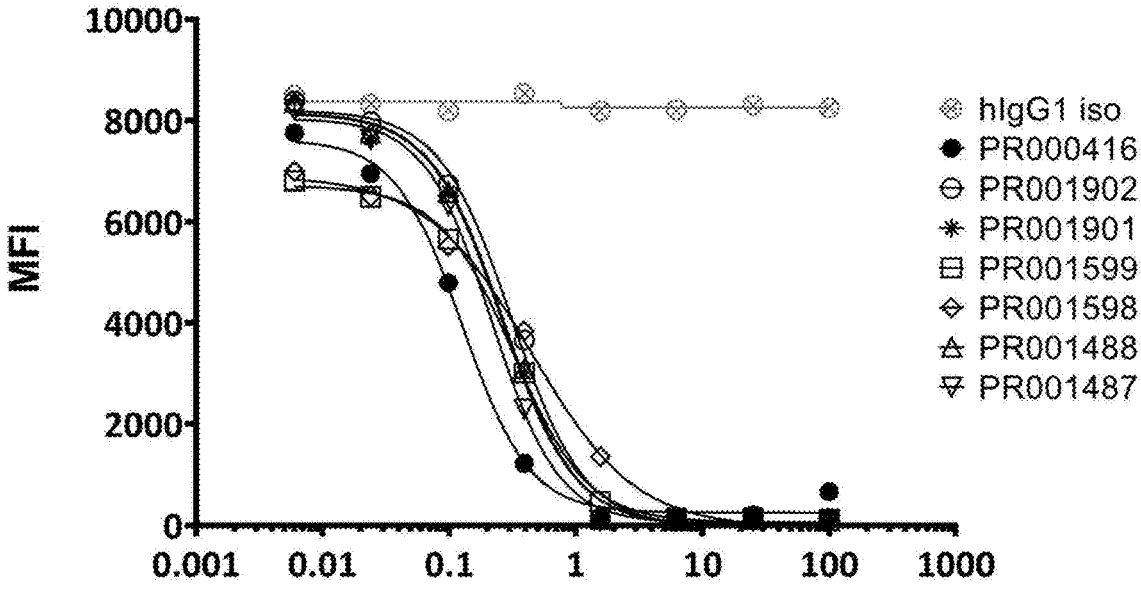
FIG. 16 shows that the fusion proteins of the present application block the binding of human PD-1 to the CHO- K1 cells overexpressing human PD-L1: (A) the fusion proteins listed in Table 21-1, (B) the fusion proteins listed in Table 21-2.
Figure 16:
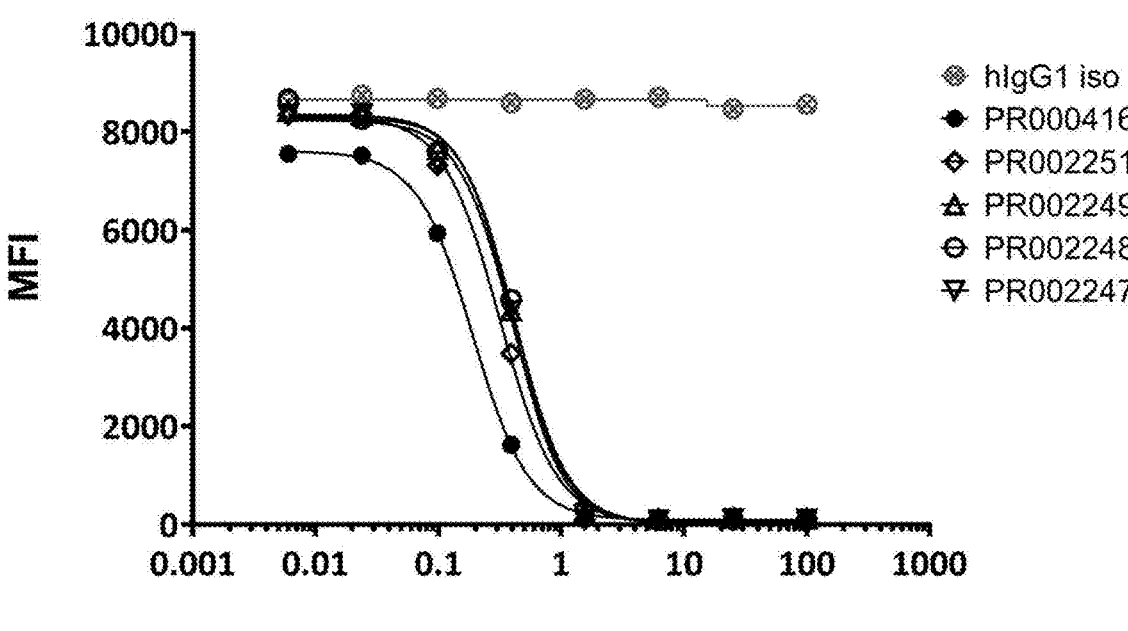

FIG. 16 (A) and Table 21-1 as well as FIG. 16 (B) and Table 21-2 show that al the fusion proteins described in the present application are capable of blocking the binding of human PD-1 to CHO-K1 cells overexpressing human PD-L1.

TABLE 21-1

| | Blocking the binding of human PD-1 to human PD-L1 that is on the cell surface |
|---|---|
| Fusion protein | IC50 (nM) |
| PR001487 | 0.2157 |
| PR001488 | 0.2661 |
| PR001598 | 0.4416 |
| PR001599 | 0.3225 |
| PR001901 | 0.2598 |
| PR001902 | 0.3107 |
| PR000416 | 0.1271 |

TABLE 21-2

| | Blocking the binding of human PD-1 to human PD-L1 that is on the cell surface |
|---|---|
| Fusion protein | IC50 (nM) |
| PR002247 | 0.3990 |
| PR002248 | 0.4178 |
| PR002249 | 0.3999 |
| PR002251 | 0.3166 |
| PR000416 | 0.1904 |

Figure 17:
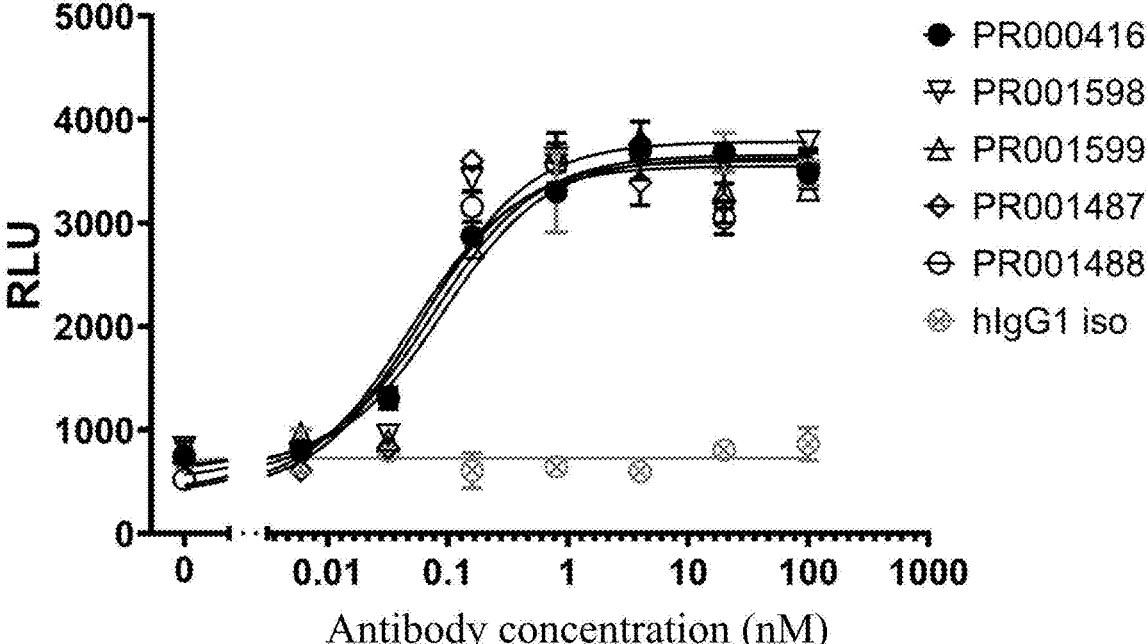
FIG. 17 shows that the inhibition of PD-1 signaling pathway by the fusion proteins of the present application.

Example 15 Detection of the Inhibitory Effect of the Fusion Proteins on PD-1 Signaling Pathway Using Reporter Gene Cell Line The reporter gene cell line was used to detect the inhibitory effect of the fusion proteins described in the present application on PD-1 signaling pathway. FIG. 17 and Table 22 show that the fusion proteins described in the present application have inhibitory effects on PD-1 signaling pathway.

TABLE 22

| | The inhibitory effect on PD-1 signaling pathway | |
|---|---|---|
| Fusion protein | Maximum fluorescence value (RLU) | EC50 (nM) |
| PR000416 | 3656 | 0.077 |
| PR001598 | 3786 | 0.068 |
| PR001599 | 3626 | 0.091 |
| PR001487 | 3600 | 0.056 |
| PR001488 | 3549 | 0.049 |

Example 16 Detection of the In Vitro Binding Effect of the Fusion Proteins to TGFB1 by Enzyme-Linked Immunosorbent Assay Human TGFB1 of the concentration of 1 μg/mL (Novoprotein, CA59) was used as antigen, and was used for the coating of the 96-well plate at 100 μL/well at 4° C. overnight. The plate was washed with 1×PBST at 200 μL/well for 3 times, 2% BSA at 200 μL/well was added, and the plate was blocked at 37° C. for 2 hrs. 1×PBST was added 200 μL/well to wash for 3 times, 5-fold concentration gradient diluted antibodies were added, wherein the highest final concentration of the antibody was 100 nM, incubated at 37° C. for 1 hr. The plate was washed with 1×PBST at 200 μL/well for 3 times, anti-human FC-HRP secondary antibody (Sigma-Aldrich, A0170, 1:4000 diluted) at 100 μL/well was added to each well, incubated at 37° C. for 1 hr. The plate was washed with 1×PBST at 200 μL/well for 3 times, then TMB was added to each well at 100 μL/well. After incubation at room temperature for 10 mins, 1M ELISA stop solution was added at 50 μL/well to stop the reaction. The microplate reader was used to detect the absorbance values at 450 nm and 570 nm. The software GraphPad Prism 8 was applied to perform data processing and plotting analysis, the parameters such as binding curves and EC50 values were obtained by four-parameter nonlinear fitting. Among them, TGFBRII-Fc is TGFBRII extracellular region fusion protein (Novoprotein, CC10), and PR001599 and PR002040 are the aforementioned control fusion protein molecules.

Figure 18:
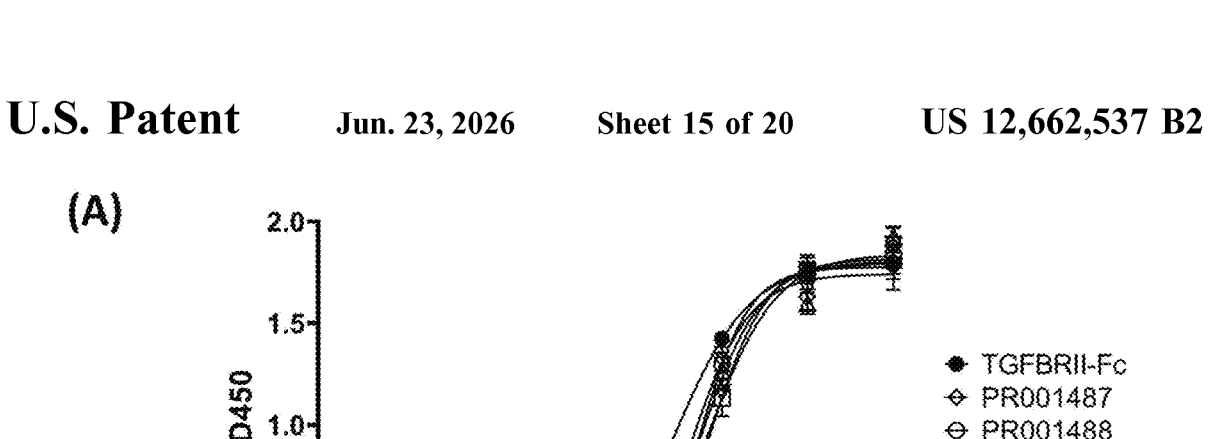
FIG. 18 shows that the fusion proteins of the present application bind to TGFB1: (A) the fusion proteins listed in Table 23-1, (B) the fusion proteins listed in Table 23-2, (C) the fusion proteins listed in Table 23-3.
Figure 18:
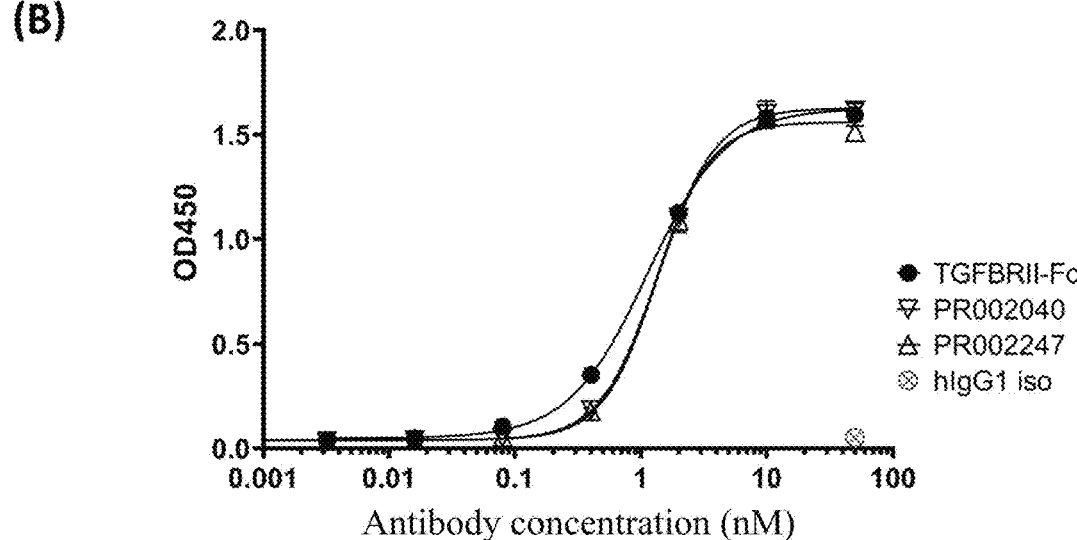
Figure 18:
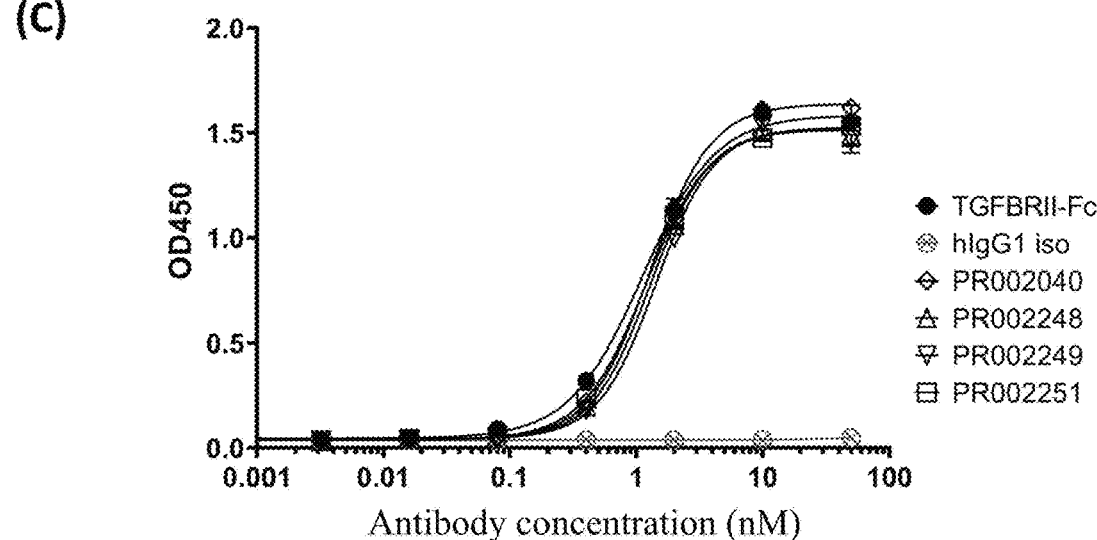

FIG. 18 (A) and Table 23-1, FIG. 18 (B) and Table 23-2, as well as FIG. 18 (C) and Table 23-3 show that all the fusion proteins described in the present application are capable of effectively binding to TGFB1, and have a drug concentration dose-dependent effect.

TABLE 23-1

| | In vitro binding to TGFB1 | |
|---|---|---|
| Fusion protein | OD Maximum value | EC50 (nM) |
| TGFBRII-Fc | 1.798 | 0.783 |
| PR001487 | 1.742 | 1.081 |
| PR001488 | 1.776 | 1.254 |
| PR001599 | 1.815 | 1.546 |
| PR001901 | 1.802 | 1.294 |
| PR001902 | 1.839 | 1.492 |

TABLE 23-2

| | In vitro binding to TGFB1 | |
| Fusion protein | OD Maximum value | EC50 (nM) |
| --- | --- | --- |
| TGFBRII-Fc | 1.626 | 1.132 |
| PR002040 | 1.627 | 1.369 |
| PR002247 | 1.560 | 1.330 |

TABLE 23-3

| | In vitro binding to TGFB1 | |
| Fusion protein | OD Maximum value | EC50 (nM) |
| --- | --- | --- |
| TGFBRII-Fc | 1.585 | 1.115 |
| PR002040 | 1.638 | 1.281 |
| PR002248 | 1.515 | 1.287 |
| PR002249 | 1.520 | 1.426 |
| PR002251 | 1.526 | 1.195 |

Example 17 the Inhibitory Effect of the Fusion Proteins on the Activation of Smad Signaling Pathway Induced by TGFB1

In this experiment, HEK-Blue™ TGFB cells (Invivogen, hkb-tgfb,) that highly express human TGFBRI and the Smad3/4 gene fused with the SEAP reporter gene were used to study the inhibitory effect of the fusion proteins on the activation of Smad signaling pathway induced by TGFB1 at cellular level. 10 µL/well, 5-fold concentration gradient dilutions of the fusion proteins to be tested were added in a 96-well plate, the highest final concentration was 50 nM. Subsequently, human TGFB1 protein (R&D Systems, 240-B/F) at a final concentration of 1 ng/mL was added at 10 µL/well into the 96-well plate. TGFB1 antibody (Biointron, B5484) and TGFBRII-Fc fusion protein (Novoprotein, CC10) were used as control molecules. 180 µL, $2.5\times10^4$ cells/well was seeded in the 96-well plate, and incubation was continued overnight in a carbon dioxide incubator. Then 20 µL of cell supernatant from each well was transferred to another 96-well plate, then 180 µL of Quanti-Blue working solution (Invivogen, rep-qb1) was added to each well, and incubation was performed at 37° C. for 1 hr. The absorbance value at 655 nm was detected on the microplate reader. The software GraphPad Prism 8 was used for data processing and graphing analysis, the parameters such as binding curves and IC50 values were obtained through four-parameter non-linear fitting.

Figure 19:
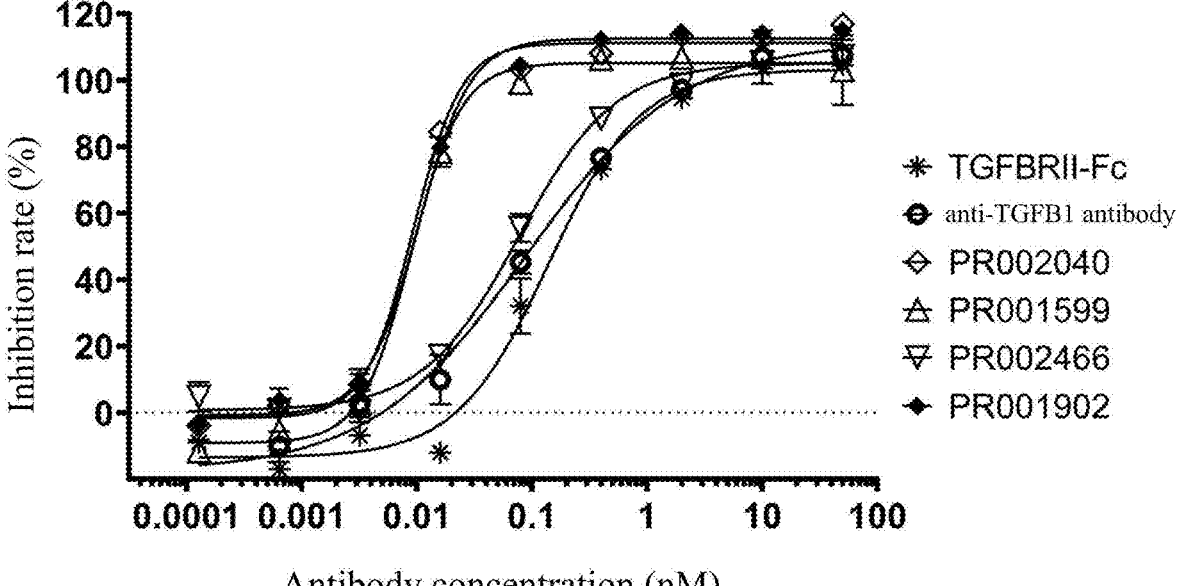
FIG. 19 shows that the inhibition of the TGFB1-induced activation of Samd signaling pathway by the fusion proteins of the present application.

The results are shown in FIG. 19 and Table 24. The fusion proteins inhibit the activity of pSMAD3 reporter induced by TGFB1 in a dose-dependent manner. PR001902 and the positive control PR001599 (M7824) have comparable efficacy and IC50; its inhibitory activity and IC50 are 8 times stronger than the positive control PR002466 (Hengrui fusion protein 9) and TGFB antibody.

TABLE 24

| | The inhibitory effect on the activation of Smad signaling pathway induced by TGFB1 | |
| Fusion protein | Maximum inhibition rate (%) | IC50 (nM) |
| --- | --- | --- |
| PR002040 | 111.2 | 0.0093 |
| PR001599 | 105.2 | 0.0090 |
| PR002466 | 105.2 | 0.0769 |
| PR001902 | 112.5 | 0.0103 |
| TGFBRII-Fc | 103.3 | 0.1402 |
| TGFB1 antibody | 111.5 | 0.0876 |

Example 18 the Results of the Determination of the Affinity of the Fusion Proteins with Human PD-L1 Using BLI The method described in Example 7.2 was used to test the affinity of the fusion proteins with human PD-L1 protein.

The results are shown in Table 25, the $K_D$ values of the affinity between the fusion proteins of the present application and human PD-L1 are all less than $1\times10^{-8}$ M.

TABLE 25

| | The affinity of the fusion proteins with human PD-L1 | | | | | | |
| Fusion protein | $K_D$ (M) | $K_D$ error | $k_{on}$ (1/Ms) | $k_{on}$ error | $k_{dis}$ (1/s) | $k_{dis}$ error | Antigen concentration (nM) |
| --- | --- | --- | --- | --- | --- | --- | --- |
| PR001488 | 1.50E−10 | 1.21E−12 | 8.07E+05 | 2.44E+03 | 1.21E−04 | 9.06E−07 | 25-1.563 |
| PR001599 | 2.82E−10 | 2.47E−12 | 5.42E+05 | 2.16E+03 | 1.53E−04 | 1.19E−06 | 25-1.563 |
| PR001902 | 6.05E−11 | 2.40E−12 | 7.44E+05 | 5.06E+03 | 4.50E−05 | 1.76E−06 | 12.5-0.78 |
| PR002249 | 5.95E−11 | 1.13E−12 | 1.07E+06 | 4.36E+03 | 6.37E−05 | 1.18E−06 | 12.5-0.78 |
| PR002251 | 9.74E−11 | 1.17E−12 | 1.17E+06 | 4.95E+03 | 1.14E−04 | 1.28E−06 | 12.5-0.78 |
| PR002466 | 7.16E−11 | 1.18E−12 | 1.28E+06 | 7.43E+03 | 9.16E−05 | 1.41E−06 | 6.25-0.39 |

Example 19 Determination of the Affinity of the Fusion Proteins with Human TGFB1 Using BLI Method First, the human TGFB1 protein (NovoProtein, CA59) was biotinylated using a biotinylation kit (EZ-Link Sulfo-NHS-LC-Biotin, ThermoFisher, A39257) according to the requirements of the instructions. Then, the affinity of the fusion proteins with human TGFB1 was determined according to the method similar to that described in Example 7.2. In particular, first the two columns of SA sensors (8 sensors were placed in each column; the sensors in the first column were called reference SA sensors, the sensors in the second column were called test SA sensors) were equilibrated in 1×PBS test buffer containing 0.02% Tween for 10 mins. Then, the biotinylated human TGFB1 was captured by the test SA sensors, the capture height was set as 0.3 nm, while the reference SA sensors were immersed in the buffer for 30 secs. The two columns of sensors were then bound with the fusion proteins to be tested in a gradient dilution (for example, the concentrations of the fusion proteins to be tested may be two-fold dilutions with 6.25-0.39 nM, and 0 nM); binding was lasted for 3 mins, and then dissociation was performed for 10 mins.

When using Octet Data Analysis software (Fortebio, version 11.0) for data analysis, the double deduction mode (double reference) was selected to deduct the reference signal, the "1:1 Global fitting" method was selected for data fitting, the kinetic parameters of the binding of antigen and antigen binding proteins were calculated, and the $k_{on}$ (1/Ms) values, $k_{dis}$ (1/s) values and $K_D$ (M) values were obtained.

The results are shown in Table 26. The fusion proteins of the present application have the $K_D$ values with human TGFB1 of less than $1 \times 10^9$ M, and show higher affinity than the control molecules PR001599 and PR002466.

TABLE 26

| The affinity with human TGFB1 | | | |
|---|---|---|---|
| Fusion protein | $K_D$ (M) | $k_{on}$ (1/Ms) | $k_{dis}$ (1/s) |
| PR001599 | 1.04E−10 | 4.10E+06 | 4.24E−04 |
| PR001902 | 7.81E−11 | 3.19E+06 | 2.50E−04 |
| PR002466 | 1.28E−10 | 4.48E+06 | 5.73E−04 |

Example 20 Determination of the Epitope Competition of Binding of the Fusion Proteins to PD-L1 Using BLI Method The epitope competition experiments were performed on the fusion proteins and the control molecules according to the method of Example 8. The results are shown in Table 27-1 and Table 27-2. The epitopes of PR001488 and PR001902 and the control molecule PR001599 or PR002466 do not completely overlap.

TABLE 27-1

| The epitope competition of fusion proteins | | | |
|---|---|---|---|
| | | The second antibody | |
| Competitive inhibition rate (%) | PR001488 | PR001599 | PR002466 |
| The first antibody PR001488 | 97.91 | 73.92 | 84.11 |

TABLE 27-2

| The epitope competition of fusion proteins | | |
|---|---|---|
| | | The second antibody |
| Competitive inhibition rate (%) | | PR001599 |
| The first antibody | PR001902 | 62.18 |

Example 21 In Vitro Detection of the Activation Effect of the Fusion Proteins on T Cells Using MLR Method In order to study the synergistic activation effect of the PD-L1/TGFB fusion proteins on T cells, human peripheral blood mononuclear cells (PBMCs) were collected and purified, the mononuclear cells (Meltenyi, 130-050-201) were isolated, and a complete medium (RPI1640 containing 50 ng/mL IL-4, 100 ng/mL GM-CSF) was used for culturing for 6 days, then 1 μg/mL of LPS was added for induction for 24 hrs to generate mature DC cells. The above-mentioned cultured cells were collected by centrifugation, washed for 4 times with PBS containing 2% FBS, resuspended in fresh medium, adjusted to a density of $2 \times 10^5$ cells/mL, and was seeded into a 96-well cell culture plate at 100 μL/well. At the same time, Pan T cells (Meltenyi, 130-096-535) were isolated from allogeneic fresh PBMCs and resuspended in fresh medium, adjusted to a cell density of $1 \times 10^6$ cells/mL, seeded into a 96-well cell culture plate at 100 μL/well. 50 μL/well of antibodies with different concentrations, and 50 μL/well of human TGFB1 protein (R&D Systems, 240-B/F) with a final concentration of 0.3 ng/mL were added into the corresponding wells of the above mentioned 96-well cell culture plate, and the cell culture plate was incubated in a 37° C., 5% $CO_2$ incubator for 5 days. The supernatants after 72 hrs and 120 hrs were collected respectively. The IL-2 ELISA kit (Thermo, 88-7025-88) was used to detect the level of IL-2 in the supernatant after 72 hrs; the IFN-γ ELISA kit (Thermo, 88-7316-88) was used to detect the level of IFN-γ in the supernatant after 120 hrs; specific operations may be according to the reagent instructions.

Figure 20:
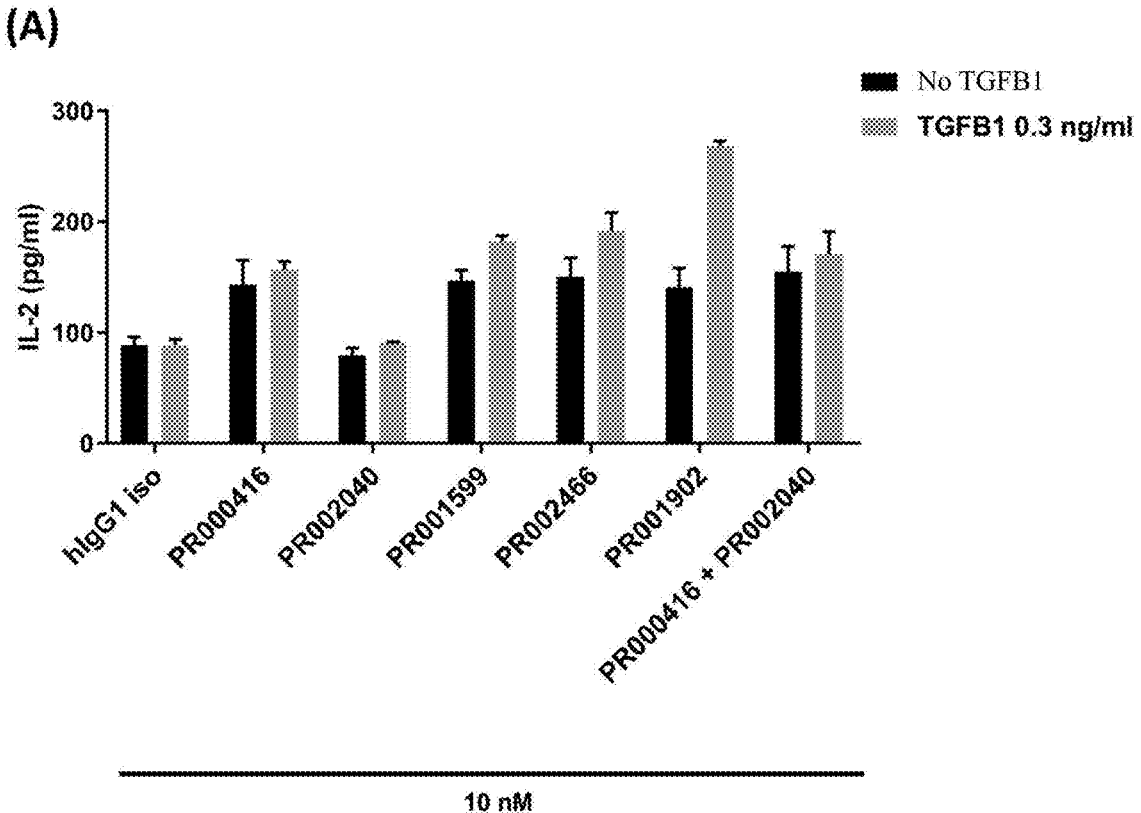
FIG. 20 shows that the level of secreting cytokines by T lymphocytes stimulated by the fusion proteins of the present application in mixed lymphocyte reaction (MLR) under the condition without or with TGFB1: (A) the levels of IL-2 in the supernatants after 72 hrs, (B) the levels of IFN-γ in the supernatants after 120 hrs.
Figure 20:
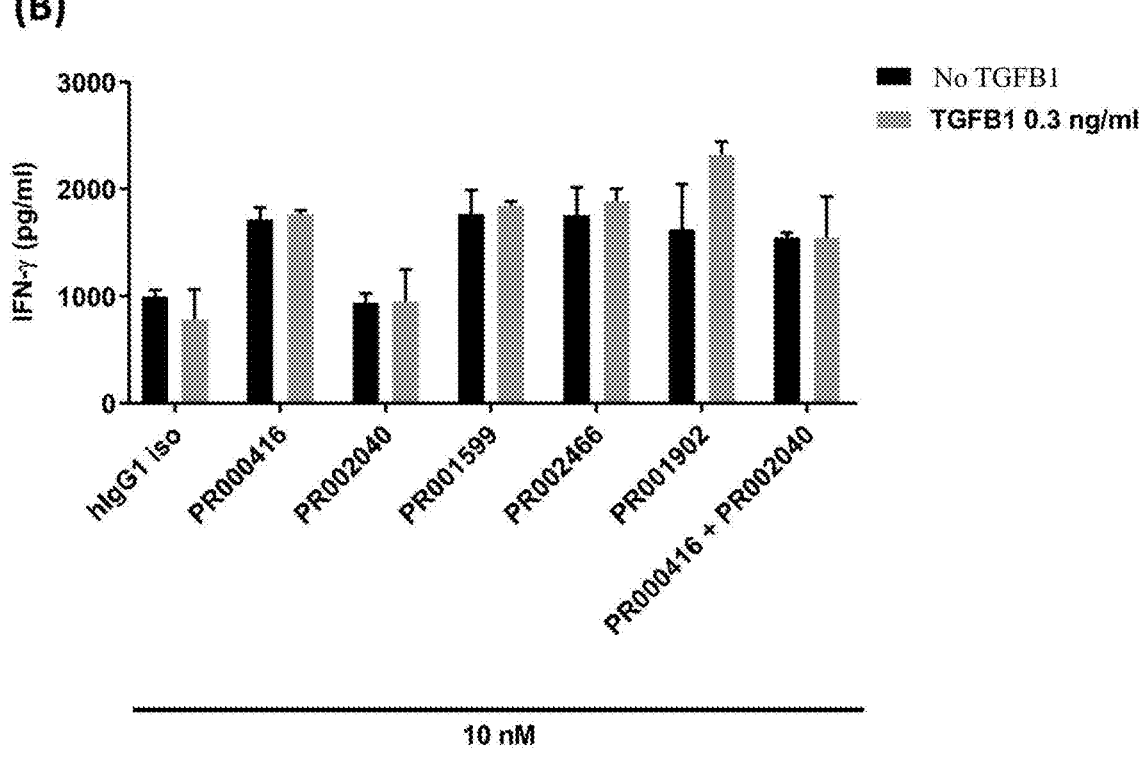

The results are shown in FIG. 20. With the addition of TGFB1, the fusion proteins are capable of enhancing the secretion of cytokines IL-2 (FIG. 20 (A)) and IFN-γ (FIG. 20 (B)) by activated T lymphocytes, and have stronger activation effect than the PD-L1 monoclonal antibody PR000416 and the positive controls PR001599 and PR002446.

Figure 21:
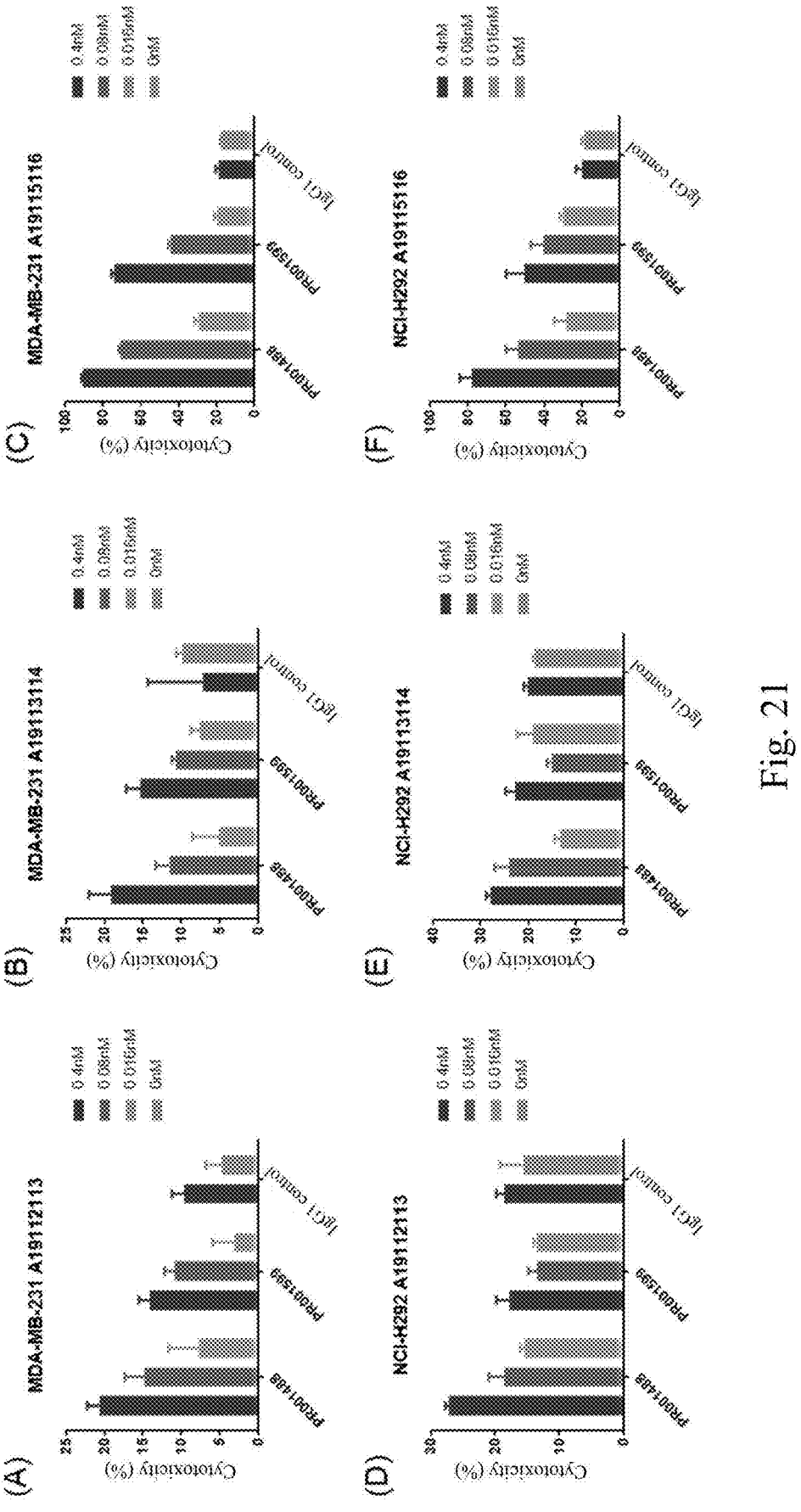
FIG. 21 shows that the results of antibody-dependent cytotoxicity of the fusion proteins of the present application: (A-C) the killing of tumor cells MDA-MB-231 by the PBMCs from three different donors; (D-F) the killing of tumor cells NCI-H292 by the PBMCs from three different donors.

Example 22 the Results of Tumor Cell-Mediated Antibody-Dependent Cytotoxicity Experiments The tumor cell-mediated antibody-dependent cytotoxicity of the fusion proteins described in the present application was detected according to the method of Example 10. In the present example, PBMCs from three donors and two tumor cell lines were used, a total of six independent ADCC experiments. The results are shown in FIG. 21 (A-F). PR001488 has a stronger ADCC effect than the positive control PR001599.

Example 23 Pharmacokinetic Study of the Fusion Proteins

The pharmacokinetic properties of the fusion proteins were tested in the present example. The method was as follows. 3 female C57BL/6 mice weighing 18-22 g were selected, and the fusion protein medicaments were administrated by intravenous injection at a dose of 9.53 mg/kg for PR001902 and 10 mg/kg for PR001488; the whole bloods were collected before administration and 0.5 hrs, 24 hrs (1 day), 2 days, 4 days, 7 days, 10 days, and 14 days after administration, and the whole bloods were standing for 30 mins to coagulate, then centrifuged at 4° C., 2,000 rpm for 5 mins, and the isolated serum samples were frozen at −80° C. until analysis. Two ELISA methods were used to quantitatively determine the drug concentration in mouse serum in the present example. ELISA method I, i.e., the Fc-end detection method, the fusion proteins containing human Fc in mouse serum were captured by goat anti-human Fc polyclonal antibody coating on 96-well plate, and then HRP-labeled goat anti-human Fc secondary antibody was added to detect; ELISA method II, i.e., TGFBRII-end detection method, the fusion proteins containing human TGFBRII domain in mouse serum was captured by human TGFB1 protein coating on 96-well plate, then HRP-labeled goat anti-human Fc secondary antibody was added to detect. The Phoenix WinNonlin software version 6.4 was used, the Noncompartmental Model (NCA) was chosen to analyze the blood drug concentration data to evaluate the pharmacokinetics.

Figure 22:
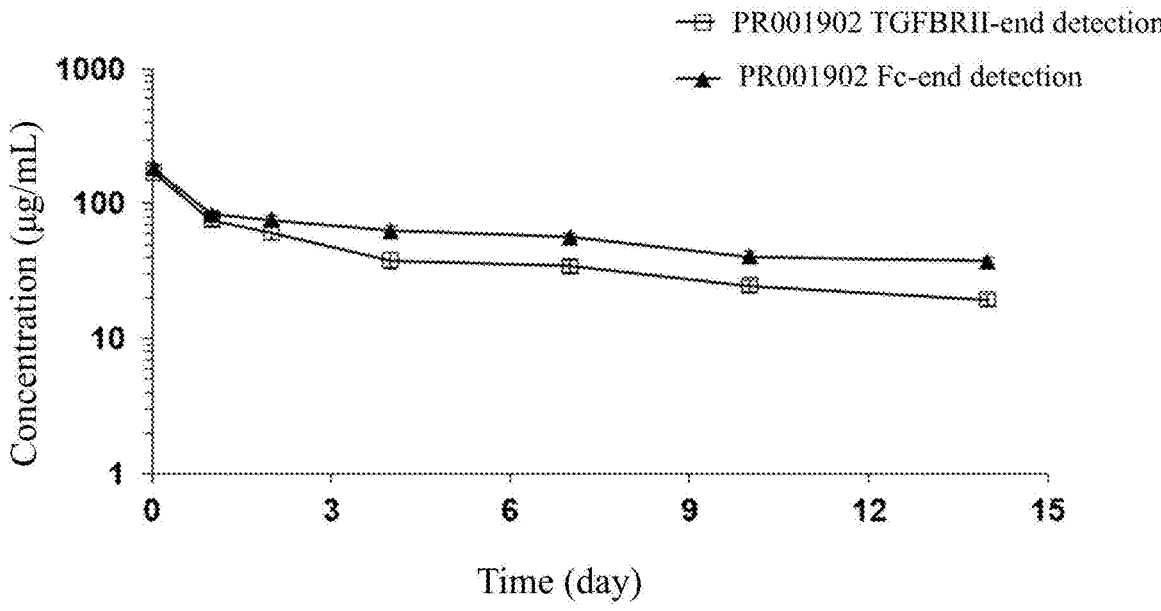
FIG. 22 shows that the pharmacokinetic results of the fusion protein PR001902 of the present application.

FIG. 22 and Table 28 show the pharmacokinetic data of the fusion protein PR001902. The results show that the half-life of PR001902 in mice is about 11 days under the Fc-end detection method; the TGFBRII-end detection method shows that the half-life of PR001902 in mice is about 8.5 days.

TABLE 28

The pharmacokinetics of PR001902

| PK parameter | Unit | PR001902 TGFBRII-end detection | | PR001902 Fc-end detection | |
|---|---|---|---|---|---|
| | | Mean ± SD | CV (%) | Mean ± SD | CV (%) |
| CL | mL/day/kg | 11.7 ± 0.90 | 8.02 | 6.67 ± 0.67 | 10.0 |
| $V_{ss}$ | mL/kg | 130 ± 16 | 12.1 | 104 ± 6 | 6.08 |
| End-point $t^{1/2}$ | day | 8.52 ± 1.35 | 15.9 | 11.0 ± 1.3 | 11.4 |
| $AUC_{last}$ | day × μg/mL | 578 ± 45 | 7.81 | 836 ± 53 | 6.36 |
| $AUC_{INF}$ | day × μg/mL | 817 ± 64 | 7.87 | 1438 ± 136 | 9.49 |

Figure 23:
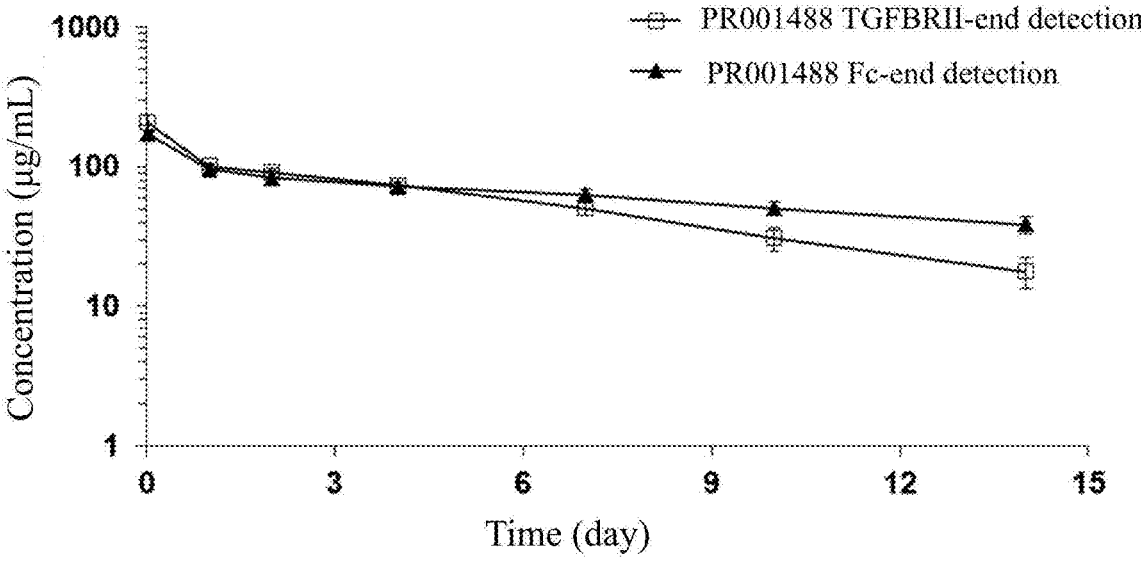
FIG. 23 shows that the pharmacokinetic results of the fusion protein PR001488 of the present application.

FIG. 23 and Table 29 show the pharmacokinetic data of the fusion protein PR001488. The results show that the half-life of PR001488 in mice is about 10 days under the Fc-end detection method; the TGFBRII-end detection method shows that the half-life of PR001488 in mice is about 5 days.

TABLE 29

The pharmacokinetics of PR001488

| PK parameter | Unit | PR001488 TGFBRII-end detection | | PR001488 Fc-end detection | |
|---|---|---|---|---|---|
| | | Mean ± SD | CV (%) | Mean ± SD | CV (%) |
| CL | mL/day/kg | 9.19 ± 1.23 | 13.4 | 5.88 ± 1.154 | 19.6 |
| $V_{ss}$ | mL/kg | 62.9 ± 7.51 | 11.9 | 82.3 ± 10.7 | 13.0 |
| End-point $t^{1/2}$ | day | 5.08 ± 1.03 | 20.2 | 10.2 ± 3.42 | 33.6 |
| $AUC_{last}$ | day × μg/mL | 818 ± 79.5 | 9.72 | 930 ± 74.4 | 8.00 |
| $AUC_{INF}$ | day × μg/mL | 952 ± 120 | 12.6 | 1511 ± 309 | 20.4 |

Example 24 Anti-Tumor Activity of the Fusion Proteins in the In Vivo Animal Model of Colon Cancer CT26-Human PD-1/PD-L1 Transgenic Mice In this example, the anti-tumor effect of the test medicaments on the immune checkpoint transplanted, humanized mouse BALB/c-human PD-1/PD-L1 (the exogenous human PD-1 transgene and human PD-L1 transgene were introduced at the same time into BALB/c mice, Jicui Yaokang Biotechnology) with mouse colon cancer cell CT26-human PDL1(tg)-mouse PDL1(KO) (the endogenous mouse PD-L1 gene of mouse colon cancer cell CT26 was knocked out and the exogenous human PD-L1 transgene was introduced, Jicui Yaokang Biotechnology) was evaluated. The CT26-human PDL1(tg)-mPDL1(KO) cells in log phase were inoculated subcutaneously into the right side of axillary back of humanized mouse BALB/c-human PD-1/PD-L1. When the average tumor volume reached to 80-120 mm³, after removing the individual mice with too large tumor volume, the mice were randomly divided into 3 groups according to the tumor volume, with 6 mice in each group. There are 3 test groups in total, namely: human IgG1 (10.4 mg/kg, human IgG1 isotype control group), M7824 (12.3 mg/kg, positive control) and PR001902 (12.2 mg/kg, the fusion protein of the present application). The intraperitoneal administrations were started on the day of grouping, once every three days for a total of 6 administrations (q3d×6). After starting the administration, the body weight and tumor volume were weighted twice a week. The calculation method of tumor volume was: tumor volume (mm³)=0.5× tumor long diameter×tumor short diameter². After the end of the experiment, the tumor-bearing mice were euthanized and the tumors were stripped and weighed. The experimental results such as the tumor volume of each group of animals and mouse body weight were calculated as mean±standard error (Mean±SEM). Multi-group comparisons were performed using one way analysis of variance (one way ANOVA) test method to compare whether there were significant differences between the various treatment groups and the control group. The data was analyzed using SPSS 18.0. P<0.05 was considered as having a significant difference.

Figure 24:
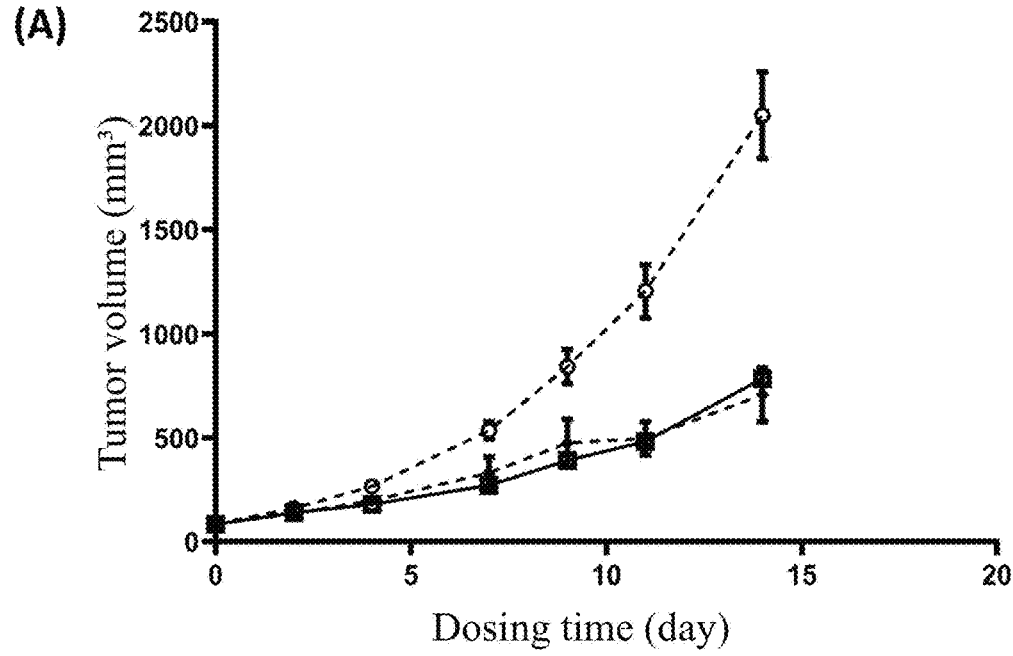
FIG. 24 shows that the anti-tumor activity of the fusion protein of the present application in a tumor animal in vivo model, the change in tumor volume (A) and the change in mouse body weight (B), respectively.
Figure 24:
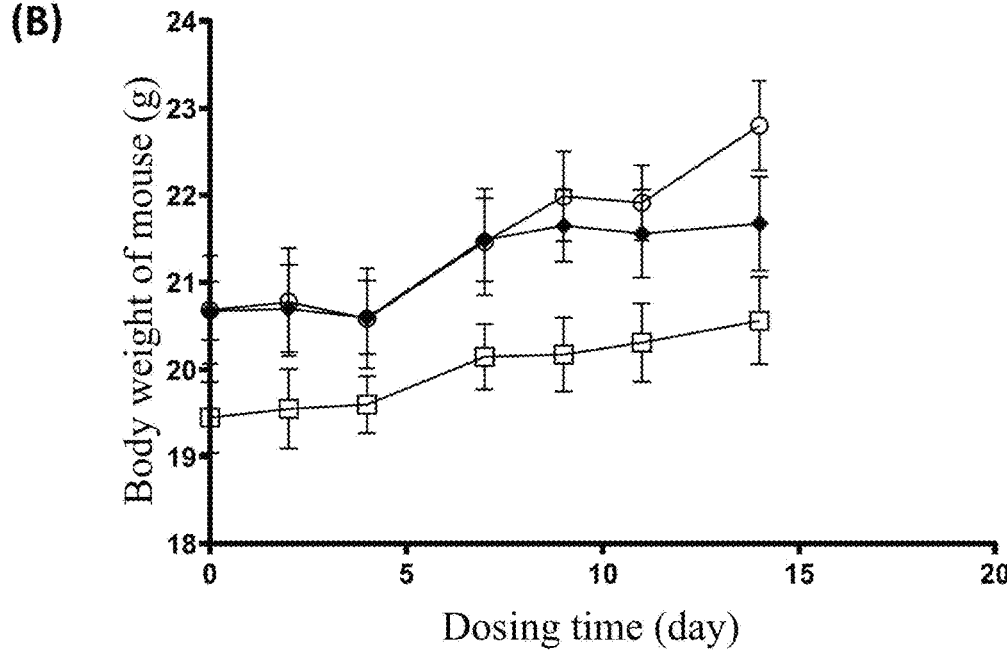

The results are shown in FIG. 24. Both the fusion protein PR001902 and the positive control M7824 are capable of significantly inhibiting the growth of subcutaneously transplanted tumors in CT26-human PD-1/PD-L1 mice; and during the experiment, the body weight of each group of animals all increased, indicating that the animals tolerate the test product well. It has no significant toxic effects on animals and has good safety.

The foregoing detailed description is provided by way of explanation and examples, and is not intended to limit the scope of the appended claims. Various changes of the embodiments listed in the present application are obvious to those of ordinary skills in the art, and are reserved within the scope of the appended claims and the equivalent solutions thereof.

The invention claimed is:

1. An isolated antigen binding protein that binds to PD-L1, comprising a light chain variable region (VL) and a heavy chain variable region (VH), wherein the VL comprises a light chain complementarity determining region (LCDR) 1, LCDR2, and LCDR3, and the VH comprises a heavy chain complementarity determining region (HCDR) 1, HCDR2, and HCDR3, wherein:

the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 29;

the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29;

the LCDR1 comprises the amino acid sequence set forth in SEQ ID NO: 51, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 29;

the LCDR1 comprises the amino acid sequence set forth in SEQ ID NO: 48; the LCDR2 comprises the amino acid sequence set forth in SEQ ID NO: 63; the LCDR3 comprises the amino acid sequence set forth in SEQ ID NO: 77; the HCDR1 comprises the amino acid sequence set forth in SEQ ID NO: 5; the HCDR2 comprises the amino acid sequence set forth in SEQ ID NO: 14; and the HCDR3 comprises the amino acid sequence set forth in SEQ ID NO: 29;

the LCDR1 comprises the amino acid sequence set forth in SEQ ID NO: 49, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29;

the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 30;

the LCDR1 comprises the amino acid sequence set forth in SEQ ID NO: 50, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 29;

the LCDR1 comprises the amino acid sequence set forth in SEQ ID NO: 50, the LCDR2 comprises the amino acid sequence set forth in SEQ ID NO: 63, the LCDR3 comprises the amino acid sequence set forth in SEQ ID NO: 79, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 31;

the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 32;

the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 14, and the HCDR3 comprises the amino acid sequence set forth in SEQ ID NO: 33;

the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 30;

the LCDR1 comprises the amino acid sequence set forth in SEQ ID NO: 48, the LCDR2 comprises the amino acid sequence set forth in SEQ ID NO: 64, the LCDR3 comprises the amino acid sequence set forth in SEQ ID NO: 78, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 30;

the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 32;

the LCDR1 comprises the amino acid sequence set forth in SEQ ID NO: 51, the LCDR2 comprises the amino acid sequence set forth in SEQ ID NO: 63, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 32;

the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 16, and the HCDR3 comprises the amino acid sequence set forth in SEQ ID NO: 33; or the LCDR1 comprises the amino acid sequence set forth in SEQ ID NO: 50, the LCDR2 comprises the amino acid sequence set forth in SEQ ID NO: 64, the LCDR3 comprises the amino acid sequence set forth in SEQ ID NO: 77, the HCDR1 comprises the amino acid sequence set forth in SEQ ID NO: 5, the HCDR2 comprises the amino acid sequence set forth in SEQ ID NO: 17, and the HCDR3 comprises the amino acid sequence set forth in SEQ ID NO: 33.

2. The isolated antigen binding protein of claim 1, wherein the VH comprises the amino acid sequence set forth in SEQ ID NO: 101, the VL comprises the amino acid sequence set forth in SEQ ID NO: 114;

the VH comprises the amino acid sequence set forth in SEQ ID NO: 90, the VL comprises the amino acid sequence set forth in SEQ ID NO: 114;

the VH comprises the amino acid sequence set forth in SEQ ID NO: 102, the VL comprises the amino acid sequence set forth in SEQ ID NO: 114;

the VH comprises the amino acid sequence set forth in SEQ ID NO: 90; the VL comprises the amino acid sequence set forth in SEQ ID NO: 108;

the VH comprises the amino acid sequence set forth in SEQ ID NO: 90, the VL comprises the amino acid sequence set forth in SEQ ID NO: 109;

the VH comprises the amino acid sequence set forth in SEQ ID NO: 91, the VL comprises the amino acid sequence set forth in SEQ ID NO: 110;

the VH comprises the amino acid sequence set forth in SEQ ID NO: 90, the VL comprises the amino acid sequence set forth in SEQ ID NO: 111;

the VH comprises the amino acid sequence set forth in SEQ ID NO: 92, the VL comprises the amino acid sequence set forth in SEQ ID NO: 112;

the VH comprises the amino acid sequence set forth in SEQ ID NO: 93, the VL comprises the amino acid sequence set forth in SEQ ID NO: 113;

the VH comprises the amino acid sequence set forth in SEQ ID NO: 95, the VL comprises the amino acid sequence set forth in SEQ ID NO: 116;

the VH comprises the amino acid sequence set forth in SEQ ID NO: 97, the VL comprises the amino acid sequence set forth in SEQ ID NO: 118;

the VH comprises the amino acid sequence set forth in SEQ ID NO: 98, the VL comprises the amino acid sequence set forth in SEQ ID NO: 118;

the VH comprises the amino acid sequence set forth in SEQ ID NO: 99, the VL comprises the amino acid sequence set forth in SEQ ID NO: 113;

the VH comprises the amino acid sequence set forth in SEQ ID NO: 100, the VL comprises the amino acid sequence set forth in SEQ ID NO: 113;

the VH comprises the amino acid sequence set forth in SEQ ID NO: 103, the VL comprises the amino acid sequence set forth in SEQ ID NO: 116; or the VH comprises the amino acid sequence set forth in SEQ ID NO: 104, the VL comprises the amino acid sequence set forth in SEQ ID NO: 116.

3. The isolated antigen binding protein of claim 1, having one or more of following properties:

1) capable of binding to PD-L1 derived from a primate with a $K_D$ value of $1 \times 10^{-8}$ M or less;

2) capable of blocking the binding of PD-1 to PD-L1;

3) capable of blocking the binding of CD80 to PD-L1;

4) capable of stimulating secretion of IFN-γ and/or IL2 in an immune cell;

5) capable of inhibiting tumor growth and/or tumor cell proliferation;

6) Binding to an epitope of PD-L1 derived from a primate that does not completely overlap with the epitope of a control antibody, wherein the control antibody comprises a LCDR1 set forth in SEQ ID NO: 52, a LCDR2 set forth in SEQ ID NO: 65 and a LCDR3 set forth in SEQ ID NO: 81, and the control antibody comprises a HCDR1 set forth in SEQ ID NO: 6, a HCDR2 set forth in SEQ ID NO: 15 and a HCDR3 set forth in SEQ ID NO: 34;

wherein the control antibody comprises a LCDR1 set forth in SEQ ID NO: 53, a LCDR2 set forth in SEQ ID NO: 66 and a LCDR3 set forth in SEQ ID NO: 82, and the control antibody comprises a HCDR1 set forth in SEQ ID NO: 5, a HCDR2 set forth in SEQ ID NO: 18 and a HCDR3 set forth in SEQ ID NO: 35; or wherein the control antibody comprises a LCDR1 set forth in SEQ ID NO: 55, a LCDR2 set forth in SEQ ID NO: 68 and a LCDR3 set forth in SEQ ID NO: 84, and the control antibody comprises a HCDR1 set forth in SEQ ID NO: 8, a HCDR2 set forth in SEQ ID NO: 20 and a HCDR3 set forth in SEQ ID NO: 37.

4. A fusion protein, comprising: a) a human TGFBRII or a fragment thereof; and b) the isolated antigen binding protein of claim 1.

5. The fusion protein of claim 4, wherein the isolated antigen binding protein comprises a heavy chain or a fragment thereof comprising the VH, and a light chain or a fragment thereof comprising the VL; and wherein the fusion protein comprises a first polypeptide and a second polypeptide, the first polypeptide comprising the heavy chain of the isolated antigen binding protein, or the fragment thereof, and the human TGFBRII or the fragment thereof; and the second polypeptide comprising the light chain of the isolated antigen binding protein, or the fragment thereof.

6. The fusion protein of claim 5, wherein the heavy chain of the isolated antigen binding protein or the fragment thereof is linked to the human TGFBRII or the fragment thereof via a peptide linker, and wherein the peptide linker comprises the amino acid sequence set forth in any one of SEQ ID NOs: 167-169.

7. The fusion protein of claim 5, wherein, the first polypeptide comprises the amino acid sequence set forth in SEQ ID NO: 143, and the second polypeptide comprises the amino acid sequence set forth in SEQ ID NO: 162;

the first polypeptide comprises the amino acid sequence set forth in SEQ ID NO: 138, and the second polypeptide comprises the amino acid sequence set forth in SEQ ID NO: 162;

the first polypeptide comprises the amino acid sequence set forth in SEQ ID NO: 139, and the second polypeptide comprises the amino acid sequence set forth in SEQ ID NO: 162;

the first polypeptide comprises the amino acid sequence set forth in SEQ ID NO: 142, and the second polypeptide comprises the amino acid sequence set forth in SEQ ID NO: 162;

the first polypeptide comprises the amino acid sequence set forth in SEQ ID NO: 147, and the second polypeptide comprises the amino acid sequence set forth in SEQ ID NO: 162;

the first polypeptide comprises the amino acid sequence set forth in SEQ ID NO: 148, and the second polypeptide comprises the amino acid sequence set forth in SEQ ID NO: 162;

the first polypeptide comprises the amino acid sequence set forth in SEQ ID NO: 145, and the second polypeptide comprises the amino acid sequence set forth in SEQ ID NO: 163; or the first polypeptide comprises the amino acid sequence set forth in SEQ ID NO: 146, and the second polypeptide comprises the amino acid sequence set forth in SEQ ID NO: 163.

8. The fusion protein of claim 5, wherein the heavy chain of the isolated antigen binding protein or the fragment thereof is linked, directly or indirectly, to the N-terminus of the human TGFBRII or the fragment thereof.

9. The fusion protein of claim 4, wherein a) is the fragment of the human TGFBRII, which comprises an extracellular domain of the human TGFBRII.

10. The fusion protein of claim 4, wherein the human TGFBRII or the fragment thereof comprises the amino acid sequence set forth in any one of SEQ ID NOs: 176-178.

11. An antibody-drug conjugate, comprising a cytotoxic agent and the isolated antigen binding protein of claim 1.

12. A pharmaceutical composition comprising the isolated antigen binding protein of claim 1 or a fusion protein, and a pharmaceutically acceptable carrier, wherein the fusion protein comprises a) a human TGFBRII or a fragment thereof; and b) the isolated antigen binding protein.

13. The pharmaceutical composition of claim 12, further comprising one or more components selected from the group consisting of a hormone formulation, a targeted small molecule formulation, a proteasome inhibitor, an imaging agent, a diagnostic agent, a chemotherapeutic agent, an oncolytic medicament, a cytotoxic agent, a cytokine, an activator of co-stimulatory molecule, an inhibitor of inhibitory molecule, and a vaccine.

14. A method of alleviating or treating a tumor, inhibiting tumor growth and/or inhibiting tumor cell proliferation in a subject in need thereof, comprising administering to the subject the isolated antigen binding protein of claim 1 or a fusion protein, wherein the fusion protein comprises: a) a human TGFBRII or a fragment thereof; and b) the isolated antigen binding protein, and wherein the tumor is a tumor with abnormal expression of PD-L1.

15. The method of claim 14, wherein the tumor is a colorectal tumor.

16. A method of inhibiting the binding of PD-L1 and/or CD80 with PD-1, comprising contacting immune cells with the isolated antigen binding protein of claim 1.

17. The isolated antigen binding protein of claim 1, wherein the isolated antigen binding protein comprises an antibody heavy chain (HC) comprising the VH and an antibody light chain (LC) comprising the VL, wherein, the LC comprises the amino acid sequence set forth in SEQ ID NO: 162, and the HC comprises the amino acid sequence set forth in SEQ ID NO: 133;

the LC comprises the amino acid sequence set forth in SEQ ID NO: 162, and the HC comprises the amino acid sequence set forth in SEQ ID NO: 134;

the LC comprises the amino acid sequence set forth in SEQ ID NO: 156, and the HC comprises the amino acid sequence set forth in SEQ ID NO: 122;

the LC comprises the amino acid sequence set forth in SEQ ID NO: 162, and the HC comprises the amino acid sequence set forth in SEQ ID NO: 137;

the LC comprises the amino acid sequence set forth in SEQ ID NO: 150, and the HC comprises the amino acid sequence set forth in SEQ ID NO: 122;

the LC comprises the amino acid sequence set forth in SEQ ID NO: 151, and the HC comprises the amino acid sequence set forth in SEQ ID NO: 122;

the LC comprises the amino acid sequence set forth in SEQ ID NO: 152, and the HC comprises the amino acid sequence set forth in SEQ ID NO: 123;

the LC comprises the amino acid sequence set forth in SEQ ID NO: 153, and the HC comprises the amino acid sequence set forth in SEQ ID NO: 122;

the LC comprises the amino acid sequence set forth in SEQ ID NO: 154, and the HC comprises the amino acid sequence set forth in SEQ ID NO: 124;

the LC comprises the amino acid sequence set forth in SEQ ID NO: 155, and the HC comprises the amino acid sequence set forth in SEQ ID NO: 125;

the LC comprises the amino acid sequence set forth in SEQ ID NO: 158, and the HC comprises the amino acid sequence set forth in SEQ ID NO: 127;

the LC comprises the amino acid sequence set forth in SEQ ID NO: 160, and the HC comprises the amino acid sequence set forth in SEQ ID NO: 129;

the LC comprises the amino acid sequence set forth in SEQ ID NO: 160, and the HC comprises the amino acid sequence set forth in SEQ ID NO: 130;

the LC comprises the amino acid sequence set forth in SEQ ID NO: 161, and the HC comprises the amino acid sequence set forth in SEQ ID NO: 131;

the LC comprises the amino acid sequence set forth in SEQ ID NO: 161, and the HC comprises the amino acid sequence set forth in SEQ ID NO: 132;

the LC comprises the amino acid sequence set forth in SEQ ID NO: 163, and the HC comprises the amino acid sequence set forth in SEQ ID NO: 135; or the LC comprises the amino acid sequence set forth in SEQ ID NO: 163, and the HC comprises the amino acid sequence set forth in SEQ ID NO: 136.

18. An isolated nucleic acid molecule encoding the antigen binding protein of claim 1 or a fusion protein comprising a) a human TGFBRII or a fragment thereof; and b) the antigen binding protein.

19. An antibody that binds to PD-L1, comprising an antibody heavy chain (HC) and an antibody light chain (LC), wherein the LC comprises the amino acid sequence set forth in SEQ ID NO: 162, and the HC comprises the amino acid sequence set forth in SEQ ID NO: 133.

20. A method of alleviating or treating a tumor in a subject in need there, comprising administering to the subject the antibody of claim 19, wherein the tumor is the tumor with abnormal expression of PD-L1.

\* \* \* \* \*